(12) United States Patent
Gnamm et al.

(10) Patent No.: US 9,115,093 B2
(45) Date of Patent: Aug. 25, 2015

(54) SUBSTITUTED BICYCLIC DIHYDROPYRIMIDINONES AND THEIR USE AS INHIBITORS OF NEUTROPHIL ELASTASE ACTIVITY

(71) Applicants: Christian Gnamm, Biberach an der Riss (DE); Thorsten Oost, Biberach an der Riss (DE); Stefan Peters, Biberach an der Riss (DE); Klaus Rudolf, Warthausen (DE)

(72) Inventors: Christian Gnamm, Biberach an der Riss (DE); Thorsten Oost, Biberach an der Riss (DE); Stefan Peters, Biberach an der Riss (DE); Klaus Rudolf, Warthausen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/184,817

(22) Filed: Feb. 20, 2014

(65) Prior Publication Data

US 2014/0249129 A1    Sep. 4, 2014

(30) Foreign Application Priority Data

Mar. 4, 2013   (EP) .................................... 13157640

(51) Int. Cl.
| | | |
|---|---|---|
| C07D 239/70 | (2006.01) |
| C07D 403/12 | (2006.01) |
| C07D 401/12 | (2006.01) |
| A61K 31/517 | (2006.01) |
| A61P 19/02 | (2006.01) |
| C07D 239/82 | (2006.01) |
| C07D 401/04 | (2006.01) |
| C07D 403/06 | (2006.01) |
| C07D 407/06 | (2006.01) |
| C07D 407/12 | (2006.01) |
| C07D 409/04 | (2006.01) |
| C07D 409/12 | (2006.01) |
| C07D 413/06 | (2006.01) |
| C07D 471/04 | (2006.01) |
| C07D 487/04 | (2006.01) |
| C07D 493/10 | (2006.01) |
| C07D 498/04 | (2006.01) |
| C07D 498/10 | (2006.01) |
| C07D 405/14 | (2006.01) |
| C07D 403/04 | (2006.01) |
| C07D 405/04 | (2006.01) |
| C07D 405/06 | (2006.01) |
| C07D 405/12 | (2006.01) |
| C07D 413/12 | (2006.01) |
| C07D 417/06 | (2006.01) |

(Continued)

(52) U.S. Cl.
CPC ............ *C07D 239/82* (2013.01); *C07D 401/04* (2013.01); *C07D 401/12* (2013.01); *C07D 403/04* (2013.01); *C07D 403/06* (2013.01); *C07D 403/12* (2013.01); *C07D 405/04* (2013.01); *C07D 405/06* (2013.01); *C07D 405/12* (2013.01); *C07D 405/14* (2013.01); *C07D 407/06* (2013.01); *C07D 407/12* (2013.01); *C07D 409/04* (2013.01); *C07D 409/12* (2013.01); *C07D 413/06* (2013.01); *C07D 413/12* (2013.01); *C07D 417/06* (2013.01); *C07D 471/04* (2013.01); *C07D 487/04* (2013.01); *C07D 487/10* (2013.01); *C07D 491/10* (2013.01); *C07D 493/10* (2013.01); *C07D 498/04* (2013.01); *C07D 498/10* (2013.01)

(58) Field of Classification Search
CPC .. C07D 239/70; C07D 403/12; C07D 401/12; C07D 239/80; A61K 31/517; A61K 45/06
USPC ........................................ 544/253; 514/258.1
See application file for complete search history.

(56) References Cited

U.S. PATENT DOCUMENTS

| 8,569,314 | B2 | 10/2013 | Von Nussbaum et al. |
| 8,580,800 | B2 | 11/2013 | Von Nussbaum et al. |
| 8,691,817 | B2 | 4/2014 | Von Nussbaum et al. |

(Continued)

FOREIGN PATENT DOCUMENTS

| CA | 2656307 A1 | 1/2008 |
| DE | 102006031314 A1 | 1/2008 |

(Continued)

OTHER PUBLICATIONS

Groutas et al. Expert Opin Ther Pat. Mar. 2011 ; 21(3): 339-354.*

(Continued)

*Primary Examiner* — Venkataraman Balasubramanian
(74) *Attorney, Agent, or Firm* — Michael P. Morris; Alan R. Stempel

(57) ABSTRACT

This invention relates to substituted bicyclic dihydropyrimidinones of formula 1

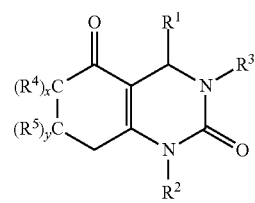

and their use as inhibitors of neutrophil elastase activity, pharmaceutical compositions containing the same, and methods of using the same as agents for treatment and/or prevention of pulmonary, gastrointestinal and genitourinary diseases, inflammatory diseases of the skin and the eye and other autoimmune and allergic disorders, allograft rejection, and oncological diseases.

13 Claims, No Drawings

(51) Int. Cl.
*C07D 487/10* (2006.01)
*C07D 491/10* (2006.01)

(56) References Cited

U.S. PATENT DOCUMENTS

| | | |
|---|---|---|
| 8,889,700 B2 | 11/2014 | Von Nussbaum et al. |
| 9,040,516 B2 | 5/2015 | Shiro et al. |
| 2009/0093477 A1 | 4/2009 | Ray et al. |
| 2011/0034433 A1 | 2/2011 | Von Nussbaum et al. |
| 2013/0065913 A1 | 3/2013 | Blench et al. |

FOREIGN PATENT DOCUMENTS

| | | |
|---|---|---|
| DE | 102007061766 A1 | 6/2009 |
| DE | 102008052013 A1 | 4/2010 |
| GB | 2392910 A | 3/2004 |
| WO | 2004024700 A1 | 3/2004 |
| WO | 2004024701 A1 | 3/2004 |
| WO | 2005021512 A1 | 3/2005 |
| WO | 2005082863 A2 | 9/2005 |
| WO | 2005082864 A1 | 9/2005 |
| WO | 2006082412 A2 | 8/2006 |
| WO | 2006136857 A1 | 12/2006 |
| WO | 2007129060 A1 | 11/2007 |
| WO | 2008135537 A1 | 11/2008 |
| WO | 2009013444 A1 | 1/2009 |
| WO | 2009037413 A1 | 3/2009 |
| WO | 2009060158 A1 | 5/2009 |
| WO | 2009060203 A1 | 5/2009 |
| WO | 2009060206 A1 | 5/2009 |
| WO | 2009080199 A1 | 7/2009 |
| WO | 2009135599 A1 | 11/2009 |
| WO | 2010078953 A1 | 7/2010 |
| WO | 2010115548 A1 | 10/2010 |
| WO | 2011110858 A1 | 9/2011 |
| WO | 2011110859 A1 | 9/2011 |
| WO | 2012002502 A1 | 1/2012 |
| WO | 2013018804 A1 | 2/2013 |

OTHER PUBLICATIONS

Turner et al., Current Pharmaceutical Design. 2, 209-224, 1996.*
Sugar et al., Diagno Microbiol. Infect. Dis. 21 129-133, 1995.*
Snyder et al., J. Med. Liban 48(4): 208-214, 2000. PubMed Abstract.*
Abstract in English for DE10 2008 052013 publication date Apr. 22, 2010.
International Search Report, PCT/ISA/210, and written opinion, pCT/ISA/237, for corresponding application PCT/EP2014/053718, date of mailing Apr. 2, 2014.
Abstract in English for DE102007061766 publication date Jun. 25, 2009.
Abstract in English for WO2012002502 publication date Jan. 5, 2012.
Sjö et al., Neutrophil elastase inhibitors: recent advances in the development of mechanism-based and nonelectrophilic inhibitors, Future Med. Chem., 2012, vol. 4, pp. 651-660.

* cited by examiner

SUBSTITUTED BICYCLIC DIHYDROPYRIMIDINONES AND THEIR USE AS INHIBITORS OF NEUTROPHIL ELASTASE ACTIVITY

This invention relates to substituted bicyclic dihydropyrimidinones of formula 1

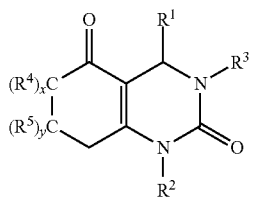

1 and their use as inhibitors of neutrophil elastase activity, pharmaceutical compositions containing the same, and methods of using the same as agents for treatment and/or prevention of pulmonary, gastrointestinal and genitourinary diseases, inflammatory diseases of the skin and the eye and other autoimmune and allergic disorders, allograft rejection, and oncological diseases.

BACKGROUND INFORMATION

The following references describe neutrophil elastase inhibitors with a monocyclic dihydropyrimidinone core: GB2392910, WO04024700, WO05082864, WO05082863, DE102006031314, US100010024, WO10115548, WO09080199, DE102007061766, WO06136857, WO06082412, WO12002502.

The following references describe neutrophil elastase inhibitors with a bicyclic tetrahydropyrrolopyrimidinedione core: WO07129060, WO08135537, US090093477, WO09013444, WO09060206, WO09060203, WO09060158, US110034433.

The following references describe neutrophil elastase inhibitors with core structures other than those herein before mentioned: WO04020412, WO04020410, WO03053930, WO10078953, WO09135599, DE102009004197, WO11110858, WO11110859, WO09060158, WO09037413, WO04024701, WO13018804, US130065913, WO13018804, WO12002502.

For a review on various inhibitors of neutrophil elastase see: P. Sjö (*Future Med. Chem.* 2012, 4, 651-660).

BRIEF SUMMARY OF THE INVENTION

Neutrophil elastase is a 29 kDa serine protease. It is expressed in bone marrow precursor cells, stored in the granula of peripheral blood granulocytes at high concentrations and it is released upon cellular activation. To the substrates of NE belong major elements of the extracellular matrix: elastin, fibronectin, laminin, collagen and proteoglycans. Neutrophil elastase activity leads to ECM degradation, increases migration and chemotaxis of mono-cytes and vascular smooth muscle cells and directly affects components of the coagulation and fibrinolytic pathways (PAI-1 and TFPI). Increased activity of neutrophil elastase is associated with chronic inflammatory and fibrotic diseases of several organs Inhibitors of neutrophil elastase will therefore have an important role for the treatment of different diseases like COPD, idiopathic pulmonary fibrosis and other fibrotic diseases, cancer, acute lung injury, acute respiratory distress syndrome, bronchiectasis, cystic fibrosis, alpha1-antitrypsin deficiency and others.

The compounds according to the present invention, including the physiologically acceptable salts, are effective as inhibitors of neutrophil elastase and exhibit favourable inhibitory potency, as determined by the half maximal inhibitory concentration ($IC_{50}$), in an enzymatic inhibition assay.

Some compounds according to the present invention, including the physiologically acceptable salts, are additionally effective as inhibitors of neutrophil serin protease proteinase 3 and exhibit favourable inhibitory potency, as determined by the half maximal inhibitory concentration ($IC_{50}$), in an enzymatic inhibition assay. This inhibitory activity on a second neutrophil serin protease may be benificial for pharmacological efficacy.

Some compounds according to the present invention, including the physiologically acceptable salts, exhibit favourable inhibitory potency, as determined by the half maximal effective concentration ($EC_{50}$), in a plasma or whole-blood assay, for instance as described in T. Stevens et al. (*J. Pharm. Exp. Ther.* 2011, 339, 313-320).

Some compounds according to the present invention, including the physiologically acceptable salts, exhibit favourable in vivo potency, as determined, for example, by the half maximal effective dose (EDO, in models of human neutrophil elastase-induced lung injury in mice, rat or hamster, for instance as described in Tremblay et al. (*Chest* 2002, 121, 582-588) or T. Stevens et al. (*J. Pharm. Exp. Ther.* 2011, 339, 313-320).

Some compounds according to the present invention, including the physiologically acceptable salts, exhibit favourable in vivo potency, as determined, for example, by the half maximal effective dose (EDO, in a model of LPS/FMLP-induced lung injury in hamster, for instance as described in Mitsuhashi et al. (*Br. J. Pharmacol.* 1999, 126, 1147-1152).

Some compounds according to the present invention, including the physiologically acceptable salts, exhibit favourable metabolic stability in an in vitro microsomal assay for metabolic stability as described in E. Kerns & L. Di (*Drug-like properties: concepts, structure design and methods: from ADME to toxicity optimization*, Elsevier, 1$^{st}$ ed, 2008), chapter 29 and references therein.

Some compounds according to the present invention, including the physiologically acceptable salts, exhibit favourable metabolic stability in an in vitro hepatocytes assay for metabolic stability as described in E. Kerns & L. Di (*Drug-like properties: concepts, structure design and methods: from ADME to toxicity optimization*, Elsevier, 1$^{st}$ ed, 2008), chapter 29 and references therein.

An improved metabolic stability in an in vitro test system is expected to translate into a reduced in vivo clearance (CL), because the metabolic conversion in the liver is reduced. Based on the pharmacokinetic equation $CL/F_{oral}=Dose/AUC$ ($F_{oral}$: oral bioavailability, AUC: area under the curve), a reduced in vivo clearance is expected to lead to higher dose-normalized systemic exposure (AUC) of the drug.

Some compounds according to the present invention, including the physiologically acceptable salts, exhibit favourable permeability in an in vitro Caco-2 cell layer method for permeability as described in E. Kerns & L. Di (*Drug-like properties: concepts, structure design and methods: from ADME to toxicity optimization*, Elsevier, 1$^{st}$ ed, 2008), chapter 26 and references therein. For an oral drug, improved permeability is expected to translate into a higher fraction of the drug absorbed in the intestinal tract, thus, resulting in higher dose-normalized systemic exposure (AUC).

Some compounds according to the present invention, including the physiologically acceptable salts, exhibit a favourable, that is low efflux ratio (permeability in the efflux direction divided by the permeability in the influx direction) in an in vitro Caco-2 or MDCK cell layer method as described in E. Kerns & L. Di (*Drug-like properties: concepts, structure design and methods: from ADME to toxicity optimization*, Elsevier, 1$^{st}$ ed, 2008), chapter 26 and 27 and references therein. For an oral drug, an improved, that is reduced efflux ratio is expected to translate into a higher fraction of the drug absorbed in the intestinal tract, thus, resulting in higher dose-normalized systemic exposure (AUC).

Some compounds according to the present invention, including the physiologically acceptable salts, exhibit favourable aqueous solubility in a kinetic or thermodynamic solubility method as described in E. Kerns & L. Di (*Drug-like properties: concepts, structure design and methods: from ADME to toxicity optimization*, Elsevier, 1$^{st}$ ed, 2008), chapter 25 and references therein. For an oral drug, improved aqueous solubility is expected to translate into a higher fraction of the drug absorbed in the intestinal tract resulting in higher dose-normalized systemic exposure (AUC).

Comparatively higher dose-normalized systemic exposure (AUC) can be advantageous in several ways: (1) If a certain systemic exposure (AUC) needs to be achieved for efficacy, the drug can be dosed in a lower amount. Lower dosages have the advantages of lower drug load (parent drug and metabolites thereof) for the patient causing potentially less side effects, and lower production costs for the drug product. (2) Comparatively higher dose-normalized systemic exposure (AUC) can lead to increased efficacy or prolonged duration of action of the drug when the same dose is applied.

Some compounds according to the present invention, including the physiologically acceptable salts, exhibit favourable metabolic stability, favourable permeability, favourable efflux ratio and favourable aqueous solubility. Accordingly, some compounds of the present invention are expected to exhibit favourable pharmacokinetic (PK) properties after oral dosing, in particular favourable systemic exposure (area under the curve, AUC), thus, leading to favourable efficacy in vivo.

Some compounds according to the present invention, including the physiologically acceptable salts, exhibit favourable pharmacokinetic (PK) properties. The PK properties can be determined in pre-clinical animal species, for example mouse, rat, hamster, dog, guinea pig, mini pig, cynomolgus monkey, rhesus monkey. The PK properties of a compound can be described, for example, by the following parameters: Mean residence time (MRT), elimination half-live ($t_{1/2}$), volume-of-distribution ($V_D$), area under the curve (AUC), clearance (CL) and bioavailability after oral administration ($F_{oral}$).

The compounds of the invention and metabolites thereof are devoid of the hydrazine sub-structure that causes structural alerts for mutagenicity and carcinogenicity as described in Benigni et al. (*Chem. Rev.* 2011, 11, 2507-2536). Thus, compounds of the invention may bear the advantage of reduced genotoxic potential and reduced risk of failure during development because of genotoxic parent compound, metabolites and/or impurities.

Some compounds according to the present invention, including the physiologically acceptable salts, exhibit favourable inhibition of cytochrome P450 (CYP) isozymes in corresponding in vitro assays for CYP isozyme inhibition as described in E. Kerns & L. Di (*Drug-like properties: concepts, structure design and methods: from ADME to toxicity optimization*, Elsevier, 1$^{st}$ ed, 2008), chapter 32 and references therein. Reduced inhibition of CYP isozymes is expected to translate into a reduced risk for undesirable drug-drug interactions which is the interference of one drug with the normal metabolic or pharmacokinetic behaviour of a co-administered drug.

Some compounds according to the present invention, including the physiologically acceptable salts, exhibit favourable, i.e. low inhibition of the hERG channel in a patch clamp assay as described in E. Kerns & L. Di (*Drug-like properties: concepts, structure design and methods: from ADME to toxicity optimization*, Elsevier, 1$^{st}$ ed, 2008), chapter 34 and references cited therein.

DETAILED DESCRIPTION OF THE INVENTION

A compound of formula 1

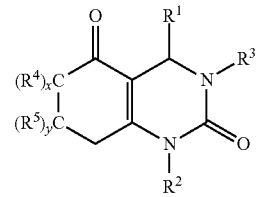

1 wherein $R^1$ is phenyl or a five- or six-membered heteroaryl, wherein one, two or three elements are replaced by an element independently selected from the group consisting of N, O and S; preferably phenyl or pyridinyl; each ring optionally substituted with one, two or three substituents independently selected from the group consisting of halogen, $O_2N$—, NC—, $H_2N$—, HO—, $R^{1.1}$, $R^{1.1}O$—, $R^{1.2}$, $R^{1.3}S$—, $R^{1.3}(O)S$— and $R^{1.3}(O)_2S$—;

$R^{1.1}$ is independently selected from the group consisting of $C_{1-6}$-alkyl-, $C_{3-6}$-cycloalkyl-, $C_{1-6}$-haloalkyl- and $C_{3-6}$-halocycloalkyl;

$R^{1.2}$ is HO—$C_{1-6}$-alkyl- or $R^{1.1}$—O—$C_{1-6}$-alkyl-;

$R^{1.3}$ is independently selected from the group consisting of H, HO—, $R^{1.1}$ and $R^{1.2}$; preferably $R^{1.1}$;

$R^2$ is phenyl or a five- or six-membered heteroaryl, wherein one or two elements are replaced by an element independently selected from the group consisting of N, O and S; preferably phenyl or pyridinyl; each ring optionally substituted with one or two substituents independently selected from the group consisting of halogen, $C_{1-4}$-alkyl-, $C_{1-4}$-haloalkyl- and $C_{1-4}$-alkyl-O—;

$R^3$ is a residue independently selected from the group consisting of $R^{3.1}$—;

$R^{3.2}(O)C$—;

$R^{3.2}O(O)C$—;

$R^{3.2}O(O)C$-A-; preferably $R^{3.2}O(O)C$—$CH_2$—;

$R^{3.2}S$—; $R^{3.2}(O)S$—; $R^{3.2}(O)_2S$—; preferably $R^{3.2}(O)_2S$—;

$(R^{3.2})_2N(O)C$—; and $(R^{3.2})_2N(O)C$-A-; preferably $(R^{3.2})_2N(O)C$—$CH_2$—;

$R^{3.1}$ is independently selected from the group consisting of H, $R^{3.3}$, $R^{3.4}$, $C_{1-6}$-alkyl-$C_{3-6}$-cycloalkyl- and $C_{3-6}$-cycloalkyl-$C_{1-6}$-alkyl-, each optionally substituted with one or two substituents independently selected from among $R^{3.1.1}$—;

$R^{3.1.1}$ is selected from the group consisting of HO—, halogen, NC—, $R^{3.3}$O—, $R^{3.5}$, $R^{3.6}$ and $R^{3.7}$ or $R^{3.1.1}$ denotes a ring independently selected from phenyl and a four-membered heterocyclic ring containing one element independently selected from among N, O, S, S(O) and S(O)$_2$ or $R^{3.1.1}$ denotes a five- or six-membered heterocyclic or heteroaryl ring containing one, two or three elements independently selected from among N, O, S, S(O) and S(O)$_2$;

each of the rings optionally substituted with one or two substituents independently selected from among HO—, O=, halogen, NC—, $R^{3.3}$, $R^{3.3}$—(O)C—, $R^{3.4}$, $R^{3.5}$, $R^{3.6}$ and $R^{3.7}$ or two substituents are together $R^{3.8}$;

$R^{3.2}$ is independently selected from among $R^{3.1}$, phenyl, a four-membered heterocyclic ring containing one element independently selected from the group consisting of N, O, S, S(O) and S(O)$_2$; or a five- or six-membered heterocyclic or heteroaryl ring containing one, two or three elements independently selected from the group consisting of N, O, S, S(O) and S(O)$_2$; each ring optionally substituted with one or two substituents independently selected from the group consisting of HO—, O=, NC—, halogen, $R^{3.3}$, $R^{3.3}$O—, $R^{3.3}$—(O)C—, $R^{3.4}$, $R^{3.5}$, $R^{3.6}$, $R^{3.7}$ or two substituents are together $R^{3.8}$;

or two $R^{3.2}$ are together a three-, four-, five- or six-membered monocyclic or a six-, seven-, eight-, nine- or ten-membered bicyclic heterocyclic or heteroaryl ring optionally containing additional to the nitrogen one or two elements independently selected from the group consisting of N, O, S, S(O) and S(O)$_2$; optionally substituted with one or two substituents, independently selected from the group consisting of HO—, F, O=, NC—, $R^{3.3}$, $R^{3.3}$O—, $R^{3.3}$—(O)C—, $R^{3.4}$, $R^{3.5}$, $R^{3.6}$, $R^{3.7}$, phenyl, a five- or six-membered heterocyclic or heteroaryl ring containing one, two or three elements independently selected from the group consisting of N, O, S, S(O) and S(O)$_2$; or two substituents are together $R^{3.8}$;

$R^{3.3}$ is independently selected from the group consisting of $C_{1-6}$-alkyl-, $C_{3-6}$-cycloalkyl-, $C_{1-6}$-haloalkyl- and $C_{3-6}$-halocycloalkyl-;

$R^{3.4}$ is HO—$C_{1-6}$-alkyl- or $R^{3.3}$—O—$C_{1-6}$-alkyl-;

$R^{3.5}$ is independently selected from the group consisting of $H_2N$—, $R^{3.3}$—HN—, $(R^{3.3})_2N$—, $R^{3.3}$—(O)C—HN— and $R^{3.3}$—(O)C—$(R^{3.3})N$—;

$R^{3.6}$ is independently selected from the group consisting of $R^{3.3}$—(O)S—, $R^{3.3}$—(O)$_2$S—, $R^{3.3}$(HN)S—, $R^{3.3}$(HN)(O)S—, $R^{3.3}$($R^{3.3}$N)S—, $R^{3.3}$($R^{3.3}$N)(O)S—, $R^{3.3}$($R^{3.4}$N)S—, $R^{3.3}$($R^{3.4}$N)(O)S—; $R^{3.3}$(NC—N)S— and $R^{3.3}$(NC—N)(O)S—;

$R^{3.7}$ is independently selected from the group consisting of HO(O)C—, $H_2N(O)C$—, $R^{3.3}$—O—(O)C—, $R^{3.3}$—NH—(O)C— and $(R^{3.3})_2N$—(O)C—;

$R^{3.8}$ is independently $C_{1-6}$-alkylene or $C_{1-6}$-haloalkylene, wherein optionally one or two CH$_2$-groups independently from each other are replaced by —HN—, —($R^{3.3}$)N—, —($R^{3.4}$)N—, —($R^{3.3}$(O)C—)N—, —($R^{3.4}$(O)C—)N—, —O—, —S—, —S(O)— and —S(O)$_2$—;

A is —CH$_2$—, —CH$_2$—CH$_2$— or —CH$_2$—CH$_2$—CH$_2$—; preferably —CH$_2$—; optionally substituted with one or two substituents independently selected from the it) group consisting of halogen, $R^{3.3}$, $R^{3.3}$O— and $R^{3.4}$ or two substituents together are $R^{3.8}$;

$R^4$ is independently selected from the group consisting of halogen, $C_{1-6}$-alkyl-, $C_{3-6}$-cycloalkyl-, $C_{1-6}$-haloalkyl-, $C_{3-6}$-halocycloalkyl-, HO—$C_{1-6}$-alkyl- and $C_{1-6}$-alkyl-O—$C_{1-6}$-alkyl-; preferably methyl or two $R^4$ are together $C_{1-6}$-alkylene or $C_{1-6}$-haloalkylene, wherein optionally one CH$_2$-group can be replaced by —O—, —S—, —S(O)— or —S(O)$_2$—;

X is 0, 1 or 2, preferably 0;

$R^5$ is independently selected from the group consisting of halogen, NC—, $R^{5.1}$; HO(O)C—, $H_2N(O)C$—, $R^{5.1}$—O—(O)C—, $R^{5.1}$—NH—(O)C—, $(R^{5.1})_2N$—(O)C—;

phenyl or a five- or six-membered heterocyclic or heteroaryl ring containing one, two or three elements independently selected from the group consisting of N, O, S, S(O) and S(O)$_2$; each ring optionally substituted with one, two or three substituents independently selected from the group consisting of halogen, HO—, O=, NC—, $O_2N$—, $H_2N$—, $R^{5.1}$, $R^{5.1}$O—, $R^{5.1}$—HN—, $(R^{5.1})_2N$—, $R^{5.1}$—(O)C—HN—, $R^{5.1}$—(O)C—$(R^{5.1})N$—, $R^{5.1}$—(O)S—, $R^{5.1}$—(O)$_2$S—, $R^{5.1}$—(HN)S—, $R^{5.1}$—(HN)(O)S—, $R^{5.1}$—($R^{5.1}$N)S—, $R^{5.1}$—($R^{5.1}$N)(O)S—, $R^{5.1}$—(NC—N)S—, $R^{5.1}$—(NC—N)(O)S—, HO(O)C—, $H_2N(O)C$—, $R^{5.1}$—O—(O)C—, $R^{5.1}$—NH—(O)C— and $(R^{5.1})_2N$—(O)C—;

$R^{5.1}$ is independently selected from the group consisting of $C_{1-6}$-alkyl-, $C_{3-6}$-cycloalkyl-, $C_{1-6}$-alkyl-$C_{3-6}$-cycloalkyl-, $C_{3-6}$-cycloalkyl-$C_{1-6}$-alkyl-, $C_{1-6}$-haloalkyl-, $C_{3-6}$-halocycloalkyl, HO—$C_{1-6}$-alkyl-, $C_{1-6}$-alkyl-O—$C_{1-6}$-alkyl-, $C_{3-6}$-cycloalkyl-O—$C_{1-6}$-alkyl-, $C_{1-6}$-haloalkyl-O—$C_{1-6}$-alkyl- and $C_{3-6}$-halocycloalkyl-O—$C_{1-6}$-alkyl-, or two $R^{5.1}$ are together $C_{1-6}$-alkylene or $C_{1-6}$-haloalkylene, wherein optionally one or two CH$_2$-groups are replaced by —HN—, —($C_{1-6}$-alkyl-)N—, —($C_{3-6}$-cycloalkyl-)N—, —($C_{1-6}$-haloalkyl-)N—, —($C_{3-6}$-halocycloalkyl-)N—, —(HO—$C_{1-6}$-alkyl-)N—, —($C_{1-6}$-alkyl-O—$C_{1-6}$-alkyl-)N—, —($C_{3-6}$-cycloalkyl-O—$C_{1-6}$-alkyl-)N—, —($C_{1-6}$-alkyl-(O)C—)N—, —($C_{3-6}$-cycloalkyl-(O)C—)N—, —($C_{1-6}$-haloalkyl-(O)C—)N—, —(HO—$C_{1-6}$-alkyl-(O)C—)N—, —($C_{1-6}$-alkyl-O—$C_{1-6}$-alkyl-(O)C—)N—, —($C_{3-6}$-cycloalkyl-O—$C_{1-6}$-alkyl-(O)C—)N—, —O—, —S—, —S(O)— and —S(O)$_2$—;

y is 0, 1 or 2, preferably 0;

or a salt thereof.

Used Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms.

In general in single groups like HO, $H_2N$, S(O), S(O)$_2$, NC (cyano), HOOC, $F_3C$ or the like, the skilled artisan can see the radical attachment point(s) to the molecule from the free valences of the group itself. For combined groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail. An asterisk is may be used in sub-formulas to indicate the bond which is connected to the core molecule as defined.

For example, the term "3-carboxypropyl-group" represents the following substituent:

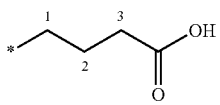

wherein the carboxy group is attached to the third carbon atom of the propyl group. The terms "1-methylpropyl-", "2,2-dimethylpropyl-" or "cyclopropylmethyl-" group represent the following groups:

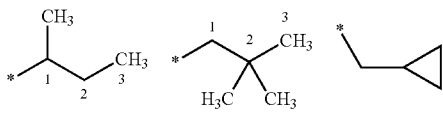

The asterisk may be used in sub-formulas to indicate the bond which is connected to the core molecule as defined.

Many of the followings terms may be used repeatedly in the definition of a formula or group and in each case have one of the meanings given above, independently of one another.

The term "substituted" as used herein, means that any one or more hydrogens on the designated atom is replaced with a selection from the indicated group, provided that the designated atom's normal valence is not exceeded, and that the substitution results in a stable compound.

The expressions "prevention", "prophylaxis", "prophylactic treatment" or "preventive treatment" used herein should be understood synonymous and in the sense that the risk to develop a condition mentioned hereinbefore is reduced, especially in a patient having elevated risk for said conditions or a corresponding anamnesis, e.g. elevated risk of developing metabolic disorder such as diabetes or obesity or another disorder mentioned herein. Thus the expression "prevention of a disease" as used herein means the management and care of an individual at risk of developing the disease prior to the clinical onset of the disease. The purpose of prevention is to combat the development of the disease, condition or disorder, and includes the administration of the active compounds to prevent or delay the onset of the symptoms or complications and to prevent or delay the development of related diseases, conditions or disorders. Success of said preventive treatment is reflected statistically by reduced incidence of said condition within a patient population at risk for this condition in comparison to an equivalent patient population without preventive treatment.

The expression "treatment" or "therapy" means therapeutic treatment of patients having already developed one or more of said conditions in manifest, acute or chronic form, including symptomatic treatment in order to relieve symptoms of the specific indication or causal treatment in order to reverse or partially reverse the condition or to delay the progression of the indication as far as this may be possible, depending on the condition and the severity thereof. Thus the expression "treatment of a disease" as used herein means the management and care of a patient having developed the disease, condition or disorder. The purpose of treatment is to combat the disease, condition or disorder. Treatment includes the administration of the active compounds to eliminate or control the disease, condition or disorder as well as to alleviate the symptoms or complications associated with the disease, condition or disorder.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

All isomeric forms (especially all stereoisomeric forms, e.g. all chiral, enantiomeric, diastereomeric and racemic forms, all tautomeric and all geometric isomeric forms) of a compound of the present invention are intended with this invention, unless the specific isomer is specifically indicated. Obviously, the isomer which is pharmacologically more potent and/or more efficacious is preferred.

It will be appreciated that the compounds of the present invention contain at least one asymmetrically substituted carbon atom, and may therefore be isolated as pure enantiomers or as a racemic or non-racemic mixture of both enantiomers. It will be appreciated that some of the compounds of the present invention contain more than one stereogenic center, i.e. more than one asymmetrically substituted carbon or sulfur atom, and may therefore be isolated as pure diastereomers or as diastereomeric mixtures, both in optically active or racemic forms.

The invention contemplates all conceivable stereoisomers, particularly the diastereomers and enantiomers mentioned herein, e.g. in substantially pure form, in enriched form (e.g. substantially free of any or all other undesired enantiomers and/or diastereomers and/or in any mixing ratio, including the racemic forms, as well as the salts thereof.

In general, substantially pure stereoisomers can be obtained according to synthetic principles known to a person skilled in the field, e.g. by separation of corresponding mixtures, by using stereochemically pure starting materials and/or by stereoselective synthesis. It is known in the art how to prepare optically active forms, such as by resolution of racemic forms or by synthesis, e.g. starting from optically active starting materials and/or by using chiral reagents.

Enantiomerically pure compounds of this invention or intermediates may be prepared via asymmetric synthesis, for example by preparation and subsequent separation of appropriate diastereomeric compounds or intermediates which can be separated by known methods (e.g. by chromatographic separation or crystallization) and/or by using chiral reagents, such as chiral starting materials, chiral catalysts or chiral auxiliaries.

Further, it is known to the person skilled in the art how to prepare enantiomerically pure compounds from the corresponding racemic mixtures, such as by chromatographic separation of the corresponding racemic mixtures on chiral stationary phases; or by resolution of a racemic mixture using an appropriate resolving agent, e.g. by means of diastereomeric salt formation of the racemic compound with optically active acids or bases, subsequent resolution of the salts and release of the desired compound from the salt; or by derivatization of the corresponding racemic compounds with optically active chiral auxiliary reagents, subsequent diastereomer separation and removal of the chiral auxiliary group; or by kinetic resolution of a racemate (e.g. by enzymatic resolution); by enantio-selective crystallization from a conglomerate of enantiomorphous crystals under suitable conditions; or by (fractional) crystallization from a suitable solvent in the presence of an optically active chiral auxiliary.

The term halogen generally denotes fluorine, chlorine, bromine and iodine.

As used herein the term "prodrug" refers to (i) an inactive form of a drug that exerts its effects after metabolic processes within the body converting it to a usable or active form, or (ii) a substance that gives rise to a pharmacologically active metabolite, although not itself active (i.e. an inactive precursor).

The terms "prodrug" or "prodrug derivative" mean a covalently-bonded derivative, carrier or precursor of the parent compound or active drug substance which undergoes at least some biotransformation prior to exhibiting its pharmacological effect(s). Such prodrugs either have metabolically cleavable or otherwise convertible groups and are rapidly transformed in vivo to yield the parent compound, for example, by hydrolysis in blood or by activation via oxidation as in case of thioether groups. Most common prodrugs include esters and amide analogs of the parent compounds. The prodrug is formulated with the objectives of improved chemical stability, improved patient acceptance and compliance, improved bioavailability, prolonged duration of action, improved organ selectivity, improved formulation (e.g., increased hydrosolubility), and/or decreased side effects (e.g., toxicity). In general, prodrugs themselves have weak or no biological activity and are stable under ordinary conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; Bioreversible Carriers in Drug Design, E. B. Roche (ed.), Elsevier, 1987, each of which is incorporated herein by reference in their entireties.

The term "pharmaceutically acceptable prodrug" as used herein means a prodrug of a compound of the invention which is, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine, 2,2'-iminobis(ethanol), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine (2,2',2"-nitrilotris-(ethanol)), tromethamine, zinc hydroxide, acetic acid, 2.2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-c amphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxyethane-sulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like. (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals H$_3$C—, H$_3$C—CH$_2$—, H$_3$C—CH$_2$—CH$_2$—, H$_3$C—CH(CH$_3$)—, H$_3$C—CH$_2$—CH$_2$—CH$_2$—, H$_3$C—CH$_2$—CH(CH$_3$)—, H$_3$C—CH(CH$_3$)—CH$_2$—, H$_3$C—C(CH$_3$)$_2$—, H$_3$C—CH$_2$—CH$_2$—CH$_2$—CH$_2$—, H$_3$C—CH$_2$—CH$_2$—CH(CH$_3$)—, H$_3$C—CH$_2$—CH(CH$_3$)—CH$_2$—, H$_3$C—CH(CH$_3$)—CH$_2$—CH$_2$—, H$_3$C—CH$_2$—C(CH$_3$)$_2$—, H$_3$C—C(CH$_3$)$_2$—CH$_2$—, H$_3$C—CH(CH$_3$)—CH(CH$_3$)— and H$_3$C—CH$_2$—CH(CH$_2$CH$_3$)—.

The term "$C_{1-n}$-alkylene" wherein n is an integer 2 to n, either alone or in combination with another radical, denotes an acyclic, straight or branched chain divalent alkyl radical containing from 1 to n carbon atoms. For example the term $C_{1-4}$-alkylene includes —CH$_2$—, —CH$_2$—CH$_2$—, —CH(CH$_3$)—, —CH$_2$—CH$_2$—CH$_2$—, —C(CH$_3$)$_2$—, —CH —(CH₂CH₃)—, —CH(CH₃)—CH₂—, —CH₂—CH(CH₃)—, —CH₂—CH₂—CH₂—CH₂—, —CH₂—CH₂—CH(CH₃)—, —CH(CH₃)—CH₂—CH₂—, —CH₂—CH(CH₃)—CH₂—, —CH₂—C(CH₃)₂—, —C(CH₃)₂—CH₂—, —CH(CH₃)—CH(CH₃)—, —CH₂—CH(CH₂CH₃)—, —CH(CH₂CH₃)—CH₂—, —CH(CH₂CH₂CH₃)—, —CH(CH(CH₃))₂— and —C(CH₃)(CH₂CH₃)—.

The term "$C_{3-n}$-cycloalkyl", wherein n is an integer from 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

By the term "halo" added to a "alkyl", "alkylene" or "cycloalkyl" group (saturated or unsaturated) is such a alkyl or cycloalkyl group wherein one or more hydrogen atoms are replaced by a halogen atom selected from among fluorine, chlorine or bromine, preferably fluorine and chlorine, particularly preferred is fluorine. Examples include: H₂FC—, HF₂C—, F₃C—.

The term "aryl" as used herein, either alone or in combination with another radical, denotes is a carbocyclic aromatic monocyclic group containing 6 carbon atoms which may be further fused to a second five- or six-membered, carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heterocyclyl" means a saturated or unsaturated mono- or polycyclic-ring system including aromatic ring system containing one or more elements selected from the group consisting of N, O, S, S(O) or S(O)₂, consisting of 3 to 14 ring atoms wherein none of the heteroatoms is part of the aromatic ring. The term "heterocyclyl" is intended to include all the possible isomeric forms; thus, the term "heterocyclyl" includes the following exemplary structures which are not depicted as radicals as each form may be attached through a covalent bond to any atom so long as appropriate valences are maintained:

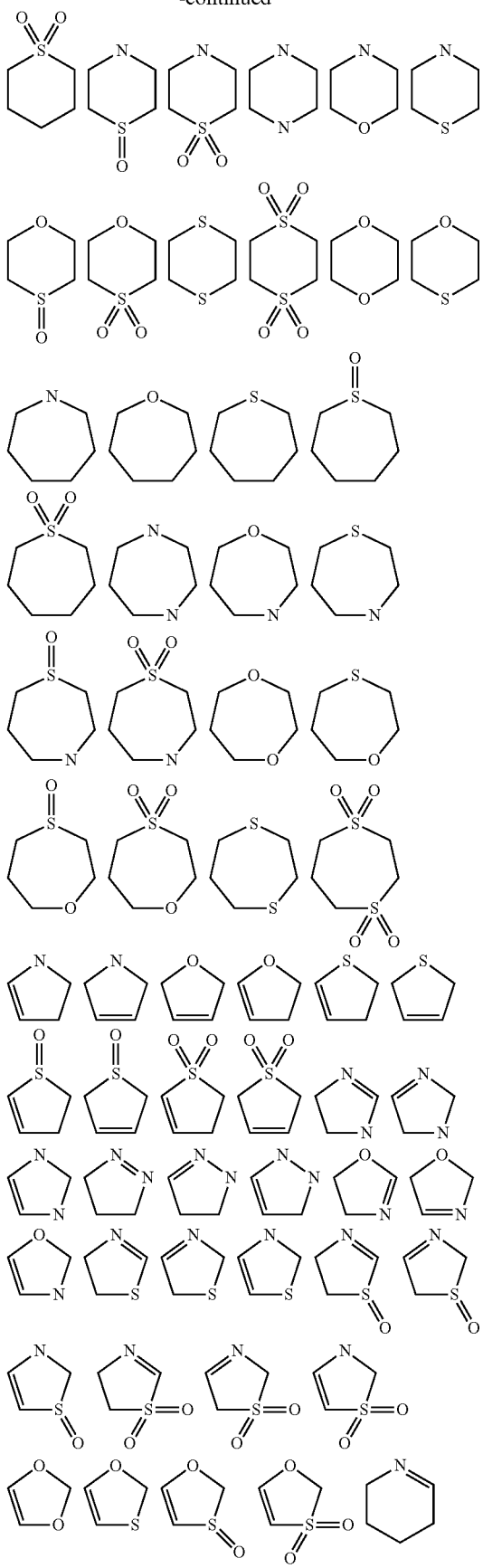

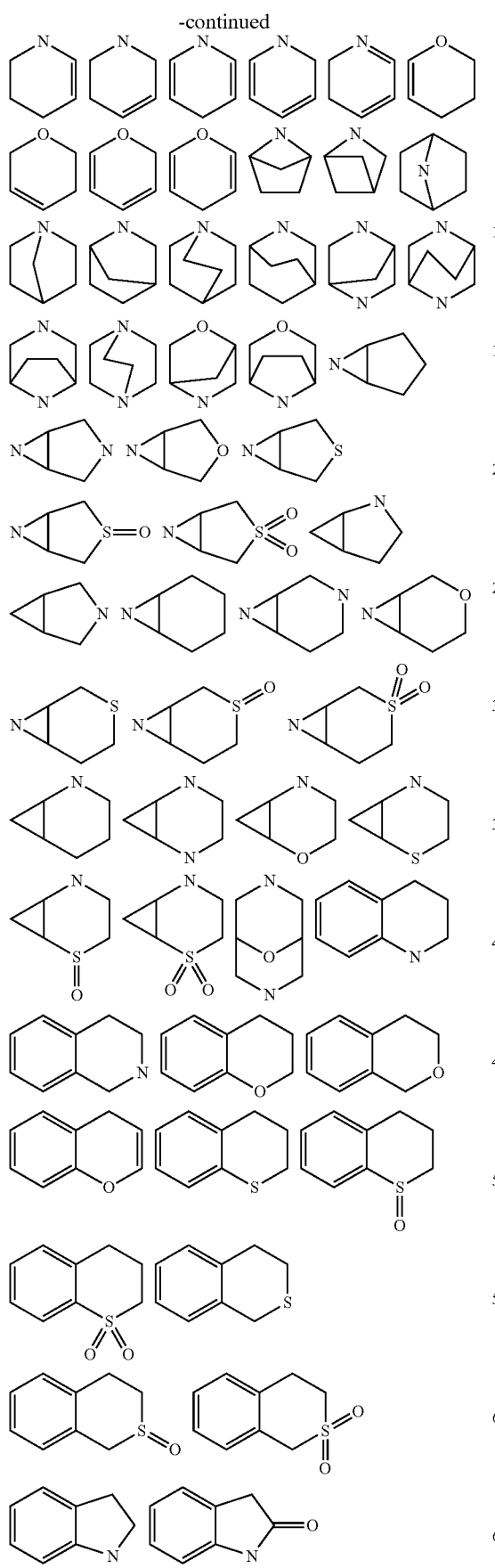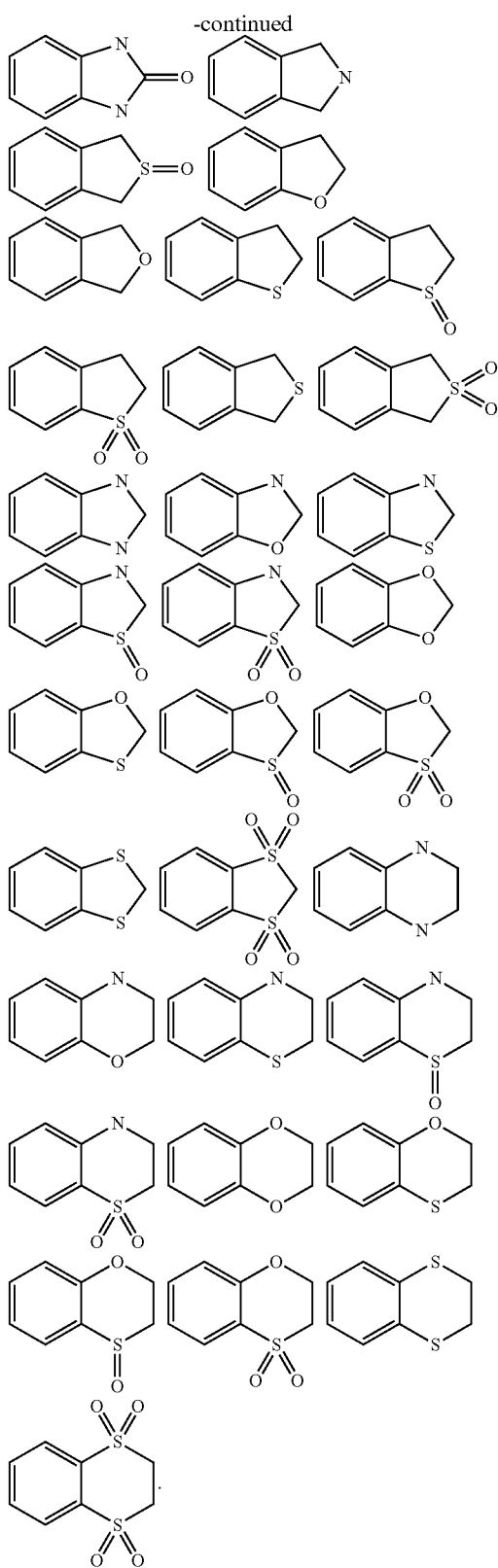
The term "heteroaryl" means a mono- or polycyclic-ring systems containing one or more elements selected from among N, O, S, S(O) and S(O)$_2$, consisting of 5 to 14 ring atoms wherein at least one of the heteroatoms is part of aromatic ring. The term "heteroaryl" is intended to include all the possible isomeric forms; Thus, the term "heteroaryl" includes the following exemplary structures which are not depicted as radicals as each form may be attached through a covalent bond to any atom so long as appropriate valences are maintained:

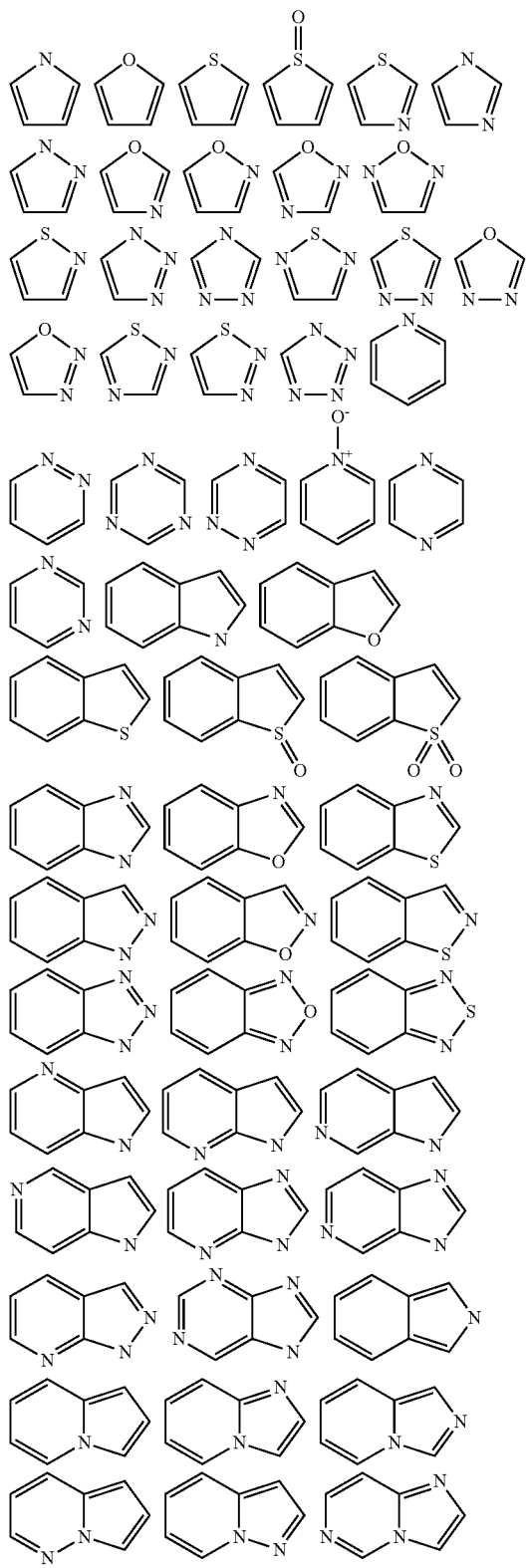

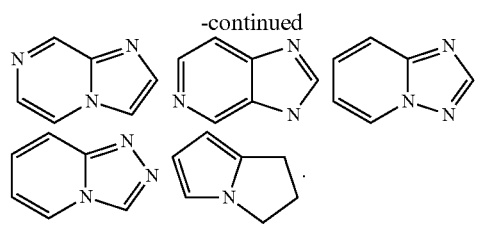

Preferred Embodiments

Preferred are the above compounds of formula 1, wherein $R^1$ is $R^{1.a}$ and $R^{1.a}$ is phenyl or pyridinyl; each ring optionally substituted by one, two or three residues independently selected from the group consisting of halogen, $O_2N-$, $NC-$, $H_2N-$, $HO-$, $R^{1.1}$, $R^{1.1}O-$, $R^{1.2}$, $R^{1.3}S-$, $R^{1.3}(O)S-$ and $R^{1.3}(O)_2S-$.

Particularly preferred are the above compounds of formula 1, wherein $R^1$ is $R^{1.a}$ and $R^{1.a}$ is phenyl, optionally substituted by one, two or three residues independently selected from the group consisting of halogen, $O_2N-$, $NC-$, $H_2N-$, $HO-$, $R^{1.1}R^{1.1}O-$, $R^{1.2}$, $R^{1.3}S-$, $R^{1.3}(O)S-$ and $R^{1.3}(O)_2S-$.

Particularly preferred are the above compounds of formula 1, wherein $R^1$ is $R^{1.a}$ and $R^{1.a}$ is pyridinyl, optionally substituted by one, two or three residues independently selected from the group consisting of halogen, $O_2N-$, $NC-$, $H_2N-$, $HO-$, $R^{1.1}$, $R^{1.1}O-$, $R^{1.2}$, $R^{1.3}S-$, $R^{1.3}(O)S-$ and $R^{1.3}(O)_2S-$.

Preferred are the above compounds of formula 1, wherein $R^1$ is $R^{1.b}$ and $R^{1.b}$ is phenyl or pyridinyl; each ring optionally substituted by one, two or three residues independently selected from the group consisting of halogen, $NC-$, $R^{1.1}$, $R^{1.3}(O)S-$ and $R^{1.3}(O)_2S-$.

Preferred are the above compounds of formula 1, wherein $R^1$ is $R^{1.c}$ and $R^{1.c}$ is phenyl or pyridinyl; each ring optionally substituted by one, two or three residues independently selected from the group consisting of halogen, $NC-$, $R^{1.1}$, $R^{1.1}(O)S-$ and $R^{1.1}(O)_2S-$.

Preferred are the above compounds of formula 1, wherein $R^1$ is $R^{1.d}$ and $R^{1.d}$ is phenyl or pyridinyl; each ring optionally substituted by one, two or three residues independently selected from the group consisting of F, Cl, $NC-$, $R^{1.1}$ and $R^{1.3}(O)_2S-$.

Preferred are the above compounds of formula 1, wherein $R^1$ is $R^{1.e}$ and $R^{1.e}$ is phenyl or pyridinyl; each ring optionally substituted by one, two or three residues independently selected from the group consisting of F, Cl, $NC-$, $R^{1.1}$, $R^{1.1}O-$ and $R^{1.1}(O)_2S-$.

Preferred are the above compounds of formula 1, wherein $R^1$ is $R^{1.f}$ and $R^{1.f}$ is phenyl or pyridinyl; each ring optionally substituted by one, two or three residues independently selected from the group consisting of F, Cl, $NC-$, Me, Et, i-Pr, t-Bu, cyclopropyl, $Me(O)_2S-$, $Et(O)_2S-$, $i-Pr(O)_2S-$, $t-Bu(O)_2S-$ and cyclopropyl$(O)_2S-$.

Preferred are the above compounds of formula 1, wherein $R^1$ is $R^{1.g}$ and $R^{1.g}$ is phenyl or pyridinyl; each ring optionally substituted by one, two or three residues independently selected from the group consisting of F, Cl, $NC-$, Me, $MeO-$, $Me(O)_2S-$ and $Et(O)_2S-$.

Preferred are the above compounds of formula 1, wherein $R^1$ is $R^{1.h}$ and $R^{1.h}$ is phenyl or pyridinyl; each ring optionally substituted by one or two residues independently selected from the group consisting of $NC-$, $Me(O)_2S-$ and $Et(O)_2S-$.

Preferred are the above compounds of formula 1, wherein $R^1$ is $R^{1.i}$ and $R^{1.i}$ is phenyl; optionally substituted by one or two residues independently selected from the group consisting of NC—, Me(O)$_2$S— and Et(O)$_2$S—.

Preferred are the above compounds of formula 1, wherein R$^1$ is R$^{1.j}$ and R$^{1.j}$ is pyridinyl; optionally substituted by one or two residues independently selected from the group consisting of NC— and Me(O)$_2$S—.

Preferred are the above compounds of formula 1, wherein R$^1$ is R$^{1.k}$ and R$^{1.k}$ is

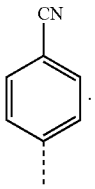

Preferred are the above compounds of formula 1, wherein R$^1$ is R$^{1.m}$ and R$^{1.m}$ is

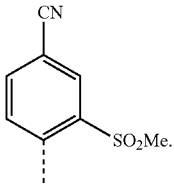

Preferred are the above compounds of formula 1, wherein R$^1$ is R$^{1.n}$ and R$^{1.n}$ is

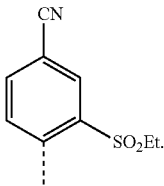

Preferred are the above compounds of formula 1, wherein R$^1$ is R$^{1.o}$ and R$^{1.o}$ is

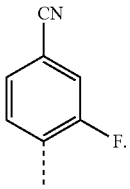

Preferred are the above compounds of formula 1, wherein R$^2$ is R$^{2.a}$ and R$^{2.a}$ is phenyl or a six-membered heteroaryl; wherein one or two elements are replaced by an element independently selected from among N, O and S; each ring optionally substituted with one or two substituents independently selected from the group consisting of halogen, C$_{1-4}$-alkyl-, C$_{1-4}$-haloalkyl- and C$_{1-4}$-alkyl-O—.

Preferred are the above compounds of formula 1, wherein R$^2$ is R$^{2.b}$ and R$^{2.b}$ is phenyl or a six-membered heteroaryl; wherein one or two elements are replaced by N; each ring optionally substituted with one or two substituents independently selected from the group consisting of halogen, C$_{1-4}$-alkyl- and C$_{1-4}$-haloalkyl-.

Preferred are the above compounds of formula 1, wherein R$^2$ is R$^{2.c}$ and R$^{2.c}$ is phenyl or pyridinyl; each optionally substituted with one or two substituents independently selected from the group consisting of halogen, C$_{1-4}$-alkyl- and C$_{1-4}$-haloalkyl-.

Preferred are the above compounds of formula 1, wherein R$^2$ is R$^{2.d}$ and R$^{2.d}$ is phenyl or pyridinyl; each optionally substituted with one or two substituents independently selected from the group consisting of F—, F$_3$C—, F$_2$HC— and FH$_2$C—.

Particularly preferred are the above compounds of formula 1, wherein R$^2$ is R$^{2.d}$ and R$^{2.d}$ is phenyl or pyridinyl; each optionally substituted with one or two substituents independently selected from the group consisting of F—, F$_3$C— and F$_2$HC—.

Preferred are the above compounds of formula 1, wherein R$^2$ is R$^{2.e}$ and R$^{2.e}$ is phenyl; optionally substituted with one or two substituents independently selected from the group consisting of F—, F$_3$C— and F$_2$HC—. Particularly preferred are the above compounds of formula 1, wherein R$^2$ is R$^{2.e}$ and R$^{2.e}$ is phenyl; optionally substituted with one or two substituents independently selected from the group consisting of F— and F$_3$C—.

Preferred are the above compounds of formula 1, wherein R$^2$ is R$^{2.f}$ and R$^{2.f}$ is pyridinyl; optionally substituted with one or two substituents independently selected from the group consisting of F—, F$_3$C— and F$_2$HC—.

Particularly preferred are the above compounds of formula 1, wherein R$^2$ is R$^{2.f}$ and R$^{2.f}$ is pyridinyl; optionally substituted with one or two substituents substituents independently selected from the group consisting of F— and F$_3$C—.

Preferred are the above compounds of formula 1, wherein R$^2$ is R$^2$ g and R$^2$ g is phenyl or pyridinyl; each optionally substituted with a substituent independently selected from the group consisting of F$_3$C—, F$_2$HC— and FH$_2$C—.

Particularly preferred are the above compounds of formula 1, wherein R$^2$ is R$^2$ g and R$^2$ g is phenyl or pyridinyl; each optionally substituted with a substituent independently selected from the group consisting of F$_3$C— and F$_2$HC—.

Preferred are the above compounds of formula 1, wherein R$^2$ is R$^{2.h}$ and R$^{2.h}$ is phenyl, optionally substituted with a substituent independently selected from the group consisting of F$_3$C—, F$_2$HC— and FH$_2$C—.

Particularly preferred are the above compounds of formula 1, wherein R$^2$ is R$^{2.h}$ and R$^{2.h}$ is phenyl, optionally substituted with a substituent independently selected from the group consisting of F$_3$C— and F$_2$HC.

Preferred are the above compounds of formula 1, wherein R$^2$ is R$^{2.i}$ and R$^{2.i}$ is pyridinyl, optionally substituted with a substituent independently selected from the group consisting of F$_3$C—, F$_2$HC— and FH$_2$C—.

Particularly preferred are the above compounds of formula 1, wherein R$^2$ is R$^{2.i}$ and R$^{2.i}$ is pyridinyl, optionally substituted with a substituent independently selected from the group consisting of F$_3$C— and F$_2$HC—.

In a preferred embodiment of the invention R$^2$ is one of the above mentioned rings carrying the above mentioned substituent in meta-position to the connection of R$^2$ with the compound of formula 1.

Preferred are the above compounds of formula 1, wherein R$^2$ is R$^{2.j}$ and R$^{2.j}$ is

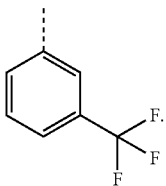

Preferred are the above compounds of formula 1, wherein $R^2$ is $R^{2.k}$ and $R^{2.k}$ is

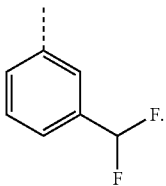

Preferred are the above compounds of formula 1, wherein $R^2$ is $R^{2.m}$ and $R^{2.m}$ is

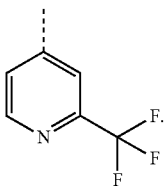

Preferred are the above compounds of formula 1, wherein $R^2$ is $R^{2.n}$ and $R^{2.n}$ is

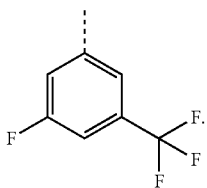

Preferred are the above compounds of formula 1, wherein $R^2$ is $R^{2.o}$ and $R^{2.o}$ is

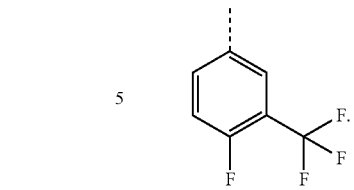

Preferred are the above compounds of formula 1, wherein $R^3$ is $R^{3.a}$ and $R^{3.a}$ is $R^{3.1}$—;
$R^{3.2}$O(O)C—;
$R^{3.2}$O(O)C—CH$_2$—;
$R^{3.2}$(O)$_2$S—;
(R$^{3.2}$)$_2$N(O)C—; and
(R$^{3.2}$)$_2$N(O)C—CH$_2$ Preferred are the above compounds of formula 1, wherein $R^3$ is $R^{3.b}$ and $R^{3.b}$ is $R^{3.1}$—;
$R^{3.2}$O(O)C—;
$R^{3.2}$(O)$_2$S—,
(R$^{3.2}$)$_2$N(O)C—; and
(R$^{3.2}$)$_2$N(O)C—CH$_2$—.

Preferred are the above compounds of formula 1, wherein $R^3$ is $R^{3.c}$ and $R^{3.c}$ is independently selected from the group consisting of HO(O)C—H$_2$C—, MeO(O)C—H$_2$C—, H$_2$N(O)C—H$_2$C—, MeHN(O)C—H$_2$C—, Me$_2$N(O)C—H$_2$C—, morpholinyl-(O)C—H$_2$C—, azetidinyl-(O)C—H$_2$C—, pyrrolidinyl-(O)C—H$_2$C—, MeHN(O)C—, EtHN(O)C—, HO(CH$_2$)$_2$HN(O)C—, HO(CMe$_2$)(CH$_2$)HN(O)C—, HO(CH$_2$)$_3$HN(O)C—, Me(O)S(CH$_2$)$_2$HN(O)C—, Me(O)$_2$S(CH$_2$)$_2$HN(O)C—, Et(O)$_2$S— and Me(O)$_2$S—.

Preferred are the above compounds of formula 1, wherein $R^3$ is $R^{3.d}$ and $R^{3.d}$ is independently selected from the group consisting of HO(O)C—H$_2$C—, MeO(O)C—H$_2$C—, H$_2$N(O)C—H$_2$C—, MeHN(O)C—H$_2$C—, Me$_2$N(O)C—H$_2$C—, morpholinyl-(O)C—H$_2$C—, azetidinyl-(O)C—H$_2$C— and pyrrolidinyl-(O)C—H$_2$C—.

Preferred are the above compounds of formula 1, wherein $R^3$ is $R^{3.e}$ and $R^{3.e}$ is independently selected from the group consisting of MeHN(O)C—, EtHN(O)C—, HO(CH$_2$)$_2$HN(O)C—, HO(CH$_2$)$_3$HN(O)C—, HO(CMe$_2$)(CH$_2$)HN(O)C—, Me(O)S(CH$_2$)$_2$HN(O)C— and Me(O)$_2$S(CH$_2$)$_2$HN(O)C—.

Preferred are the above compounds of formula 1, wherein $R^3$ is selected from the examples (E#) 1 to 54 of Table $R^3$—Embodiments of the invention for $R^3$, $R^{3.2}$, $R^{3.3}$, $R^{3.4}$, $R^{3.5}$, $R^{3.6}$, $R^{3.7}$, $R^{3.8}$ (if present):

TABLE 1

$R^3$ - Embodiments of the inventions

| E# | $R^3$ | $R^{3.2}$ | $R^{3.3}$ | $R^{3.4}$ | $R^{3.5}$ | $R^{3.6}$ | $R^{3.7}$ | $R^{3.8}$ |
|---|---|---|---|---|---|---|---|---|
| 1. | $R^{3.1.a}$ | | $R^{3.3.a}$ | $R^{3.4.b}$ | $R^{3.5.b}$ | $R^{3.6.b}$ | $R^{3.7.b}$ | |
| 2. | $R^{3.1.b}$ | | $R^{3.3.a}$ | $R^{3.4.b}$ | | | | |
| 3. | $R^{3.1.c}$ | | $R^{3.3.a}$ | $R^{3.4.b}$ | $R^{3.5.b}$ | $R^{3.6.b}$ | $R^{3.7.b}$ | $R^{3.8.b}$ |
| 4. | $R^{3.1.d}$ | | $R^{3.3.a}$ | $R^{3.4.b}$ | $R^{3.5.b}$ | $R^{3.6.b}$ | $R^{3.7.b}$ | |
| 5. | H | | | | | | | |
| 6. | Me | | | | | | | |
| 7. | NC—CH$_2$— | | | | | | | |
| 8. | $R^{3.2}$O(O)C— | $R^{3.2.a}$ | $R^{3.3.a}$ | $R^{3.4.b}$ | $R^{3.5.b}$ | $R^{3.6.b}$ | $R^{3.7.b}$ | $R^{3.8.b}$ |
| 9. | $R^{3.2}$O(O)C— | $R^{3.2.b}$ | $R^{3.3.a}$ | $R^{3.4.b}$ | | | | |
| 10. | $R^{3.2}$O(O)C— | $R^{3.2.c}$ | | | | | | |
| 11. | $R^{3.2}$O(O)C— | $R^{3.2.d}$ | $R^{3.3.a}$ | $R^{3.4.b}$ | $R^{3.5.b}$ | $R^{3.6.b}$ | $R^{3.7.b}$ | $R^{3.8.b}$ |
| 12. | $R^{3.2}$O(O)C— | $R^{3.2.h}$ | | | | | | |
| 13. | $R^{3.2}$O(O)C—CH$_2$— | $R^{3.2.a}$ | $R^{3.3.a}$ | $R^{3.4.b}$ | $R^{3.5.b}$ | $R^{3.6.b}$ | $R^{3.7.b}$ | $R^{3.8.b}$ |

TABLE 1-continued

R³ - Embodiments of the inventions

| E# | R³ | R³·² | R³·³ | R³·⁴ | R³·⁵ | R³·⁶ | R³·⁷ | R³·⁸ |
|---|---|---|---|---|---|---|---|---|
| 14. | R³·²O(O)C—CH₂— | R³·²·ᵇ | R³·³·ᵃ | R³·⁴·ᵇ | | | | |
| 15. | R³·²O(O)C—CH₂— | R³·²·ᶜ | | | | | | |
| 16. | R³·²O(O)C—CH₂— | R³·²·ᵈ | R³·³·ᵃ | R³·⁴·ᵇ | R³·⁵·ᵇ | R³·⁶·ᵇ | R³·⁷·ᵇ | R³·⁸·ᵇ |
| 17. | R³·²O(O)C—CH₂— | R³·²·ʰ | | | | | | |
| 18. | R³·²(O)₂S— | R³·²·ᵃ | R³·³·ᵃ | R³·⁴·ᵇ | R³·⁵·ᵇ | R³·⁶·ᵇ | R³·⁷·ᵇ | R³·⁸·ᵇ |
| 19. | R³·²(O)₂S— | R³·²·ᵇ | R³·³·ᵃ | R³·⁴·ᵇ | | | | |
| 20. | R³·²(O)₂S— | R³·²·ᶜ | | | | | | |
| 21. | R³·²(O)₂S— | R³·²·ᵈ | R³·³·ᵃ | R³·⁴·ᵇ | R³·⁵·ᵇ | R³·⁶·ᵇ | R³·⁷·ᵇ | R³·⁸·ᵇ |
| 22. | R³·²(O)₂S— | Me; | | | | | | |
| 23. | R³·²(O)₂S— | R³·²·ʰ | | | | | | |
| 24. | R³·²HN(O)C— | R³·²·ᵃ | R³·³·ᵃ | R³·⁴·ᵇ | R³·⁵·ᵇ | R³·⁶·ᵇ | R³·⁷·ᵇ | R³·⁸·ᵇ |
| 25. | R³·²HN(O)C— | R³·²·ᵇ | R³·³·ᵃ | R³·⁴·ᵇ | | | | |
| 26. | R³·²HN(O)C— | R³·²·ᶜ | | | | | | |
| 27. | R³·²HN(O)C— | R³·²·ᵈ | R³·³·ᵃ | R³·⁴·ᵇ | R³·⁵·ᵇ | R³·⁶·ᵇ | R³·⁷·ᵇ | R³·⁸·ᵇ |
| 28. | R³·²HN(O)C— | R³·²·ʰ | | | | | | |
| 29. | R³·²HN(O)C— | H | | | | | | |
| 30. | R³·²HN(O)C— | Me | | | | | | |
| 31. | R³·²HN(O)C— | Et | | | | | | |
| 32. | R³·²HN(O)C— | cyclo-PR | | | | | | |
| 33. | R³·²HN(O)C— | iso-PR | | | | | | |
| 34. | R³·²HN(O)C— | HO(CH₂)₂— | | | | | | |
| 35. | R³·²HN(O)C— | HO(CMe₂)CH₂— | | | | | | |
| 36. | R³·²HN(O)C— | HO(CH₂)₃— | | | | | | |
| 37. | R³·²HN(O)C— | F₂CH—CH₂— | | | | | | |
| 38. | R³·²HN(O)C—CH₂— | R³·²·ᵃ | R³·³·ᵃ | R³·⁴·ᵇ | R³·⁵·ᵇ | R³·⁶·ᵇ | R³·⁷·ᵇ | R³·⁸·ᵇ |
| 39. | R³·²HN(O)C—CH₂— | R³·²·ᵇ | R³·³·ᵃ | R³·⁴·ᵇ | | | | |
| 40. | R³·²HN(O)C—CH₂— | R³·²·ᶜ | | | | | | |
| 41. | R³·²HN(O)C—CH₂— | R³·²·ᵈ | R³·³·ᵃ | R³·⁴·ᵇ | R³·⁵·ᵇ | R³·⁶·ᵇ | R³·⁷·ᵇ | R³·⁸·ᵇ |
| 42. | R³·²HN(O)C—CH₂— | R³·²·ʰ | | | | | | |
| 43. | (R³·²)₂N(O)C— | R³·²·ᵃ | R³·³·ᵃ | R³·⁴·ᵇ | R³·⁵·ᵇ | R³·⁶·ᵇ | R³·⁷·ᵇ | R³·⁸·ᵇ |
| 44. | (R³·²)₂N(O)C— | R³·²·ᵇ | R³·³·ᵃ | R³·⁴·ᵇ | | | | |
| 45. | (R³·²)₂N(O)C— | R³·²·ᵉ | R³·³·ᵃ | R³·⁴·ᵇ | R³·⁵·ᵇ | R³·⁶·ᵇ | R³·⁷·ᵇ | R³·⁸·ᵇ |
| 46. | (R³·²)₂N(O)C— | R³·²·ᶠ | R³·³·ᵃ | R³·⁴·ᵇ | R³·⁵·ᵇ | R³·⁶·ᵇ | R³·⁷·ᵇ | R³·⁸·ᵇ |
| 47. | (R³·²)₂N(O)C— | R³·²·ᵍ | R³·³·ᵃ | R³·⁴·ᵇ | R³·⁵·ᵇ | R³·⁶·ᵇ | R³·⁷·ᵇ | R³·⁸·ᵇ |
| 48. | (R³·²)₂N(O)C—CH₂— | R³·²·ᵃ | R³·³·ᵃ | R³·⁴·ᵇ | R³·⁵·ᵇ | R³·⁶·ᵇ | R³·⁷·ᵇ | R³·⁸·ᵇ |
| 49. | (R³·²)₂N(O)C—CH₂— | R³·²·ᵇ | R³·³·ᵃ | R³·⁴·ᵇ | | | | |
| 50. | (R³·²)₂N(O)C—CH₂— | R³·²·ᶜ | | | | | | |
| 51. | (R³·²)₂N(O)C—CH₂— | R³·²·ᵈ | R³·³·ᵃ | R³·⁴·ᵇ | R³·⁵·ᵇ | R³·⁶·ᵇ | R³·⁷·ᵇ | R³·⁸·ᵇ |
| 52. | (R³·²)₂N(O)C—CH₂— | R³·²·ᵉ | R³·³·ᵃ | R³·⁴·ᵇ | R³·⁵·ᵇ | R³·⁶·ᵇ | R³·⁷·ᵇ | R³·⁸·ᵇ |
| 53. | (R³·²)₂N(O)C—CH₂— | R³·²·ᶠ | R³·³·ᵃ | R³·⁴·ᵇ | R³·⁵·ᵇ | R³·⁶·ᵇ | R³·⁷·ᵇ | R³·⁸·ᵇ |
| 54. | (R³·²)₂N(O)C—CH₂— | R³·²·ᵍ | R³·³·ᵃ | R³·⁴·ᵇ | R³·⁵·ᵇ | R³·⁶·ᵇ | R³·⁷·ᵇ | R³·⁸·ᵇ |

Preferred are the above compounds of formula 1, wherein $R^{3.1}$ is $R^{3.1.a}$ and $R^{3.1.a}$ is selected from among H, $R^{3.3}$, $R^{3.4}$, $C_{1-6}$-alkyl-$C_{3-6}$-cycloalkyl- and $C_{3-6}$-cycloalkyl-$C_{1-6}$-alkyl-, each optionally substituted with one or two substituents independently selected from among $R^{3.1.1}$; and $R^{3.1.1}$ is selected from among HO—, halogen, NC—, $R^{3.3}$O—, $R^{3.5}$, $R^{3.6}$ and $R^{3.7}$.

Preferred are the above compounds of formula 1, wherein $R^{3.1}$ is $R^{3.1.b}$ and $R^{3.1.b}$ is selected from among H, $R^{3.3}$, $R^{3.4}$, $C_{1-6}$-alkyl-$C_{3-6}$-cycloalkyl- and $C_{3-6}$-cycloalkyl-$C_{1-6}$-alkyl-.

Preferred are the above compounds of formula 1, wherein $R^{3.1}$ is $R^{3.1.c}$ and $R^{3.1.c}$ is selected from among H, $R^{3.4}$ and $C_{1-6}$-alkyl-, optionally substituted with one or two substituents independently selected from among $R^{3.11}$; and $R^{3.1.1}$ is a ring independently selected from the group consisting of phenyl, a four-membered heterocyclic ring containing one element independently selected from the group consisting of N, O, S, S(O) and S(O)₂; or $R^{3.1.1}$ denotes a five- or six-membered heterocyclic or heteroaryl ring containing one, two or three elements independently selected from among N, O, S, S(O) and S(O)₂; each of the rings optionally substituted with one or two substituents independently selected from among HO—, O═, halogen, NC—, $R^{3.3}$, $R^{3.3}$O—, $R^{3.3}$—(O)C—, $R^{3.4}$, $R^{3.5}$, $R^{3.6}$ and $R^{3.7}$ or two substituents are together $R^{3.8}$.

Preferred are the above compounds of formula 1, wherein $R^3$ is $R^{3.1.d}$ and $R^{3.1.d}$ is selected from among H, $R^{3.4}$ and $C_{1-6}$-alkyl-, optionally substituted with one or two substituents independently selected from among $R^{3.1.1}$; and $R^{3.1.1}$ is a ring independently selected from among phenyl and a five- or six-membered heterocyclic or heteroaryl ring containing one, two or three elements independently selected from among N, O, S, S(O) and S(O)₂;

each of the rings optionally substituted with one or two substituents independently selected from HO—, O═, halogen, NC—, $R^{3.3}$, $R^{3.3}$O—, $R^{3.3}$—(O)C—, $R^{3.4}$, $R^{3.5}$, $R^{3.6}$ and $R^{3.7}$.

Preferred are the above compounds of formula 1, wherein $R^{3.2}$ is $R^{3.2.a}$ and $R^{3.2.a}$ is $R^{3.1.a}$.

Preferred are the above compounds of formula 1, wherein $R^{3.2}$ is $R^{3.2.b}$ and $R^{3.2.b}$ is $R^{3.1.b}$.

Preferred are the above compounds of formula 1, wherein $R^{3.2}$ is $R^{3.2.c}$ and $R^{3.2.c}$ is phenyl.

Preferred are the above compounds of formula 1, wherein $R^{3.2}$ is $R^{3.2.d}$ and $R^{3.2.d}$ is a five- or six-membered heterocyclic or heteroaryl ring containing one, two or three elements independently selected from N, O, S, S(O) and S(O)₂; each ring optionally substituted with one or two substituents independently selected from HO—, O═, NC—, halogen, $R^{3.3}$, $R^{3.3}$O—, $R^{3.3}$—(O)C—, $R^{3.4}$, $R^{3.5}$, $R^{3.6}$ and $R^{3.7}$ or two substituents are together $R^{3.8}$.

Preferred are the above compounds of formula 1, wherein $R^{3.2}$ is $R^{3.2.e}$ and two $R^{3.2.e}$ are together a three-, four-, five- or six-membered monocyclic or a six-, seven-, eight-, nine- or ten-membered bicyclic heterocyclic or heterocyclic ring optionally containing additional to the nitrogen one or two elements independently selected from among N, O, S, S(O) and S(O)$_2$; optionally substituted with one or two substituents, independently selected from among HO—, F, O=, NC—, $R^{3.3}$, $R^{3.3}$O—, $R^{3.3}$—(O)C—, $R^{3.4}$, $R^{3.5}$, $R^{3.7}$ and $R^{3.6}$ or two substituents are together $R^{3.8}$.

Preferred are the above compounds of formula 1, wherein $R^{3.2}$ is $R^{3.2.f}$ and two $R^{3.2.f}$ are together a three-, four-, five- or six-membered heterocyclic or heteroaryl ring optionally containing additional to the nitrogen one or two elements independently selected from among N, O, S, S(O) and S(O)$_2$; optionally substituted with one or two substituents, independently selected from among HO—, F, O=, NC—, $R^{3.3}$, $R^{3.3}$O—, $R^{3.3}$—(O)C—, $R^{3.4}$, $R^{3.5}$, $R^{3.7}$ and $R^{3.6}$ or two substituents are together $R^{3.8}$.

Preferred are the above compounds of formula 1, wherein $R^{3.2}$ is $R^{3.2.g}$ and two $R^{3.2.g}$ are together a six-, seven-, eight-, nine- or ten-membered bicyclic heterocyclic or heteroaryl ring optionally containing additional to the nitrogen one or two elements independently selected from among N, O, S, S(O) and S(O)$_2$; optionally substituted with one or two substituents, independently selected from among HO—, F, O=, NC—, $R^{3.3}$, $R^{3.3}$O—, $R^{3.3}$—(O)C—, $R^{3.4}$, $R^{3.5}$, $R^{3.7}$ and $R^{3.6}$ or two substituents are together $R^{3.8}$.

Preferred are the above compounds of formula 1, wherein $R^{3.2}$ is $R^{3.2.h}$ and $R^{3.2.h}$ is selected from among H, Me, Et, n-Pr, i-Pr and cyclopropyl.

Preferred are the above compounds of formula 1, wherein $R^{3.2}$ is $R^{3.2.i}$ and $R^{3.2.i}$ is selected from among H, Me, Et, i-Pr, cyclopropyl, HO(CH$_2$)$_2$—, HO(CMe$_2$)(CH$_2$)— and HO(CH$_2$)$_3$—.

Preferred are the above compounds of formula 1, wherein $R^{3.3}$ is $R^{3.3.a}$ and $R^{3.3.a}$ is selected from among Me, Et, n-Pr, i-Pr, n-Bu, t-Bu, cyclopropyl, cyclobutyl, cyclopentyl, cyclohexyl, F$_3$C—, F$_2$HC—, F$_3$C—CH$_2$—, F$_2$HC—CH$_2$— and FH$_2$C—CH$_2$—.

Preferred are the above compounds of formula 1, wherein $R^{3.4}$ is $R^{3.4.a}$ and $R^{3.4.a}$ is selected from among HO—CH$_2$—, HO—CH$_2$—CH$_2$—, HO—CH$_2$—CH$_2$—CH$_2$—, $R^{3.3.a}$O—CH$_2$—, $R^{3.3.a}$O—CH$_2$—CH$_2$— and $R^{3.3.a}$O—CH$_2$—CH$_2$—CH$_2$—.

Preferred are the above compounds of formula 1, wherein $R^{3.4}$ is $R^{3.4.b}$ and $R^{3.4.b}$ is selected from among HO—CH$_2$—, HO—CH$_2$—CH$_2$—, HO—CH$_2$—CH$_2$—CH$_2$—, MeO-CH$_2$—, MeO-CH$_2$—CH$_2$—, MeO-CH$_2$—CH$_2$—CH$_2$—, EtO-CH$_2$— EtO-CH$_2$—CH$_2$— and EtO-CH$_2$—CH$_2$—CH$_2$—.

Preferred are the above compounds of formula 1, wherein $R^{3.5}$ is $R^{3.5.a}$ and $R^{3.5.a}$ is selected from among H$_2$N—, $R^{3.3.a}$HN—, $(R^{3.3.a})_2$N—, $R^{3.3.a}$ (O)C—HN— and $R^{3.3.a}$—(O)C—$(R^{3.3.a})$N—.

Preferred are the above compounds of formula 1, wherein $R^{3.5}$ is $R^{3.5.b}$ and $R^{3.5.b}$ is selected from among H$_2$N—, MeHN—, (Me)$_2$N—, EtHN—, (Et)$_2$N—, Et(Me)N—, i-PrHN—, (i-Pr)(Me)N—, t-BuHN—, (t-Bu)(Me)N—, Me(O)C—HN—, Et(O)C—HN—, n-Pr(O)C—HN—, i-Pr(O)C—HN—, t-Bu(O)C—HN—, Me(O)C-(Me)N—, Et(O)C-(Me)N—, n-Pr(O)C-(Me)N—, i-Pr(O)C-(Me)N— and t-Bu(O)C-(Me)N—.

Preferred are the above compounds of formula 1, wherein $R^{3.6}$ is $R^{3.6.a}$ and $R^{3.6.a}$ is selected from among $R^{3.3.a}$(O)S—, $R^{3.3.a}$(O)$_2$S—, $R^{3.3.a}$(HN)S—, $R^{3.3.a}$(HN)(O)S—, $R^{3.3.a}$($R^{3.3.a}$N)S—, $R^{3.3.a}$($R^{3.3.a}$N)(O)S—, $R^{3.3.a}$($R^{3.4.a}$N)S—, $R^{3.3.a}$($R^{3.4.a}$N)(O)S—, $R^{3.3.a}$(NC—N)S— and $R^{3.3.a}$(NC—N)(O)S—.

Preferred are the above compounds of formula 1, wherein $R^{3.6}$ is $R^{3.6.b}$ and $R^{3.6.b}$ is selected from among Me(O)S—, Et(O)S—, i-Pr(O)S—, Me(O)$_2$S—, Et(O)$_2$S—, i-Pr(O)$_2$S—, Me(HN)S—, Et(HN)S—, i-Pr(HN)S—, Me(HN)(O)S—, Et(HN)(O)S—, i-Pr(HN)(O)S—, Me(MeN)S—, Et(MeN) S—, i-Pr(MeN)S—, Me(MeN)(O)S—, Et(MeN)(O)S—, i-Pr (MeN)(O)S—, Me(HOCH$_2$CH$_2$N)S—, Et(HOCH$_2$CH$_2$N) S—, i-Pr(HOCH$_2$CH$_2$N)S—, Me(HOCH$_2$CH$_2$N)(O)S—, Et(HOCH$_2$CH$_2$N)(O)S—, i-Pr(HOCH$_2$CH$_2$N)(O)S—, Me(MeOCH$_2$CH$_2$N)S—, Et(MeOCH$_2$CH$_2$N)S—, i-Pr (MeOCH$_2$CH$_2$N)S—, Me(MeOCH$_2$CH$_2$N)(O)S—, Et(MeOCH$_2$CH$_2$N)(O)S— and i-Pr(MeOCH$_2$CH$_2$N)(O) S—, Preferred are the above compounds of formula 1, wherein $R^{3.7}$ is $R^{3.7.a}$ and $R^{3.7.a}$ is selected from among HO(O)C—, H$_2$N(O)C—, $R^{3.3.a}$0(O)C—, $R^{3.3.a}$NH(O)C— and $(R^{3.3.a})_2$N (O)C—.

Preferred are the above compounds of formula 1, wherein $R^{3.7}$ is $R^{3.7.b}$ and $R^{3.7.b}$ is selected from among HO(O)C—, H$_2$N(O)C—, MeO(O)C—, EtO(O)C—, i-PrO(O)C—, t-BuO(O)C—, MeNH(O)C—, EtNH(O)C—, i-PrNH(O) C—, t-BuNH(O)C—, (Me)$_2$N(O)C—, (Et)$_2$N(O)C—, (i-Pr) (Me)N(O)C—, (t-Bu)(Me)N(O)C—, Et(Me)N(O)C—, i-Pr (Me)N(O)C— and t-Bu(Me)N(O)C—.

Preferred are the above compounds of formula 1, wherein $R^{3.8}$ is $R^{3.8.a}$ and $R^{3.8.a}$ is independently selected from the group consisting of —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, wherein optionally one or two CH$_2$-groups are replaced by —HN—, -MeN—, -EtN—, -(Me(O)C—)N—, -(Et(O)C—)N—, -(MeO(O)C—)N—, -(EtO(O)C—)N—, —O—, —S—, —S(O)—, —S(O)$_2$—.

Preferred are the above compounds of formula 1, wherein $R^{3.8}$ is $R^{3.8.b}$ and $R^{3.8.b}$ is selected from among —CH$_2$—, —CH$_2$CH$_2$—, —CH$_2$CH$_2$CH$_2$—, —CH$_2$CH$_2$CH$_2$CH$_2$— and —CH$_2$CH$_2$CH$_2$CH$_2$CH$_2$—, wherein optionally one or two CH$_2$-groups are replaced by —HN—, -MeN—, -EtN—, —O—, —S—, —S(O)—, —S(O)$_2$-.

Preferred are the above compounds of formula 1, wherein A is $A^a$ and $A^a$ is —CH$_2$—, optionally substituted with one or two substituents independently selected from the group consisting of halogen, $R^{3.3}$, $R^{3.3}$O— and $R^{3.4}$ or two substituents together are —CH$_2$CH$_2$—.

Preferred are the above compounds of formula 1, wherein $R^3$ is a residue independently selected from the group consisting of $R^{3.1}$—;

$R^{3.2}$O(O)C— or $R^{3.2}$O(O)C—CH$_2$—;

$R^{3.2}$(O)$_2$S—; and $(R^{3.2})_2$N(O)C— or $(R^{3.2})_2$N(O)C—CH$_2$—;

$R^3$ is independently selected from the group consisting of H, $R^{3.3}$, $R^{3.4}$, C$_{1-6}$-alkyl-C$_{3-6}$-cycloalkyl- and C$_{3-6}$-cycloalkyl-C$_{1-6}$-alkyl-, each optionally substituted with one or two substituents independently selected from among $R^{3.11}$—;

$R^{3.1.1}$ is selected from the group consisting of HO—, halogen, NC—, $R^{3.3}$O—, $R^{3.5}$, $R^{3.6}$ and $R^{37}$; or $R^{3.1.1}$ denotes a ring independently selected from among phenyl and a four-membered heterocyclic ring containing one element independently selected from among N, O, S, S(O) and S(O)$_2$; or $R^{3.1.1}$ denotes a five- or six-membered heterocyclic or heteroaryl ring containing one, two or three elements independently selected from among N, O, S, S(O) and S(O)$_2$; each of the rings as defined for $R^{3.1.1}$ is optionally substituted with one or two substituents independently selected from among HO—, O=, halogen, $R^{3.3}$, $R^{3.3}O—$, $R^{3.3}—(O)C—$, $R^{3.4}$, $R^{3.5}$, $R^{3.6}$ and $R^{3.7}$ or two substituents are together $R^{3.8}$;

$R^{3.2}$ is independently selected from the group consisting of $R^{3.1}$, phenyl or a five- or six-membered heterocyclic or heteroaryl ring containing one, two or three elements independently selected from the group consisting of N, O, S, S(O) or S(O)$_2$; each ring optionally substituted with one or two substituents independently selected from the group consisting of HO—, O═, NC—, halogen, $R^{3.3}$, $R^{3.3}O—$, $R^{3.3}—(O)C—$, $R^{3.4}$, $R^{3.5}$, $R^{3.6}$ and $R^{3.7}$ or two substituents are together $R^{3.8}$; or two $R^{3.2}$ are together a five- or six-membered monocyclic or an eight-, nine- or ten-membered bicyclic heterocyclic or heteroaryl ring optionally containing additional to the nitrogen one or two elements independently selected from the group consisting of N, O, S, S(O) and S(O)$_2$; optionally substituted with one or two substituents, independently selected from the group consisting of HO—, F, O═, $R^{3.3}$, $R^{3.3}O—$, $R^{3.3}—(O)C—$, $R^{3.4}$, $R^{3.5}$, $R^{3.7}$ and $R^{3.6}$ or two substituents are together $R^{3.8}$;

$R^{3.3}$ is independently selected from the group consisting of $C_{1-6}$-alkyl-, $C_{3-6}$-cycloalkyl-, $C_{1-6}$-haloalkyl- and $C_{3-6}$-halocycloalkyl-;

$R^{3.4}$ is HO—$C_{1-6}$-alkyl- or $R^{3.3}$—O—$C_{1-6}$-alkyl-;

$R^{3.5}$ is independently selected from the group consisting of $H_2N—$, $R^{3.3}—HN—$, $(R^{3.3})_2N—$ and $R^{3.3}—(O)C—HN—$;

$R^{3.6}$ is independently selected from the group consisting of $R^{3.3}—(O)S—$, $R^{3.3}—(O)_2S—$, $R^{3.3}(HN)S—$, $R^{3.3}(HN)(O)S—$, $R^{3.3}(R^{3.3}N)S—$, $R^{3.3}(R^{3.3}N)(O)S—$, $R^{3.3}(R^{3.4}N)S—$ and $R^{3.3}(R^{3.4}N)(O)S—$;

$R^{3.7}$ is independently selected from the group consisting of HO(O)C—, $H_2N(O)C—$, $R^{3.3}—O—(O)C—$, $R^{3.3}—NH—(O)C—$ and $(R^{3.3})_2N—(O)C—$;

$R^{3.8}$ is independently selected from the group consisting of $C_{1-6}$-alkylene and $C_{1-6}$-haloalkylene, wherein optionally one or two CH$_2$-groups are replaced independently from each other by —HN—, —$(R^{3.3})N—$, —$(R^{3.4})N—$, —$(R^{3.3}(O)C—)N—$, —$(R^{3.4}(O)C—)N—$, —O—, —S—, —S(O)— or —S(O)$_2$—;

or a salt thereof.

Preferred are the above compounds of formula 1, wherein A is $A^b$ and $A^b$ is —CH$_2$—, optionally substituted with one or two substituents independently selected from the group consisting of F, Me, Et, i-Pr, MeO, EtO, HOCH$_2$O— and MeOCH$_2$—.

Preferred are the above compounds of formula 1, wherein A is $A^c$ and $A^c$ is —CH$_2$—, optionally substituted with a substituent independently selected from among F and Me.

Preferred are the above compounds of formula 1, wherein A is $A^d$ and $A^d$ is —CH$_2$—.

Preferred are the above compounds of formula 1, wherein $R^4$ is $R^{4.a}$ and $R^{4.a}$ is independently selected from the group consisting of fluorine, $C_{1-6}$-alkyl-, $C_{3-6}$-cycloalkyl-, $C_{1-6}$-haloalkyl-, $C_{3-6}$-halocycloalkyl-, HO—$C_{1-6}$-alkyl- and $C_{1-6}$-alkyl-O—$C_{1-6}$-alkyl-; or two $R^{4.a}$ are together $C_{1-6}$-alkylene or $C_{1-6}$-haloalkylene, wherein optionally one CH$_2$-group can be replaced by —O—.

Preferred are the above compounds of formula 1, wherein $R^4$ is $R^{4.b}$ and $R^{4.b}$ is independently selected from the group consisting of fluorine, $C_{1-4}$-alkyl-, $C_{3-4}$-cycloalkyl-, $C_{1-4}$-haloalkyl-, $C_{3-4}$-halocycloalkyl-, HO—$C_{1-4}$-alkyl- and $C_{1-4}$-alkyl-O—$C_{1-4}$-alkyl-; or two $R^{4.b}$ are together $C_{1-6}$-alkylene or $C_{1-6}$-haloalkylene.

Preferred are the above compounds of formula 1, wherein $R^4$ is $R^{4.c}$ and $R^{4.c}$ is independently selected from the group consisting of fluorine, $C_{1-4}$-alkyl-, $C_{3-4}$-cycloalkyl-, $C_{1-4}$-haloalkyl-, $C_{3-4}$-halocycloalkyl-, HO—$C_{1-4}$-alkyl- and $C_{1-4}$-alkyl-O—$C_{1-4}$-alkyl-.

Preferred are the above compounds of formula 1, wherein $R^4$ is $R^{4.d}$ and $R^{4.d}$ is independently selected from the group consisting of fluorine, methyl, ethyl, n-propyl, isopropyl, cyclopropyl, n-butyl, isobutyl, cyclobutyl, tert-butyl, HO—CH$_2$—, HO—CH$_2$CH$_2$— and HO—CH$_2$CH$_2$CH$_2$—.

Preferred are the above compounds of formula 1, wherein $R^4$ is $R^{4.e}$ and $R^{4.e}$ is fluorine or methyl.

Particularly preferred are the above compounds of formula 1, wherein $R^4$ is $R^{4.e}$ and $R^{4.e}$ is methyl.

Preferred are the above compounds of formula 1, wherein x is 2, and $R^4$ is $R^{4.f}$, wherein $R^{4.f}$ denotes independently from each other $C_{1-4}$-alkyl-.

Particularly preferred are the above compounds of formula 1, wherein x is 2, and $R^4$ is methyl.

Preferred are the above compounds of formula 1, wherein x is $x^a$ and $x^a$ is 0 or 1.

Preferred are the above compounds of formula 1, wherein x is $x^b$ and $x^b$ is 0.

Preferred are the above compounds of formula 1, wherein $R^5$ is $R^{5.a}$ and $R^{5.a}$ is independently selected from the group consisting of fluorine, NC—, $R^{5.1}$;

HO(O)C—, $H_2N(O)C—$, $R^{5.1}—O—(O)C—$, $R^{5.1}—NH—(O)C—$, $(R^{5.1})_2N—(O)C—$;

phenyl or a five- or six-membered heterocyclic or heteroaryl ring containing one or two elements independently selected from the group consisting of N, O, S, S(O) and S(O)$_2$; each ring optionally substituted with one, two or three substituents independently selected from the group consisting of halogen, HO—, O═, NC—, $O_2N—$, $H_2N—$, $R^{5.1}$ and $R^{5.1}O—$;

and $R^{5.1}$ is $R^{5.1.a}$ and $R^{5.1.a}$ is independently selected from the group consisting of $C_{1-6}$-alkyl-, $C_{3-6}$-cycloalkyl-, $C_{1-6}$-alkyl-$C_{3-6}$-cycloalkyl-, $C_{3-6}$-cycloalkyl-$C_{1-6}$-alkyl-, $C_{1-6}$-haloalkyl-, $C_{3-6}$-halocycloalkyl-, HO—$C_{1-6}$-alkyl-, $C_{1-6}$-alkyl-O—$C_{1-6}$-alkyl-, $C_{3-6}$-cycloalkyl-O—$C_{1-6}$-alkyl-, $C_{1-6}$-haloalkyl-O—$C_{1-6}$-alkyl- and $C_{3-6}$-halocycloalkyl-O—$C_{1-6}$-alkyl-; or two $R^{5.1.a}$ are together $C_{1-6}$-alkylene or $C_{1-6}$-haloalkylene, wherein optionally one CH$_2$-group is replaced by —HN—, —$(C_{1-6}$-alkyl-$)N—$, —$(C_{3-6}$-cycloalkyl-$)N—$, —$(HO—C_{1-6}$-alkyl-$)N—$, —$(C_{1-6}$-alkyl-O—$C_{1-6}$-alkyl-$)N—$, —$(C_{1-6}$-alkyl-(O)C—$)N—$, —$(C_{3-6}$-cycloalkyl-(O)C—$)N—$, —$(HO—C_{1-6}$-alkyl-(O)C—$)N—$, —$(C_{1-6}$-alkyl-O—$C_{1-6}$-alkyl-(O)C—$)N—$, —O—, —S—, —S(O)— or —S(O)$_2$—;

Preferred are the above compounds of formula 1, wherein $R^5$ is $R^{5.b}$ and $R^{5.b}$ is independently selected from the group consisting of fluorine, $R^{5.1}$, HO(O)C—, $H_2N(O)C—$, $R^{5.1}—O—(O)C—$, $R^{5.1}—NH—(O)C—$ and $(R^{5.1})_2N—(O)C—$; and $R^{5.1}$ is $R^{5.1.b}$ and $R^{5.1.b}$ is independently selected from the group consisting of $C_{1-6}$-alkyl-, $C_{3-6}$-cycloalkyl-, $C_{1-6}$-haloalkyl-, $C_{3-6}$-halocycloalkyl-, HO—$C_{1-6}$-alkyl-, $C_{1-6}$-alkyl-O—$C_{1-6}$-alkyl-, $C_{3-6}$-cycloalkyl-O—$C_{1-6}$-alkyl-, $C_{1-6}$-haloalkyl-O—$C_{1-6}$-alkyl- and $C_{3-6}$-halocycloalkyl-O—$C_{1-6}$-alkyl-; or two $R^{5.1}$ are together $C_{1-6}$-alkylene or $C_{1-6}$-haloalkylene; wherein optionally one CH$_2$-group is replaced by —O—;

Preferred are the above compounds of formula 1, wherein $R^5$ is $R^{5.c}$ and $R^{5.c}$ is independently selected from the group consisting of $R^{5.1}$, HO(O)C— and $H_2N(O)C—$; and $R^{5.1}$ is $R^{5.1.c}$ and $R^{5.1.c}$ is independently selected from the group consisting of methyl, ethyl, n-propyl, isopropyl, cyclopropyl, n-butyl, isobutyl, cyclobutyl, tert-butyl, $F_3C—$, HO—CH$_2$—, HO—CH$_2$CH$_2$—, HO—CH$_2$CH$_2$CH$_2$—, CH$_3$—O—CH$_2$—, CH$_3$—O—CH$_2$CH$_2$— and CH$_3$—O—CH$_2$CH$_2$CH$_2$—.

Preferred are the above compounds of formula 1, wherein R$^5$ is R$^{5.c}$ and R$^{5.c}$ is independently selected from the group consisting of R$^{5.1}$, HO(O)C— and H$_2$N(O)C—; and R$^{5.1}$ is R$^{5.1.d}$ and R$^{5.1.d}$ is independently selected from the group consisting of methyl, ethyl, n-propyl, isopropyl, cyclopropyl, n-butyl, isobutyl, cyclobutyl, tert-butyl and F$_3$C—.

Preferred are the above compounds of formula 1, wherein R$^5$ is R$^{5.a}$ and R$^{5.a}$ is independently selected from the group consisting of MeO(O)C—, HO(O)C—, H$_2$N(O)C—, Ph, thiophene-2-yl, Me and F$_3$C—.

Preferred are the above compounds of formula 1, wherein R$^5$ is R$^{5.e}$ and R$^{5.e}$ is independently selected from the group consisting of MeO(O)C—, HO(O)C—, H$_2$N(O)C— and Me-.

Preferred are the above compounds of formula 1, wherein y is 2, and R$^5$ is R$^{5.f}$, wherein R$^{5.f}$ denotes independently from each other C$_{1-4}$-alkyl-.

Particularly preferred are the above compounds of formula 1, wherein y is 2, and R$^{5.f}$ is methyl.

Preferred are the above compounds of formula 1, wherein y is y$^a$ and y$^a$ is 0 or 1.

Preferred are the above compounds of formula 1, wherein y is y$^b$ and y$^b$ is 0.

Preferred is a compound of formula 1, wherein

R$^1$ is R$^{1.c}$ and R$^{1.c}$ is phenyl or pyridinyl; each ring optionally substituted by one, two or three residues independently selected from the group consisting of halogen, NC—, R$^{1.1}$, R$^{1.1}$O— and R$^{1.1}$(O)$_2$S—;

R$^2$ is R$^{2.b}$ and R$^{2.b}$ is phenyl or a six-membered heteroaryl; wherein one or two elements are replaced by N; each ring optionally substituted with one or two substituents independently selected from the group consisting of halogen, C$_{1-4}$-alkyl- and C$_{1-4}$-haloalkyl-;

R$^3$ is a residue independently selected from the group consisting of

R$^{3.1}$—;

R$^{3.2}$O(O)C—;

R$^{3.2}$(O)$_2$S—; and (R$^{3.2}$)$_2$N(O)C— or (R$^{3.2}$)$_2$N(O)C—CH$_2$—.

R$^{3.1}$ is independently selected from the group consisting of H, R$^{3.3}$, R$^{3.4}$, C$_{1-6}$-alkyl-C$_{3-6}$-cycloalkyl- and C$_{3-6}$-cycloalkyl-C$_{1-6}$-alkyl-, each optionally substituted with one or two substituents independently selected from among R$^{3.1.1}$;

R$^{3.1.1}$ is selected from the group consisting of HO—, halogen, NC—, R$^{3.3}$O—, R$^{3.5}$, R$^{3.6}$ and R$^{3.7}$ or R$^{3.1.1}$ denotes a ring independently selected from among phenyl and a four-membered heterocyclic ring containing one element independently selected from N, O, S, S(O) and S(O)$_2$; or R$^{3.1.1}$ denotes a five- or six-membered heterocyclic or heteroaryl ring containing one, two or three elements independently selected from N, O, S, S(O) and S(O)$_2$; each of the rings optionally substituted with one or two substituents independently selected from HO—, O═, halogen, R$^{3.3}$, R$^{3.3}$O—, R$^{3.3}$—(O)C—, R$^{3.4}$ R$^{3.5}$, R$^{3.6}$ and R$^{37}$ or two substituents are together R$^{3.8}$;

R$^{3.2}$ is independently selected from the group consisting of R$^{3.1}$, phenyl or a five- or six-membered heterocyclic or heteroaryl ring containing one, two or three elements independently selected from the group consisting of N, O, S, S(O) and S(O)$_2$; each ring optionally substituted with one or two substituents independently selected from the group consisting of HO—, O═, NC—, halogen, R$^{3.3}$, R$^{3.3}$O—, R$^{3.3}$—(O)C—, R$^{3.4}$, R$^{3.5}$, R$^{3.6}$, R$^{3.7}$ or two substituents are together R$^{3.8}$;

or two R$^{3.2}$ are together a five- or six-membered monocyclic or an eight-, nine- or ten-membered bicyclic heterocyclic or heteroaryl ring optionally containing additional to the nitrogen one or two elements independently selected from the group consisting of N, O, S, S(O) and S(O)$_2$; optionally substituted with one or two substituents, independently selected from the group consisting of HO—, F, O═, R$^{3.3}$, R$^{3.3}$O—, R$^{3.3}$—(O)C—, R$^{3.4}$, R$^{3.5}$, R$^{3.7}$ and R$^{3.6}$ or two substituents are together R$^{3.8}$;

R$^{3.3}$ is independently selected from the group consisting of C$_{1-6}$-alkyl-, C$_{3-6}$-cycloalkyl-, C$_{1-6}$-haloalkyl- and C$_{3-6}$-halocycloalkyl-;

R$^{3.4}$ is HO—C$_{1-6}$-alkyl- or R$^{3.3}$—O—C$_{1-6}$-alkyl-;

R$^{3.5}$ is independently selected from the group consisting of H$_2$N—, R$^{3.3}$—HN—, (R$^{3.3}$)$_2$N— and R$^{3.3}$—(O)C—HN—;

R$^{3.6}$ is independently selected from the group consisting of R$^{3.3}$—(O)S—, R$^{3.3}$—(O)$_2$S—, R$^{3.3}$(HN)S—, R$^{3.3}$(HN)(O)S—, R$^{3.3}$(R$^{3.3}$N)S—, R$^{3.3}$(R$^{3.3}$N)(O)S—, R$^{3.3}$(R$^{3.4}$N)S— and R$^{3.3}$(R$^{3.4}$N)(O)S—;

R$^{3.7}$ is independently selected from the group consisting of HO(O)C—, H$_2$N(O)C—, R$^{3.3}$—O—(O)C—, R$^{3.3}$—NH—(O)C— and (R$^{3.3}$)$_2$N—(O)C—;

R$^{3.8}$ is independently selected from the group consisting of C$_{1-6}$-alkylene or C$_{1-6}$-haloalkylene, wherein optionally one or two CH$_2$-groups independently from each other are replaced by —HN—, —(R$^{3.3}$)N—, —(R$^{3.4}$)N—, —(R$^{3.3}$(O)C—)N—, —(R$^{3.4}$(O)C—)N—, —O—, —S—, —S(O)— or —S(O)$_2$—;

R$^4$ is R$^{4.a}$ and R$^{4.a}$ is independently selected from the group consisting of fluorine, C$_{1-6}$-alkyl-, C$_{3-6}$-cycloalkyl-, C$_{1-6}$-haloalkyl-, C$_{3-6}$-halocycloalkyl-, HO—C$_{1-6}$-alkyl- and C$_{1-6}$-alkyl-O—C$_{1-6}$-alkyl-; or two R$^{4.a}$ are together C$_{1-6}$-alkylene or C$_{1-6}$-haloalkylene, wherein optionally one CH$_2$-group can be replaced by —O—;

x is 0, 1 or 2; preferably 0;

R$^5$ is R$^{5.a}$ and R$^{5.a}$ is independently selected from the group consisting of fluorine, NC—, R$^{5.1}$;

HO(O)C—, H$_2$N(O)C—, R$^{5.1}$—O—(O)C—, R$^{5.1}$—NH—(O)C—, (R$^{5.1}$)$_2$N—(O)C—;

phenyl or a five- or six-membered heterocyclic or heteroaryl ring containing one or two elements independently selected from the group consisting of N, O, S, S(O) and S(O)$_2$; each ring optionally substituted with one, two or three substituents independently selected from the group consisting of halogen, HO—, O═, NC—, O$_2$N—, H$_2$N—, R$^{5.1}$ and R$^{5.1}$O—;

R$^{5.1}$ is R$^{5.1.a}$ and R$^{5.1.a}$ is independently selected from the group consisting of C$_{1-6}$-alkyl-, C$_{3-6}$-cycloalkyl-, C$_{1-6}$-haloalkyl-, C$_{3-6}$-halocycloalkyl-, HO—C$_{1-6}$-alkyl-, C$_{1-6}$-alkyl-O—C$_{1-6}$-alkyl-, C$_{3-6}$-cycloalkyl-O—C$_{1-6}$-alkyl-, C$_{1-6}$-haloalkyl-O—C$_{1-6}$-alkyl-, and C$_{3-6}$-halocycloalkyl-O—C$_{1-6}$-alkyl-; or two R$^{5.1.a}$ are together C$_{1-6}$-alkylene or C$_{1-6}$-haloalkylene, wherein optionally one CH$_2$-group is replaced by —HN—, —(C$_{1-6}$-alkyl-)N—, —(C$_{3-6}$-cycloalkyl-)N—, —(HO—C$_{1-6}$-alkyl-)N—, —(C$_{1-6}$-alkyl-O—C$_{1-6}$-alkyl-)N—, —(C$_{1-6}$-alkyl-(O)C—)N—, —(C$_{3-6}$-cycloalkyl-(O)C—)N—, (HO—C$_{1-6}$-alkyl-(O)C—)N—, (C$_{1-6}$-alkyl-O—C$_{1-6}$-alkyl-(O)C—)N—, —O—, —S—, —S(O)— or —S(O)$_2$—;

y is 0, 1 or 2; preferably 0;

or a salt thereof.

Preferred is a compound of formula 1, wherein
$R^1$ is $R^{1.g}$ g and $R^{1.g}$ is phenyl or pyridinyl; each ring optionally substituted by one, two or three residues independently selected from the group consisting of F, Cl, NC—, Me, MeO—, Me(O)$_2$S— and Et(O)$_2$S—;
$R^2$ is $R^{2.d}$ and $R^{2.d}$ is phenyl or pyridinyl; each optionally substituted with one or two substituents independently selected from the group consisting of fluorine, CF$_3$— and CF$_2$H—;
$R^3$ is selected of the examples (E#) 1 to 54 of the Table $R^3$—Embodiments of the invention;
$R^4$ is $R^{4.b}$ and $R^{4.b}$ is independently selected from the group consisting of fluorine, C$_{1-4}$-alkyl-, C$_{3-4}$-cycloalkyl-, C$_{1-4}$-haloalkyl-, C$_{3-4}$-halocycloalkyl-, HO—C$_{1-4}$-alkyl- and C$_{1-4}$-alkyl-O—C$_{1-4}$-alkyl-; or two $R^{4.b}$ are together C$_{1-6}$-alkylene or C$_{1-6}$-haloalkylene.
x is 0, 1 or 2; preferably 0;
$R^5$ is $R^{5.b}$ and $R^{5.b}$ is independently selected from the group consisting of fluorine, $R^{5.1}$ HO(O)C—, H$_2$N(O)C—, $R^{5.1}$—O—(O)C—, $R^{5.1}$—NH—(O)C— and ($R^{5.1}$)$_2$N—(O)C—;
$R^{5.1}$ is $R^{5.1.b}$ and $R^{5.1.b}$ is independently selected from the group consisting of C$_{1-6}$-alkyl-, C$_{3-6}$-cyclo alkyl-, C$_{1-6}$-halo alkyl-, C$_{3-6}$-halocycloalkyl-, HO—C$_{1-6}$-alkyl-, C$_{1-6}$-alkyl-O—C$_{1-6}$-alkyl-, C$_{3-6}$-cycloalkyl-O—C$_{1-6}$-alkyl-, C$_{1-6}$-haloalkyl-O—C$_{1-6}$-alkyl- and C$_{3-6}$-halocyclo alkyl-O—C$_{1-6}$-alkyl-; or two $R^{5.1}$ are together C$_{1-6}$-alkylene or C$_{1-6}$-haloalkylene; wherein optionally one CH$_2$-group is replaced by —O—;
y is 0, 1 or 2; preferably 0;
or a salt thereof.

Preferred is a compound of formula 1, wherein
$R^1$ is $R^{1.h}$ and $R^{1.h}$ is phenyl or pyridinyl; each ring optionally substituted by one or two residues independently selected from the group consisting of NC—, Me(O)$_2$S and Et(O)$_2$S;
Particularly preferred are the above compounds of formula 1, wherein $R^1$ is $R^{1.i}$ and $R^{1.i}$ is phenyl; optionally substituted by one or two residues independently selected from the group consisting of NC—, Me(O)$_2$S— and Et(O)$_2$S—;
Particularly preferred are the above compounds of formula 1, wherein $R^1$ is $R^{1.j}$ and $R^{1.j}$ is pyridinyl; optionally substituted by one or two residues independently selected from the group consisting of NC— and Me(O)$_2$S—;
$R^2$ is $R^{2.d}$ and $R^{2.d}$ is phenyl or pyridinyl; each optionally substituted with one or two substituents independently selected from the group consisting of F—, F$_3$C— and F$_2$HC—;
$R^3$ is selected of the examples (E#) 1 to 54 of the Table $R^3$—Embodiments of the invention;
$R^4$ is $R^{4.c}$ and $R^{4.c}$ is independently selected from the group consisting of fluorine, C$_{1-4}$-alkyl-, C$_{3-4}$-cycloalkyl-, C$_{1-4}$-haloalkyl-, C$_{3-4}$-halocycloalkyl-, HO—C$_{1-4}$-alkyl- and C$_{1-4}$-alkyl-O—C$_{1-4}$-alkyl-.
x is 0, 1 or 2; preferably 0;
$R^5$ is $R^{5.c}$ and $R^{5.c}$ is independently selected from the group consisting of $R^{5.1}$, HO(O)C— and H$_2$N(O)C—;
$R^{5.1}$ is $R^{5.1.c}$ and $R^{5.1.c}$ is independently selected from the group consisting of methyl, ethyl, n-propyl, isopropyl, cyclopropyl, n-butyl, isobutyl, cyclobutyl, tert-butyl, F$_3$C—, HO—CH$_2$—, HO—CH$_2$CH$_2$—, HO—CH$_2$CH$_2$CH$_2$—, CH$_3$—O—CH$_2$—, CH$_3$—O—CH$_2$CH$_2$— and CH$_3$—O—CH$_2$CH$_2$CH$_2$—.
y is y$^a$ and y$^a$ is 0 or 1; preferably 0;
or a salt thereof.

Preferred is a compound of formula 1, wherein
$R^1$ is $R^{1.h}$ and $R^{1.h}$ is phenyl or pyridinyl; each ring optionally substituted by one or two residues independently selected from the group consisting of NC—, Me(O)$_2$S and Et(O)$_2$S;
Particularly preferred are the above compounds of formula 1, wherein $R^1$ is $R^{1.i}$ and $R^{1.i}$ is phenyl; optionally substituted by one or two residues independently selected from the group consisting of NC—, Me(O)$_2$S— and Et(O)$_2$S—;
Particularly preferred are the above compounds of formula 1, wherein $R^1$ is $R^{1.j}$ and $R^{1.j}$ is pyridinyl; optionally substituted by one or two residues independently selected from the group consisting of NC— and Me(O)$_2$S—;
$R^2$ is $R^{2.d}$ and $R^{2.d}$ is phenyl or pyridinyl; each optionally substituted with one or two substituents independently selected from F—, F$_3$C— and F$_2$HC—;
$R^3$ is one of the examples (E#) 2, 4, 5, 6, 7, 8, 12, 13, 17, 22, 23, 28, 29, 30, 31, 32, 33, 34, 35, 36, 37, 38, 43, 44, 48, 53 selected from the examples of the Table $R^3$—Embodiments of the invention;
$R^4$ is $R^{4.d}$ and $R^{4.d}$ is independently selected from the group consisting of fluorine, methyl, ethyl, n-propyl, isopropyl, cyclopropyl, n-butyl, isobutyl, cyclobutyl, tert-butyl, HO—CH$_2$—, HO—CH$_2$CH$_2$— and HO—CH$_2$CH$_2$CH$_2$—.
x is 0, 1 or 2; preferably 0;
$R^5$ is $R^{5.c}$ and $R^{5.c}$ is independently selected from $R^{5.1}$, HO(O)C— and H$_2$N(O)C—;
$R^{5.1}$ is $R^{5.1.c}$ and $R^{5.1.c}$ is independently selected from the group consisting of methyl, ethyl, n-propyl, isopropyl, cyclopropyl, n-butyl, isobutyl, cyclobutyl, tert-butyl, F$_3$C—, HO—CH$_2$—, HO—CH$_2$CH$_2$—, HO—CH$_2$CH$_2$CH$_2$—, CH$_3$—O—CH$_2$—, CH$_3$—O—CH$_2$CH$_2$— and CH$_3$—O—CH$_2$CH$_2$CH$_2$—.
y is y$^a$ and y$^a$ is 0 or 1; preferably 0;
or a salt thereof.

Preferred is a compound of formula 1, wherein
$R^1$ is $R^{1.h}$ and $R^{1.h}$ is phenyl or pyridinyl; each ring optionally substituted by one or two residues independently selected from the group consisting of NC—, Me(O)$_2$S and Et(O)$_2$S;
Particularly preferred are the above compounds of formula 1, wherein $R^1$ is $R^{1.i}$ and $R^{1.i}$ is phenyl; optionally substituted by one or two residues independently selected from the group consisting of NC—, Me(O)$_2$S— and Et(O)$_2$S—;
Particularly preferred are the above compounds of formula 1, wherein $R^1$ is $R^{1.j}$ and $R^{1.j}$ is pyridinyl; optionally substituted by one or two residues independently selected from the group consisting of NC— and Me(O)$_2$S—;
$R^2$ is $R^{2.d}$ and $R^{2.d}$ is phenyl or pyridinyl; each optionally substituted with one or two substituents independently selected from F—, F$_3$C— and F$_2$HC—;
$R^3$ is one of the examples (E#) 2, 4, 5, 6, 7, 8, 12, 13, 17, 22, 23, 28, 29, 30, 31, 32, 33, 34, 35, 36, 37, 38, 43, 44, 48, 53 selected from the examples of the Table $R^3$—Embodiments of the invention;
$R^4$ is $R^{4.f}$ and $R^{4.f}$ is independently selected from the group consisting of fluorine, methyl, ethyl, n-propyl, isopropyl, cyclopropyl, n-butyl, isobutyl, cyclobutyl, tert-butyl, HO—CH$_2$—, HO—CH$_2$CH$_2$— and HO—CH$_2$CH$_2$CH$_2$—.
x is 0, 1 or 2; preferably 0;
$R^5$ is $R^{5.e}$ and $R^{5.e}$ is independently selected from the group consisting of MeO(O)C—, HO(O)C—, H$_2$N(O)C— and Me-;
y is y$^a$ and y$^a$ is 0 or 1; preferably 0;
or a salt thereof.

Preferred is a compound of formula 1, wherein
$R^1$ is $R^{1.h}$ and $R^{1.h}$ is phenyl or pyridinyl; each ring optionally substituted by one or two residues independently selected from the group consisting of NC—, Me(O)$_2$S and Et(O)$_2$S;
  Particularly preferred are the above compounds of formula 1, wherein $R^1$ is $R^{1.i}$ and $R^{1.i}$ is phenyl; optionally substituted by one or two residues independently selected from the group consisting of NC—, Me(O)$_2$S— and Et(O)$_2$S—;
  Particularly preferred are the above compounds of formula 1, wherein $R^1$ is $R^{1.j}$ and $R^{1.j}$ is pyridinyl; optionally substituted by one or two residues independently selected from the group consisting of NC— and Me(O)$_2$S—;
$R^2$ is $R^{2.g}$ and $R^{2.g}$ is phenyl or pyridinyl; each optionally substituted with a substituent independently selected from among F$_3$C— and F$_2$HC—;
$R^3$ is one of the examples (E#) 2, 4, 5, 6, 7, 8, 18, 22, 23, 24, 28, 29, 30, 31, 32, 33, 34, 35, 36, 37, 38, 41, 42, 48, 53 selected from the examples of the Table $R^3$—Embodiments of the invention;
$R^4$ is methyl;
x is 0, 1 or 2; preferably 0;
$R^5$ is $R^{5.e}$ and $R^{5.e}$ is independently selected from the group consisting of MeO(O)C—, HO(O)C—, H$_2$N(O)C— and Me;
y is $y^a$ and $y^a$ is 0 or 1; preferably 0;
or a salt thereof.
  Preferred is a compound of formula 1, wherein
$R^1$ is $R^{1.h}$ and $R^{1.h}$ is phenyl or pyridinyl; each ring optionally substituted by one or two residues independently selected from the group consisting of NC—, Me(O)$_2$S and Et(O)$_2$S;
  Particularly preferred are the above compounds of formula 1, wherein $R^1$ is $R^{1.i}$ and $R^{1.i}$ is phenyl; optionally substituted by one or two residues independently selected from the group consisting of NC—, Me(O)$_2$S— and Et(O)$_2$S—;
  Particularly preferred are the above compounds of formula 1, wherein $R^1$ is $R^{1.j}$ and $R^{1.j}$ is pyridinyl; optionally substituted by one or two residues independently selected from the group consisting of NC— and Me(O)$_2$S—;
$R^2$ is $R^{2.g}$ and $R^{2.g}$ is phenyl or pyridinyl; each optionally substituted with a substituent independently selected from F$_3$C— or F$_2$HC—;
$R^3$ is one of the examples (E#) 5, 6, 7, 22, 29, 30, 31, 32, 33, 34, 35, 36, 37 selected from the examples of the Table $R^3$—Embodiments of the invention;
x is $x^b$ and $x^b$ is 0;
y is $y^b$ and $y^b$ is 0;
or a salt thereof.
  Preferred is a compound of formula 1, wherein $R^1$ is $R^{1.c}$ and $R^{1.c}$ is phenyl or pyridinyl; each ring optionally substituted by one, two or three residues independently selected from the group consisting of F, Cl, NC—, $R^{1.1}$, $R^{1.1}$O— and $R^{13}$(O)$_2$S—; and
  $R^{1.1}$ is independently selected from the group consisting of C$_{1-6}$-alkyl-, C$_{3-6}$-cycloalkyl-, C$_{1-6}$-haloalkyl- and C$_{3-6}$-halocycloalkyl-;
  $R^{1.2}$ is HO—C$_{1-6}$-alkyl- or $R^{1.1}$—O—C$_{1-6}$-alkyl-;
  $R^{13}$ is independently selected from the group consisting of H, HO—, $R^{1.1}$ and $R^{1.2}$;
or a salt thereof.

Preferred of all of the above mentioned embodiments of the invention is a compound of formula 1, wherein configuration of formula 1 is according to formula 1'

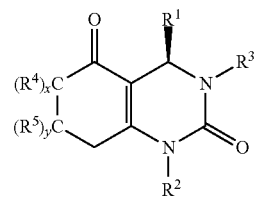

or a salt thereof.

PREPARATION

The compounds according to the present invention and their intermediates may be obtained using methods of synthesis which are known to the one skilled in the art and described in the literature of organic synthesis. Preferably, the compounds are obtained in analogous fashion to the methods of preparation explained more fully hereinafter, in particular as described in the experimental section. In some cases, the order in carrying out the reaction steps may be varied. Variants of the reaction methods that are known to the one skilled in the art but not described in detail here may also be used. The general processes for preparing the compounds according to the invention will become apparent to the one skilled in the art studying the following schemes. Starting materials are commercially available or may be prepared by methods that are described in the literature or herein, or may be prepared in an analogous or similar manner. Any functional groups in the starting materials or intermediates may be protected using conventional protecting groups. These protecting groups may be cleaved again at a suitable stage within the reaction sequence using methods familiar to the one skilled in the art.

Compounds of the invention VI are accessible using the synthetic route illustrated in Scheme 1; $R^I$, $R^{E.1}$, $R^{E.2}$ have the meanings as defined hereinbefore and hereinafter.

SCHEME 1

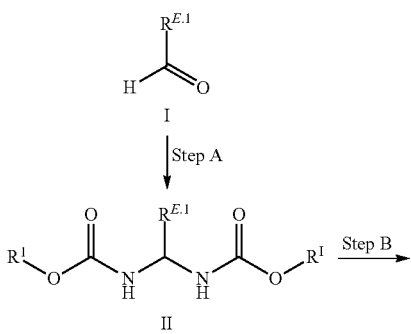

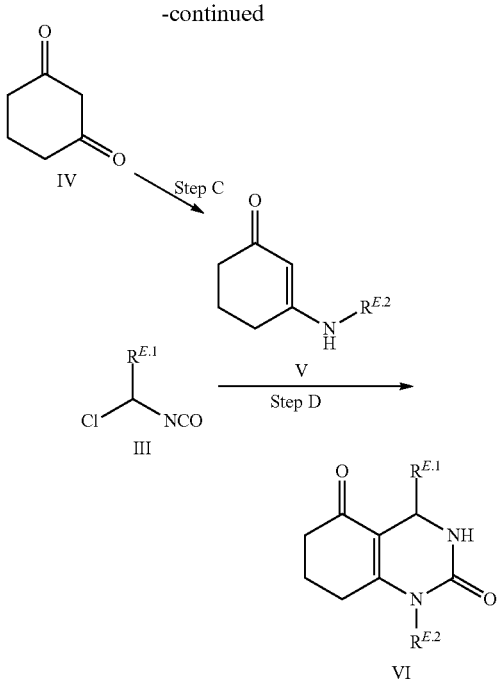

Intermediates II (Step A, intermediate I→intermediate II) can be prepared as described in Vovk et al. (*Synlett* 2006, 3, 375-378) or in PL2004/369318, by heating an aliphatic or aromatic aldehyde I with a carbamate, for example methyl carbamate, ethyl carbamate (urethane) or benzyl carbamate in the presence of a strong Brønsted or a Lewis acid, for example sulfuric acid, hydrogen chloride, p-toluenesulfonic acid, Amberlyst 15, tetrafluoro-boric acid, trifluoroacetic acid or boron trifluoride, either without solvent as a melt or in a suitable solvent, such as benzene, toluene, acetonitrile, diethyl ether, chloroform, acetic anhydride or mixtures thereof. The reaction takes place within 1 to 24 hours. Preferred reaction temperatures are between room temperature and 160° C., or the boiling point of the solvent, respectively. Preferably the reaction is done with molten ethyl carbamate as reactant and a catalytic amount of concentrated sulfuric acid at temperatures of 140-160° C. without any further solvent.

The chlorination (Step B, intermediate II→intermediate III) can be done as described in Vovk et al. (*Synlett* 2006, 3, 375-378) and Sinitsa et al. (*J. Org. Chem. USSR* 1978, 14, 1107) by heating intermediate II together with a chlorinating agent, for example phosphorous pentachloride, phosphoryl chloride or sulfuryl chloride in an organic solvent, for example benzene or toluene. The reaction takes place within 1 to 24 hours. Preferred reaction temperatures are between 50° C. and 150° C.

Alternatively, intermediates III can be prepared as described in Jochims et al. (*Chem. Ber.* 1982, 115, 860-870) by α-halogenation of aliphatic isocyanates, for example benzyl iso-cyanate, using for example a bromination agent, for example N-bromosuccinimide Isocyanates can be synthesized as described in U.S. Pat. No. 6,207,665 and in Charalambides et al. (*Synth. Commun.* 2007, 37, 1037-1044), by reacting an amine precursor with phosgene.

Intermediates V (Step C, intermediate IV→intermediates V) can be prepared as described in Ali et al. (*Aust. J. Chem.* 2005, 58, 870-876) and Scott et al. (*J. Med. Chem.* 1993, 36, 1947-1955) by direct condensation of cyclohexane-1,3-dione (IV) with an amine, optionally in a suitable solvent under reflux, for example benzene or toluene with azeotropic removal of water.

Alternatively, intermediates V can be prepared as described in Chen et al. (*Synth. Commun.* 2010, 40, 2506-2510) and Tietcheu et al. (*J. Heterocyclic Chem.* 2002, 39, 965-973) by reacting cyclohexane-1,3-dione (IV) and an aliphatic or aromatic amine in the presence of a catalyst, for example Ytterbium triflate [Yb(OTf)$_3$] or an acid, for example hydrogen chloride or p-toluenesulfonic acid, optionally in a solvent, for example water, acetic acid, acetonitrile, benzene, toluene. The reaction takes place within 1-24 hours. Preferred reaction temperatures are between room temperature and 120° C., most preferred room temperature.

Alternatively, intermediates V can be prepared in analogy to a procedure described in Mariano et al. (*J. Org. Chem.* 1984, 49, 220-228) by reacting an amine with 3-chloro-2-cyclohexen-1-one, which can be prepared from cyclohexane-1,3-dione.

Compounds according to the present invention (Step D, intermediates III→compounds of the invention VI) can be prepared as described in Vovk et al. (*Synlett* 2006, 3, 375-378), to Vovk et al. (*Russ. J. Org. Chem.* 2010, 46, 709-715) and Kushnir et al. (*Russ. J. Org. Chem.* 2011, 47, 1727-1732) by reacting intermediates III with intermediates V in an organic solvent, for example dichloromethane, chloroform, benzene or toluene. The reaction takes place within 1-24 hours. Preferred reaction temperatures are between 0° C. and 100° C.

Compounds of the invention VI are alternatively accessible using the synthetic route illustrated in Scheme 2; $R^{II}$, $R^{E.1}$, $R^{E.2}$ have the meanings as defined hereinbefore and hereinafter.

SCHEME 2

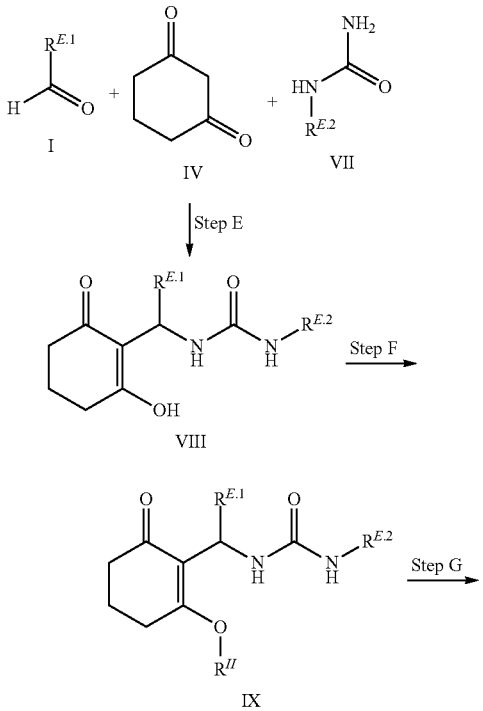

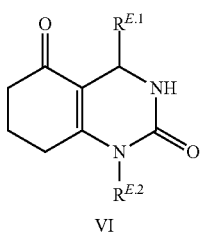

VI

Intermediates VIII can be prepared following a procedure described in Zhu et al. (*Heterocycles* 2005, 65, 133-142) by reacting an aldehyde I with cyclohexane-1,3-dione (IV) and a substituted urea VII in the presence of trimethylsilyl chloride as Lewis acid in a mixture of acetonitrile and N,N-dimethylformamide. The reaction takes place within 1-72 hours. Preferred reaction temperatures are between room temperature and 100° C. Alternatively, as described amongst others in Kappe et al. (*Org. React.* 2004, 63, 1-116), other Brønsted or Lewis acids can be used as catalyst, for example HCl, $H_2SO_4$, citric acid, acetic acid, trifluoroacetic acid, para-toluenesulfonic acid, $H_3PO_4$, polyphosphoric acid, $Me_3SiI$, LiBr, $KHSO_4$, $Al_2O_3$, $HBF_4$, $BF_3.Et_2O$, $FeCl_2$, $SnCl_2$ or $SiO_2$ and the reaction can be carried out in other organic solvents, for example ethanol, methanol, tetrahydrofuran, acetic acid, 1-butyl-3-methylimidazolium bromide, acetic acetate, tert-butyl methyl ether, chloroform or in water. Alternatively, as described in US2011/34433, a suitable catalyst can be prepared by heating triethyl phosphate and phosphorouos pentoxide at 50° C. over night.

The alkylation of enol VIII (Step F, intermediates VIII→intermediates IX) can be carried out by reacting the enol VIII with a suitable alkylating reagent, for example methyl iodide, ethyl bromide, dimethyl sulfate, diazomethane or trimethyloxonium tetrafluoroborate in the presence of a base, for example triethylamine, N,N-diisopropylethylamine, piperidine, pyridine, potassium carbonate, sodium hydroxide, potassium tert-butoxide, sodium hydride, lithium diisopropylamide, potassium hexamethyldisilazide, lithium hexamethyldisilazide, an organolithium reagent, for example tert-butyllithium or a Grignard reagent, for example isopropylmagnesiumchloride in an organic solvent, for example N,N-dimethylformamide, tetrahydrofuran, 1,4-dioxane, acetonitrile, dichloromethane, dimethylsulfoxide or toluene. The reaction takes place within 1-24 hours. Preferred reaction temperatures are between room temperature and 100° C.

Alternatively, the enol VIII can be activated by converting it into a sulfonylate, for example its corresponding methanesulfonylate, para-toluenesulfonylate or trifluoromethanesulfonylate by reacting it with the appropriate sulfonylating reagent, for example methanesulfonyl chloride or trifluoromethanesulfonic anhydride, optionally in the presence of a base, for example pyridine, triethylamine or N,N-diisopropylethylamine in an organic solvent, for example N,N-dimethylformamide, tetrahydrofuran, 1,4-dioxane, acetonitrile or dichloromethane.

Alternatively, the enol VIII can be activated as described in WO11094953 by converting it into its corresponding vinyl chloride using $POCl_3$ in chloroform.

The cyclization (Step G, intermediates IX→compounds of the invention VI) can be achieved by reacting an enolether IX with a suitable base, for example sodium or potassium tert-butoxide, sodium hydride, sodium hydroxide or lithium diisopropylamide in an organic solvent, for example dichloromethane, chloroform, N,N-dimethylformamide or acetonitrile. Alternatively, as described in Zanatta et al. (*Bioorg. Med. Chem. Lett.* 2006, 14, 3174-3184), para-toluenesulfonic acid can be used instead of abovementioned bases.

Compounds according to the present invention X, XI, XII, XIII and XIV are accessible via the synthetic routes depicted in scheme 3; $R^{III}$, $R^{IV}$, $R^{V}$, $R^{E.1}$, $R^{E.2}$, $R^{E.3}$ have the meanings as defined hereinbefore and hereinafter.

SCHEME 3

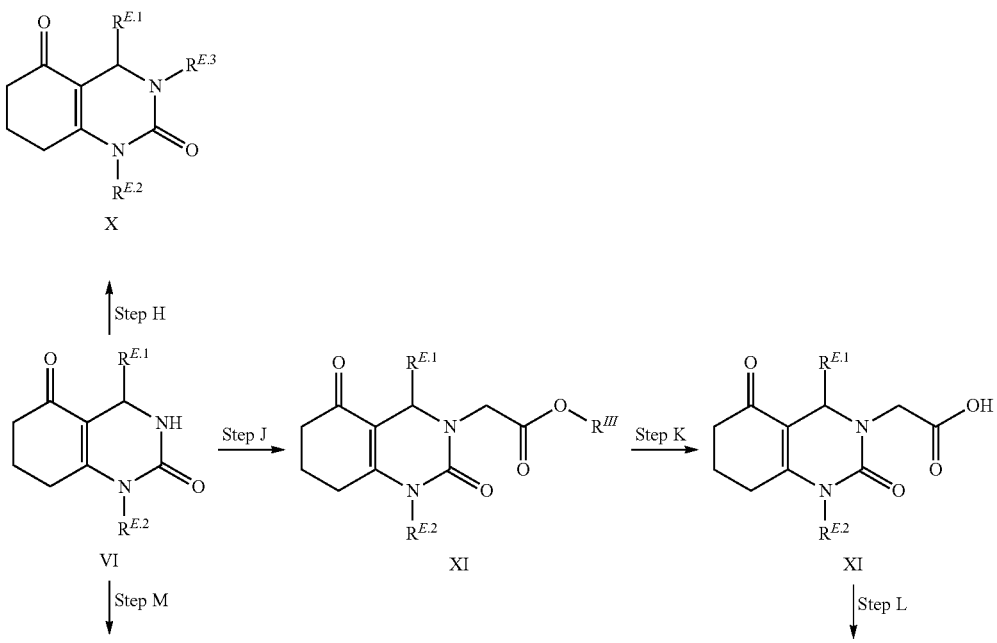

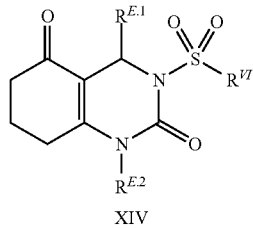

XIV

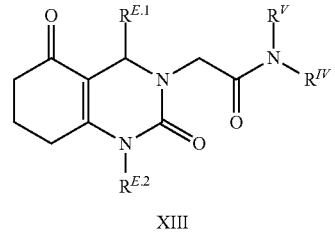

XIII

Compounds of the invention X (Step H, compounds of the invention VI→compounds of the invention X, $R^{E.3}$=alkyl or substituted alkyl) can be prepared as described in WO04024700 by reacting compounds of the invention VI with an alkylating agent, for example a dialkyl sulfate, for example dimethyl sulfate, an alkyl halide, for example methyl iodide or an alkyl sulfonylate, for example benzyl tosylate, in the presence of a suitable base, for example sodium hydride, sodium hydroxide, cesium carbonate, lithium diisopropylamide, potassium hexamethyldisilazide, lithium hexamethyldisilazide, an organolithium reagent, for example tert-butyllithium or a Grignard reagent, for example isopropylmagnesiumchloride, in an organic solvent, for example tetrahydrofuran, N,N-dimethylformamide, acetonitrile, 1,4-dioxane, dichloromethane or toluene. The reaction takes place within 1-72 hours. Preferred reaction temperatures are between 0° C. and 100° C.

Compounds of the invention XI (Step J, compounds of the invention VI→compounds of the invention XI) can be prepared in analogy to compounds of the invention X (Step H, compounds of the invention VI →compounds of the invention X), using an appropriate alkyl haloacetate as alkylating agent, for example methyl bromoacetate.

Compounds of the invention XII (Step K, compounds of the invention XI→compounds of the invention XII) can be prepared as described in WO04024700, by reacting compounds of the invention XI with water in the presence of a suitable base, for example sodium hydroxide, potassium hydroxide, caesium hydroxide, lithium hydroxide, sodium carbonate, potassium carbonate, sodium methoxide or sodium ethoxide in a suitable solvent, for example water, methanol, ethanol, propanol, N,N-dimethylformamide, tetrahydrofuran, 1,4-dioxane, acetonitrile or mixtures thereof. The reaction takes place within 1-72 hours. Preferred reaction temperatures are between 0° C. and 100° C.

The amide coupling (Step L, compounds of the invention XII→compounds of the invention XIII) can be achieved by reacting the carboxylic acid intermediate XII with amines $R^{IV}NH_2$ or $R^{IV}R'NH$ in the presence of an amide coupling reagent, for example N,N,N',N'-tetramethyl-O-(benzotriazol-1-yl)uronium tetrafluoroborate (TBTU) or N,N,N',N'-tetramethyl-O-(benzotriazol-1-yl)uronium hexafluorophosphate (HB TU), in the presence of a base, for example triethylamine, N,N-diisopropylethylamine or N-methylmorpholine in an organic solvent, for example N-methyl-2-pyrrolidone N,N-dimethyl-formamide, N,N-dimethylacetamide or mixtures thereof. The reaction takes place within 1-72 hours. Preferred reaction temperatures are between 0° C. and 50° C., most preferred room temperature.

Compounds of the invention XIV (Step M, compounds of the invention VI→compounds of the invention XIV, $R^{VI}$=alkyl or aryl) can be prepared as described in WO07137874, by reacting compounds of the invention VI with a sulfonylating agent, for example methanesulfonyl chloride or para-toluenesulfonyl chloride in the presence of a base, for example sodium hydride, lithium diisopropylamide, potassium hexamethyldisilazide, lithium hexamethyldisilazide, an organolithium reagent, for example tert-butyllithium or a Grignard reagent, for example iso-propylmagnesiumchloride, in an organic solvent, for example tetrahydrofuran, N,N-dimethylformamide, acetonitrile, 1,4-dioxane or dichloromethane. The reaction takes place within 1-72 hours. Preferred reaction temperatures are between 0° C. and room temperature.

Compounds according to the present invention XVI and XVII are accessible via the synthetic routes depicted in scheme 4; $R^{IV}$, $R^V$, $R^{VII}$, $R^{E.1}$, $R^{E.2}$ have the meanings as defined hereinbefore and hereinafter.

SCHEME 4

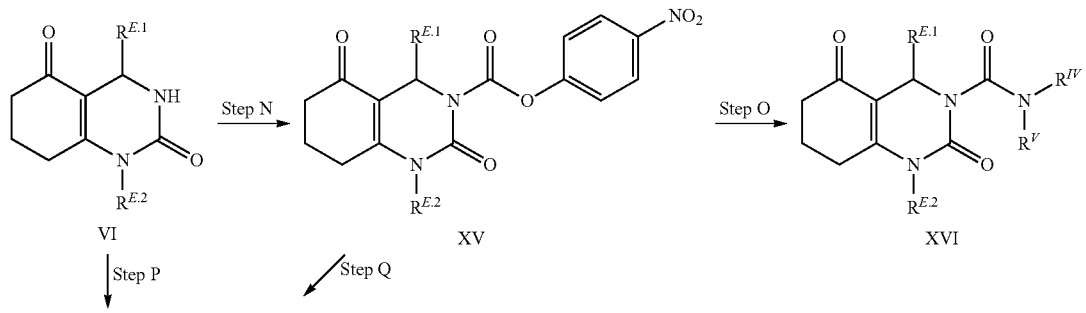

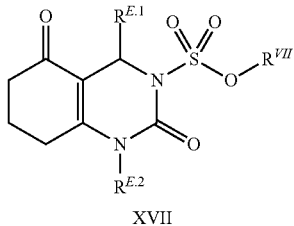

XVII

Intermediates XV (Step N, compounds of the invention VI→intermediates XV) can be prepared as described in WO09080199, by reacting compounds of the invention VI with 4-nitrophenyl chloroformate in the presence of a base, for example triethylamine, N,N-diisopropylethylamine or N-methylmorpholine, optionally in the presence of a catalyst, for example 4-dimethylaminopyridine, in an organic solvent, for example dichloromethane, tetrahydrofuran, acetonitrile or N,N-dimethylformamide. The reaction takes place within 1-24 hours. Preferred reaction temperatures are between 0° C. and 50° C., most preferred room temperature.

Compounds of the invention XVI (Step O, intermediates XV→compounds of the invention XVI) can be prepared as described in WO09080199, by reacting intermediates XV with an amine $R^{IV}NH_2$ or $R^{IV}R^VNH$ in an organic solvent, for example dichloromethane, acetonitrile, tetrahydrofuran, 1,4-dioxane, toluene or N,N-dimethylformamide. The reaction takes place within 1-72 hours. Preferred reaction temperatures are between 0° C. and 50° C., most preferred room temperature.

Compounds of the invention XVII (Step P, compounds of the invention VI→compounds of the invention XVII) can be prepared as described in WO07046513 or JP2000273087, by reacting compounds of the invention VI with a suitable chloroformate $ClCO_2R^{VII}$, for example methyl chloroformate or benzyl chloroformate, in the presence of a suitable base, for example potassium carbonate, sodium hydride, sodium hydroxide, lithium diisopropylamide, potassium hexamethyldisilazide, lithium hexamethyldisilazide, an organolithium reagent, for example tert-butyllithium or a Grignard reagent, for example iso-propylmagnesiumchloride, in an organic solvent, for example tetrahydrofuran, N,N-dimethyl-formamide, acetonitrile, 1,4-dioxane, dichloromethane or toluene. The reaction takes place within 1-72 hours. Preferred reaction temperatures are between 0° C. and 100° C.

Alternatively, compounds of the invention XVII (Step Q, intermediates XV→compounds of the invention XVII) can be prepared as described in WO03101917 or WO11085211, by reacting intermediates XV with a suitable alcohol, for example methanol, iso-propanol, 2-methoxyethanol, 2,2-dimethyl-1-propanol or benzyl alcohol, in the presence of a suitable base, for example potassium carbonate, potassium tert-butoxide or sodium hexamethyldisilazide in an organic solvent, for example tetrahydrofuran, N,N-dimethylformamide, acetonitrile, dichloromethane or dimethylsulfoxide. The reaction takes place within 1-72 hours. Preferred reaction temperatures are between 0° C. and 100° C., most preferred room temperature.

Additionally to the synthetic route depicted in Scheme 1, compounds of the invention VI are also accessible using the synthetic route depicted in Scheme 5. $R^{E.1}$, $R^{E.2}$ have the meanings as defined hereinbefore and hereinafter.

SCHEME 5

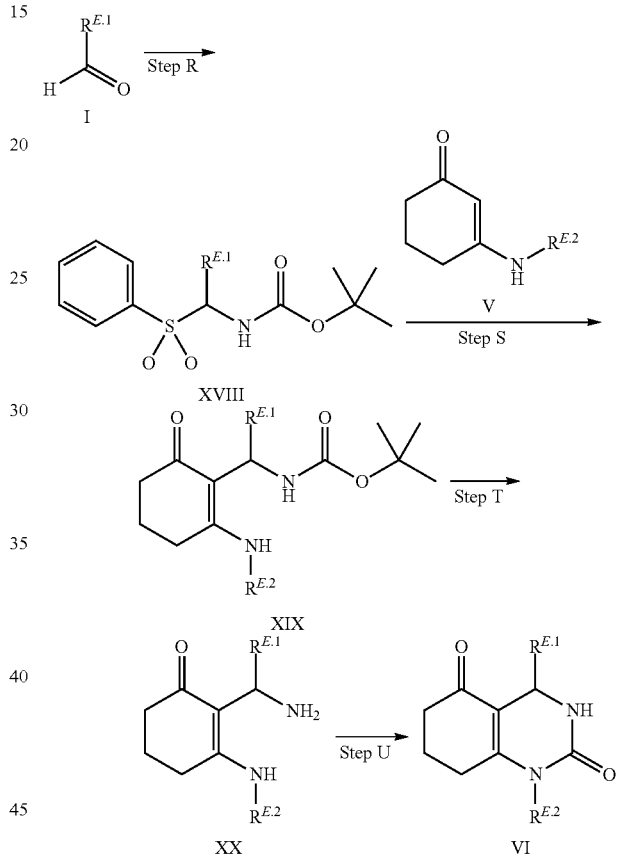

Intermediates XVIII (Step R, intermediate I→intermediate XVIII) can be prepared as described in Best et al. (*J. Am. Chem. Soc.* 2012, 134, 18193-18196) or in Yang et al. (*Org. Synth.* 2009, 86, 11-17), by reacting an aromatic aldehyde I with a suitable sulfinate, for example sodium benzenesulfinic acid, and a suitable carbamate, for example methyl carbamate or tert-butyl carbamate, in the presence of a suitable acid, for example formic acid, in a suitable solvent, for example tetrahydrofuran, ethanol, methanol or a mixture of solvents, for example tetrahydrofuran and water. Alternatively, as described in Reingruber et al. (*Adv. Synth. Catal.* 2009, 351, 1019-1024) or in WO06136305, a suitable lewis acid, for example trimethylsilyl chloride, can be used as acid and acetonitrile or toluene can be used as solvent. The reaction takes place within 1-6 days. Preferred reaction temperatures are between 0° C. and 50° C., most preferred room temperature.

Intermediates XIX (Step S, intermediate XVIII→intermediate XIX) can be prepared in analogy to the method described for the preparation of compounds of the invention VI (Scheme 1, Step D, intermediate III→compound of the invention VI), by reacting intermediates XVIII with intermediates V in the presence of a suitable base, for example sodium hydride or sodium tert-butoxide, in a suitable organic solvent, for example tetrahydrofuran or 2-methyltetrahydrofuran. The reaction takes place within 1-24 h. Preferred reaction temperatures are between 0° C. and 50° C., most preferred room temperature.

Intermediates XX (Step T, intermediate XIX→intermediate XX) can be prepared by reacting intermediates XIX with a suitable acid, for example hydrogen chloride, in a suitable solvent, for example 1,4-dioxane. The reaction takes place between 1-72 hours. Preferred reaction temperatures are between 0° C. and room temperature, most preferred room temperature.

Compounds of the invention VI (Step U, intermediate XX→compound of the invention VI) can be prepared as described in Csütörtöki et al. (*Tetrahedron Lett.* 2011, 67, 8564-8571) or in WO11042145, by reacting intermediates XX with a suitable reagent, for example phosgene, triphosgene or carbonyl diimidazole, in the presence of a suitable base, for example triethylamine, N,N-diisopropylethylamine, pyridine or sodium carbonate, in a suitable solvent, for example acetonitrile, dichloromethane or toluene. The reaction takes place between 1-72 hours. Preferred reaction temperatures are between 0° C. and 50° C., most preferred room temperature.

Additionally to the synthetic route depicted in Scheme 2, compounds of the invention VI are also accessible using the synthetic route depicted in Scheme 6, $R^{E.1}$, $R^{E.2}$ have the meanings as defined hereinbefore and hereinafter.

SCHEME 6

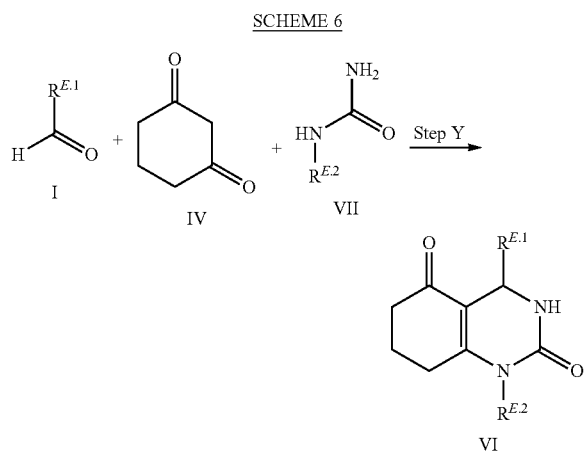

Compounds of the invention VI (Step Y, starting materials I, IV and VII→compounds of the invention VI) can be prepared following a procedure described in WO09080199 and WO05082864, by reacting an aldehyde I, a suitable 1,3-dione IV and an unsubstituted or monosubstituted urea VII with a reagent prepared by reacting a mixture of phosphorus pentoxide and a suitable trialkyl phosphate, for example triethyl phosphate at 50° C. over night, in a suitable solvent, for example tert-butyl methyl ether. The reaction takes place within 1-72 h. Preferred reaction temperatures are between room temperature and the boiling point of the employed solvent.

Preliminary Remarks

The term room temperature denotes a temperature of about 20° C. As a rule, $^1$H NMR spectra and/or mass spectra have been obtained of the compounds prepared. Compounds given with a specific configuration at a stereocenter are isolated as pure isomers.

The retention times given are measured under the following conditions (TFA: trifluoroacetic acid, DEA: diethylamine, $scCO_2$: supercritical carbon dioxide):

| Method Name: V001_006 | | | | |
|---|---|---|---|---|
| Column: XBridge C18, 4.6 × 30 mm, 3.5 μm | | | | |
| Column Supplier: Waters | | | | |
| Gradient/Solvent Time [min] | % Solvent [$H_2O$, 0.1% TFA] | % Solvent [acetonitrile] | Flow [ml/min] | Temp [° C.] |
| 0.0 | 95 | 5 | 4.8 | 60 |
| 1.6 | 0 | 100 | 4.8 | 60 |
| 1.85 | 0 | 100 | 4.8 | 60 |
| 1.9 | 95 | 5 | 4.8 | 60 |

| Method Name: V011_S01 | | | | |
|---|---|---|---|---|
| Column: XBridge C18, 4.6 × 30 mm, 3.5 μm | | | | |
| Column Supplier: Waters | | | | |
| Gradient/Solvent Time [min] | % Solvent [$H_2O$, 0.1% $NH_3$] | % Solvent [acetonitrile] | Flow [ml/min] | Temp [° C.] |
| 0.0 | 97 | 3 | 5 | 60 |
| 0.2 | 97 | 3 | 5 | 60 |
| 1.6 | 0 | 100 | 5 | 60 |
| 1.7 | 0 | 100 | 5 | 60 |

| Method Name: V012_S01 | | | | |
|---|---|---|---|---|
| Column: XBridge C18, 4.6 × 30 mm, 3.5 μm | | | | |
| Column Supplier: Waters | | | | |
| Gradient/Solvent Time [min] | % Solvent [$H_2O$, 0.1% TFA] | % Solvent [acetonitrile] | Flow [ml/min] | Temp [° C.] |
| 0.0 | 97 | 3 | 5 | 60 |
| 0.2 | 97 | 3 | 5 | 60 |
| 1.6 | 0 | 100 | 5 | 60 |
| 1.7 | 0 | 100 | 5 | 60 |

| Method Name: W018_S01 | | | | |
|---|---|---|---|---|
| Column: Sunfire C18, 4.6 × 30 mm, 2.5 μm | | | | |
| Column Supplier: Waters | | | | |
| Gradient/Solvent Time [min] | % Solvent [$H_2O$, 0.1% TFA] | % Solvent [acetonitrile] | Flow [ml/min] | Temperature [° C.] |
| 0.0 | 97 | 3 | 4 | 60 |
| 0.15 | 97 | 3 | 3 | 60 |
| 2.15 | 0 | 100 | 3 | 60 |
| 2.20 | 0 | 100 | 4.5 | 60 |
| 2.40 | 0 | 100 | 4.5 | 60 |

Method Name: X012_S01  
Column: Xbridge BEH C18, 2.1 × 30 mm, 1.7 μm  
Column Supplier: Waters

| Gradient/Solvent Time [min] | % Solvent [H$_2$O, 0.1% TFA] | % Solvent [acetonitrile] | Flow [ml/min] | Temperature [° C.] |
|---|---|---|---|---|
| 0.0 | 99 | 1 | 1.6 | 60 |
| 0.02 | 99 | 1 | 1.6 | 60 |
| 1.00 | 0 | 100 | 1.6 | 60 |
| 1.10 | 0 | 100 | 1.6 | 60 |

Method Name: X018_S01  
Column: Sunfire C18, 2.1 × 30 mm, 2.5 μm  
Column Supplier: Waters

| Gradient/Solvent Time [min] | % Solvent [H$_2$O, 0.1% TFA] | % Solvent [acetonitrile] | Flow [ml/min] | Temperature [° C.] |
|---|---|---|---|---|
| 0.0 | 99 | 1 | 1.5 | 60 |
| 0.02 | 99 | 1 | 1.5 | 60 |
| 1.00 | 0 | 100 | 1.5 | 60 |
| 1.10 | 0 | 100 | 1.5 | 60 |

Method Name: Z002_002  
Column: Sunfire C18, 3 × 30 mm, 2.5 μm  
Column Supplier: Waters

| Gradient/Solvent Time [min] | % Solvent [H$_2$O, 0.1% TFA] | % Solvent [methanol] | Flow [ml/min] | Temperature [° C.] |
|---|---|---|---|---|
| 0.0 | 50 | 50 | 2.2 | 60 |
| 0.05 | 50 | 50 | 2.2 | 60 |
| 1.40 | 0 | 100 | 2.2 | 60 |
| 1.80 | 0 | 100 | 2.2 | 60 |

Method Name: Z003_001  
Column: XBridge C18, 3 × 30 mm, 2.5 μm  
Column Supplier: Waters

| Gradient/Solvent Time [min] | % Solvent [H$_2$O, 0.1% NH$_3$] | % Solvent [methanol] | Flow [ml/min] | Temperature [° C.] |
|---|---|---|---|---|
| 0.0 | 95 | 5 | 2.2 | 60 |
| 0.05 | 95 | 5 | 2.2 | 60 |
| 1.40 | 0 | 100 | 2.2 | 60 |
| 1.80 | 0 | 100 | 2.2 | 60 |

Method Name: Z003_004  
Column: XBridge C18, 3 × 30 mm, 2.5 μm  
Column Supplier: Waters

| Gradient/Solvent Time [min] | % Solvent [H$_2$O, 0.1% NH$_3$] | % Solvent [methanol] | Flow [ml/min] | Temperature [° C.] |
|---|---|---|---|---|
| 0.0 | 95 | 5 | 1.9 | 60 |
| 0.20 | 95 | 5 | 1.9 | 60 |
| 1.55 | 0 | 100 | 1.9 | 60 |
| 1.60 | 0 | 100 | 2.4 | 60 |
| 1.80 | 0 | 100 | 2.4 | 60 |

Method Name: Z005_001  
Column: Stablebond C18, 3 × 30 mm, 1.8 μm  
Column Supplier: Waters

| Gradient/Solvent Time [min] | % Solvent [H$_2$O, 0.1% TFA] | % Solvent [methanol] | Flow [ml/min] | Temperature [° C.] |
|---|---|---|---|---|
| 0.0 | 95 | 5 | 2.2 | 60 |
| 0.05 | 95 | 5 | 2.2 | 60 |
| 1.40 | 0 | 100 | 2.2 | 60 |
| 1.80 | 0 | 100 | 2.2 | 60 |

Method Name: Z011_S03  
Column: XBridge C18, 3 × 30 mm, 2.5 μm  
Column Supplier: Waters

| Gradient/Solvent Time [min] | % Solvent [H$_2$O, 0.1% NH$_3$] | % Solvent [acetonitrile] | Flow [ml/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

Method Name: Z012_S04  
Column: XBridge C18, 3 × 30 mm, 2.5 μm  
Column Supplier: Waters

| Gradient/Solvent Time [min] | % Solvent [H$_2$O, 0.1% TFA] | % Solvent [acetonitrile] | Flow [ml/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

Method Name: Z017_S04  
Column: Stablebond C18, 3 × 30 mm, 1.8 μm  
Column Supplier: Waters

| Gradient/Solvent Time [min] | % Solvent [H$_2$O, 0.1% TFA] | % Solvent [acetonitrile] | Flow [ml/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

Method Name: Z018_S04  
Column: Sunfire C18, 3 × 30 mm, 2.5 μm  
Column Supplier: Waters

| Gradient/Solvent Time [min] | % Solvent [H$_2$O, 0.1% TFA] | % Solvent [acetonitrile] | Flow [ml/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |

Method Name: Z018_S04
Column: Sunfire C18, 3 × 30 mm, 2.5 µm
Column Supplier: Waters

| Gradient/Solvent Time [min] | % Solvent [H$_2$O, 0.1% TFA] | % Solvent [acetonitrile] | Flow [ml/min] | Temperature [° C.] |
|---|---|---|---|---|
| 1.25 | 0 | 100 | 3 | 60 |
| 1.40 | 0 | 100 | 3 | 60 |

Method Name: 001_CA03
Column: Sunfire C18, 4.6 × 30 mm, 3.5 µm
Column Supplier: Waters

| Gradient/Solvent Time [min] | % Solvent [H$_2$O, 0.1% TFA] | % Solvent [acetonitrile] | Flow [ml/min] | Temperature [° C.] |
|---|---|---|---|---|
| 0.0 | 98 | 2 | 2.5 | 60.0 |
| 1.5 | 0 | 100 | 2.5 | 60.0 |
| 1.8 | 0 | 100 | 2.5 | 60.0 |

Method Name: 001_CA04
Column: XBridge C18, 4.6 × 30 mm, 3.5 µm
Column Supplier: Waters

| Gradient/Solvent Time [min] | % Solvent [H$_2$O, 0.1% NH$_3$] | % Solvent [acetonitrile] | Flow [ml/min] | Temperature [° C.] |
|---|---|---|---|---|
| 0.0 | 80.0 | 20.0 | 2.0 | 60.0 |
| 1.7 | 0.0 | 100.0 | 2.0 | 60.0 |
| 2.5 | 0.0 | 100.0 | 2.0 | 60.0 |

Method Name: 004_CA01
Column: Sunfire C18, 4.6 × 30 mm, 3.5 µm
Column Supplier: Waters

| Gradient/Solvent Time [min] | % Solvent [H$_2$O, 0.1% TFA] | % Solvent [acetonitrile] | Flow [ml/min] | Temperature [° C.] |
|---|---|---|---|---|
| 0.0 | 98.0 | 2.0 | 2.5 | 60.0 |
| 1.5 | 0.0 | 100.0 | 2.5 | 60.0 |
| 1.8 | 0.0 | 100.0 | 2.5 | 60.0 |

Method Name: 004_CA05
Column: XBridge C18, 3.0 × 30 mm, 2.5 µm
Column Supplier: Waters

| Gradient/Solvent Time [min] | % Solvent [H$_2$O, 0.1% NH$_3$] | % Solvent [acetonitrile] | Flow [ml/min] | Temperature [° C.] |
|---|---|---|---|---|
| 0.0 | 98.0 | 2.0 | 2.0 | 60.0 |
| 1.2 | 0.0 | 100.0 | 2.0 | 60.0 |
| 1.4 | 0.0 | 100.0 | 2.0 | 60.0 |

Method Name: I_ADH_20_MeOH_DEA
Column: Chiralpak ADH 4.6 × 250 mm, 5 µm
Column Supplier: Daicel

| Gradient/Solvent Time [min] | % Solvent [MeOH, 0.2% DEA] | % Solvent [scCO$_2$] | Flow [ml/min] | Temperature [° C.] | Back Pressure [bar] |
|---|---|---|---|---|---|
| 10 min | 20 | 80 | 4 | 40 | 100 |

Method Name: I_ASH_20_IPROP_DEA
Column: Chiralpak ASH 4.6 × 250 mm, 5 µm
Column Supplier: Daicel

| Gradient/Solvent Time [min] | % Solvent [iso-PrOH, 0.2% DEA] | % Solvent [scCO$_2$] | Flow [ml/min] | Temperature [° C.] | Back Pressure [bar] |
|---|---|---|---|---|---|
| 10 min | 20 | 80 | 4 | 40 | 100 |

Method Name: I_IA_25_IPROP_DEA
Column: Chiralpak IA 4.6 × 250 mm, 5 µm
Column Supplier: Daicel

| Gradient/Solvent Time [min] | % Solvent [iso-PrOH, 0.2% DEA] | % Solvent [scCO$_2$] | Flow [ml/min] | Temperature [° C.] | Back Pressure [bar] |
|---|---|---|---|---|---|
| 10 min | 25 | 75 | 4 | 40 | 150 |

Method Name: I_IB_20_MeOH_DEA
Column: Chiralpak IB 4.6 × 250 mm, 5 µm
Column Supplier: Daicel

| Gradient/Solvent Time [min] | % Solvent [MeOH, 0.2% DEA] | % Solvent [scCO$_2$] | Flow [ml/min] | Temperature [° C.] | Back Pressure [bar] |
|---|---|---|---|---|---|
| 10 min | 20 | 80 | 4 | 40 | 150 |

Method Name: I_IB_30_MeOH_DEA
Column: Chiralpak IB 4.6 × 250 mm, 5 µm
Column Supplier: Daicel

| Gradient/Solvent Time [min] | % Solvent [MeOH, 0.2% DEA] | % Solvent [scCO$_2$] | Flow [ml/min] | Temperature [° C.] | Back Pressure [bar] |
|---|---|---|---|---|---|
| 10 min | 30 | 70 | 4 | 40 | 150 |

Method Name: I_IB_20_IPROP_DEA
Column: Chiralpak IB 4.6 × 250 mm, 5 µm
Column Supplier: Daicel

| Gradient/Solvent Time [min] | % Solvent [iso-PrOH, 0.2% DEA] | % Solvent [scCO$_2$] | Flow [ml/min] | Temperature [° C.] | Back Pressure [bar] |
|---|---|---|---|---|---|
| 10 min | 20 | 80 | 4 | 40 | 150 |

Method Name: I_IC_20_MeOH_DEA
Column: Chiralpak IC 4.6 × 250 mm, 5 μm
Column Supplier: Daicel

| Gradient/ Solvent Time [min] | % Solvent [MeOH, 0.2% DEA] | % Solvent [scCO$_2$] | Flow [ml/min] | Temperature [° C.] | Back Pressure [bar] |
|---|---|---|---|---|---|
| 10 min | 20 | 80 | 4 | 40 | 100 |

Method Name: I_IC_25_IPROP_DEA
Column: Chiralpak IC 4.6 × 250 mm, 5 μm
Column Supplier: Daicel

| Gradient/ Solvent Time [min] | % Solvent [iso-PrOH, 0.2% DEA] | % Solvent [scCO$_2$] | Flow [ml/min] | Temperature [° C.] | Back Pressure [bar] |
|---|---|---|---|---|---|
| 10 min | 25 | 75 | 4 | 40 | 100 |

Method Name: 001_CA07
Column: SunFire C18, 2.1 × 50 mm, 2.5 μm
Column Supplier: Waters

| Gradient/ Solvent Time [min] | % Solvent [H$_2$O, 0.1% TFA] | % Solvent [acetonitrile] | Flow [ml/min] | Temperature [° C.] |
|---|---|---|---|---|
| 0.0 | 95 | 5 | 1.5 | 60.0 |
| 0.75 | 0 | 100 | 1.5 | 60.0 |
| 0.85 | 0 | 100 | 1.5 | 60.0 |

Method Name: 002_CA03
Column: SunFire C18, 3.0 × 30 mm, 2.5 μm
Column Supplier: Waters

| Gradient/ Solvent Time [min] | % Solvent [H$_2$O, 0.1% TFA] | % Solvent [acetonitrile] | Flow [ml/min] | Temperature [° C.] |
|---|---|---|---|---|
| 0.0 | 99 | 1 | 2.0 | 60.0 |
| 0.90 | 0 | 100 | 2.0 | 60.0 |
| 1.1 | 0 | 100 | 2.0 | 60.0 |

Method Name: 005_CA01
Column: SunFire C18, 3.0 × 30 mm, 2.5 μm
Column Supplier: Waters

| Gradient/ Solvent Time [min] | % Solvent [H$_2$O, 0.1% TFA] | % Solvent [acetonitrile] | Flow [ml/min] | Temperature [° C.] |
|---|---|---|---|---|
| 0.0 | 98 | 2 | 2.0 | 60.0 |
| 1.2 | 0 | 100 | 2.0 | 60.0 |
| 1.4 | 0 | 100 | 2.0 | 60.0 |

Method Name: X012_S01
Column: Xbridge BEH C18, 2.1 × 30 mm, 1.7 μm
Column Supplier: Waters

| Gradient/ Solvent Time [min] | % Solvent [H$_2$O, 0.1% TFA] | % Solvent [acetonitrile] | Flow [ml/min] | Temperature [° C.] |
|---|---|---|---|---|
| 0.0 | 99 | 1 | 1.3 | 60 |
| 0.02 | 99 | 1 | 1.3 | 60 |
| 1.00 | 0 | 100 | 1.3 | 60 |
| 1.10 | 0 | 100 | 1.3 | 60 |

Assignment of Absolute Configurations

The absolute configuration of example 18A has been assigned unambiguously by X-ray structure analysis to be (S). This (S)-enantiomer (example 18A) is significantly more potent with respect to the inhibition of neutrophil elastase than the (R)-enantiomer (example 18B), as can be seen from the measured IC$_{50}$ values of 4.8 nM (example 18A) and 2509 nM (example 18B), respectively. The absolute configuration of all other pure enantiomers described has been assigned in analogy to example 18A, that is, the more potent enantiomer (the eutomer) with respect to the inhibition of neutrophil elastase, i.e. the enantiomer with the lower IC$_{50}$ value has been assigned to have the same absolute configuration as example 18A. Obviously, in this context the term "absolute configuration" does not refer to the stereodescriptors (R) or (S) as they depend on the individual substitution pattern, but to the three-dimensional orientation of the substituents that are attached to the sterocenter.

SYNTHESES OF STARTING MATERIALS

Unless stated otherwise, all starting materials are commercially available and are used as they are obtained from the supplier.

The following starting materials were prepared as described in the literature cited: 3-(3-(Trifluoromethyl)phenylamino)cyclohex-2-enone: *Aust. J. Chem.* 2005, 58, 870-876, 1-Bromo-4-(chloro(isocyanato)methyl)benzene: *Synlett* 2006, 3, 375-378.

The synthesis of the following starting materials has been described before in the literature cited:

5,5-Dimethyl-3-(3-(trifluoromethyl)phenylamino)cyclohex-2-enone: *Org. Lett.* 2000, 2, 1109-1112; 1-(4-fluoro-3-(trifluoromethyl)phenyl)urea: WO09135599; 1-(3-fluoro-5-(trifluoromethyl)phenyl)urea: WO09135599.

SYNTHESES OF INTERMEDIATES

Intermediate 1

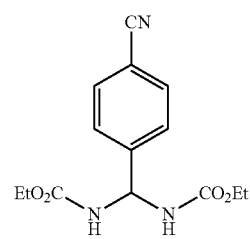

Diethyl (4-Cyanophenyl)methylenedicarbamate

In a three-necked round bottom flask equipped with a drying tube filled with calcium chloride and an inlet for nitrogen, 4-formylbenzonitrile (25.0 g, 191 mmol) and ethyl carbamate (37.4 g, 419 mmol) are heated at 145° C. The flask is being purged with a flow of nitrogen, and concentrated sulfuric acid (ca. 200 μL, ca. 3 mmol) is added slowly drop by drop. After 7 h the solidified reaction mixture is cooled to room temperature, crushed, mixed thoroughly with water and dried. Yield: 53.0 g; ESI mass spectrum: [M+H]$^+$=314; Retention time HPLC: 0.88 min (V011_S01).

Intermediate 2

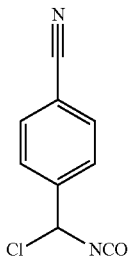

4-(Chloro(isocyanato)methyl)benzonitrile

Phosphorous pentachloride (83.3 g, 400 mmol) is added to a suspension of diethyl (4-cyanophenyl)methylenedicarbamate (intermediate 1, 53.0 g, 182 mmol) in benzene (200 mL) and the mixture is heated at reflux for 2 h. The benzene is evaporated and the mixture is then purified by distillation under reduced pressure. The first fraction (ca. 40° C., ca. 0.01 mbar) is discarded. The second fraction (ca. 110° C., ca. 0.6 mbar) is collected. Yield: 28.4 g; ESI mass spectrum: [M+MeOH—HCl+1-1]$^+$=189; Retention time HPLC: it) 0.65 min (Z003_004).

Intermediate 3

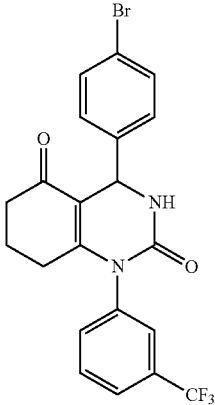 [SMILES: O=C1CCCC2=C1C(c1ccc(Br)cc1)NC(=O)N2c1cccc(C(F)(F)F)c1]

4-(4-Bromophenyl)-1-(3-(trifluoromethyl)phenyl)-3,4,7,8-tetrahydroquinazoline-2,5(1H,6H)-dione A solution of 1-bromo-4-(chloro(isocyanato)methyl)benzene (4.25 g, 17.24 mmol) in dichloromethane (30 mL) is added to a solution of 3-(3-(trifluoromethyl)phenylamino)-cyclohex-2-enone (4.00 g, 15.67 mmol) in dichloromethane (60 mL) and the resulting mixture is heated at reflux for 3 h and stirred at room temperature over night. All volatiles are evaporated and the residue is purified by flash chromatography on silica (gradient dichloromethane/methanol 100:0 to 98:2). Yield: 5.10 g; ESI mass spectrum: [($^{79}$Br)-M+H]$^+$=465, [($^{81}$Br)-M+H]$^+$=467; Retention time HPLC: 1.44 min (V001_006).

Intermediate 4

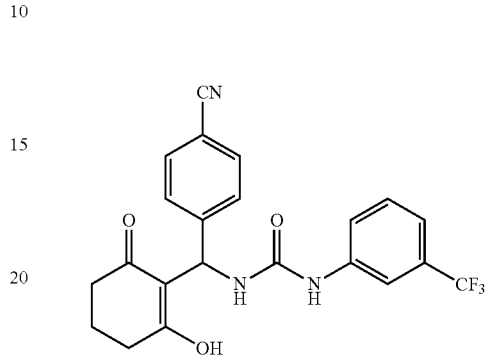

1-((4-Cyanophenyl)(2-hydroxy-6-oxocyclohex-1-enyl)methyl)-3-(3-(trifluoromethyl)-phenyl)urea Trimethylsilyl chloride (50.7 mL, 400 mmol) is added to a solution of cyclohexane-1,3-dione (11.2 g, 100 mmol), 4-formylbenzonitrile (13.8 g, 105 mmol) and 1-(3-(trifluoromethyl)phenyl)urea (20.4 g, 100 mmol) in a mixture of N,N-dimethylformamide (100 mL) and acetonitrile (150 mL), and the mixture is stirred at room temperature over night. The reaction mixture is poured into a mixture of water and ice (2 L) and stirred for 2 h. The mixture is filtered and the precipitate is dried under reduced pressure. Yield: 41.9 g; ESI mass spectrum [M+H]$^+$=430, Retention time HPLC: 0.91 min (Z018_S04).

Intermediate 5

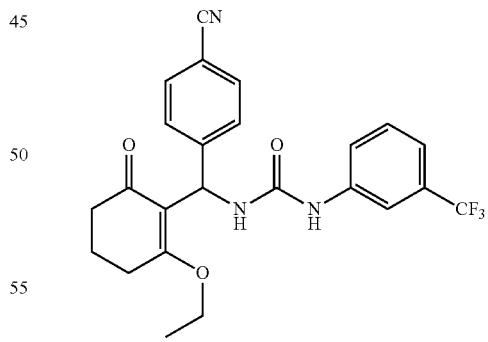

1-((4-Cyanophenyl)(2-ethoxy-6-oxocyclohex-1-enyl)methyl)-3-(3-(trifluoromethyl)-phenyl)urea N,N-Diisopropylethylamine (9.41 mL, 54.0 mmol) is added to a suspension of 14(4-cyanophenyl)(2-hydroxy-6-oxocyclohex-1-enyl)methyl)-3-(3-(trifluoromethyl)phenyl)urea (intermediate 4, 10.00 g, 23.29 mmol) in dichloromethane (200 mL). Triethyloxonium tetrafluoroborate (8.85 g, 46.6 mmol) is added and the mixture is stirred at room temperature for 20 min. The mixture is washed three times with water and then concentrated under reduced pressure. Yield: 10.08 g; ESI mass spectrum [M+H]$^+$=458, Retention time HPLC: 0.98 min (Z018_S04).

Intermediate 6

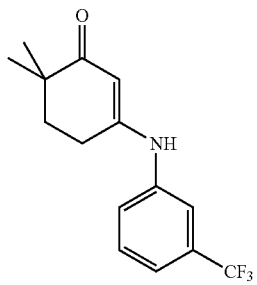 [SMILES: CC1(C)CCC(Nc2cccc(C(F)(F)F)c2)=CC1=O]

6,6-Dimethyl-3-(3-(trifluoromethyl)phenylamino)cyclohex-2-enone

A mixture of 4,4-dimethylcyclohexane-1,3-dione (563 mg, 4.02 mmol), 3-(trifluoromethyl)aniline (500 µL, 645 mg, 4.02 mmol), Ytterbium(III) trifluormethanesulfonate (12.5 mg, 20 µmol, 0.5 mol %) and N,N-dimethylformamide (2.5 mL) is stirred at room temperature over night. Methanol and water are added and the mixture is filtered. The precipitate is washed with water and dried under reduced pressure. Yield: 654 mg; ESI mass spectrum [M+H]$^+$=284, Retention time HPLC: 1.18 min (Z005_001).

Intermediate 7

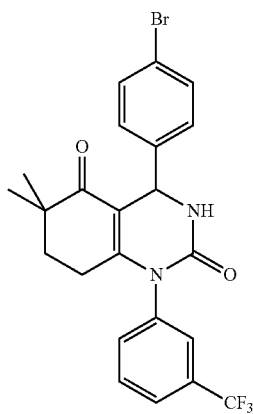 [SMILES: CC1(C)CCC2=C(C1=O)C(c1ccc(Br)cc1)NC(=O)N2c1cccc(C(F)(F)F)c1]

4-(4-Bromophenyl)-6,6-dimethyl-1-(3-(trifluoromethyl)phenyl)-3,4,7,8-tetrahydroquinazoline-2,5(1H,6H)-dione A solution of 1-bromo-4-(chloro(isocyanato)methyl)benzene (569 mg, 2.31 mmol) in dichloromethane (5 mL) is added to a solution of 6,6-dimethyl-3-(3-(trifluoromethyl)phenylamino)cyclohex-2-enone (intermediate 6, 654 mg, 2.31 mmol) in dichloromethane (15 mL), and the resulting mixture is heated at reflux for 4 h and stirred at room temperature over night. Another portion of 1-bromo-4-(chloro(isocyanato)methyl)benzene (283 mg, 1.15 mmol) is added and the mixture is heated at reflux for 24 h. The mixture is cooled to room temperature and all volatiles are evaporated. The residue is purified by flash chromatography on silica (gradient cyclohexane/ethyl acetate 90:10 to 60:40). Yield: 372 mg; ESI mass spectrum: [($^{79}$Br)-M+H]$^+$=493, [($^{81}$Br)-M+H]$^+$=495; Retention time HPLC: 1.37 min (Z005_001).

Intermediate 8

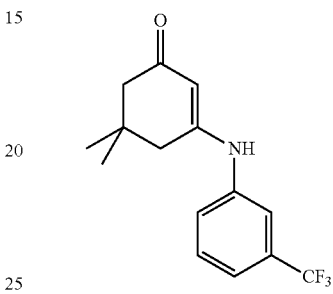

5,5-Dimethyl-3-(3-(trifluoromethyl)phenylamino)cyclohex-2-enone

The title compound is prepared in analogy to 6,6-dimethyl-3-(3-(trifluoromethyl)phenyl-amino)cyclohex-2-enone (intermediate 6), using 5,5-dimethylcyclohexane-1,3-dione (1.13 g, 8.04 mmol) as starting material. Yield: 1.73 g, ESI mass spectrum [M+H]$^+$=284, Retention time HPLC: 1.18 min (Z005_001).

Intermediate 9

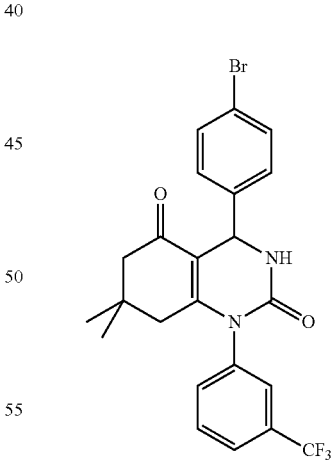

4-(4-Bromophenyl)-7,7-dimethyl-1-(3-(trifluoromethyl)phenyl)-3,4,7,8-tetrahydroquinazoline-2,5(1H,6H)-dione A solution of 1-bromo-4-(chloro(isocyanato)methyl)benzene (435 mg, 1.77 mmol) in dichloromethane (5 mL) is added to a solution of 5,5-dimethyl-3-(3-(trifluoromethyl)phenylamino)cyclohex-2-enone (intermediate 8, 500 mg, 1.77 mmol) in dichloromethane (15 mL) and the mixture is heated at reflux over night. All volatiles are evaporated and the residue is purified by flash chromatography on silica (gradient cyclohexane/ethyl acetate 90:10 to 60:40). Yield: 389 mg; ESI mass spectrum: [($^{79}$Br)-M+H]$^+$=493, [($^{81}$Br)-M+H]$^+$=495; Retention time HPLC: 1.38 min (Z002_002).

Intermediate 10

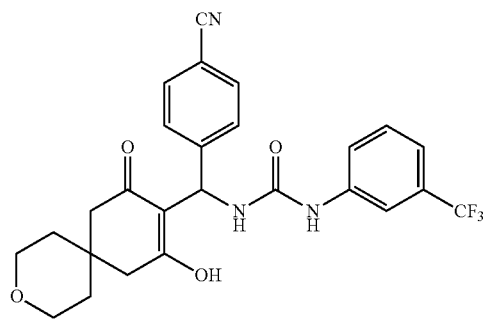 [SMILES: N#Cc1ccc(C(NC(=O)Nc2cccc(C(F)(F)F)c2)C2=C(O)CC3(CCOCC3)CC2=O)cc1]

1-((4-cyanophenyl)(8-hydroxy-10-oxo-3-oxaspiro [5.5]undec-8-en-9-yl)methyl)-3-(3-(trifluoromethyl) phenyl)urea Trimethylsilyl chloride (275 µL, 2.17 mmol) is added to a solution of 3-oxaspiro[5.5]un-decane-8,10-dione (360 mg, 1.98 mmol), 4-formylbenzonitrile (259 mg, 1.98 mmol) and 1-(3-(trifluoromethyl)phenyl)urea (403 mg, 1.98 mmol) in a mixture of N,N-dimethyl-formamide (1.5 mL) and acetonitrile (2.5 mL), and the mixture is heated at 50° C. for 1 h. The reaction mixture is cooled to room temperature and poured into a mixture of water and ice. The precipitate is filtered and dried under reduced pressure. Yield: 712 mg; ESI mass spectrum [M+H]$^+$=500, Retention time HPLC: 1.12 min (V012_S01).

Intermediate 11

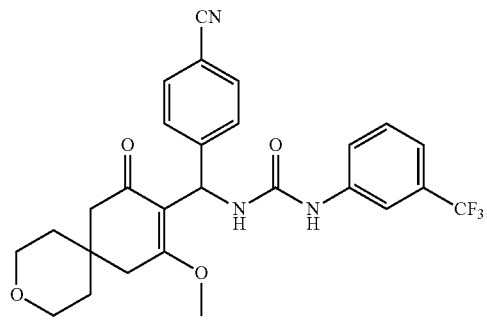 [SMILES: COC1=C(C(NC(=O)Nc2cccc(C(F)(F)F)c2)c2ccc(C#N)cc2)C(=O)CC2(CCOCC2)C1]

1-((4-Cyanophenyl)(8-methoxy-10-oxo-3-oxaspiro [5.5]undec-8-en-9-yl)methyl)-3-(3-(trifluoromethyl) phenyl)urea Trimethyloxonium tetrafluoroborate (320 mg, 2.16 mmol) is added to a solution of 1-((4-cyanophenyl)(8-hydroxy-10-oxo-3-oxaspiro[5.5]undec-8-en-9-yl)methyl)-3-(3-(trifluoromethyl)phenyl)urea (intermediate 10, 712 mg, 1.43 mmol) and N,N-diisopropylethylamine (490 µL, 2.81 mmol) in dichloromethane (20 mL). The mixture is stirred at room temperature for 30 min and washed with water. The organic layer is concentrated under reduced pressure, and the residue is purified by reversed phase HPLC (Waters Xbridge™-C$_{18}$, gradient of acetonitrile in water, 0.1% TFA). Yield: 380 mg; ESI mass spectrum [M+H]$^+$=514, Retention time HPLC: 1.18 min (V012_S01).

Intermediate 12

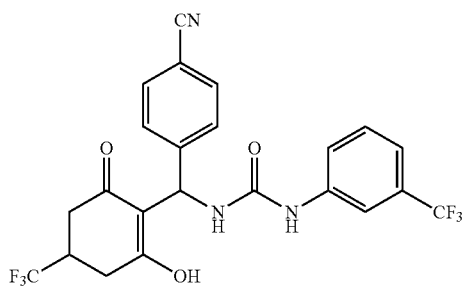 [SMILES: N#Cc1ccc(C(NC(=O)Nc2cccc(C(F)(F)F)c2)C2=C(O)CC(C(F)(F)F)CC2=O)cc1]

1-((4-Cyanophenyl)(2-hydroxy-6-oxo-4-(trifluoromethyl)cyclohex-1-enyl)methyl)-3-(3-(trifluoromethyl) phenyl)urea Trimethylsilyl chloride (775 µL, 6.11 mmol) is added to a solution of 5-(trifluoromethyl)-cyclohexane-1,3-dione (1.00 g, 5.55 mmol), 4-formylbenzonitrile (728 mg, 5.55 mmol) and 1-(3-(trifluoromethyl)phenyl)urea (1.13 g, 5.55 mmol) in a mixture of N,N-dimethylform-amide (4.3 mL) and acetonitrile (8.3 mL), and the mixture is stirred at room temperature for 1 h. The reaction mixture is cooled to room temperature and poured into a mixture of water and ice. The precipitate is filtered and dried under reduced pressure. Yield: 2.38 g; ESI mass spectrum [M+H]$^+$=498, Retention time HPLC: 0.75 min (V011_S01).

Intermediate 13

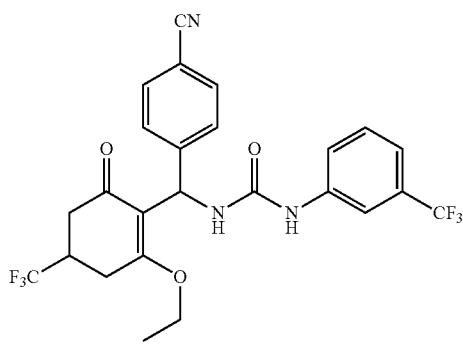 [SMILES: CCOC1=C(C(NC(=O)Nc2cccc(C(F)(F)F)c2)c2ccc(C#N)cc2)C(=O)CC(C(F)(F)F)C1]

1-((4-Cyanophenyl)(2-ethoxy-6-oxo-4-(trifluoromethyl)cyclohex-1-enyl)methyl)-3-(3-(trifluoromethyl) phenyl)urea Triethyloxonium tetrafluoroborate (1.82 g, 9.57 mmol) is added to a mixture of N,N-diisopropylethylamine (1.92 mL, 11.0 mmol) and 1-((4-cyanophenyl)(2-hydroxy-6-oxo-4-(trifluoromethyl)cyclohex-1-enyl)methyl)-3-(3-(trifluoromethyl)phenyl)urea (intermediate 12, 2.38 g, 4.79 mmol) in dichloromethane (30 mL). The mixture is stirred at room temperature for 1 h and washed three times with water. The organic layer is dried over Na$_2$SO$_4$ and concentrated under reduced pressure. Yield: 1.66 g; ESI mass spectrum [M+H]$^+$=525, Retention time HPLC: 1.25 min (V011_S01).

Intermediate 14

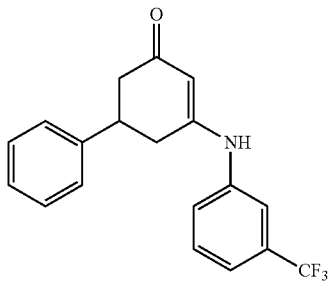 [SMILES: O=C1C=C(Nc2cccc(C(F)(F)F)c2)CC(c2ccccc2)C1]

5-Phenyl-3-(3-(trifluoromethyl)phenylamino)cyclohex-2-enone

A mixture of 5-phenylcyclohexane-1,3-dione (1.51 g, 8.04 mmol), 3-(trifluoromethyl)-aniline (1.00 mL, 1.29 g, 8.04 mmol), Ytterbium(III) trifluormethanesulfonate (25 mg, 40 μmol, 0.5 mol %) and N,N-dimethylformamide (2.5 mL) is stirred at room temperature over night. Methanol and water are added and the mixture is filtered. The precipitate is dissolved in a mixture of N,N-dimethylformamide, methanol and some drops of aqueous ammonia. Water is added and the precipitate is filtered. Yield: 1.51 g; ESI mass spectrum [M+H]$^+$=332, Retention time HPLC: 1.09 min (Z003_001).

Intermediate 15

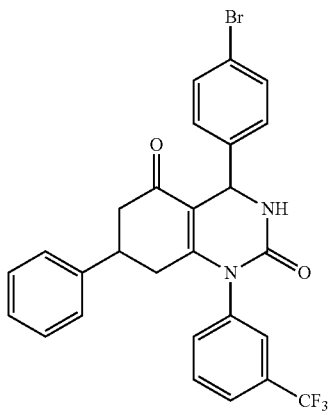 [SMILES: O=C1CC(c2ccccc2)CC2=C1C(c1ccc(Br)cc1)NC(=O)N2c1cccc(C(F)(F)F)c1]

4-(4-Bromophenyl)-7-phenyl-1-(3-(trifluoromethyl)phenyl)-3,4,7,8-tetrahydroquinazoline-2,5(1H,6H)-dione A solution of 1-bromo-4-(chloro(isocyanato)methyl)benzene (201 mg, 0.815 mmol) in dichloromethane (3 mL) is added to a solution of 5-phenyl-3-(3-(trifluoromethyl)phenyl-amino)cyclohex-2-enone (intermediate 14, 270 mg, 0.815 mmol) in dichloromethane (7 mL), and the mixture is heated at reflux for 4 h and cooled to room temperature. After 2 d the mixture is concentrated under reduced pressure and the residue is purified by flash chromatography on silica (gradient cyclohexane/ethyl acetate 90:10 to 60:40). Yield: 195 mg; ESI mass spectrum: [($^{79}$Br)-M+H]$^+$=541, [($^{81}$Br)-M+H]$^+$=543; Retention time HPLC: 1.42 min, 1.44 min (1:1 mixture of diastereomers) (Z002_002).

Intermediate 16

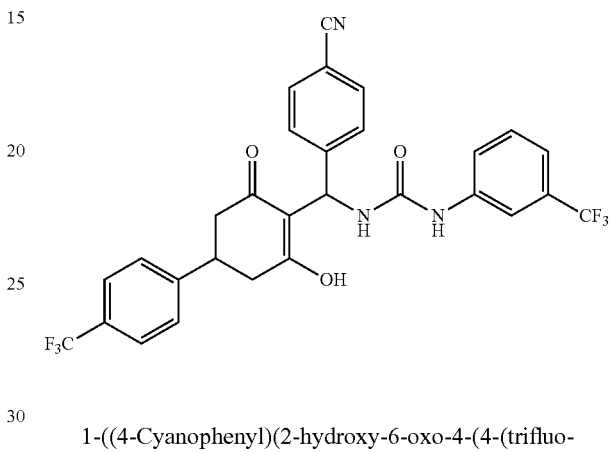

1-((4-Cyanophenyl)(2-hydroxy-6-oxo-4-(4-(trifluoromethyl)phenyl)cyclohex-1-enyl)-methyl)-3-(3-(trifluoromethyl)phenyl)urea The title compound is prepared in analogy to 1-((4-cyanophenyl)(2-hydroxy-6-oxo-4-(tri-fluoromethyl)cyclohex-1-enyl)methyl)-3-(3-(trifluoromethyl)phenyl)urea (intermediate 12), using 5-(4-(trifluoromethyl)phenyl)cyclohexane-1,3-dione (500 mg, 1.95 mmol) as starting material. Yield: 930 mg; ESI mass spectrum [M+H]$^+$=574, Retention time HPLC: 0.85 min (V011_S01).

Intermediate 17

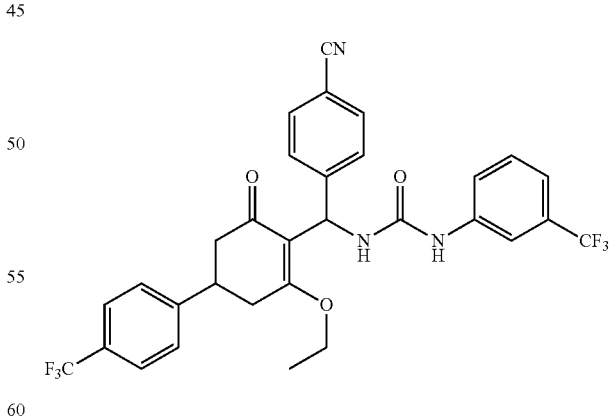

1-((4-Cyanophenyl)(2-ethoxy-6-oxo-4-(4-(trifluoromethyl)phenyl)cyclohex-1-enyl)-methyl)-3-(3-(trifluoromethyl)phenyl)urea The title compound is prepared in analogy to 1-((4-cyanophenyl)(2-ethoxy-6-oxo-4-(tri-fluoromethyl)cyclohex- 1-enyl)methyl)-3-(3-(trifluoromethyl)phenyl)urea (intermediate 13), using 1-((4-cyanophenyl)(2-hydroxy-6-oxo-4-(4-(trifluoromethyl)phenyl)cyclohex-1-enyl)-methyl)-3-(3-(trifluoromethyl)phenyl)urea (intermediate 16, 930 mg, 1.62 mmol) as starting material. Yield: 825 mg; ESI mass spectrum [M+H]$^+$=602, Retention time HPLC: 1.37 min (V011_S01).

Intermediate 18

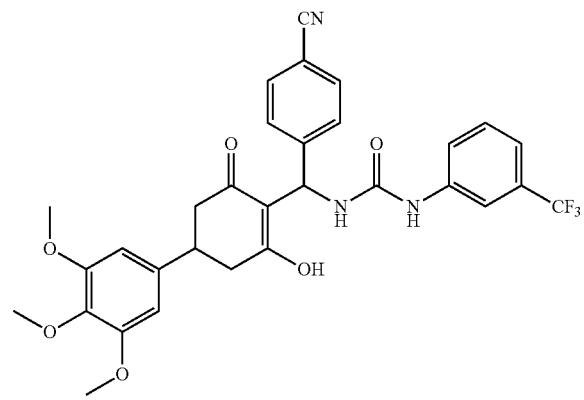 [SMILES: COc1cc(C2CC(=O)C(C(NC(=O)Nc3cccc(C(F)(F)F)c3)c3ccc(C#N)cc3)=C(O)C2)cc(OC)c1OC]

1-((4-Cyanophenyl)(2-hydroxy-6-oxo-4-(3,4,5-trimethoxyphenyl)cyclohex-1-enyl)-methyl)-3-(3-(trifluoromethyl)phenyl)urea The title compound is prepared in analogy to 1-((4-cyanophenyl)(2-hydroxy-6-oxo-4-(tri-fluoromethyl)cyclohex-1-enyl)methyl)-3-(3-(trifluoromethyl)phenyl)urea (intermediate 12), using 5-(3,4,5-trimethoxyphenyl)cyclohexane-1,3-dione (300 mg, 1.08 mmol) as starting material. Yield: 590 mg; ESI mass spectrum [M+H]$^+$=596, Retention time HPLC: 0.76 min (V011_S01).

Intermediate 19

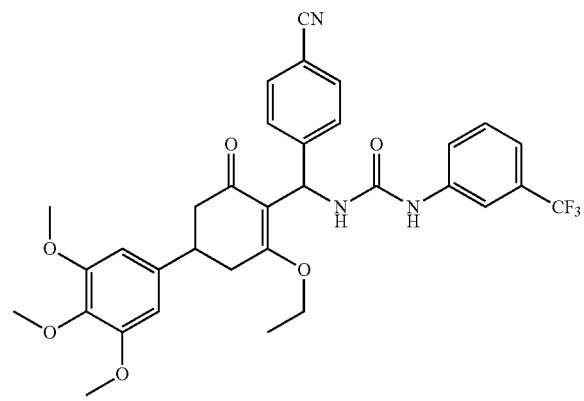 [SMILES: CCOC1=C(C(NC(=O)Nc2cccc(C(F)(F)F)c2)c2ccc(C#N)cc2)C(=O)CC(c2cc(OC)c(OC)c(OC)c2)C1]

1-((4-Cyanophenyl)(2-ethoxy-6-oxo-4-(3,4,5-trimethoxyphenyl)cyclohex-1-enyl)-methyl)-3-(3-(trifluoromethyl)phenyl)urea The title compound is prepared in analogy to 1-((4-cyanophenyl)(2-ethoxy-6-oxo-4-(tri-fluoromethyl)cyclohex- 1-enyl)methyl)-3-(3-(trifluoromethyl)phenyl)urea (intermediate 13), using 1-((4-cyanophenyl)(2-hydroxy-6-oxo-4-(3,4,5-trimethoxyphenyl)cyclohex-1-enyl)-methyl)-3-(3-(trifluoromethyl)phenyl)urea (intermediate 18, 680 mg, 1.14 mmol) as starting material. Yield: 684 mg; ESI mass spectrum [M+H]$^+$=624, Retention time HPLC: 1.27 min (V011_S01).

Intermediate 20

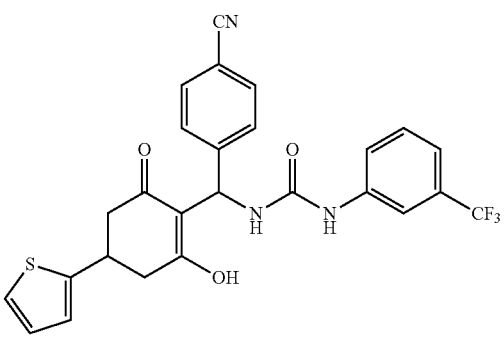 [SMILES: N#Cc1ccc(C(NC(=O)Nc2cccc(C(F)(F)F)c2)C2=C(O)CC(c3cccs3)CC2=O)cc1]

1-((4-Cyanophenyl)(2-hydroxy-6-oxo-4-(thiophen-2-yl)cyclohex-1-enyl)methyl)3-(3-(trifluoromethyl)phenyl)urea Trimethylsilyl chloride (216 µL, 1.70 mmol) is added to a solution of 5-(thiophen-2-yl)-cyclohexane-1,3-dione (300 mg, 1.54 mmol), 4-formylbenzonitrile (202 mg, 1.54 mmol) and 1-(3-(trifluoromethyl)phenyl)urea (315 mg, 1.54 mmol) in a mixture of N,N-dimethyl-formamide (1.2 mL) and acetonitrile (2.3 mL). The mixture is stirred at room temperature over night and poured into a mixture of water and ice. The precipitate is filtered and dried under reduced pressure. Yield: 444 mg; ESI mass spectrum [M+H]$^+$=512, Retention time HPLC: 0.75 min (V011_S01).

Intermediate 21

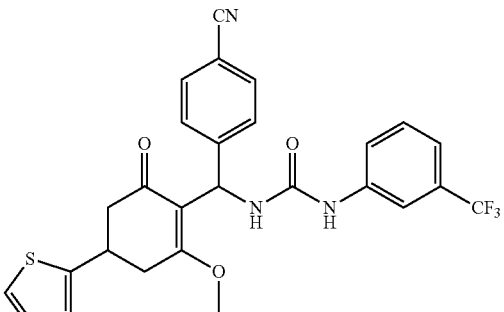

1-((4-Cyanophenyl)(2-ethoxy-6-oxo-4-(thiophen-2-yl)cyclohex-1-enyl)methyl)-3-(3-(tri-fluoromethyl)phenyl)urea The title compound is prepared in analogy to 1-((4-cyanophenyl)(2-ethoxy-6-oxo-4-(tri-fluoromethyl)cyclohex-1-enyl)methyl)-3-(3-(trifluoromethyl)phenyl)urea (intermediate 13), using 1-((4-cyanophenyl)(2-hydroxy-6-oxo-4-(thiophen-2-yl)cyclohex-1-enyl)methyl)-3-(3-(trifluoromethyl)phenyl)urea (intermediate 20, 444 mg, 0.87 mmol) as starting material. Yield: 507 mg; ESI mass spectrum [N+H]$^+$=540, Retention time HPLC: 1.29 min (V011_S01).

Intermediate 22

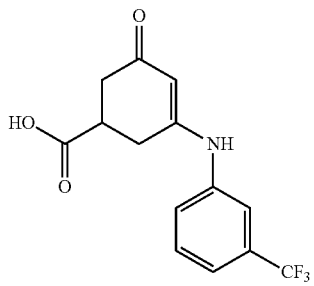 [SMILES: O=C1C=C(Nc2cccc(C(F)(F)F)c2)CC(C(=O)O)C1]

5-Oxo-3-(3-(trifluoromethyl)phenylamino)cyclohex-3-enecarboxylic acid

A mixture of 3,5-dioxocyclohexanecarboxylic acid (1.00 g, 6.41 mmol), 3-(trifluoromethyl)aniline (880 μL, 1.14 g, 4.05 mmol), Ytterbium(III) trifluormethanesulfonate (20 mg, 32 μmol, 0.5 mol %) and N,N-dimethylformamide (3 mL) is stirred at room temperature over night. Water and aqueous sodium hydroxide are added and the mixture is washed with diethyl ether. The organic layer is discarded, and the aqueous layer is acidified with aqueous hydrogen chloride and extracted with diethyl ether. The organic layer is dried over Na$_2$SO$_4$ and concentrated under reduced pressure. Yield: 1.30 g; ESI mass spectrum [M+H]$^+$=300, Retention time HPLC: 1.08 min (V001_006).

Intermediate 23

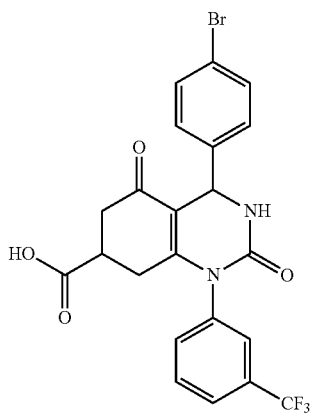 [SMILES: O=C1CC(C(=O)O)CC2=C1C(c1ccc(Br)cc1)NC(=O)N2c1cccc(C(F)(F)F)c1]

4-(4-Bromophenyl)-2,5-dioxo-1-(3-(trifluoromethyl)phenyl)-1,2,3,4,5,6,7,8-octahydroquinazoline-7-carboxylic acid A solution of 1-bromo-4-(chloro(isocyanato)methyl)benzene (1.07 g, 4.34 mmol) in dichloromethane (5 mL) is added to a solution of 5-oxo-3-(3-(trifluoromethyl)phenyl-amino)cyclohex-3-enecarboxylic acid (intermediate 22, 1.30 g, 4.34 mmol) in dichloromethane (15 mL) and the mixture is heated at reflux for 3 h. Water and aqueous sodium hydroxide solution are added and the mixture is washed with diethyl ether. The organic layer is discarded and the aqueous layer is acidified with aqueous hydrogen chloride and extracted twice with diethyl ether. The organic layers are combined, dried over Na$_2$SO$_4$ and concentrated under reduced pressure. Yield: 770 mg; ESI mass spectrum: [($^{79}$Br)-M+H]$^+$=509, [($^{81}$Br)-M+H]$^+$=511; Retention time HPLC: 1.25 min, 1.35 min (1:1 mixture of diastereomers) (V001_006).

Intermediate 24

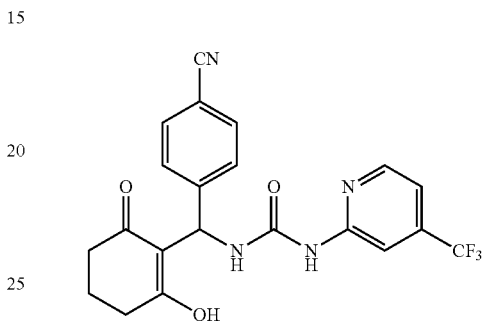

1-((4-cyanophenyl)(2-hydroxy-6-oxocyclohex-1-enyl)methyl)-3-(4-(trifluoromethyl)-pyridin-2-yl)urea Trimethylsilyl chloride (125 μL, 0.982 mmol) is added to a solution of cyclohexane-1,3-dione (100 mg, 0.892 mmol), 4-formylbenzonitrile (117 mg, 0.892 mmol) and 1-(4-(trifluoromethyl)pyridin-2-yl)urea (183 mg, 0.892 mmol) in a mixture of N,N-dimethylformamide (670 μL) and acetonitrile (1.2 mL), and the mixture is heated at 50° C. for 1 h. The reaction mixture is cooled to room temperature and poured into a mixture of water and ice. The mixture is filtered, and the precipitate is washed with water and dried under reduced pressure. Yield: 293 mg; ESI mass spectrum [M+H]$^+$=431, Retention time HPLC: 0.63 min (V011_S01).

Intermediate 25

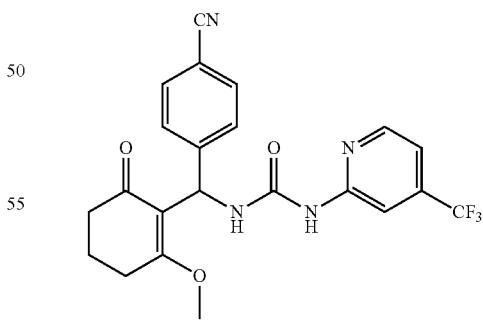

1-((4-cyanophenyl)(2-methoxy-6-oxocyclohex-1-enyl)methyl)-3-(4-(trifluoromethyl)-pyridin-2-yl)urea Trimethyloxonium tetrafluoroborate (185 mg, 1.25 mmol) is added to a solution of N,N-diisopropylethylamine (210 μL, 1.21 mmol) and 1-((4-cyanophenyl)(2-hydroxy-6-oxocyclohex-1-enyl)methyl)-3-(4-(trifluoromethyl)pyridin-2-yl)urea (intermediate 24, 264 mg, 0.613 mmol). The mixture is stirred at room temperature for 1 h and extracted with water. The organic phase is dried over Na$_2$SO$_4$ and concentrated under reduced pressure. Yield: 200 mg; ESI mass spectrum [M+H]$^+$=445, Retention time HPLC: 1.08 min (V011_S01).

Intermediate 26

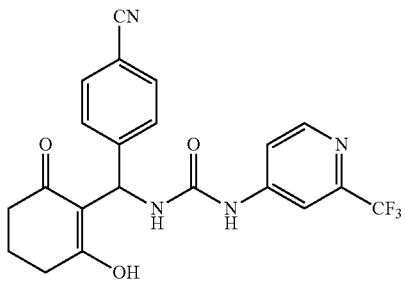 [SMILES: N#Cc1ccc(C(NC(=O)Nc2ccnc(C(F)(F)F)c2)C2=C(O)CCCC2=O)cc1]

1-((4-Cyanophenyl)(2-hydroxy-6-oxocyclohex-1-enyl)methyl)-3-(2-(trifluoromethyl)-pyridin-4-yl)urea Trimethylsilyl chloride (187 μL, 1.47 mmol) is added to a solution of cyclohexane-1,3-dione (150 mg, 1.34 mmol), 4-formylbenzonitrile (175 mg, 1.34 mmol) and 1-(2-(trifluoromethyl)pyridin-4-yl)urea (274 mg, 1.34 mmol) in a mixture of N,N-dimethyl-formamide (1.0 mL) and acetonitrile (1.8 mL), and the mixture is stirred at room temperature for 1.5 h. The reaction mixture is cooled to room temperature and poured into a mixture of water and ice. The mixture is filtered, and the precipitate is washed with water and dried under reduced pressure. Yield: 410 mg; ESI mass spectrum [M+H]$^+$=431, Retention time HPLC: 0.60 min (V011_S01).

Intermediate 27

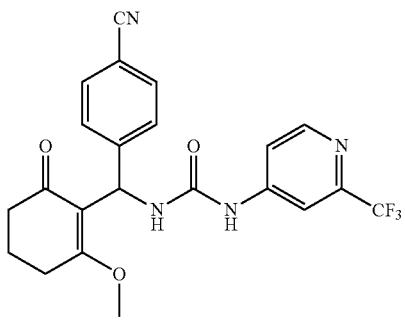 [SMILES: COC1=C(C(NC(=O)Nc2ccnc(C(F)(F)F)c2)c2ccc(C#N)cc2)C(=O)CCC1]

1-((4-Cyanophenyl)(2-methoxy-6-oxocyclohex-1-enyl)methyl)-3-(2-(trifluoromethyl)-pyridin-4-yl)urea Trimethyloxonium tetrafluoroborate (47 mg, 0.318 mmol) is added to a solution of N,N-diisopropylethylamine (72 μL, 0.412 mmol) and 1-((4-cyanophenyl)(2-hydroxy-6-oxocyclohex-1-enyl)methyl)-3-(2-(trifluoromethyl)pyridin-4-yl) urea (intermediate 26, 90 mg, 0.209 mmol) in dichloromethane (10 mL). The mixture is stirred at room temperature for 1 h and extracted three times with water. The organic phase is dried over Na$_2$SO$_4$ and concentrated under reduced pressure. Yield: 100 mg; ESI mass spectrum [M+H]$^+$=445, Retention time HPLC: 1.05 min (V012_S01).

Intermediate 28

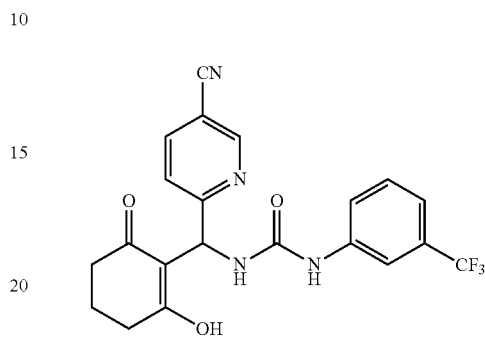

1-((5-Cyanopyridin-2-yl)(2-hydroxy-6-oxocyclohex-1-enyl)methyl)-3-(3-(trifluoromethyl)phenyl)urea Trimethylsilyl chloride (125 μL, 0.98 mmol) is added to a solution of cyclohexane-1,3-s dione (100 mg, 0.89 mmol), 6-formylnicotinonitrile (118 mg, 0.89 mmol) and 1-(3-(trifluoromethyl)phenyl)urea (182 mg, 0.89 mmol) in a mixture of N,N-dimethyl-formamide (670 μL) and acetonitrile (1.2 mL), and the mixture is stirred at room temperature for 1.5 h. The reaction mixture is cooled to room temperature and poured into a mixture of water and ice. The mixture is filtered, and the precipitate is washed with water and dried under reduced pressure. Yield: 330 mg; ESI mass spectrum [M+H]$^+$=431, Retention time HPLC: 0.63 min (V011_S01).

Intermediate 29

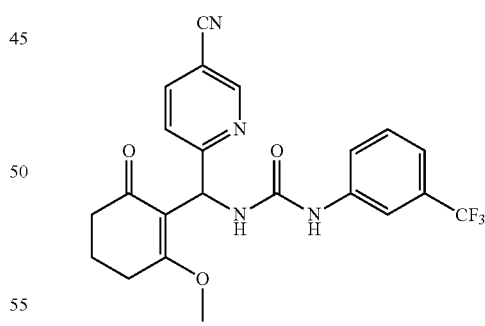

1-((5-Cyanopyridin-2-yl)(2-methoxy-6-oxocyclohex-1-enyl)methyl)-3-(3-(trifluoromethyl)phenyl) urea The title compound is prepared in analogy to 1-((4-cyanophenyl)(2-methoxy-6-oxocyclohex-1-enyl)methyl)-3-(4-(trifluoromethyl)pyridin-2-yl)urea (intermediate 25) using 1-((5-cyanopyridin-2-yl)(2-hydroxy-6-oxocyclohex-1-enyl)methyl)-3-(3-(trifluoromethyl)phenyl) urea (intermediate 28, 330 mg, 0.767 mmol) as starting material. Yield: 203 mg; ESI mass spectrum [M+H]⁺=445, Retention time HPLC: 1.05 min (V011_S01).

Intermediate 30

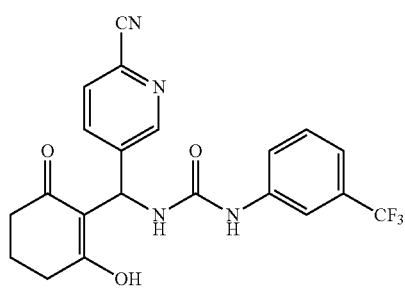 [SMILES: N#Cc1ccc(C(NC(=O)Nc2cccc(C(F)(F)F)c2)C2=C(O)CCCC2=O)cn1]

1-((6-cyanopyridin-3-yl)(2-hydroxy-6-oxocyclohex-1-enyl)methyl)-3-(3-(trifluoromethyl)phenyl)urea Trimethylsilyl chloride (125 µL, 0.982 mmol) is added to a solution of cyclohexane-1,3-dione (100 mg, 0.892 mmol), 5-formylpicolinonitrile (118 mg, 0.892 mmol) and 1-(3-(trifluoromethyl)phenyl)urea (183 mg, 0.829 mmol) in a mixture of N,N-dimethylformamide (670 µL) and acetonitrile (1.2 mL), and the mixture is heated at 50° C. for 1 h. The reaction mixture is cooled to room temperature and poured into a mixture of water and ice. The mixture is filtered, and the precipitate is washed with water and dried under reduced pressure. Yield: 346 mg; ESI mass spectrum [M+H]⁺=431, Retention time HPLC: 0.67 min (V011_S01).

Intermediate 31

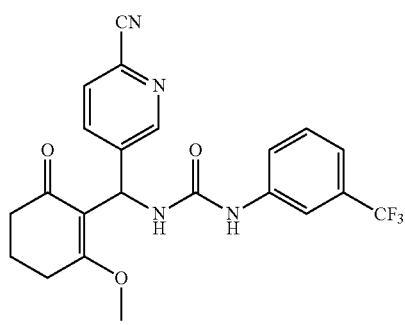 [SMILES: COC1=C(C(NC(=O)Nc2cccc(C(F)(F)F)c2)c2ccc(C#N)nc2)C(=O)CCC1]

1-((6-Cyanopyridin-3-yl)(2-methoxy-6-oxocyclohex-1-enyl)methyl)-3-(3-(trifluoromethyl)phenyl)urea Trimethyloxonium tetrafluoroborate (121 mg, 0.82 mmol) is added to a solution of N,N-diisopropylethylamine (276 µL, 1.58 mmol) and 1-((6-cyanopyridin-3-yl)(2-hydroxy-6-oxocyclohex-1-enyl)methyl)-3-(3-(trifluoromethyl)phenyl)urea (intermediate 30, 346 mg, 0.804 mmol) in dichloromethane (10 mL). The mixture is stirred at room temperature overnight, and another portion of trimethyloxonium tetrafluoroborate (121 mg, 0.82 mmol) is added. After 1 h the mixture is diluted with dichloromethane, and washed with water and saturated aqueous sodium chloride solution. The organic layer is dried over Na₂SO₄ and concentrated under reduced pressure. Yield: 300 mg; ESI mass spectrum [M+H]⁺=445, Retention time HPLC: 1.09 min (V011_S01).

Intermediate 32

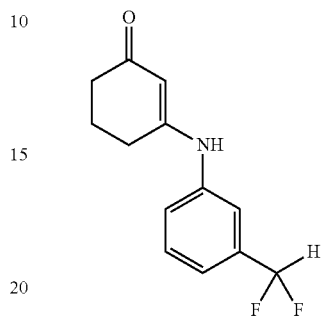

3-(3-(Difluoromethyl)phenylamino)cyclohex-2-enone

A mixture of cyclohexane-1,3-dione (2.00 g, 17.84 mmol), 3-(difluoromethyl)aniline (2.55 g, 17.82 mmol) and Ytterbium(III) trifluormethanesulfonate (111 mg, 178 µmol, 1.0 mol %) is stirred at room temperature for 2 h. Methanol and water are added and the mixture is extracted twice with dichloromethane. The combined organic layers are dried over Na₂SO₄ and concentrated under reduced pressure. The residue is purified by flash chromatography on silica (gradient cyclohexane/ethyl acetate 1:1 to ethyl acetate). Yield: 2.76 g; ESI mass spectrum [M+H]⁺=237, Retention time HPLC: 0.40 min (X012_S01).

Intermediate 33

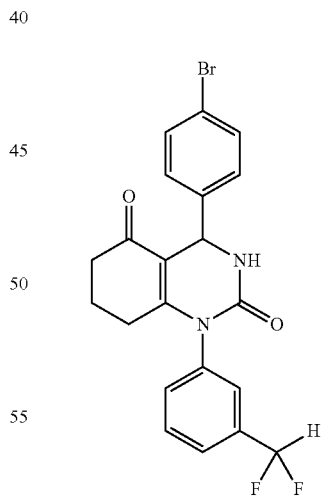

4-(4-Bromophenyl)-1-(3-(difluoromethyl)phenyl)-3,4,7,8-tetrahydroquinazoline-2,5(1H,6H)-dione A solution of 1-bromo-4-(chloro(isocyanato)methyl)benzene (400 mg, 1.62 mmol) in dichloromethane (2.5 mL) is added to a solution of 3-(3-(difluoromethyl)phenylamino)-cyclohex-2-enone (intermediate 32, 385 mg, 1.62 mmol) in dichloromethane (2.5 mL). The mixture is heated at reflux for 2 h and cooled to room temperature. Water is added and the mixture is extracted twice with dichloromethane. The combined organic layers are dried over Na$_2$SO$_4$ and concentrated under reduced pressure. The residue is purified by flash chromatography on silica (gradient cyclohexane/ethyl acetate 80:20 to ethyl acetate. Yield: 350 mg; ESI mass spectrum: [($^{79}$Br)-M+H]$^+$=447, [($^{81}$Br)-M+H]$^+$=449; Retention time HPLC: 0.61 min (X012_S01).

Intermediate 34

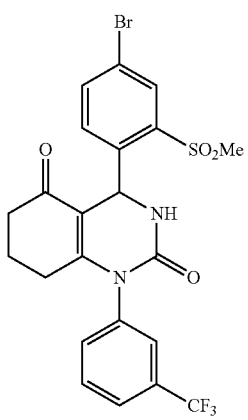 [SMILES: CS(=O)(=O)c1cc(Br)ccc1C1NC(=O)N(c2cccc(C(F)(F)F)c2)C2=C1C(=O)CCC2]

4-(4-Bromo-2-(methylsulfonyl)phenyl)-1-(3-(trifluoromethyl)phenyl)-3,4,7,8-tetrahydroquinazoline-2,5(1H,6H)-dione A mixture of triethyl phosphate (400 μL, 428 mg, 2.35 mmol) and phosphorous pentoxide (216 mg, 1.52 mmol) is heated at 50° C. over night and dilutet with tert-butyl methyl ether (10 mL). Cyclohexane-1,3-dione (320 mg, 2.85 mmol), 4-bromo-2-(methylsulfonyl)benz-aldehyde (500 mg, 1.90 mmol) and 1-(3-(trifluoromethyl)phenyl)urea (388 mg, 1.90 mmol) are added, and the mixture is heated at reflux over night and concentrated under reduced pressure. The residue is purified by reversed phase HPLC (Agilent ZORBAX™+SB-C$_{18}$, gradient of acetonitrile in water, 0.15% formic acid). Yield: 80 mg; ESI mass spectrum [($^{79}$Br)-M+H]$^+$=543, [($^{81}$Br)-M+H]$^+$=545, Retention time HPLC: 1.06 min (Z017_S04).

Intermediate 35

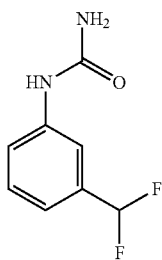 [SMILES: NC(=O)Nc1cccc(C(F)F)c1]

1-(3-(Difluoromethyl)phenyl)urea

Water (10 mL) is added dropwise to a mixture of 3-(difluoromethyl)aniline (2.00 g, 13.97 mmol) in glacial acetic acid (6 mL). A solution of sodium cyanate (1.00 g, 15.38 mmol) in water (10 mL) is added dropwise, and the mixture is stirred at room temperature for 4 h. The precipitate is filtered, washed with water and dried under reduced pressure. Yield: 1.80 g; ESI mass spectrum [M+H]$^+$=187, Retention time HPLC: 0.70 min (Z012_S04).

Intermediate

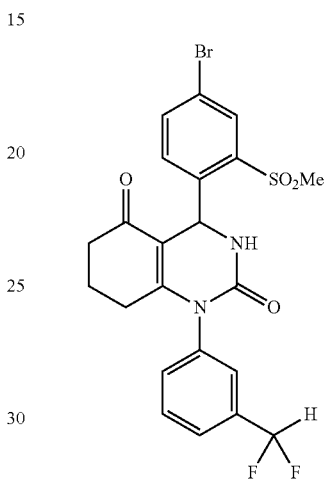

4-(4-Bromo-2-(methylsulfonyl)phenyl)-1-(3-(difluoromethyl)phenyl)-3,4,7,8-tetrahydroquinazoline-2,5(1H,6H)-dione The title compound is prepared in analogy to 4-(4-bromo-2-(methylsulfonyl)phenyl)-1-(3-(trifluoromethyl)phenyl)-3,4,7,8-tetrahydroquinazoline-2,5(1H,6H)-dione (intermediate 34), using 1-(3-(difluoromethyl)phenyl)urea (intermediate 35, 707 mg, 3.80 mmol) as starting material. Yield: 319 mg; ESI mass spectrum [($^{79}$Br)-M+H]$^+$=525, [($^{81}$Br)-M+H]$^+$=527, Retention time HPLC: 1.01 min (Z017_S04).

Intermediate 37

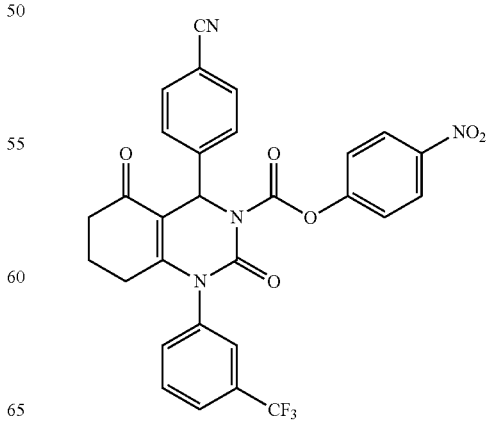

4-Nitrophenyl 4-(4-Cyanophenyl)-2,5-dioxo-1-(3-(trifluoromethyl)phenyl)-1,2,5,6,7,8-hexahydro-quinazoline-3(4H)-carboxylate N,N-Diisopropylethylamine (1.65 mL, 9.72 mmol) and 4-dimethylaminopyridine (59 mg, 0.49 mmol) are added to a solution of 4-(2,5-dioxo-1-(3-(trifluoromethyl)phenyl)-1,2,3,4,5,6,7,8-octahydroquinazolin-4-yl)-benzonitrile (example 1, 1.00 g, 2.43 mmol) in dichloromethane (6 mL), and the mixture is cooled in an ice bath. A solution of 4-nitrophenyl chloroformate (540 mg, 2.67 mmol) in dichloromethane (2 mL) is added, and the mixture is warmed to room temperature. After 3 h another portion of 4-nitrophenyl chloroformate (980 mg, 4.86 mmol) and N,N-diisopropylethylamine (830 µL, 4.86 mmol) are added, and the mixture is stirred over night. Water is added and the mixture is extracted twice with dichloromethane. The combined organic layers are dried over Na$_2$SO$_4$ and concentrated under reduced pressure. The residue is purified twice by flash chromatography on silica (first purification: gradient cyclohexane/ethyl acetate 100:0 to 70:30, second purification: gradient cyclohexane/ethyl acetate 100:0 to 50:50). Yield: 374 mg; ESI mass spectrum [M+H]$^+$=577, Retention time HPLC: 0.92 min (Z018_S04).

Intermediate 38

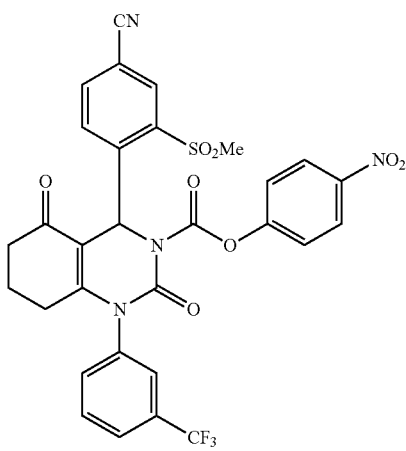 [SMILES: CS(=O)(=O)c1cc(C#N)ccc1C1C2=C(CCCC2=O)N(c2cccc(C(F)(F)F)c2)C(=O)N1C(=O)Oc1ccc([N+](=O)[O-])cc1]

4-Nitrophenyl 4-(4-Cyano-2-(methylsulfonyl)phenyl)-2,5-dioxo-1-(3-(trifluoromethyl)-phenyl)-1,2,5,6,7,8-hexahydroquinazoline-3(4H)-carboxylate A microwave vessel is charged with a mixture of 4-(1-(3-(trifluoromethyl)phenyl)-2,5-dioxo-1,2,3,4,5,6,7,8-octahydroquinazolin-4-yl)-3-(methylsulfonyl)benzonitrile (example 18, 50 mg, 0.10 mmol), 4-nitrophenyl chloroformate (31 mg, 0.15 mmol) and a tip of a spatula of 4-dimethylaminopyridine in toluene (3 mL). Triethylamine (0.1 mL) is added, and the mixture is heated in a microwave at 150° C. for 10 min. Another portion of 4-nitrophenyl chloroformate (31 mg, 0.15 mmol) is added and the mixture is heated again at 150° C. for 20 min. All volatiles are evaporated and the residue is purified by reversed phase HPLC (Agilent ZORBAX™ SB-C$_{18}$, gradient of acetonitrile in water, 0.15% formic acid). Yield: 32 mg; ESI mass spectrum M+H]$^+$=655, Retention time HPLC: 1.10 min (Z017_S04).

Intermediate 39

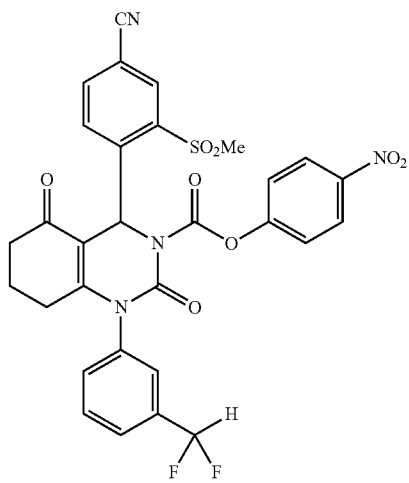 [SMILES: CS(=O)(=O)c1cc(C#N)ccc1C1C2=C(CCCC2=O)N(c2cccc(C(F)F)c2)C(=O)N1C(=O)Oc1ccc([N+](=O)[O-])cc1]

4-Nitrophenyl 4-(4-Cyano-2-(methylsulfonyl)phenyl)-1-(3-(difluoromethyl)phenyl)-2,5-dioxo-1,2,5,6,7,8-hexahydroquinazoline-3(4H)-carboxylate The title compound is prepared in analogy to 4-nitrophenyl 4-(4-cyano-2-(methylsulfonyl)-phenyyl)-2,5-dioxo-1-(3-(trifluoromethyl)phenyl)-1,2,5,6,7,8-hexahydroquinazoline-3(4H)-carboxylate (intermediate 38), using 4-(1-(3-(difluoromethyl)phenyl)-2,5-dioxo-1,2,3,4,5,6,7,8-octahydroquinazolin-4-yl)-3-(methylsulfonyl)benzonitrile (example 19, 100 mg, 0.212 mmol) as starting material and purifying the product by preparative HPLC (first purification: Waters SunFire™-C$_{18}$, gradient of acetonitrile in water, 0.1% formic acid, second purification: Agilent ZORBAX™ SB-C$_{18}$, gradient of acetonitrile in water, 0.15% formic acid). Yield: 16 mg, ESI mass spectrum [M+H]$^+$=637, Retention time HPLC: 1.06 min (Z017_S04).

Intermediate

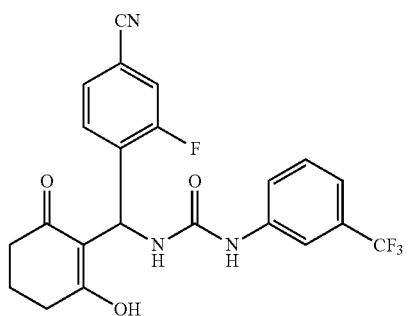 [SMILES: N#Cc1ccc(C(NC(=O)Nc2cccc(C(F)(F)F)c2)C2=C(O)CCCC2=O)c(F)c1]

1-((4-Cyano-2-fluorophenyl)(2-hydroxy-6-oxocyclohex-1-enyl)methyl)-3-(3-(trifluoromethyl)phenyl) urea Trimethylsilyl chloride (1 M in dichloromethane, 4.90 mL, 4.90 mmol) is added to a solution of cyclohexane-1,3-dione (0.50 g, 4.46 mmol), 3-fluoro-4-formylbenzonitrile (0.67 g, 4.46 mmol) and 1-(3-(trifluoromethyl)phenyl)urea (0.91 g, 4.46 mmol) in a mixture of N,N-dimethylformamide (2.0 mL) and acetonitrile (2.0 mL). The mixture is stirred at room temperature for 45 min and then poured into ice water. The mixture is stirred over night at room temperature, and the precipitate is filtered and dried. Yield: 1.8 g; ESI mass spectrum [M+H]$^+$=448, Retention time HPLC: 1.02 min (Z018_S04).

Intermediate 41

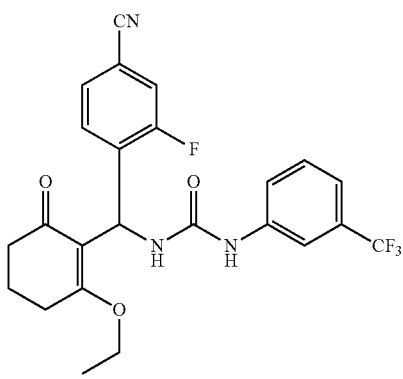 [SMILES: CCOC1=C(C(NC(=O)Nc2cccc(C(F)(F)F)c2)c2ccc(C#N)cc2F)C(=O)CCC1]

1-((4-Cyano-2-fluorophenyl)(2-ethoxy-6-oxocyclohex-1-enyl)methyl)-3-(3-(trifluoromethyl)phenyl) urea Triethyloxonium tetrafluoroborate (1.60 g, 8.42 mmol) is added to a solution of 1-((4-cyano-2-fluorophenyl)(2-hydroxy-6-oxocyclohex-1-enyl)methyl)-3-(3-(trifluoromethyl)phenyl)urea (intermediate 40 1.80 g, 4.02 mmol) and N,N-diisopropylethylamine (1.60 mL, 9.2 mmol) in dichloromethane (15 mL), and the mixture is stirred at room temperature for 20 min Water is added, and the phases are separated. The organic layer is dried over Na$_2$SO$_4$ and concentrated under reduced pressure. Yield: 1.82 g; ESI mass spectrum [M+H]$^+$=476, Retention time HPLC: 1.11 min (Z018_S04).

Intermediate 42

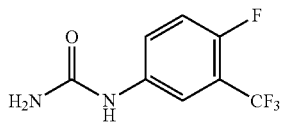 [SMILES: NC(=O)Nc1ccc(F)c(C(F)(F)F)c1]

1-(4-fluoro-3-(trifluoromethyl)phenyl)urea

Water (2.5 mL) is added slowly to a mixture of 4-fluoro-3-(trifluoromethyl)aniline (500 mg, 2.79 mmol) in glacial acetic acid (1.5 mL). A solution of sodium cyanate (200 mg, 3.07 mmol) in water (2.5 mL) is added slowly, and the mixture is stirred at room temperature for 4 h. The mixture is extracted twice with dichloromethane, and the combined organic layers are concentrated under reduced pressure. Yield: 588 mg; ESI mass spectrum [M+H]$^+$=223; Retention time HPLC: 0.87 min (Z018_S04).

Intermediate 43

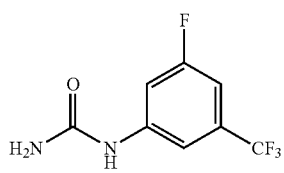

1-(3-Fluoro-5-(trifluoromethyl)phenyl)urea

The title compound is prepared in analogy to 1-(4-fluoro-3-(trifluoromethyl)phenyl)urea (intermediate 42), using 5-fluoro-3-(trifluoromethyl)aniline (1.00 g, 5.58 mmol) as starting material. Yield: 630 mg; ESI mass spectrum [M+H]$^+$=223; Retention time HPLC: 0.91 min (Z018_S04).

Intermediate 44

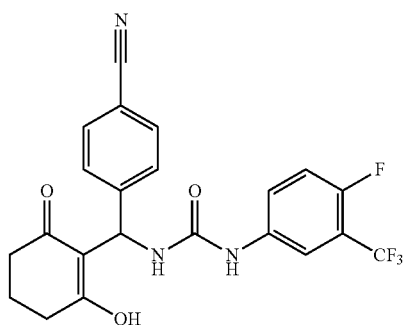 [SMILES: N#Cc1ccc(C(NC(=O)Nc2ccc(F)c(C(F)(F)F)c2)C2=C(O)CCCC2=O)cc1]

1-((4-Cyanophenyl)(2-hydroxy-6-oxocyclohex-1-enyl)methyl)-3-(4-fluoro-3-(trifluoromethyl)phenyl) urea A mixture of triethyl phosphate (620 μL, 3.66 mmol) and phosphorous pentoxide (346 mg, 2.44 mmol) is heated at 50° C. over night and dilutet with tert-butyl methyl ether (7 mL). Cyclohexane-1,3-dione (513 mg, 4.57 mmol), 1-(4-fluoro-3-(trifluoromethyl)phenyl)urea (677 mg, 3.05 mmol) and 4-formylbenzonitrile (400 mg, 3.05 mmol) are added, and the mixture is heated at 55° C. for 3 h. All volatiles are removed under reduced pressure. The residue is dissolved in methanol, and the mixture is purified by reversed phase HPLC (Waters SunFire™-C$_{18}$, gradient of acetonitrile in water, 0.1% formic acid). Yield: 551 mg; ESI mass spectrum [M+H]⁺=448; Retention time HPLC: 1.04 min (Z018_S04).

Intermediate 45

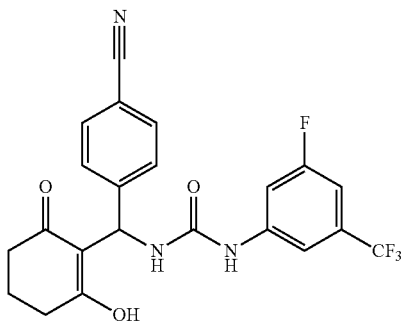 [SMILES: N#Cc1ccc(C(NC(=O)Nc2cc(F)cc(C(F)(F)F)c2)C2=C(O)CCCC2=O)cc1]

1-((4-Cyanophenyl)(2-hydroxy-6-oxocyclohex-1-enyl)methyl)-3-(3-fluoro-5-(trifluoromethyl)phenyl)urea The title compound is prepared in analogy to 1-((4-cyanophenyl)(2-hydroxy-6-oxocyclohex-1-enyl)methyl)-3-(4-fluoro-3-(trifluoromethyl)phenyl)urea (intermediate 44), using 1-(3-fluoro-5-(trifluoromethyl)phenyl)urea (intermediate 43, 630 mg, 1.99 mmol) as starting material. Yield: 378 mg; ESI mass spectrum [M+H]⁺=448; Retention time HPLC: 1.07 min (Z018_S04).

Intermediate 46

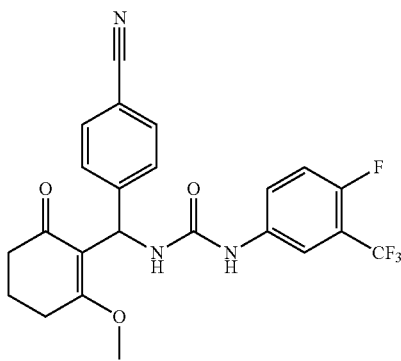 [SMILES: COC1=C(C(NC(=O)Nc2ccc(F)c(C(F)(F)F)c2)c2ccc(C#N)cc2)C(=O)CCC1]

1-((4-Cyanophenyl)(2-methoxy-6-oxocyclohex-1-enyl)methyl)-3-(4-fluoro-3-(trifluoromethyl)phenyl)urea N,N-Diisopropylethylamine (450 µL, 2.59 mmol) and trimethyloxonium tetrafluoroborate (331 mg, 2.24 mmol) are added to a mixture of 1-((4-cyanophenyl)(2-hydroxy-6-oxocyclohex-1-enyl)methyl)-3-(4-fluoro-3-(trifluoromethyl)phenyl)urea (intermediate 44, 500 mg, 1.12 mmol) in dichloromethane (4.0 mL), and the mixture is stirred at room temperature for 20 min Dichloromethane (20 mL) is added, and the phases are separated. The organic layer is washed three times with water and concentrated under reduced pressure. Yield: 567 mg; ESI mass spectrum [M+H]⁺=462; Retention time HPLC: 1.09 min (Z018_S04).

Intermediate 47

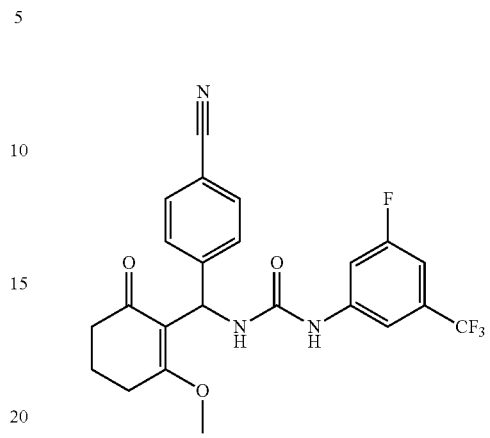

1-((4-Cyanophenyl)(2-methoxy-6-oxocyclohex-1-enyl)methyl)-3-(3-fluoro-5-(trifluoromethyl)phenyl)urea The title compound is prepared in analogy to 1-((4-cyanophenyl)(2-methoxy-6-oxocyclohex-1-enyl)methyl)-3-(4-fluoro-3-(trifluoromethyl)phenyl)urea (intermediate 46), using 1-((4-cyanophenyl)(2-hydroxy-6-oxocyclohex-1-enyl)methyl)-3-(3-fluoro-5-(trifluoromethyl)phenyl)urea (intermediate 45, 378 mg, 0.85 mmol) as starting material. Yield: 367 mg; ESI mass spectrum [M+H]⁺=462; Retention time HPLC: 1.11 min (Z018_S04).

Intermediate 48

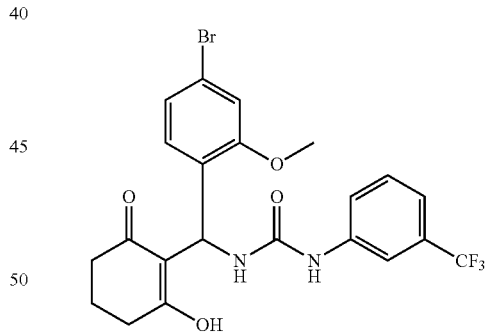

1-((4-Bromo-2-methoxyphenyl)(2-hydroxy-6-oxocyclohex-1-enyl)methyl)-3-(3-(trifluoromethyl)phenyl)urea A mixture of cyclohexane-1,3-dione (700 mg, 6.24 mmol), 4-bromo-2-methoxybenz-aldehyde (1.35 g, 6.28 mmol) and 1-(3-(trifluoromethyl)phenyl)urea (1.27 g, 6.24 mmol) in N,N-dimethylformamide (2.0 mL) and acetonitrile (3.0 mL) is stirred at room temperature for 20 min Trimethylsilyl chloride (1 M in dichloromethane, 9.0 mL, 9.0 mmol) is added, and the mixture is stirred at room temperature for 30 min and poured into ice water. The mixture is stirred for 3 h and concentrated under reduced pressure. The residue is purified by reversed phase HPLC (Waters Xbridge™-$C_{18}$, gradient of acetonitrile in water, 0.1% $NH_3$). Yield: 900 mg; ESI mass spectrum [($^{79}$Br)-M+H]$^+$=513, [($^{81}$Br)-M+H]$^+$=515; Retention time HPLC: 0.68 min (Z011_S03).

Intermediate 49

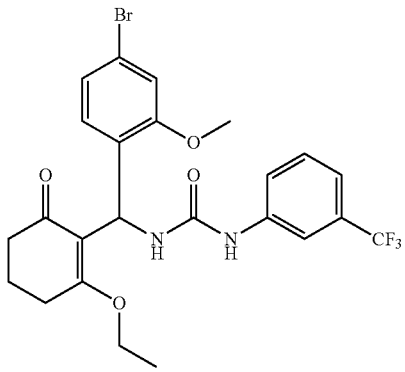 [SMILES: CCOC1=C(C(NC(=O)Nc2cccc(C(F)(F)F)c2)c2ccc(Br)cc2OC)C(=O)CCC1]

1-((4-Bromo-2-methoxyphenyl)(2-ethoxy-6-oxocyclohex-1-enyl)methyl)-3-(3-(tri-fluoromethyl)phenyl)urea The title compound is prepared in analogy to 1-((4-cyano-2-fluorophenyl)(2-ethoxy-6-oxocyclohex-1-enyl)methyl)-3-(3-(trifluoromethyl)phenyl)urea (intermediate 41) using ici 1-((4-bromo-2-methoxyphenyl)(2-hydroxy-6-oxocyclohex-1-enyl)methyl)-3-(3-(trifluoromethyl)phenyl)urea (intermediate 48, 900 mg, 1.75 mmol) as starting material. Yield: 910 mg; ESI mass spectrum [($^{79}$Br)-M+H]$^+$=541, [($^{81}$Br)-M+H]$^+$=543; Retention time HPLC: 0.92 min (Z011_S03).

Intermediate 50

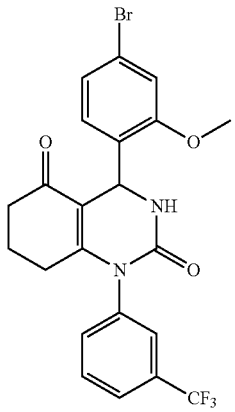 [SMILES: COc1cc(Br)ccc1C1NC(=O)N(c2cccc(C(F)(F)F)c2)C2=C1C(=O)CCC2]

4-(4-Bromo-2-methoxyphenyl)-1-(3-(trifluoromethyl)phenyl)-3,4,7,8-tetrahydroquinazoline-2,5(1H,6H)-dione Sodium tert-butoxide (175 mg, 1.82 mmol) is added to a solution of 1-((4-bromo-2-methoxyphenyl)(2-ethoxy-6-oxocyclohex-1-enyl)methyl)-3-(3-(trifluoromethyl)phenyl)-urea (intermediate 49, 760 mg, 1.40 mmol) in acetonitrile (4 mL), and the mixture is shaked in an ultrasound bath for 20 min Water is added, and the mixture is extracted with dichloromethane. The combined organic layers are dried over $Na_2SO_4$ and concentrated under reduced pressure. The residue is purified by reversed phase HPLC (Waters Xbridge™-$C_{18}$, gradient of acetonitrile in water, 0.1% $NH_3$). Yield: 41 mg; ESI mass spectrum [($^{79}$Br)-M+H]$^+$=495, [($^{81}$Br)-M+H]$^+$=497; Retention time HPLC: 0.96 min (Z011_S03).

Intermediate 51

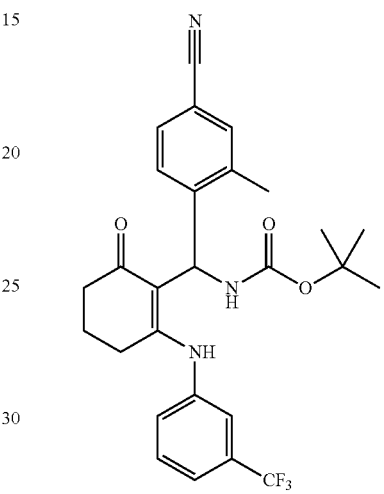

tert-Butyl (4-Cyano-2-methylphenyl)(6-oxo-2-(3-(trifluoromethyl)phenylamino)-cyclohex-1-enyl) methylcarbamate Step 1 tert-Butyl (4-Cyano-2-methylphenyl)(phenylsulfonyl)methylcarbamate

Formic acid (3.3 mL, 88 mmol) is added to a mixture of tert-butyl carbamate (1.61 g, 13.8 mmol), 4-formyl-3-methylbenzonitrile (2.00 g, 13.8 mmoo) and sodium benzenesulfinate (2.26 g, 13.8 mmol) in a mixture of tetrahydrofuran (7 mL) and water (18 mL), and the mixture is stirred at room temperature for 4 days. The tetrahydrofuran is removed under reduced pressure. The precipitate is filtered and dried. Yield: 3.77 g.

Step 2 tert-Butyl (4-Cyano-2-methylphenyl)(6-oxo-2-(3-(trifluoromethyl)phenylamino)cyclohex-1-enyl)methylcarbamate Sodium hydride (60% in mineral oil, 150 mg, 3.75 mmol) is added in portions to a mixture of tert-butyl (4-cyano-2-methylphenyl)(phenylsulfonyl)methylcarbamate (step 1, 1.88 g, 3.41 mmol) and 2-methyltetrahydrofuran (10 mL), and the mixture is stirred at room temperature for 30 min 3-(3-(Trifluoromethyl)phenylamino)cyclohex-2-enone (869 mg, 3.41 mmol) is added, and the mixture is stirred for 2 h. Water is added, and the mixture is extracted with dichloromethane. The phases are separated, and the organic layer is concentrated under reduced pressure. The residue is purified by reversed phase HPLC (Waters Xbridge™-C$_{18}$, gradient of acetonitrile in water, 0.1% TFA). Yield: 1.57 g; ESI mass spectrum [M+H]$^+$=500; Retention time HPLC: 0.79 min (X012_S01).

Intermediate 52

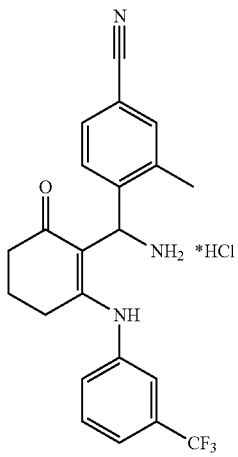 [SMILES: Cc1cc(C#N)ccc1C(N)C1=C(Nc2cccc(C(F)(F)F)c2)CCCC1=O]

4-(Amino(6-oxo-2-(3-(trifluoromethyl)phenylamino)cyclohex-1-enyl)methyl)-3-methylbenzonitrile hydrochloride Hydrogen chloride (4 M in 1,4-dioxane, 5.50 mL, 22.0 mmol) is added to a solution of tert-butyl (4-cyano-2-methylphenyl)(6-oxo-2-(3-(trifluoromethyl)phenylamino)cyclohex-1-enyl)methylcarbamate (intermediate 51, 1.57 g, 3.14 mmol) in 1,4-dioxane (10 mL), and the mixture is stirred at room temperature over night. All volatiles are removed under reduced pressure, and the residue is treated with tert-butyl methyl ether. The precipitate is filtered and dried. Yield: 1.18 g; ESI mass spectrum [M+H]$^+$=400; Retention time HPLC: 0.56 min (X012_S01).

Intermediate 53

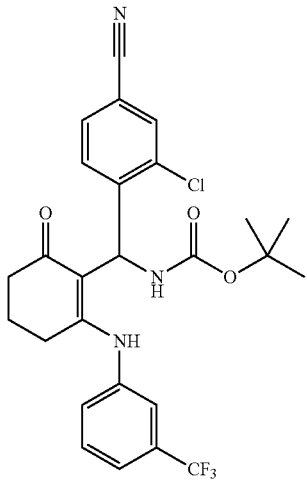 [SMILES: CC(C)(C)OC(=O)NC(C1=C(Nc2cccc(C(F)(F)F)c2)CCCC1=O)c1ccc(C#N)cc1Cl]

tert-Butyl (2-Chloro-4-cyanophenyl)(6-oxo-2-(3-(trifluoromethyl)phenylamino)cyclohex-1-enyl)methylcarbamate The title compound is prepared in analogy to tert-butyl (4-cyano-2-methylphenyl)(6-oxo-2-(3-(trifluoromethyl)phenylamino)cyclohex-1-enyl)methylcarbamate (intermediate 51), using 3-chloro-4-formylbenzonitrile (500 mg, 6.04 mmol) as starting material. Yield: 1.05 g; ESI mass spectrum [M+H]$^+$=520; Retention time HPLC: 0.81 min (X012_S01).

Intermediate 54

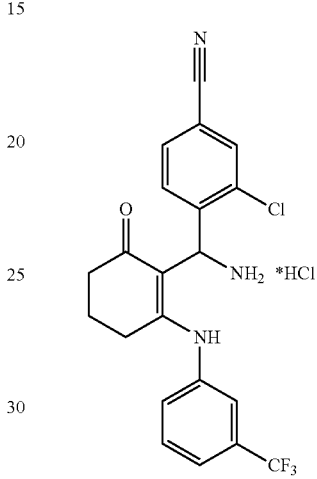

4-(Amino(6-oxo-2-(3-(trifluoromethyl)phenylamino)cyclohex-1-enyl)methyl)-3-chloro-benzonitrile hydrochloride Hydrogen chloride (4 M in 1,4-dioxane, 4.0 mL, 16.2 mmol) is added to a solution of tert-butyl (2-chloro-4-cyanophenyl)(6-oxo-2-(3-(trifluoromethyl)phenylamino)cyclohex-1-enyl)methylcarbamate (intermediate 53, 1.05 g, 2.02 mmol) in 1,4-dioxane (5 mL), and the mixture is stirred at room temperature over night. All volatiles are removed under reduced pressure, and the residue is treated with tert-butyl methyl ether. The precipitate is filtered and dried. Yield: 690 mg; ESI mass spectrum [M+H]$^+$=420; Retention time HPLC: 0.57 min (X012_S01).

Intermediate 55

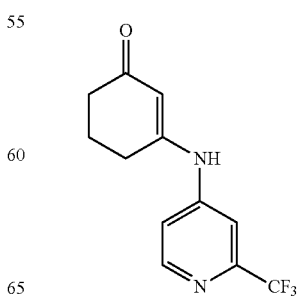

3-(2-(trifluoromethyl)pyridin-4-ylamino)cyclohex-2-enone

A mixture of cyclohexane-1,3-dione (2.00 g, 17.8 mmol), 4-amino-2-trifluormethylpyridine (2.89 g, 17.8 mmol) and glacial acetic acid (10 mL) is heated at 130° C. for 4 h. The mixture cooled at room temperature, diluted with ethyl acetate and extracted three times with water. The phases are separated, and the aqueous layer is extracted with ethyl acetate. The combined organic layers are dried over $Na_2SO_4$ and concentreated under reduced pressure. The residue is purified by flash chromatography on silica (gradient dichloromethane/is methanol 95:5). Yield: 940 mg; ESI mass spectrum $[M+H]^+$=257; Retention time HPLC: 0.80 min (V011_S01).

Intermediate 56

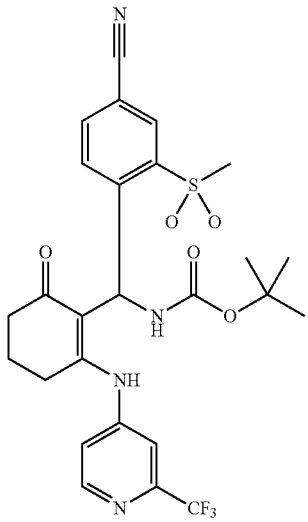 [SMILES: CC(C)(C)OC(=O)NC(C1=C(Nc2ccnc(C(F)(F)F)c2)CCCC1=O)c1ccc(C#N)cc1S(C)(O)O]

tert-Butyl (4-Cyano-2-(methylsulfonyl)phenyl)(6-oxo-2-(2-(trifluoromethyl)pyridin-4-ylamino)cyclohex-1-enyl)methylcarbamate Step 1 tert-Butyl (4-Cyano-2-(methylsulfonyl)phenyl)(phenylsulfonyl)methylcarbamate

Formic acid (4.1 mL, 109 mmol) is added to a mixture of tert-butyl carbamate (2.00 g, 17.1 mmol), 4-formyl-3-(methylsulfonyl)benzonitrile (3.57 g, 17.1 mmol) and sodium benzenesulfinate (2.80 g, 17.1 mmol) in a mixture of tetrahydrofuran (12 mL) and water (48 mL), and the mixture is stirred at room temperature for 5 days. Water (60 mL) is added, and the precipitated is filtered, washed with water and dried. Yield: 5.00 g.

Step 2 tert-Butyl (4-Cyano-2-(methylsulfonyl)phenyl)(6-oxo-2-(2-(trifluoromethyl)pyridin-4-ylamino)cyclohex-1-enyl)methylcarbamate Sodium hydride (60% in mineral oil, 153 mg, 3.84 mmol) is added in portions to a mixture of tert-butyl (4-cyano-2-(methylsulfonyl)phenyl)(phenylsulfonyl)methylcarbamate (step 1, 1.60 g, 3.20 mmol based on 90% purity) and 2-methyltetrahydrofuran (15 mL), and the mixture is stirred at room temperature for 20 min. 3-(2-(Trifluoromethyl)pyridin-4-yl-amino)cyclohex-2-enone (intermediate 55, 940 mg, 3.70 mmol) is added, and the mixture is stirred for 2 h. Water is added, and the phases are separated. The organic layer is washed with water and concentrated under reduced pressure. The residue is purified by flash chromatography on silica (gradient dichloromethane/methanol 99:1 to 97/3). Yield: 2.10 g; ESI mass spectrum $[M+H]^+$=565; Retention time HPLC: 0.67 min (X012_S02).

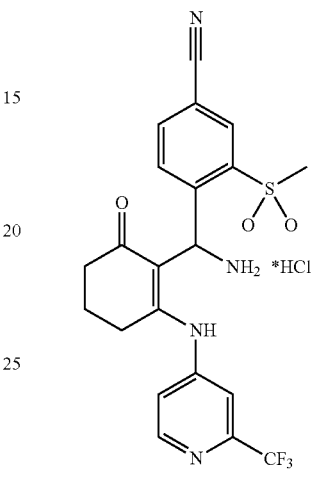

Intermediate 57

4-(Amino(6-oxo-2-(2-(trifluoromethyl)pyridin-4-ylamino)cyclohex-1-enyl)methyl)-3-(methylsulfonyl)benzonitrile hydrochloride Hydrogen chloride (4 M in 1,4-dioxane, 4.7 mL, 18.6 mmol) is added to a solution of tert-butyl (4-cyano-2-(methylsulfonyl)phenyl)(6-oxo-2-(2-(trifluoromethyl)pyridin-4-ylamino)-cyclohex-1-enyl)methylcarbamate (intermediate 56, 2.10 g, 3.72 mmol) in acetonitrile (15 mL), and the mixture is stirred at room temperature for 3 h. All volatiles are removed under reduced pressure, and the residue is recrystallized from acetonitrile. Yield: 970 mg; ESI mass spectrum $[M+H]^+$=465; Retention time HPLC: 0.45 min (X012_S01).

Intermediate 58

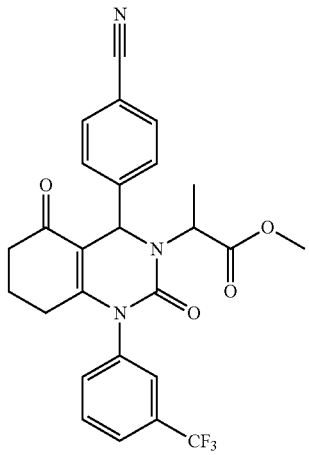 [SMILES: COC(=O)C(C)N1C(=O)N(c2cccc(C(F)(F)F)c2)C2=C(C(=O)CCC2)C1c1ccc(C#N)cc1]

Methyl 2-(4-(4-Cyanophenyl)-2,5-dioxo-1-(3-(trifluoromethyl)phenyl)-1,2,5,6,7,8-hexahydroquinazolin-3(4H)-yl)propanoate Cesium carbonate (713 mg, 2.19 mmol) is added to a solution of 4-(2,5-dioxo-1-(3-(trifluoromethyl)phenyl)1,2,3,4,5,6,7,8octahydroquinazolin-4-yl)-benzonitrile (example 1, 300 mg, 0.73 mmol) and methyl 2-bromopropanoate (244 mg, 1.46 mmol) in N,N-dimethylformamide (10 mL), and the mixture is stirred at 50° C. for 6 h and at room temperature over night. Water is added, and the mixture is extracted with dichloromethane. The organic layer is extracted with water and brine, dried over MgSO$_4$ and concentrated under reduced pressure. Yield: 353 mg; ESI mass spectrum [M+H]$^+$=498; Retention time HPLC: 0.97 min (Z018_S04).

Intermediate 59

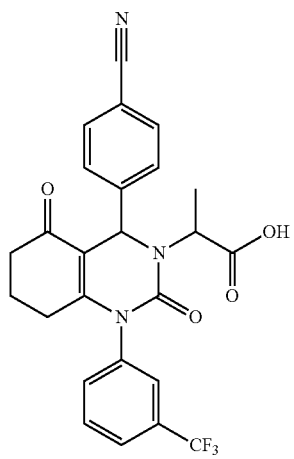 [SMILES: CC(C(=O)O)N1C(=O)N(c2cccc(C(F)(F)F)c2)C2=C(C(=O)CCC2)C1c1ccc(C#N)cc1]

2-(4-(4-Cyanophenyl)-2,5-dioxo-1-(3-(trifluoromethyl)phenyl)-1,2,5,6,7,8-hexahydroquinazolin-3(4H)-yl)propanoic acid Aqueous lithium hydroxide (2 M, 1.06 mL, 2.12 mmol) is added to a solution of methyl 2-(4-(4-cyanophenyl)-2,5-dioxo-1-(3-(trifluoromethyl)phenyl)-1,2,5,6,7,8-hexahydroquinazolin-3(4H)-yl)propanoate (intermediate 58, 350 mg, 0.70 mmol), and the mixture is stirred at room temperature over night. Water and dichloromethane are added, and the phases are separated. The organic layer is discarded, and the aqueous layer is acidified with aqueous hydrogen chloride (1 M) and extracted with dichloromethane. The organic phase is dried over MgSO$_4$ and concentrated under reduced pressure. Yield: 274 mg; ESI mass spectrum [M+H]$^+$=484; Retention time HPLC: 0.90 min (Z018_S04).

Intermediate 60

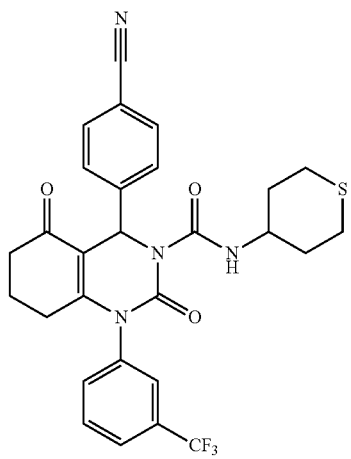 [SMILES: N#Cc1ccc(C2C3=C(CCCC3=O)N(c3cccc(C(F)(F)F)c3)C(=O)N2C(=O)NC2CCSCC2)cc1]

4-(4-Cyanophenyl)-2,5-dioxo-N-(tetrahydro-2H-thiopyran-4-yl)-1-(3-(trifluoromethyl)phenyl)-1,2,5,6,7,8-hexahydroquinazoline-3(4H)-carboxamide Tetrahydro-2H-thiopyran-4-amine (76 mg, 0.65 mmol) is added to a solution of 4-nitrophenyl 4-(4-cyanophenyl)-2,5-dioxo-1-(3-(trifluoromethyl)phenyl)1,2,5,6,7,8-hexahydroquinazoline-3(4H)-carboxylate (intermediate 37, 220 mg, 0.32 mmol) in acetonitrile (6 mL), and the mixture is stirred at room temperature for 30 min and purified by reversed phase HPLC (Waters SunFire™-C$_{18}$, gradient of acetonitrile in water, 0.1% TFA). Yield: 168 mg; ESI mass spectrum [M+H]$^+$=555; Retention time HPLC: 1.19 min (Z018_S04).

SYNTHESES OF EXAMPLES

Example 1

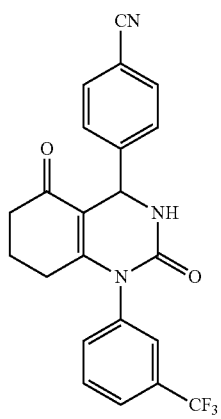 [SMILES: N#Cc1ccc(C2NC(=O)N(c3cccc(C(F)(F)F)c3)C3=C2C(=O)CCC3)cc1]

4-(2,5-Dioxo-1-(3-(trifluoromethyl)phenyl)-1,2,3,4,5,6,7,8-octahydroquinazolin-4-yl)-benzonitrile Method A:
Under an atmosphere of argon, a mixture of 4-(4-bromophenyl)-1-(3-(trifluoromethyl)-phenyl)-3,4,7,8-tetrahydroquinazoline-2,5(1H,6H)-dione (intermediate 3, 5.10 g, 10.96 mmol), zinc cyanide (1.50 g, 12.8 mmol) and tetrakis(triphenylphosphine)-palladium(O) (600 mg, 0.52 mmol) in N,N-dimethylformamide (5 mL) is heated at 90° C. for 2 h. Water is added and the mixture is filtered. The precipitate is purified by flash chromatography on silica (gradient dichloromethane/methanol 100:0 to 98:2). Yield: 2.40 g; ESI mass spectrum [M+H]$^+$=412; Retention time HPLC: 1.29 min (V001_006).

Method B:

A solution of 4-(chloro(isocyanato)methyl)benzonitrile (intermediate 2, 2.20 g, 11.4 mmol) in dichloromethane (15 mL) is added to a solution of 3-(3-(trifluoromethyl)phenylamino)-cyclohex-2-enone (2.24 g, 8.78 mmol) and the mixture is heated at reflux for 4 h. All volatiles are evaporated and the residue is purified by flash chromatography on silica (gradient cyclohexane/ethyl acetate 80:20 to 40:60). Yield: 550 mg; ESI mass spectrum [M+H]$^+$=412; Retention time HPLC: 1.29 min (V001_006).

Methode C:

Sodium tert-butoxide (2.55 g, 26.5 mmol) is added to a mixture of 1-((4-cyanophenyl)-(2-ethoxy-6-oxocyclohex-1-enyl)methyl)-3-(3-(trifluoromethyl)phenyl)urea (intermediate 5, 10.1 g, 22.1 mmol) and acetonitrile (100 mL). After 20 min the mixture is filtered and the precipitate is washed with acetonitrile and methyl tert-butyl ether. The precipitate is mixed with water (300 mL) and the suspension is stirred for 1 h. The precipitate is filtered again and dried under reduced pressure. Yield: 5.24 g; ESI mass spectrum [M+H]$^+$=412; Retention time HPLC: 0.88 min (Z018_S04).

Examples 1A and 1B: Enantiomers of 1

The enantiomers of racemic 4-(2,5-dioxo-1-(3-(trifluoromethyl)phenyl)-1,2,3,4,5,6,7,8-octahydroquinazolin-4-yl)-benzonitrile (example 1, 260 mg, 462 mmol) are separated by preparative supercritical fluid chromatography on a chiral phase (Daicel Chiralpak ADH, 2×10 mm×250 mm, 5 µm, 15% MeOH+0.2% diethylamine in supercritical CO$_2$, 40° C., 120 bar back pressure).

Example 1A

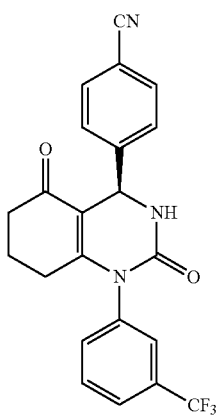 [SMILES: N#Cc1ccc([C@H]2NC(=O)N(c3cccc(C(F)(F)F)c3)C3=C2C(=O)CCC3)cc1]

(R)-4-(2,5-Dioxo-1-(3-(trifluoromethyl)phenyl)-1,2,3,4,5,6,7,8-octahydroquinazolin-4-yl)benzonitrile Yield: 75 mg; ESI mass spectrum [M+H]$^+$=412; Retention time: 3.45 min (late eluting enantiomer) (I_ADH_20_MeOH_DEA).

Example 1B

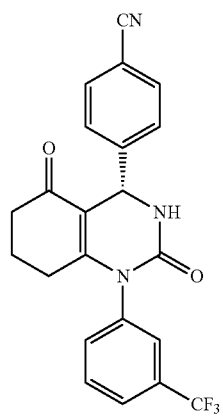 [SMILES: N#Cc1ccc([C@@H]2NC(=O)N(c3cccc(C(F)(F)F)c3)C3=C2C(=O)CCC3)cc1]

(S)-4-(2,5-Dioxo-1-(3-(trifluoromethyl)phenyl)-1,2,3,4,5,6,7,8-octahydroquinazolin-4-yl)benzonitrile Yield: 75 mg; ESI mass spectrum [M+H]$^+$=412; Retention time: 3.02 min (early eluting enantiomer) (I_ADH_20_MeOH_DEA).

Example 2

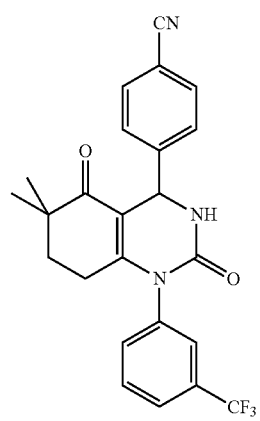 [SMILES: CC1(C)CCC2=C(C1=O)C(c1ccc(C#N)cc1)NC(=O)N2c1cccc(C(F)(F)F)c1]

4-(6,6-Dimethyl-2,5-dioxo-1-(3-(trifluoromethyl)phenyl)-1,2,3,4,5,6,7,8-octahydroquinazolin-4-yl)benzonitrile Under an atmosphere of argon, a mixture of 4-(4-bromophenyl)-6,6-dimethyl-1-(3-(tri-fluoromethyl)phenyl)-3,4,7,8-tetrahydroquinazoline-2,5(1H,6H)-dione (intermediate 7, 372 mg, 0.754 mmol), zinc cyanide (110 mg, 0.937 mmol) and tetrakis(triphenyl-phosphine)palladium(O) (50 mg, 43 μmol) in N,N-dimethylformamide (2 mL) is heated at 110° C. over night. Water is added and the mixture is filtered. The precipitate is purified by flash chromatography on silica (gradient cyclohexane/ethyl acetate 80:20 to 60:40). Yield: 220 mg; ESI mass spectrum [M+H]⁺=440; Retention time HPLC: 1.26 min (Z005_001).

Example 3

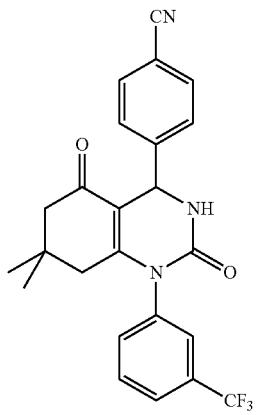

4-(7,7-Dimethyl-2,5-dioxo-1-(3-(trifluoromethyl)phenyl)-1,2,3,4,5,6,7,8-octahydroquinazolin-4-yl)benzonitrile The title compound is prepared in analogy to 4-(6,6-dimethyl-2,5-dioxo-1-(3-(trifluoromethyl)phenyl)-1,2,3,4,5,6,7,8-octahydroquinazolin-4-yl)benzonitrile (example 2), using 4-(4-bromophenyl)-7,7-dimethyl-1-(3-(trifluoromethyl)phenyl)-3,4,7,8-tetrahydroquinazoline-2,5(1H,6H)-dione (intermediate 9, 389 mg, 0.789 mmol) as starting material. Yield: 125 mg; ESI mass spectrum [M+H]⁺=440; Retention time HPLC: 1.22 min (Z005_001).

Example 4

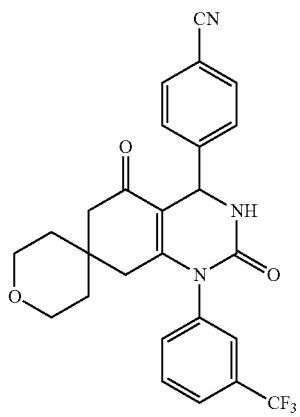 [SMILES: N#Cc1ccc(C2NC(=O)N(c3cccc(C(F)(F)F)c3)C3=C2C(=O)CC2(CCOCC2)C3)cc1]

4-(2',5'-Dioxo-1'-(3-(trifluoromethyl)phenyl)-2,2',3,3',4',5,5',6,6',8'-decahydro-1'H-spiro[pyran-4,7'-quinazoline]-4'-yl)benzonitrile Potassium tert-butoxide (49 mg, 0.44 mmol) is added to a solution of 1-((4-cyanophenyl)-(8-methoxy-10-oxo-3-oxaspiro[5.5]undec-8-en-9-yl)methyl)-3-(3-(trifluoromethyl)phenyl)urea (intermediate 11, 224 mg, 0.44 mmol) in N,N-dimethylformamide (3 mL). The mixture is stirred at room temperature over night and then purified by reversed phase HPLC (Waters Xbridge™-C₁₈, gradient of acetonitrile in water, 0.1% TFA). Yield: 21 mg; ESI mass spectrum [M+H]⁺=482, Retention time HPLC: 1.04 min (V011_S01).

Example 5

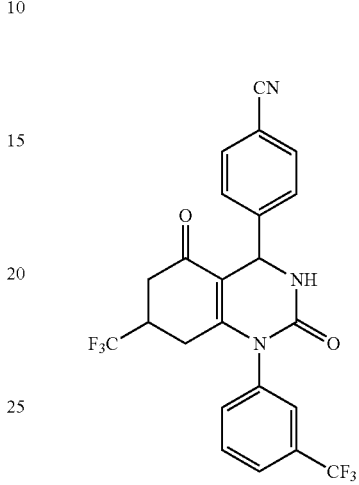

4-(2,5-Dioxo-7-(trifluoromethyl)-1-(3-(trifluoromethyl)phenyl)-1,2,3,4,5,6,7,8-octahydroquinazolin-4-yl)benzonitrile Sodium tert-butoxide (364 mg, 3.79 mmol) is added to a solution of 1-((4-cyanophenyl)-(2-ethoxy-6-oxo-4-(trifluoromethyl)cyclohex-1-enyl)methyl)-3-(3-(trifluoromethyl)phenyl)urea (intermediate 13, 1.66 g, 3.16 mmol) in acetonitrile (19 mL) and the mixture is stirred at room temperature over night. All volatiles are evaporated and the residue is purified by reversed phase HPLC (Waters Xbridge™-C₁₈, gradient of acetonitrile in water, 0.1% TFA). Yield: 90 mg; ESI mass spectrum [M+H]⁺=480, Retention time HPLC: 1.17 min (V011_S01).

Example 6

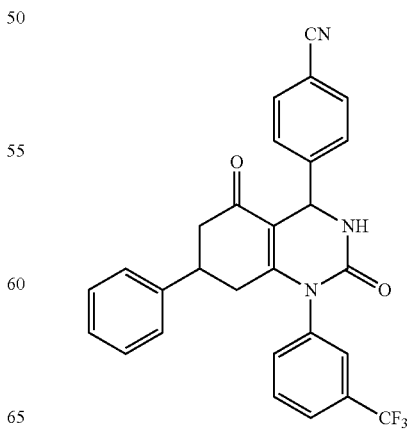

4-(2,5-dioxo-7-phenyl-1-(3-(trifluoromethyl)phe-
nyl)-1,2,3,4,5,6,7,8-octahydroquinazolin-4-yl)ben-
zonitrile The title compound is prepared in analogy to 4-(6,6-dimethyl-2,5-dioxo-1-(3-(trifluoromethyl)phenyl)-1,2,3,4,5,6,7,8-octahydroquinazolin-4-yl)benzonitrile (example 2), using 4-(4-bromophenyl)-7-phenyl-1-(3-(trifluoromethyl)phenyl)-3,4,7,8-tetrahydroquinazoline-2,5(1H,6H)-dione (intermediate 15, 287 mg, 0.53 mmol) as starting material. Yield: 82 mg; ESI mass spectrum [M+H]$^+$=488, Retention time HPLC: 1.13 min, 1.50 min (1:1 mixture of diastereomers) (Z003_001).

Example 7

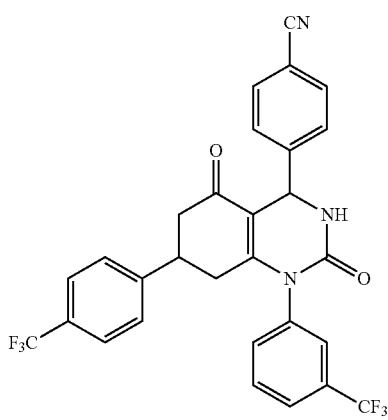 [SMILES: N#Cc1ccc(C2NC(=O)N(c3cccc(C(F)(F)F)c3)C3=C2C(=O)CC(c2ccc(C(F)(F)F)cc2)C3)cc1]

4-(2,5-Dioxo-1-(3-(trifluoromethyl)phenyl)-7-(4-(trifluoromethyl)phenyl)-1,2,3,4,5,6,7,8-octahydroquinazolin-4-yl)benzonitrile Sodium tert-butoxide (211 mg, 2.19 mmol) is added to a solution of 1-((4-cyanophenyl)-(2-ethoxy-6-oxo-4-(4-(trifluoromethyl)phenyl)cyclohex-1-enyl)methyl)-3-(3-(trifluoromethyl)phenyl)urea (intermediate 17, 825 mg, 1.37 mmol) in acetonitrile (12 mL) and the mixture is stirred at room temperature over night. Water is added and the mixture is extracted with ethyl acetate. The organic layer is dried over Na$_2$SO$_4$ and concentrated under reduced pressure. The residue is purified by flash chromatography on silica (gradient cyclohexane/ethyl acetate 100:0 to 0:100). Yield: 135 mg; ESI mass spectrum [M+H]$^+$=556, Retention time HPLC: 1.27 min, 1.29 min (1:1 mixture of diastereomers) (V011_S01).

Example 8

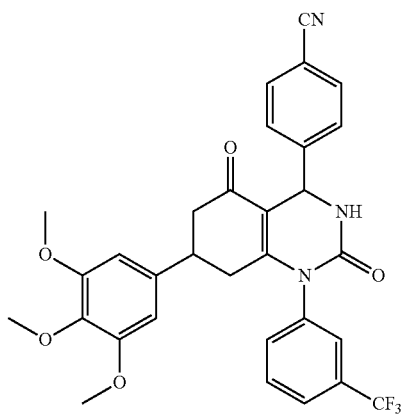 [SMILES: COc1cc(C2CC(=O)C3=C(C2)N(c2cccc(C(F)(F)F)c2)C(=O)NC3c2ccc(C#N)cc2)cc(OC)c1OC]

4-(2,5-Dioxo-1-(3-(trifluoromethyl)phenyl)-7-(3,4,5-trimethoxyphenyl)-1,2,3,4,5,6,7,8-octahydroquinazolin-4-yl)benzonitrile Sodium tert-butoxide (126 mg, 1.32 mmol) is added to a solution of 1-((4-cyanophenyl)-(2-ethoxy-6-oxo-4-(3,4,5-trimethoxyphenyl)cyclohex-1-enyl)methyl)-3-(3-(trifluoromethyl)phenyl)urea (intermediate 19, 684 mg, 1.10 mmol) in acetonitrile (8 mL) and the mixture is stirred at room temperature for 2 h. Water is added and the mixture is extracted with ethyl acetate. The organic layer is dried over Na$_2$SO$_4$ and concentrated under reduced pressure. The residue is purified by reversed phase HPLC (Waters Xbridge™-C$_{18}$, gradient of acetonitrile in water, 0.1% TFA). Yield: 190 mg; ESI mass spectrum [M+H]$^+$=578, Retention time HPLC: 1.13 min, 1.14 min (1:1 mixture of diastereomers) (V011_S01).

Example 9

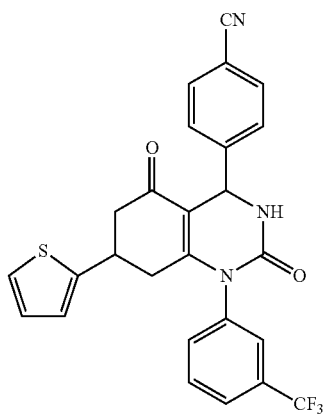 [SMILES: N#Cc1ccc(C2NC(=O)N(c3cccc(C(F)(F)F)c3)C3=C2C(=O)CC(c2cccs2)C3)cc1]

4-(2,5-Dioxo-7-(thiophen-2-yl)-1-(3-(trifluoromethyl)phenyl)-1,2,3,4,5,6,7,8-octahydroquinazolin-4-yl)benzonitrile Sodium tert-butoxide (108 mg, 1.13 mmol) is added to a solution of 1-((4-cyanophenyl)-(2-ethoxy-6-oxo-4-(thiophen-2-yl)cyclohex-1-enyl)methyl)-3-(3-(trifluoromethyl)phenyl)-urea (intermediate 21, 507 mg, 0.94 mmol) in acetonitrile (6 mL) and the mixture is stirred at room temperature over night. Water is added and the mixture is extracted with ethyl acetate. The organic layer is dried over $Na_2SO_4$ and concentrated under reduced pressure. The residue is purified two times by reversed phase HPLC (first purification: Waters Xbridge™-$C_{18}$, gradient of acetonitrile in water, 0.1% TFA; second purification: Waters Xbridge™-$C_{18}$, gradient of acetonitrile in water, 0.1% $NH_3$). Yield: 31 mg; ESI mass spectrum $[M+H]^+=494$, Retention time HPLC: 1.18 min, 1.20 min (1:1 mixture of diastereomers) (V011_S01).

Example 10

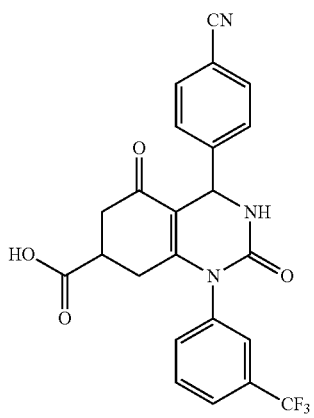 [SMILES: N#Cc1ccc(C2NC(=O)N(c3cccc(C(F)(F)F)c3)C3=C2C(=O)CC(C(=O)O)C3)cc1]

4-(4-Cyanophenyl)-2,5-dioxo-1-(3-(trifluoromethyl)phenyl)-1,2,3,4,5,6,7,8-octahydroquinazoline-7-carboxylic acid Under an atmosphere of argon, a mixture of 4-(4-Bromophenyl)-2,5-dioxol-(3-(trifluoromethyl)phenyl)-1,2,3,4,5,6,7,8-octahydroquinazoline-7-carboxylic acid (intermediate 23, 760 mg, 1.49 mmol), zinc cyanide (300 mg, 2.56 mmol) and tetrakis(triphenylphosphine)-palladium(O) (170 mg, 0.15 mol) in N,N-dimethylformamide (8 mL) is heated at 110° C. over night. Water is added and the mixture is filtered. The precipitate is purifed by flash chromatography on silica (gradient dichloromethane/methanol 100:0 to 99:1). Yield: it) 210 mg; ESI mass spectrum $[M+H]^+=456$; Retention time HPLC: 0.61 min, 0.64 min (1:1 mixture of diastereomers) (VO11_S01

Example 11

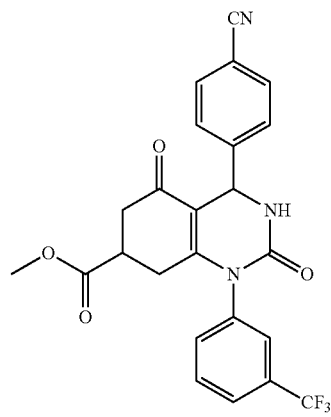 [SMILES: COC(=O)C1CC(=O)C2=C(C1)N(c1cccc(C(F)(F)F)c1)C(=O)NC2c1ccc(C#N)cc1]

Methyl 4-(4-Cyanophenyl)-2,5-dioxo-1-(3-(trifluoromethyl)phenyl)-1,2,3,4,5,6,7,8-octahydroquinazoline-7-carboxylate A mixture of 4-(4-cyanophenyl)-2,5-dioxo-1-(3-(trifluoromethyl)phenyl)-1,2,3,4,5,6,7,8-octahydroquinazoline-7-carboxylic acid (example 10, 70 mg, 0.154 mmol) and hydrogen chloride (1.3 M in methanol, 1.0 mL, 1.3 mmol) is stirred at 50° C. for 72 h.

All volatiles are evaporated and the residue is purified by reversed phase HPLC (Waters Xbridge™-$C_{18}$, gradient of methanol in water, 0.1% TFA). Yield: 11 mg; ESI mass spectrum $[M+H]^+=470$; Retention time HPLC: 1.19 min, 1.21 min (1:1 mixture of diastereomers) (V001_006).

Example 12

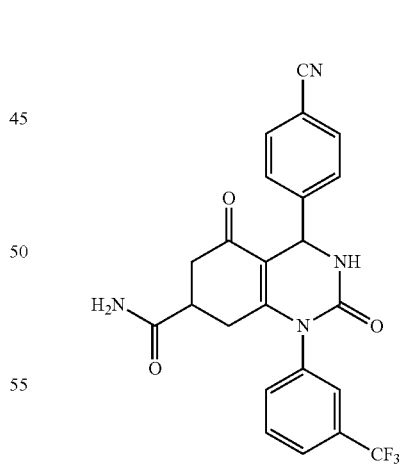

4-(4-Cyanophenyl)-2,5-dioxo-1-(3-(trifluoromethyl)phenyl)-1,2,3,4,5,6,7,8-octahydroquinazoline-7-carboxamide N,N,N',N'-Tetramethyl-O-(benzotriazol-1-yl)uronium tetrafluoroborate (50 mg, 0.16 mmol) and N,N-diisopropylethylamine (60 μL, 0.34 mmol) are added to a solution of 4-(4-cyanophenyl)-2,5-dioxo-1-(3-(trifluoromethyl)phenyl)-1,2,3,4,5,6,7,8-octahydroquinazoline-7-carboxylic acid (example 10, 70 mg, 0.154 mmol) in N,N-dimethylformamide (1.0 mL). After 10 min aqueous ammonia (35%, 0.5 mL) is added and the mixture is stirred at room temperature for 1 h. Water is added and the mixture is extracted with diethyl ether. The organic layer is concentrated under reduced pressure, and the residue is purified by reversed phase HPLC (Waters Xbridge™-C$_{18}$, gradient of methanol in water, 0.1% TFA). Yield: 15 mg; ESI mass spectrum [M+H]$^+$=455; Retention time HPLC: 1.02 min (V001_006).

Example 13

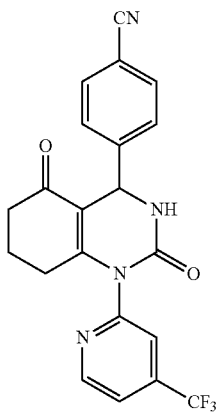

4-(2,5-Dioxo-1-(4-(trifluoromethyl)pyridin-2-yl)-1,2,3,4,5,6,7,8-octahydroquinazolin-4-yl)benzonitrile Potassium tert-butoxide (47 mg, 0.421 mmol) is added to a solution of 1-((4-cyanophenyl)-(2-methoxy-6-oxocyclohex-1-enyl)methyl)-3-(6-(trifluoromethyl)pyridin-2-yl)urea (intermediate 25, 200 mg, 0.405 mmol) in N,N-dimethylformamide (3 mL). The mixture is stirred at room temperature for 1 h and concentrated under reduced pressure. The residue is purified by reversed phase HPLC (Waters Xbridge™-C$_{18}$, gradient of acetonitrile in water, 0.1% NH$_3$). Yield: 9 mg; ESI mass spectrum [M+H]$^+$=413; Retention time HPLC: 1.02 min (V012_S01).

Example 14

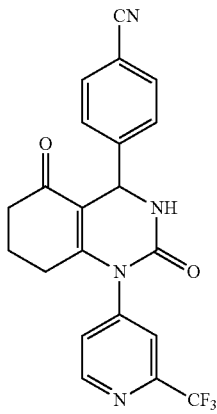

4-(2,5-Dioxo-1-(2-(trifluoromethyl)pyridin-4-yl)-1,2,3,4,5,6,7,8-octahydroquinazolin-4-yl)benzonitrile Potassium tert-butoxide (15.8 mg, 0.140 mmol) is added to a solution of 1-((4-cyanophenyl)(2-methoxy-6-oxocyclohex-1-enyl)methyl)-3-(2-(trifluoromethyl)pyridin-4-yl)urea (intermediate 27, 60 mg, 0.135 mmol) in N,N-dimethylformamide (1 mL). The mixture is stirred at room temperature over night and then purified by reversed phase HPLC (Waters Xbridge™-C$_{18}$, gradient of acetonitrile in water, 0.1% TFA). Yield: 9 mg; ESI mass spectrum [M+H]$^+$=413; Retention time HPLC: 1.01 min (V012_S01).

Example 15

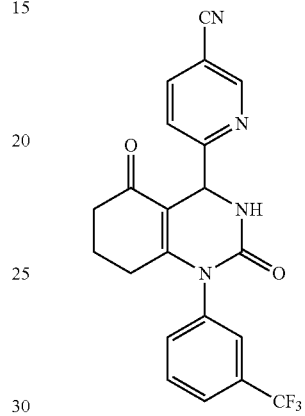

6-(2,5-Dioxo-1-(3-(trifluoromethyl)phenyl)-1,2,3,4,5,6,7,8-octahydroquinazolin-4-yl)-nicotinonitrile Potassium tert-butoxide (53 mg, 0.475 mmol) is added to a solution of 14(5-cyanopyridin-2-yl)(2-methoxy-6-oxocyclohex-1-enyl)methyl)-3-(3-(trifluoromethyl)phenyl)urea (intermediate 29, 203 mg, 0.458 mmol) in N,N-dimethylformamide (4 mL). The mixture is stirred at room temperature over night, and another portion of potassium tert-butoxide (26 mg, 0.23 mmol) is added. After 30 min, the mixture is concentrated under reduced pressure, and the residue is purified by reversed phase HPLC (Waters Xbridge-C$_{18}$, gradient of acetonitrile in water, 0.1% NH$_3$). Yield: 5 mg; ESI mass spectrum [M+H]$^+$=413; Retention time HPLC: 1.02 min (V011_S01).

Example 16

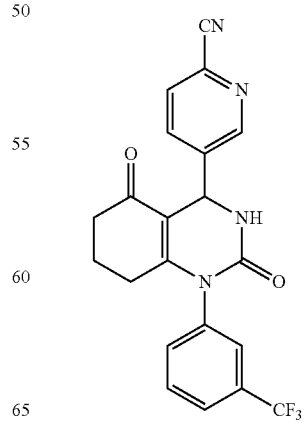

5-(2,5-dioxo-1-(3-(trifluoromethyl)phenyl)-1,2,3,4,5,6,7,8-octahydroquinazolin-4-yl)-picolinonitrile Potassium tert-butoxide (63 mg, 0.56 mmol) is added to a solution of 14(6-cyanopyridin-3-yl)(2-methoxy-6-oxocyclohex-1-enyl)methyl)-3-(3-(trifluoromethyl)phenyl)urea (intermediate 31, 240 mg, 0.54 mmol) in N,N-dimethylformamide (5 mL). The mixture is stirred at room temperature for 30 min and concentrated under reduced pressure. The residue is purified by reversed phase HPLC (Waters Xbridge™-C$_{18}$, gradient of acetonitrile in water, 0.1% NH$_3$). Yield: 30 mg; ESI mass spectrum [M+H]$^+$=413; Retention time HPLC: 1.02 min (V011_S01).

Example 17

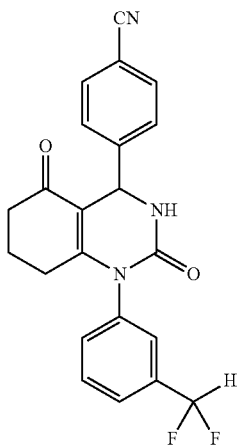 [SMILES: N#Cc1ccc(C2NC(=O)N(c3cccc(C(F)F)c3)C3=C2C(=O)CCC3)cc1]

4-(1-(3-(Difluoromethyl)phenyl)-2,5-dioxo-1,2,3,4,5,6,7,8-octahydroquinazolin-4-yl)-benzonitrile Under an atmosphere of argon, a mixture of 4-(4-bromophenyl)-1-(3-(difluoromethyl)-phenyl)-3,4,7,8-tetrahydroquinazoline-2,5(1H,6H)-dione (intermediate 33, 75 mg, 0.168 mmol), zinc cyanide (34 mg, 0.290 mmol) and tetrakis (triphenylphosphine)-palladium(0) (20 mg, 17 µmol) in N,N-dimethylformamide (1 mL) is heated at 110° C. for 2 h and cooled to room temperature. Water is added and the mixture is extracted twice with dichloromethane. The combined organic layers are dried over Na$_2$SO$_4$ and concentrated under reduced pressure. The residue is purified by flash chromatography on silica (gradient cyclohexane/ethyl acetate 100:0 to 0:100). Yield: 30 mg; ESI mass spectrum [M+H]$^+$=394; Retention time HPLC: 0.53 min (X012_S01).

Example 18

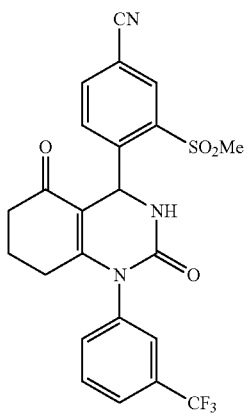 [SMILES: CS(=O)(=O)c1cc(C#N)ccc1C1NC(=O)N(c2cccc(C(F)(F)F)c2)C2=C1C(=O)CCC2]

4-(2,5-Dioxo-1-(3-(trifluoromethyl)phenyl)-1,2,3,4,5,6,7,8-octahydroquinazolin-4-yl)-3-(methylsulfonyl)benzonitrile Under an atmosphere of argon, a mixture of 4-(4-bromo-2-(methylsulfonyl)phenyl)-1-(3-(trifluoromethyl)phenyl)-3,4,7,8-tetrahydroquinazoline-2,5(1H,6H)-dione (intermediate 34), zinc cyanide (22 mg, 0.191 mmol) and tetrakis (triphenylphosphine)-palladium(0) (17 mg, 15 pot) in N,N-dimethylformamide (1 mL) is heated at 110° C. over night. Water is added and the mixture is filtered. The precipitate is purifed by flash chromatography on silica (gradient cyclohexane/ethyl acetate 80:20 to 50:50). Yield: 47 mg; ESI mass spectrum [M+H]$^+$=490; Retention time HPLC: 0.98 min (Z012_S04).

Examples 18A and 18B

Enantiomers of Example 18

The enantiomers of racemic 4-(2,5-dioxo-1-(3-(trifluoromethyl)phenyl)-1,2,3,4,5,6,7,8-octahydroquinazolin-4-yl)-3-(methylsulfonyl)benzonitrile (example 18, 40 mg, 82 µmol) are separated by preparative supercritical fluid chromatography on a chiral phase (Daicel Chiralpak IB, 10 mm×250 mm, 5 µm, 20% MeOH+0.2% diethylamine in supercritical CO$_2$, 40° C., 120 bar back pressure).

Example 18A

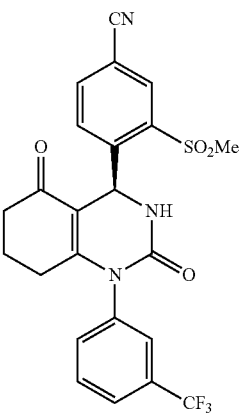 [SMILES: CS(=O)(=O)c1cc(C#N)ccc1[C@H]1NC(=O)N(c2cccc(C(F)(F)F)c2)C2=C1C(=O)CCC2]

(S)-4-(2,5-Dioxo-1-(3-(trifluoromethyl)phenyl)-1,2,3,4,5,6,7,8-octahydroquinazolin-4-yl)-3-(methylsulfonyl)benzonitrile Yield: 14 mg; ESI mass spectrum [M+H]$^+$=490; Retention time: 1.99 min (early eluting enantiomer) (I_IB_20_MeOH_DEA).

Example 18B

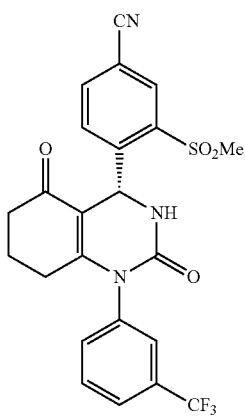 [SMILES: CS(=O)(=O)c1cc(C#N)ccc1[C@@H]1NC(=O)N(c2cccc(C(F)(F)F)c2)C2=C1C(=O)CCC2]

(R)-4-(2,5-Dioxo-1-(3-(trifluoromethyl)phenyl)-1,2,
3,4,5,6,7,8-octahydroquinazolin-4-yl)-3-(methylsulfonyl)benzonitrile Yield: 9 mg; ESI mass spectrum [M+H]$^+$=490; Retention time: 2.66 min (late eluting enantiomer) (I_IB_20_MeOH_DEA).

Example 19

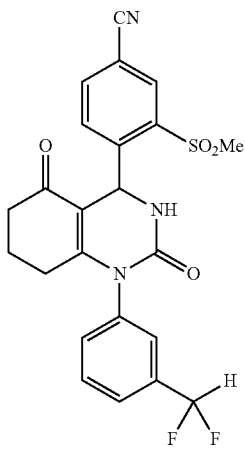 [SMILES: CS(=O)(=O)c1cc(C#N)ccc1C1NC(=O)N(c2cccc(C(F)F)c2)C2=C1C(=O)CCC2]

4-(1-(3-(Difluoromethyl)phenyl)-2,5-dioxo-1,2,3,4,
5,6,7,8-octahydroquinazolin-4-yl)-3-(methylsulfonyl)benzonitrile The title compound is prepared in analogy to 4-(2,5-dioxo-1-(3-(trifluoromethyl)phenyl)-1,2,3,4,5,6,7,8-octahydroquinazolin-4-yl)-3-(methyl sulfonyl)benzonitrile (example 18), using 4-(4-bromo-2-(methylsulfonyl)phenyl)-1-(3-(difluoromethyl)phenyl)-3,4,7,8-tetrahydroquinazoline-2,5(1H,6H)-dione (intermediate 36) as starting material. Yield: 185 mg; ESI mass spectrum [M+H]$^+$=472; Retention time HPLC: 0.93 min (Z012_S04).

Examples 19A and 19B

Enantiomers of Example 19

The enantiomers of racemic 4-(1-(3-(difluoromethyl)phenyl)-2,5-dioxo-1,2,3,4,5,6,7,8-octahydroquinazolin-4-yl)-3-(methylsulfonyl)benzonitrile (example 19, 130 mg, 0.276 mmol) are separated by preparative supercritical fluid chromatography on a is chiral phase (Daicel Chiralpak IB, 10×250 mm, 5 μm, 15% MeOH+0.2% diethylamine in supercritical $CO_2$, 40° C., 120 bar back pressure).

Example 19A

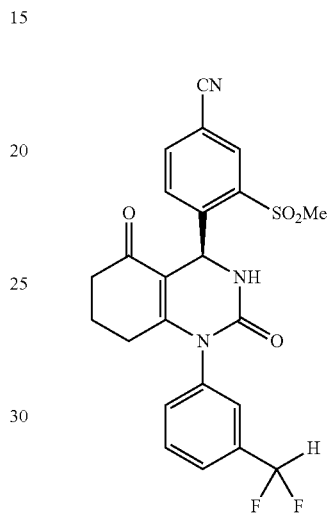

(S)-4-(1-(3-(Difluoromethyl)phenyl)-2,5-dioxo-1,2,
3,4,5,6,7,8-octahydroquinazolin-4-yl)-3-(methylsulfonyl)benzonitrile Yield: 47 mg; ESI mass spectrum [M+H]$^+$=472; Retention time: 4.93 min (early eluting enantiomer) (I_IB_20_IPROP_DEA).

Example 19B

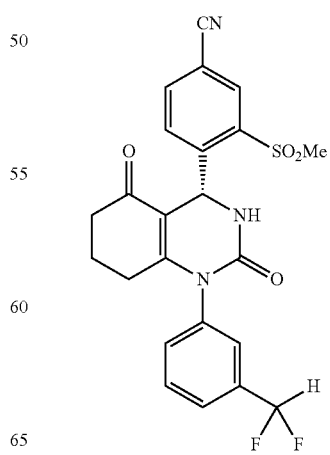

(R)-4-(1-(3-(Difluoromethyl)phenyl)-2,5-dioxo-1,2,3,4,5,6,7,8-octahydroquinazolin-4-yl)-3-(methylsulfonyl)benzonitrile Yield: 50 mg; ESI mass spectrum [M+H]⁺=472; Retention time: 5.55 min (late eluting enantiomer) (I_IB_20_IPROP_DEA).

Example 20

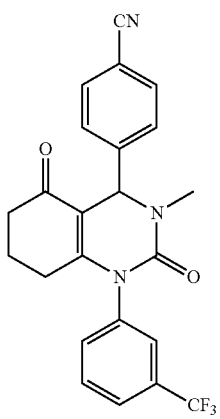

4-(1-(3-(Trifluoromethyl)phenyl)-3-methyl-2,5-dioxo-1,2,3,4,5,6,7,8-octahydroquinazolin-4-yl)benzonitrile Lithium diisopropylamide (2.0 M in tetrahydrofuran, 265 µL, 0.53 mmol) is added at 0° C. to a solution of 4-(2,5-dioxo-1-(3-(trifluoromethyl)phenyl)-1,2,3,4,5,6,7,8-octahydroquinazolin-4-yl)-benzonitrile (example 1, 200 mg, 0.486 mmol) in N,N-dimethylformamide (10 mL). Methyl iodide (40 µL, 0.64 mmol) is added and the mixture is stirred for 1 h. Water is added and the mixture is extracted twice with dichloromethane. The combined organic layers are concentrated under reduced pressure, and the residue is purified by reversed phase HPLC (Waters Xbridge™-C₁₈, gradient of acetonitrile in water, 0.1% TFA). Yield: 50 mg; ESI mass spectrum [M+H]⁺=426; Retention time HPLC: 1.29 min (V001_006).

Examples 20A and 20B

Enantiomers of Example 20

The enantiomers of racemic 4-(1-(3-(Trifluoromethyl)phenyl)-3-methyl-2,5-dioxo-1,2,3,4,5,6,7,8-octahydroquinazolin-4-yl)benzonitrile (example 20, 70 mg, 165 µmol) are separated by preparative supercritical fluid chromatography on a chiral phase (Daicel Chiralpak IC, 10 mm×250 mm, 5 µm, 20% MeOH+0.2% diethylamine in supercritical CO₂, 40° C., 120 bar back pressure).

Example 20A

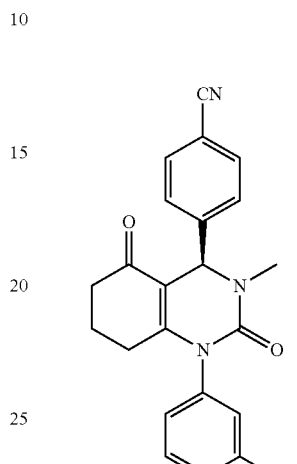

(R)-4-(1-(3-(Trifluoromethyl)phenyl)-3-methyl-2,5-dioxo-1,2,3,4,5,6,7,8-octahydroquinazolin-4-yl)benzonitrile Yield: 28 mg; ESI mass spectrum [M+H]⁺=426; Retention time: 3.76 min (early eluting enantiomer) (I_IC_20_MeOH_DEA).

Example 20B

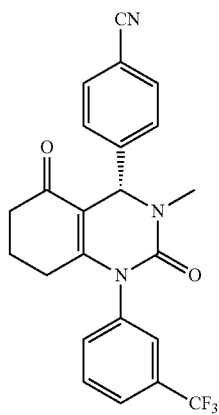 [SMILES: CN1C(=O)N(c2cccc(C(F)(F)F)c2)C2=C(C(=O)CCC2)[C@@H]1c1ccc(C#N)cc1]

(S)-4-(1-(3-(Trifluoromethyl)phenyl)-3-methyl-2,5-dioxo-1,2,3,4,5,6,7,8-octahydroquinazolin-4-yl)benzonitrile Yield: 29 mg; ESI mass spectrum [M+H]⁺=426; Retention time: 4.93 min (late eluting enantiomer) (I_IC_20_MeOH_DEA).

Example 21

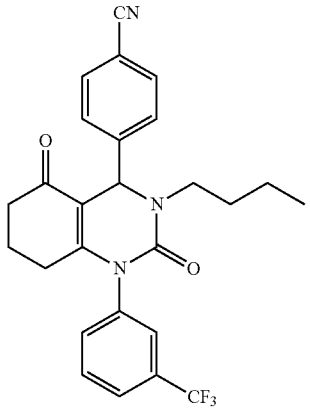 [SMILES: CCCCN1C(=O)N(c2cccc(C(F)(F)F)c2)C2=C(C(=O)CCC2)C1c1ccc(C#N)cc1]

4-(3-Butyl-1-(3-(trifluoromethyl)phenyl)-2,5-dioxo-1,2,3,4,5,6,7,8-octahydroquinazolin-4-yl)benzonitrile Lithium diisopropylamide (2.0 M in tetrahydrofuran, 135 µL, 0.27 mmol) is added at 0° C. to a solution of 4-(2,5-dioxo-1-(3-(trifluoromethyl)phenyl)-1,2,3,4,5,6,7,8-octahydroquinazolin-4-yl)-benzonitrile (example 1, 100 mg, 0.243 mmol) in N,N-dimethylformamide (5 mL). n-Butyl iodide (30 µL, 0.264 mmol) is added, and the mixture is warmed to room temperature and stirred for 2 h. Another portion of n-Butyl iodide (15 µL, 0.132 mmol) is added and the mixture is stirred over night and purified by reversed phase HPLC (Waters Xbridge™-C₁₈, gradient of acetonitrile in water, 0.1% TFA). Yield: 28 mg; ESI mass spectrum [M+H]⁺=468; Retention time HPLC: 1.47 min (V001_006).

Example 22

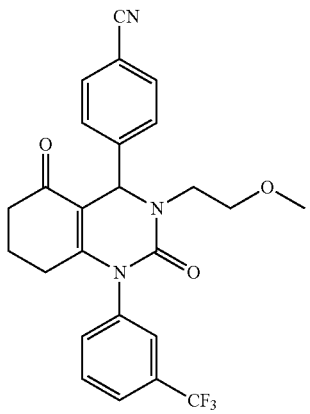 [SMILES: COCCN1C(=O)N(c2cccc(C(F)(F)F)c2)C2=C(C(=O)CCC2)C1c1ccc(C#N)cc1]

4-(1-(3-(Trifluoromethyl)phenyl)-3-(2-methoxyethyl)-2,5-dioxo-1,2,3,4,5,6,7,8-octahydroquinazolin-4-yl)benzonitrile The title compound is prepared in analogy to 4-(3-butyl-1-(3-(trifluoromethyl)phenyl)-2,5-dioxo-1,2,3,4,5,6,7,8-octahydroquinazolin-4-yl)benzonitrile (example 21), using 1-bromo-2-methoxyethane as alkylating agent. Yield: 15 mg; ESI mass spectrum [M+H]⁺=470; Retention time HPLC: 1.33 min (V001_006).

Example 23

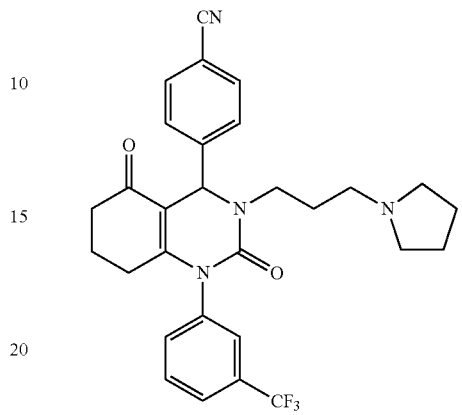

4-(1-(3-(Trifluoromethyl)phenyl)-2,5-dioxo-3-(3-(pyrrolidin-1-yl)propyl)-1,2,3,4,5,6,7,8-octahydroquinazolin-4-yl)benzonitrile In a first flask, lithium diisopropylamide (2.0 M in tetrahydrofuran, 135 µL, 0.27 mmol) is added at 0° C. to a solution of 4-(2,5-dioxo-1-(3-(trifluoromethyl)phenyl)-1,2,3,4,5,6,7,8-octahydroquinazolin-4-yl)-benzonitrile (example 1, 100 mg, 0.243 mmol) in N,N-dimethyl-formamide (3 mL, solution A). In another flask, lithium diisopropylamide (2.0 M in tetrahydrofuran, 135 µL, 0.27 mmol) is added to a solution of 1-(3-bromopropyl)pyrrolidine hydrobromide (70 mg, 0.256 mmol) in N,N-dimethylformamide (2 mL, solution B). This solution is then added to solution A and the resulting mixture is stirred at room temperature over night. Water is added, and the mixture is extracted twice with dichloromethane. The combined organic layers are dried over Na₂SO₄ and concentrated under reduced pressure. The residue is purified by reversed phase HPLC (Waters Xbridge-C₁₈, gradient of methanol in water, 0.1% TFA). Yield: 15 mg; ESI mass spectrum [M+H]⁺=523; Retention time HPLC: 1.15 min (V001_006).

Example 24

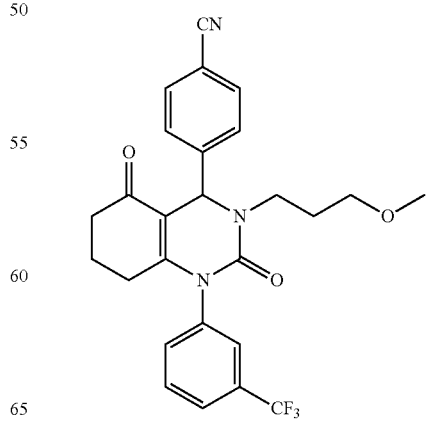

4-(1-(3-(Trifluoromethyl)phenyl)-3-(3-methoxypropyl)-2,5-dioxo-1,2,3,4,5,6,7,8-octahydroquinazolin-4-yl)benzonitrile Under an atmosphere of argon, a mixture of 4-(2,5-dioxo-1-(3-(trifluoromethyl)phenyl)-1,2,3,4,5,6,7,8-octahydroquinazolin-4-yl)-benzonitrile (example 1, 50 mg, 0.091 mmol) and 1-bromo-3-methoxypropane (15 mg, 0.10 mmol) in N,N-dimethylformamide (2 mL) is treated with lithium diisopropylamide (2.0 M in tetrahydrofuran, 55 µL, 0.11 mmol). The mixture is stirred at room temperature for 1 h and then purified by reversed phase HPLC (Waters SunFire™-C$_{18}$, gradient of acetonitrile in water, 0.1% TFA). Yield: 4 mg; ESI mass spectrum [M+H]$^+$=484; Retention time HPLC: 0.86 min (X018_S01).

The following examples of Table 2 are prepared in analogy to 4-(1-(3-(trifluoromethyl)-phenyl)-3-(3-methoxypropyl)-2,5-dioxo-1,2,3,4,5,6,7,8-octahydroquinazolin-4-yl)benzonitrite (example 24), replacing 1-bromo-3-methoxypropane with the appropriate alkyl halide as alkylating agent.

TABLE 2

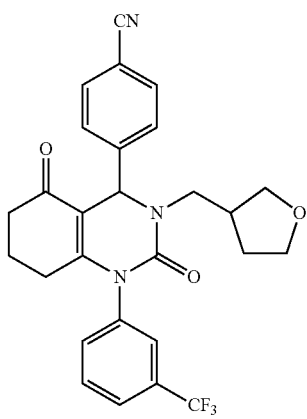 [SMILES: N#Cc1ccc(C2C3=C(CCCC3=O)N(c3cccc(C(F)(F)F)c3)C(=O)N2CC2CCOC2)cc1]

| Example | R$^3$ | MS [M + H]$^+$ | Retention time [min] | HPLC-Method |
|---|---|---|---|---|
| 24.1 | | 506 | 1.73 | W018_S01 |
| 24.2 | | 506 | 0.81 | X018_S01 |
| 24.3 | | 506 | 0.82 | X018_S01 |

Example 25

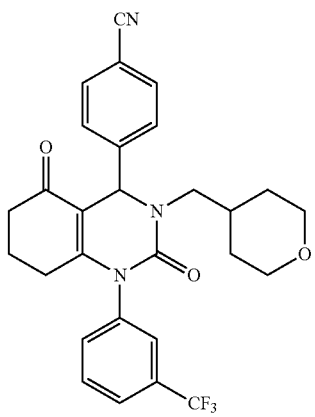 [SMILES: N#Cc1ccc(C2C3=C(CCCC3=O)N(c3cccc(C(F)(F)F)c3)C(=O)N2CC2CCOCC2)cc1]

4-(1-(3-(Trifluoromethyl)phenyl)-2,5-dioxo-3-((tetrahydrofuran-3-yl)methyl)-1,2,3,4,5,6,7,8-octahydroquinazolin-4-yl)benzonitrile Potassium carbonate (67 mg, 0.486 mmol) is added to a solution of 4-(2,5-dioxo-1-(3-(tri-fluoromethyl)phenyl)-1,2,3,4,5,6,7,8-octahydroquinazolin-4-yl)-benzonitrile (example 1, 100 mg, 0.243 mmol) in N,N-dimethylformamide (3 mL). 3-(Bromomethyl)tetrahydrofuran (60 mg, 0.365 mmol) is added, and the mixture is stirred at room temperature for 1 h and purified by reversed phase HPLC (Waters Xbridge™-C$_{18}$, gradient of acetonitrile in water, 0.1% NH$_3$). Yield: 12 mg; ESI mass spectrum [M+H]$^+$=496; Retention time HPLC: 0.91 min (Z011_S03).

Example 26

4-(1-(3-(Trifluoromethyl)phenyl)-2,5-dioxo-3-((tetrahydro-2H-pyran-4-yl)methyl)-1,2,3,4,5,6,7,8-octahydroquinazolin-4-yDbenzonitrile The title compound is prepared in analogy to 4-(1-(3-(trifluoromethyl)phenyl)-2,5-dioxo-3-((tetrahydrofuran-3-yl)methyl)-1,2,3,4,5,6,7,8-octahydroquinazolin-4-yl)benzonitrile (example 25), using 4-(bromomethyl)tetrahydro-2H- pyran as alkylating agent and stiffing the reaction mixture at room temperature for 2 d. Yield: 24 mg; ESI mass spectrum [M+H]⁺=510; Retention time HPLC: 0.92 min (Z011_S03).

Example 27

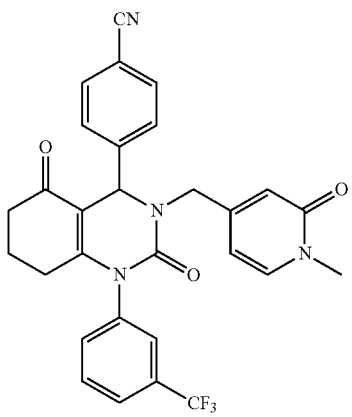 [SMILES: Cn1ccc(CN2C(=O)N(c3cccc(C(F)(F)F)c3)C3=C(C(=O)CCC3)C2c2ccc(C#N)cc2)cc1=O]

4-(1-(3-(Trifluoromethyl)phenyl)-3-((1-methyl-2-oxo-1,2-dihydropyridin-4-yl)methyl)-2,5-dioxo-1,2,3,4,5,6,7,8-octahydroquinazolin-4-yl)benzonitrile The title compound is prepared in analogy to 4-(1-(3-(trifluoromethyl)phenyl)-2,5-dioxo-3-((tetrahydrofuran-3-yl)methyl)-1,2,3,4,5,6,7,8-octahydroquinazolin-4-yl)benzonitrile (example 25), using 4-(chloromethyl)-1-methylpyridin-2(1H)-one as alkylating agent and stirring the reaction mixture at room temperature for 24 h. Yield: 60 mg; ESI mass spectrum [M+H]⁺=533; Retention time HPLC: 0.84 min (Z011_S03).

Example 28

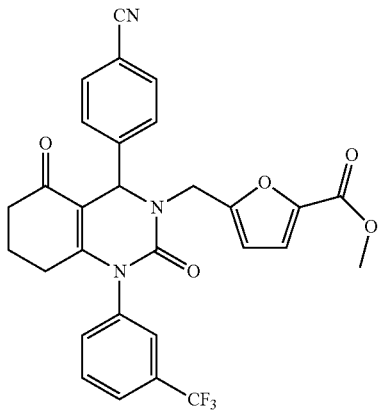 [SMILES: COC(=O)c1ccc(CN2C(=O)N(c3cccc(C(F)(F)F)c3)C3=C(C(=O)CCC3)C2c2ccc(C#N)cc2)o1]

Methyl 5-((4-(4-Cyanophenyl)-2,5-dioxo-1-(3-(trifluoromethyl)phenyl)-1,2,5,6,7,8-hexahydroquinazolin-3(4H)-yl)methyl)furan-2-carboxylate The title compound is prepared in analogy to 4-(1-(3-(trifluoromethyl)-phenyl)-2,5-dioxo-3-((tetrahydrofuran-3-yl) methyl)-1,2,3,4,5,6,7,8-octahydroquinazolin-4-yl)benzonitrile (example 25), using methyl 5-(chloromethyl)furan-2-carboxylate as alkylating agent and stirring the reaction mixture at room temperature for 5 d. Yield: 50 mg; ESI mass spectrum [M+H]⁺=550; Retention time HPLC: 0.94 min (Z011_S03).

Example 29

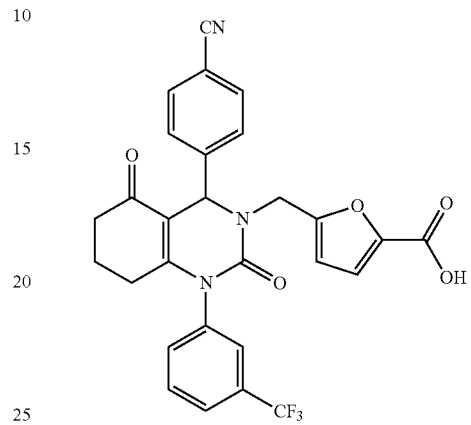

5-((4-(4-Cyanophenyl)-2,5-dioxo-1-(3-(trifluoromethyl)phenyl)-1,2,5,6,7,8-hexahydroquinazolin-3(4H)-yl)methyl)furan-2-carboxylic acid Aqueous sodium hydroxide solution (1.0 M, 100 µL, 100 µmol) is added to a solution of methyl 5-((4-(4-cyanophenyl)-2,5-dioxo-1-(3-(trifluoromethyl)phenyl)-1,2,5,6,7,8-hexahydroquinazolin-3(4H)-yl)methyl)furan-2-carboxylate (example 28, 25 mg, 45 µmol) in tetrahydrofuran (2 mL), and the mixture is at room temperature over night. Another portion of aqueous sodium hydroxide solution (4 M, 100 µL, 400 µmol) is added and stiffing was continued over night. The mixture was acidified with aqueous hydrogen chloride solution to (1 M, 100 µL, 100 µmol) and purified by reversed phase HPLC (Waters Xbridge™-C₁₈, gradient of acetonitrile in water, 0.1% TFA). Yield: 11 mg; ESI mass spectrum [M+H]⁺=536; Retention time HPLC: 0.91 min (Z018_S04).

Example 30

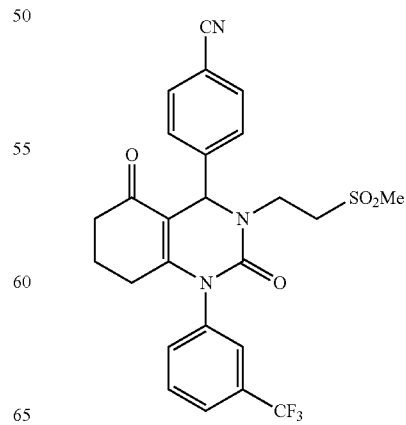

4-(3-(2-(Methylsulfonyl)ethyl)-2,5-dioxo-1-(3-(trifluoromethyl)phenyl)-1,2,3,4,5,6,7,8-octahydroquinazolin-4-yl)benzonitrile Potassium carbonate (67 mg, 0.486 mmol) and 1-bromo-2-(methylsulfonyl)ethane (68 mg, 0.365 mmol) are added to a solution of 4-(2,5-dioxo-1-(3-(trifluoromethyl)phenyl)-1,2,3,4,5,6,7,8-octahydroquinazolin-4-yl)-benzonitrile (example 1, 100 mg, 0.243 mmol) in N,N-dimethylformamide (3 mL). The mixture is heated at 50° C. for 3 d and then purified by reversed phase HPLC (first purification: Waters Xbridge™-C$_{18}$, gradient of acetonitrile in water, 0.1% NH$_3$; second purification: Waters Xbridge™-C$_{18}$, gradient of acetonitrile in water, 0.1% TFA). Yield: 22 mg; ESI mass spectrum [M+H]$^+$=518; Retention time HPLC: 0.86 min (Z011_S03).

Example 31

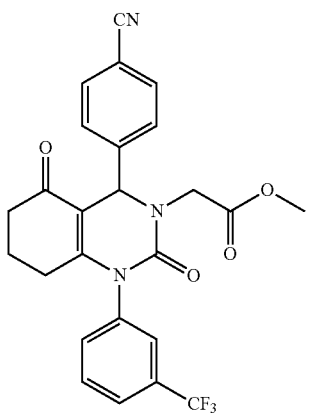 [SMILES: COC(=O)CN1C(=O)N(c2cccc(C(F)(F)F)c2)C2=C(C(=O)CCC2)C1c1ccc(C#N)cc1]

Methyl 2-(4-(4-Cyanophenyl)-2,5-dioxo-1-(3-(trifluoromethyl)phenyl)-1,2,5,6,7,8-hexahydroquinazolin-3(4H)-yl)acetate A solution of 4-(2,5-dioxo-1-(3-(trifluoromethyl)phenyl)-1,2,3,4,5,6,7,8-octahydroquinazolin-4-yl)-benzonitrile (example 1, 3.56 g, 6.12 mmol) in a mixture of N,N-dimethylformamide (10 mL) and acetonitrile (30 mL) is cooled at 0° C. in an ice bath. Lithium diisopropylamide (2.0 M in tetrahydrofuran, 6.7 mL, 13.4 mmol) is added while the temperature is kept below 5° C. Methyl bromoacetate is added dropwise while the temperature is kept below 10° C. After 1.5 h the ice bath is removed and stirring is continued over night. The mixture is concentrated under reduced pressure and the residue is purified by preparative HPLC (Waters SunFire™-C$_{18}$, gradient of acetonitrile in water, 0.1% TFA). Yield: 1.87 g; ESI mass spectrum [M+H]$^+$=484; Retention time HPLC: 0.95 min (Z018_S04).

Examples 31A and 31B

Enantiomers of Example 31

The enantiomers of racemic methyl 2-(4-(4-cyanophenyl)-2,5-dioxo-1-(3-(trifluoromethyl)-phenyl)-1,2,5,6,7,8-hexahydroquinazolin-3(4H)-yl)acetate (example 31, 220 mg, 0.46 mmol) are separated by preparative supercritical fluid chromatography on a chiral phase (Daicel Chiralpak IC, 10 mm×250 mm, 5 μm, 25% iso-PrOH+0.2% diethylamine in supercritical CO$_2$, 40° C., 120 bar back pressure).

Example 31A

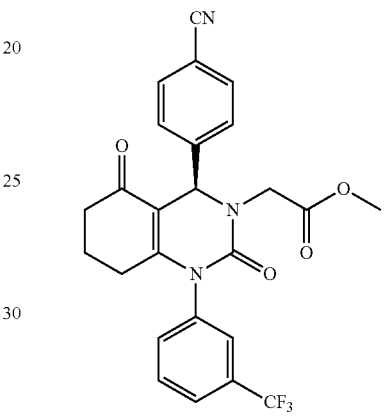

(R)-Methyl 2-(4-(4-Cyanophenyl)-2,5-dioxo-1-(3-(trifluoromethyl)phenyl)-1,2,5,6,7,8-hexahydroquinazolin-3(4H)-yl)acetate Yield: 30 mg; ESI mass spectrum [M+H]$^+$=484; Retention time: 6.66 min (early eluting enantiomer) (I_IC_25_IPROP_DEA).

Example 31B

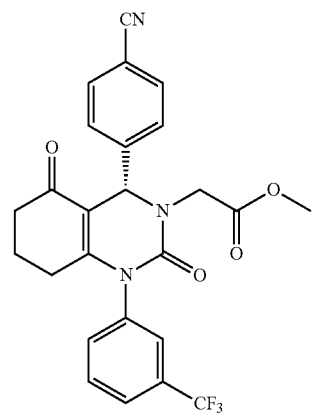 [SMILES: COC(=O)CN1C(=O)N(c2cccc(C(F)(F)F)c2)C2=C(C(=O)CCC2)[C@@H]1c1ccc(C#N)cc1]

(S)-Methyl 2-(4-(4-Cyanophenyl)-2,5-dioxo-1-(3-(trifluoromethyl)phenyl)-1,2,5,6,7,8-hexahydroquinazolin-3(4H)-yl)acetate Yield: 30 mg; ESI mass spectrum [M+H]⁺=484; Retention time: 9.33 min (late eluting enantiomer) (I_IC_25_IPROP_DEA).

Example 32

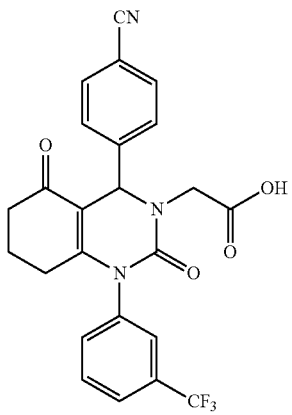 [SMILES: N#Cc1ccc(C2C3=C(CCCC3=O)N(c3cccc(C(F)(F)F)c3)C(=O)N2CC(=O)O)cc1]

2-(4-(4-Cyanophenyl)-2,5-dioxo-1-(3-(trifluoromethyl)phenyl)-1,2,5,6,7,8-hexahydroquinazolin-3(4H)-yl)acetic acid Aqueous sodium hydroxide solution (1 M, 7.27 mL, 7.27 mmol) is added to a solution of methyl 2-(4-(4-cyanophenyl)-2,5-dioxo-1-(3-(trifluoromethyl)phenyl)-1,2,5,6,7,8-hexahydroquinazolin-3(4H)-yl)acetate (example 31, 1.76 g, 3.64 mmol) in 1,4-dioxane (15 mL) and the mixture is stirred at room temperature for 1 h. Water (80 mL) is added and the mixture is extracted twice with diethyl ether. The organic phase is discarded and the aqueous phase is acidified with aqueous hydrogen chloride (1 M) and extracted three times with diethyl ether. The combined organic layers are washed with water and saturated aqueous sodium chloride, and concentrated under reduced pressure. Yield: 1.69 g; ESI mass spectrum [M+H]⁺=470; Retention time: 0.88 min (Z018_S04).

Example 32A

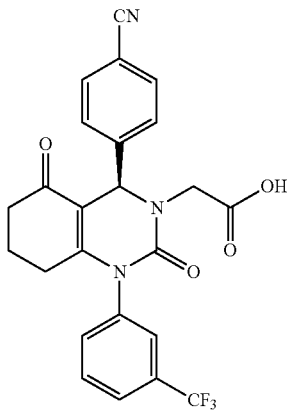 [SMILES: N#Cc1ccc([C@@H]2C3=C(CCCC3=O)N(c3cccc(C(F)(F)F)c3)C(=O)N2CC(=O)O)cc1]

(R)-2-(4-(4-Cyanophenyl)-2,5-dioxo-1-(3-(trifluoromethyl)phenyl)-1,2,5,6,7,8-hexahydroquinazolin-3(4H)-yl)acetic acid The title compound is prepared in analogy to 2-(4-(4-cyanophenyl)-2,5-dioxo-1-(3-(tri-fluoromethyl)phenyl)-1,2,5,6,7,8-hexahydroquinazolin-3(4H)-yl)acetic acid (example 32), using (R)-methyl 2-(4-(4-cyanophenyl)-2,5-dioxo-1-(3-(trifluoromethyl)phenyl)-1,2,5,6,7,8-hexahydroquinazolin-3(4H)-yl)acetate (example 31A, 30 mg, 62 μmol) as starting material. Yield: 27 mg; ESI mass spectrum [M+H]⁺=470; Retention time: 1.09 min (V001_006).

Example 32B

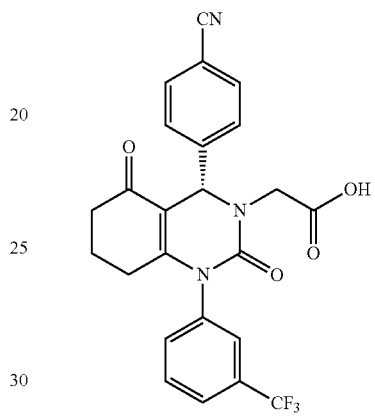

(S)-2-(4-(4-Cyanophenyl)-2,5-dioxo-1-(3-(trifluoromethyl)phenyl)-1,2,5,6,7,8-hexahydroquinazolin-3(4H)-yl)acetic acid The title compound is prepared in analogy to 2-(4-(4-cyanophenyl)-2,5-dioxo-1-(3-(tri-fluoromethyl)phenyl)-1,2,5,6,7,8-hexahydroquinazolin-3(4H)-yl)acetic acid (example 32), using (S)-methyl 2-(4-(4-cyanophenyl)-2,5-dioxo-1-(3-(trifluoromethyl)phenyl)-1,2,5,6,7,8-hexahydroquinazolin-3(4H)-yl)acetate (example 31B, 30 mg, 62 μmol) as starting material. Yield: 23 mg; ESI mass spectrum [M+H]⁺=470; Retention time: 1.09 min (V001_006).

Example 33

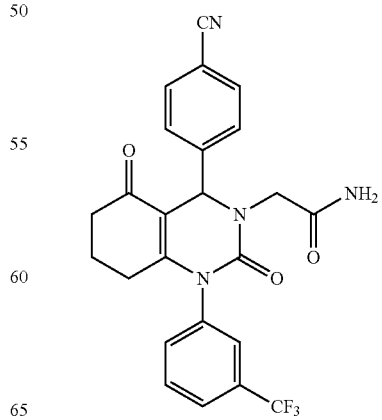

2-(4-(4-Cyanophenyl)-2,5-dioxo-1-(3-(trifluoromethyl)phenyl)-1,2,5,6,7,8-hexahydroquinazolin-3(4H)-yl)acetamide O-(7-Azabenzotriazol-1-yl)-N,N,N',N'-tetramethyluronium hexafluorophosphate (38 mg, 100 µmol) and triethylamine (70 µL, 500 µmol) is added to a solution of 2-(4-(4-cyanophenyl)-2,5-dioxo-1-(3-(trifluoromethyl)phenyl)-1,2,5,6,7,8-hexahydroquinazolin-3(4H)-yl)acetic acid (example 32, 47 mg, 100 µmol) in N,N-dimethylformamide (0.5 mL). After 20 min ammonia (0.5 M in 1,4-dioxane, 200 µL, 100 µmol) is added, and the mixture is stirred at room temperature for 2 h and purified by preparative HPLC (Waters Xbridge™-$C_{18}$, gradient of acetonitrile in water, 0.1% $NH_3$). Yield: 29 mg; ESI mass spectrum $[M+H]^+$=469; Retention time HPLC: 0.84 min (Z018_S04).

Example 34

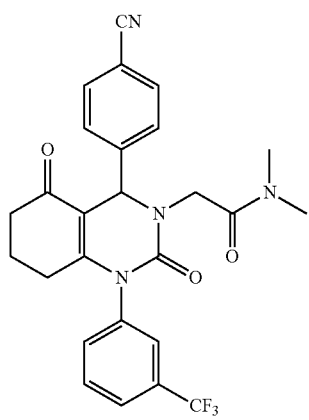 [SMILES: CN(C)C(=O)CN1C(=O)N(c2cccc(C(F)(F)F)c2)C2=C(C(=O)CCC2)C1c1ccc(C#N)cc1]

2-(4-(4-Cyanophenyl)-2,5-dioxo-1-(3-(trifluoromethyl)phenyl)-1,2,5,6,7,8-hexahydroquinazolin-3(4H)-yl)-N,N-dimethylacetamide The title compound is prepared in analogy to 2-(4-(4-cyanophenyl)-2,5-dioxo-1-(3-(tri-fluoromethyl)phenyl)-1,2,5,6,7,8-hexahydroquinazolin-3(4H)-yl)acetamide (example 33), using dimethylamine (2.0 M in tetrahydrofuran, 0.5 mL, 1.0 mmol) as amine. Yield: 32 mg; ESI mass spectrum $[M+H]^+$=497; Retention time HPLC: 1.62 min (Z011_S03).

Examples 34A and 34B

Enantiomers of Example 34

The enantiomers of racemic 2-(4-(4-cyanophenyl)-2,5-dioxo-1-(3-(trifluoromethyl)phenyl)-1,2,5,6,7,8-hexahydroquinazolin-3(4H)-yl)-N,N-dimethylacetamide (example 34, 147 mg, 0.296 mmol) are separated by preparative supercritical fluid chromatography on a chiral phase (Daicel Chiralpak IA, 10 mm×250 mm, 5 µm, 25% iso-PrOH+0.2% diethylamine in supercritical $CO_2$, 40° C., 120 bar back pressure).

Example 34A

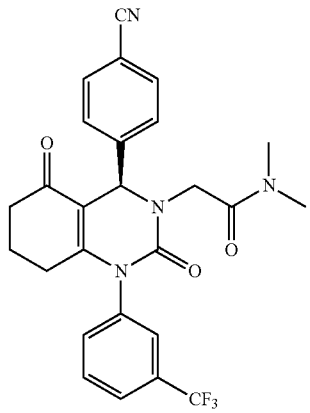 [SMILES: CN(C)C(=O)CN1C(=O)N(c2cccc(C(F)(F)F)c2)C2=C(C(=O)CCC2)[C@H]1c1ccc(C#N)cc1]

(R)-2-(4-(4-Cyanophenyl)-2,5-dioxo-1-(3-(trifluoromethyl)phenyl)-1,2,5,6,7,8-hexahydroquinazolin-3(4H)-yl)-N,N-dimethylacetamide Yield: 51 mg; ESI mass spectrum $[M+H]^+$=497; Retention time: 1.8 min (early eluting enantiomer) (I_IA_25_IPROP_DEA).

Example 34B

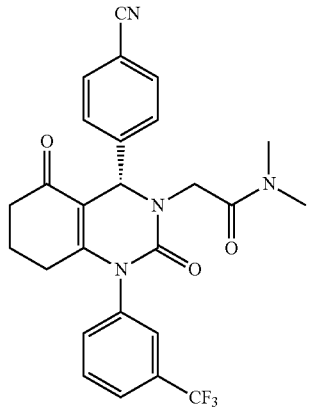

(S)-2-(4-(4-Cyanophenyl)-2,5-dioxo-1-(3-(trifluoromethyl)phenyl)-1,2,5,6,7,8-hexahydroquinazolin-3(4H)-yl)-N,N-dimethylacetamide Yield: 53 mg; ESI mass spectrum [M+H]$^+$=497; Retention time: 2.8 min (late eluting enantiomer) (I_IA_25_IPROP_DEA).

Example 35

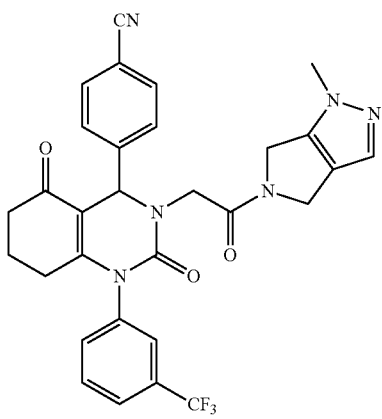 [SMILES: Cn1ncc2c1CN(C(=O)CN1C(=O)N(c3cccc(C(F)(F)F)c3)C3=C(C(=O)CCC3)C1c1ccc(C#N)cc1)C2]

4-(3-(2-(1-Methylpyrrolo[3,4-c]pyrazol-5(1H,4H,6H)-yl)-2-oxoethyl)-2,5-dioxo-1-(3-(trifluoromethyl)phenyl)-1,2,3,4,5,6,7,8-octahydroquinazolin-4-yl)benzonitrile N,N,N',N'-Tetramethyl-O-(benzotriazol-1-yl)uronium tetrafluoroborate (161 mg, 0.50 mmol) and triethylamine (210 µL, 1.51 mmol) are added to a mixture of 2-(4-(4-cyanophenyl)-2,5-dioxo-1-(3-(trifluoromethyl)phenyl)-1,2,5,6,7,8-hexahydroquinazolin-3(4H)-yl)acetic acid (example 32, 235 mg, 0.50 mmol) in N,N-dimethylformamide (2 mL). After 5 min a solution of 1-methyl-1,4,5,6-tetrahydropyrrolo[3,4-c]pyrazole (123 mg, 1.00 mmol) in N,N-dimethylformamide (3 mL) is added, and the mixture is stirred over night and purified by preparative HPLC (Waters Xbridge™-C$_{18}$, gradient of acetonitrile in water, 0.1% NH$_3$). Yield: 86 mg; ESI mass spectrum [M+H]$^+$=575; Retention time HPLC: 0.86 min (Z011_S03).

Examples 35A and 35B

Enantiomers of Example 35

The enantiomers of racemic 4-(3-(2-(1-methylpyrrolo[3,4-c]pyrazol-5(1H,4H,6H)-yl)-2-oxoethyl)-2,5-dioxo-1-(3-(trifluoromethyl)phenyl)-1,2,3,4,5,6,7,8-octahydroquinazolin-4-yl)benzobenitrile (example 35, 86 mg, 0.150 mmol) are separated by preparative supercritical fluid chromatography on a chiral phase (Daicel Chiralpak AS-H, 10 mm×250 mm, 5 µm, 20% iso-PrOH+0.2% diethylamine in supercritical CO$_2$, 40° C., 120 bar back pressure).

Example 35A

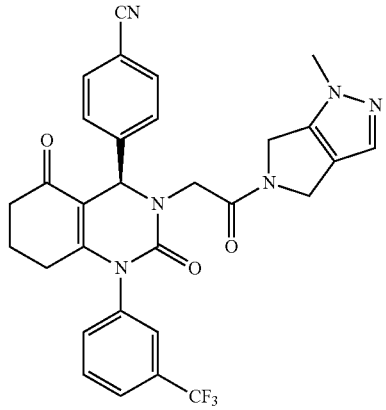 [SMILES: Cn1ncc2c1CN(C(=O)CN1C(=O)N(c3cccc(C(F)(F)F)c3)C3=C(C(=O)CCC3)[C@H]1c1ccc(C#N)cc1)C2]

(R)-4-(3-(2-(1-Methylpyrrolo[3,4-c]pyrazol-5(1H,4H,6H)-yl)-2-oxoethyl)-2,5-dioxo-1-(3-(trifluoromethyl)phenyl)-1,2,3,4,5,6,7,8-octahydroquinazolin-4-yl)benzonitrile Yield: 27 mg; ESI mass spectrum [M+H]$^+$=575; Retention time: 2.3 min (early eluting enantiomer) (I_ASH_20_IPROP_DEA).

Example 35B

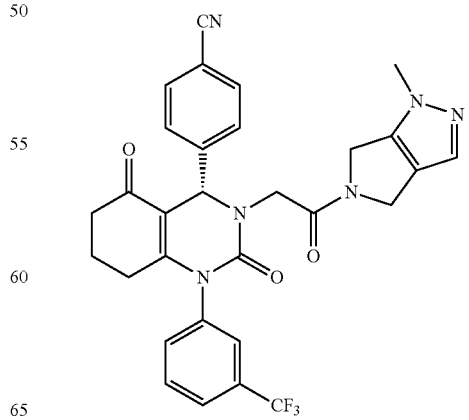

111

(S)-4-(3-(2-(1-Methylpyrrolo[3,4-c]pyrazol-5(1H, 4H,6H)-yl)-2-oxoethyl)-2,5-dioxo-1-(3-(trifluoromethyl)phenyl)-1,2,3,4,5,6,7,8-octahydroquinazolin-4-yl)benzonitrile Yield: 28 mg; ESI mass spectrum [M+H]$^+$=575; Retention time: 2.9 min (late eluting enantiomer) (I_ASH_20_IPROP_DEA).

Example 36

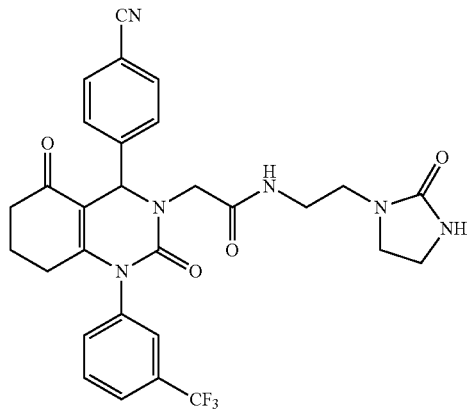 [SMILES: N#Cc1ccc(C2C3=C(CCCC3=O)N(c3cccc(C(F)(F)F)c3)C(=O)N2CC(=O)NCCN2CCNC2=O)cc1]

112

2-(4-(4-Cyanophenyl)-2,5-dioxo-1-(3-(trifluoromethyl)phenyl)-1,2,5,6,7,8-hexahydroquinazolin-3 (4H)-yl)-N-(2-(2-oxohnidazolidin-1-yDethyl)acetamide O-(7-Azabenzotriazol-1-yl)-N,N,N',N'-tetramethyluronium hexafluorophosphate (38 mg, 100 μmol) and triethylamine (35 μL, 250 μmol) are added to a solution of 2-(4-(4-cyanophenyl)-2,5-dioxo-1-(3-(trifluoromethyl)phenyl)-1,2,5,6,7,8-hexahydroquinazolin-3(4H)-yl)acetic acid (example 32, 47 mg, 100 μmol) in N,N-dimethylformamide (0.5 mL). After 30 min a solution of 1-(2-aminoethyl)imidazolidin-2-one (18 mg, 0.140 mmol) and triethylamine (35 μL, 250 μL) in N,N-dimethylformamide (0.5 mL) is added, and the mixture is stirred at room temperature over night and purified by preparative HPLC (Waters Xbridge™-C$_{18}$, gradient of acetonitrile in water, 0.1% NH$_3$). Yield: 25 mg; ESI mass spectrum [M+H]$^+$=581; Retention time HPLC: 0.97 min (001_CA04).

The following examples of Table 3 are prepared in analogy to 2-(4-(4-cyanophenyl)-2,5-dioxo-1-(3-(trifluoromethyl)phenyl)-1,2,5,6,7,8-hexahydroquinazolin-3(4H)-yl)-N-(2-(2-oxo-imidazolidin-1-yl)ethyl)acetamide (example 36) replacing 1-(2-aminoethyl)imidazolidin-2-one with the appropriate amine as starting material.

TABLE 3

| Example | R$^3$ | MS [M + H]$^+$ | Retention time [min] | HPLC-Method |
|---|---|---|---|---|
| 36.1 | ![acetamide N-methyl] | 483 | 1.09 | 004_CA01 |
| 36.2 | ![acetamide N-cyclopropyl] | 509 | 1.14 | 004_CA01 |
| 36.3 | ![acetamide N-cyclopropylmethyl] | 523 | 1.21 | 004_CA01 |

TABLE 3-continued
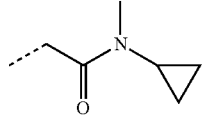
| Example | R³ | MS [M + H]⁺ | Retention time [min] | HPLC-Method |
|---|---|---|---|---|
| 36.4 | 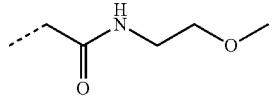 | 523 | 1.23 | 004_CA01 |
| 36.5 | 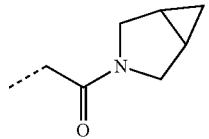 | 527 | 0.70 | 004_CA05 |
| 36.6 | 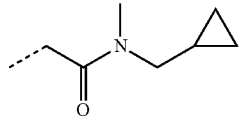 | 535 | 0.77 | 004_CA05 |
| 36.7 | 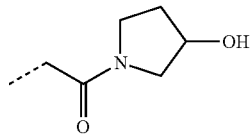 | 537 | 1.27 | 004_CA01 |
| 36.8 | 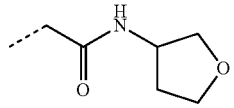 | 539 | 0.85 | 2018_S04 |
| 36.9 | 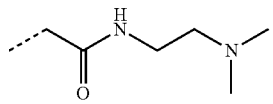 | 539 | 1.10 | 004_CA01 |
| 36.10 | 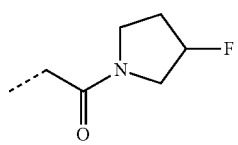 | 540 | 0.85 | 004_CA01 |
| 36.11 | | 541 | 1.18 | 004_CA01 |

TABLE 3-continued
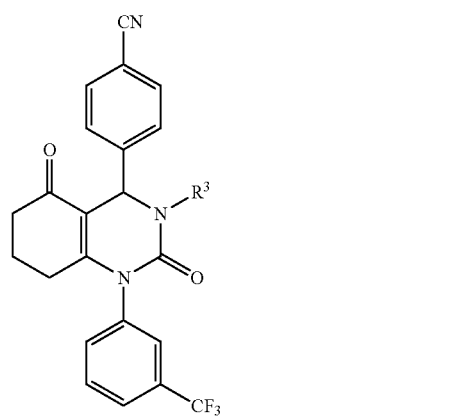
| Example | R³ | MS [M + H]⁺ | Retention time [min] | HPLC-Method |
|---|---|---|---|---|
| 36.12 | -C(O)N(CH₃)CH₂CH₂OCH₃ | 541 | 1.17 | 004_CA01 |
| 36.13 | -C(O)NHCH₂CH₂CH₂OCH₃ | 541 | 1.33 | 004_CA01 |
| 36.14 | -C(O)NHCH₂C(CH₃)₂OH | 541 | 0.69 | 004_CA05 |
| 36.15 | -C(O)NHCH₂-(2-furyl) | 549 | 1.22 | 004_CA01 |
| 36.16 | -C(O)-(5-azaspiro[2.4]heptan-5-yl) | 549 | 1.27 | 004_CA01 |
| 36.17 | -C(O)-(2-azaspiro[3.3]heptan-2-yl) | 549 | 1.28 | 004_CA01 |
| 36.18 | -C(O)-(3,4-dimethylpyrrolidin-1-yl) | 551 | 0.77 | 004_CA05 |

TABLE 3-continued

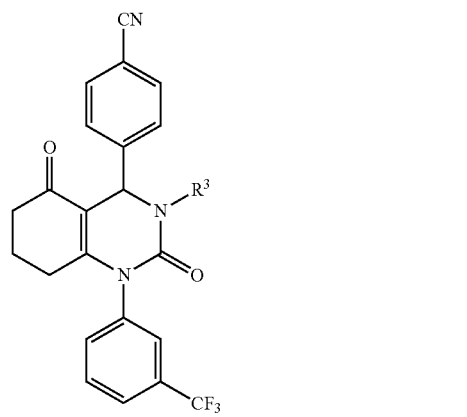

| Example | R³ | MS [M + H]⁺ | Retention time [min] | HPLC-Method |
|---|---|---|---|---|
| 36.19 | (1-(4-methylpiperidinyl)carbonylmethyl) | 551 | 1.33 | 004_CA01 |
| 36.20 | (N-(2-oxopyrrolidin-3-yl)carbamoylmethyl) | 552 | 1.01 | 004_CA01 |
| 36.21 | (1-(3-oxopiperazinyl)carbonylmethyl) | 552 | 0.65 | 004_CA05 |
| 36.22 | (N-((tetrahydrofuran-3-yl)methyl)carbamoylmethyl) | 553 | 1.11 | 004_CA01 |
| 36.23 | (1-(3-methoxypyrrolidinyl)carbonylmethyl) | 553 | 0.73 | 004_CA05 |
| 36.24 | (N-((tetrahydrofuran-2-yl)methyl)carbamoylmethyl) | 553 | 0.73 | 004_CA05 |
| 36.25 | (1-(3-hydroxy-3-methylpyrrolidinyl)carbonylmethyl) | 553 | 0.69 | 004_CA05 |

TABLE 3-continued

| Example | R³ | MS [M + H]⁺ | Retention time [min] | HPLC-Method |
|---|---|---|---|---|
| 36.26 | -CH2-C(O)-NH-CH2CH2-NH-C(O)-CH3 | 554 | 1.02 | 004_CA01 |
| 36.27 | -CH2-C(O)-NH-CH2CH2CH2-O-CH3 | 555 | 1.19 | 004_CA01 |
| 36.28 | -CH2-C(O)-thiomorpholine | 555 | 1.24 | 004_CA01 |
| 36.29 | -CH2-C(O)-NH-CH2CH2-S(O)-CH3 | 559 | 0.99 | 004_CA01 |
| 36.30 | -CH2-C(O)-NH-CH2CH2-(1-imidazolyl) | 563 | 0.86 | 004_CA01 |
| 36.31 | -CH2-C(O)-NH-CH2-(1-methyl-pyrazol-4-yl) | 563 | 1.06 | 004_CA01 |
| 36.32 | -CH2-C(O)-NH-CH2CH2-(1-pyrazolyl) | 563 | 1.11 | 004_CA01 |
| 36.33 | -CH2-C(O)-NH-CH2-(1-methyl-pyrazol-3-yl) | 563 | 1.09 | 004_CA01 |

TABLE 3-continued

| Example | R³ | MS [M + H]⁺ | Retention time [min] | HPLC-Method |
|---|---|---|---|---|
| 36.34 | | 563 | 1.33 | 004_CA01 |
| 36.35 | | 565 | 1.07 | 004_CA01 |
| 36.36 | | 566 | 1.01 | 004_CA01 |
| 36.37 | | 566 | 0.67 | 004_CA05 |
| 36.38 | | 566 | 0.86 | 004_CA01 |
| 36.39 | | 566 | 0.87 | 004_CA01 |
| 36.40 | | 567 | 1.19 | 004_CA01 |

TABLE 3-continued
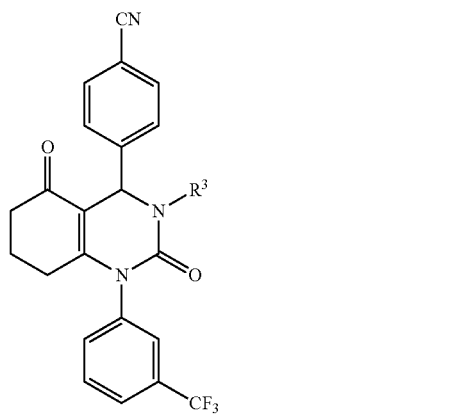
| Example | R³ | MS [M + H]⁺ | Retention time [min] | HPLC-Method |
|---|---|---|---|---|
| 36.41 | | 567 | 1.15 | 004_CA01 |
| 36.42 | | 567 | 0.73 | 004_CA05 |
| 36.43 | | 568 | 0.87 | 004_CA01 |
| 36.44 | | 571 | 1.30 | 004_CA01 |
| 36.45 | | 571 | 1.03 | 004_CA01 |
| 36.46 | | 572 | 1.03 | 004_CA01 |
| 36.47 | | 573 | 1.32 | 004_CA01 |

TABLE 3-continued

| Example | R³ | MS [M + H]⁺ | Retention time [min] | HPLC-Method |
|---|---|---|---|---|
| 36.48 | pyrrolo-pyrazine acetyl | 574 | 1.28 | 004_CA01 |
| 36.49 | imidazo-pyrazine acetyl | 575 | 0.88 | 004_CA01 |
| 36.50 | 1-methyl-pyrazolo-pyrrole acetyl | 575 | 1.11 | 004_CA01 |
| 36.51 | pyrazolo-pyrazine acetyl | 575 | 0.72 | 004_CA05 |
| 36.52 | (6-oxo-1,6-dihydropyridin-3-yl)methyl acetamide | 576 | 0.98 | 004_CA01 |
| 36.53 | (1-methyl-6-oxo-1,6-dihydropyridin-3-yl) acetamide | 576 | 1.04 | 004_CA01 |
| 36.54 | N-methyl-N-((1-methyl-1H-pyrazol-4-yl)methyl) acetamide | 577 | 0.89 | Z018_S04 |

TABLE 3-continued

[Structure: A bicyclic scaffold with CN-phenyl group at position 4, R³ on N3, and 3-(trifluoromethyl)phenyl on N1, with ketone groups]

| Example | R³ | MS [M + H]⁺ | Retention time [min] | HPLC-Method |
|---------|-----|-------------|---------------------|-------------|
| 36.55 | [piperazine-N-cyclopropyl acyl] | 578 | 0.88 | 004_CA01 |
| 36.56 | [octahydropyrrolo[1,2-a]pyrazine acyl] | 578 | 0.87 | 004_CA01 |
| 36.57 | [acetamide-CH₂-(1-methyl-5-oxopyrrolidin-2-yl)] | 580 | 1.03 | 004_CA01 |
| 36.58 | [acetamide-CH₂CH₂-(2-oxopyrrolidin-1-yl)] | 580 | 1.06 | 004_CA01 |
| 36.59 | [acetamide-CH₂-(1-methyl-5-oxopyrrolidin-3-yl)] | 580 | 1.03 | 004_CA01 |
| 36.60 | [1-acetyl-piperazine acyl] | 580 | 1.07 | 004_CA01 |
| 36.61 | [acetamide-(1-methyl-6-oxopiperidin-3-yl)] | 580 | 1.03 | 004_CA01 |

TABLE 3-continued
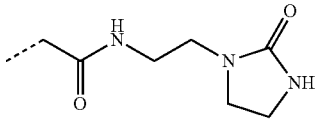
| Example | R³ | MS [M + H]⁺ | Retention time [min] | HPLC-Method |
|---|---|---|---|---|
| 36.62 | 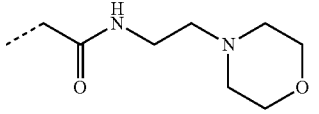 | 581 | 1.02 | 004_CA01 |
| 36.63 | 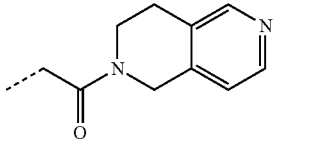 | 582 | 0.68 | 004_CA05 |
| 36.64 | 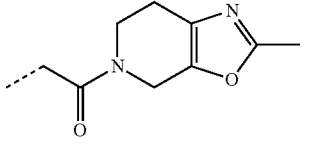 | 586 | 0.88 | 004_CA01 |
| 36.65 | 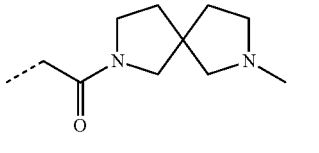 | 590 | 1.17 | 004_CA01 |
| 36.66 | 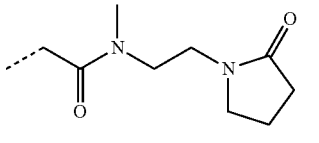 | 592 | 0.86 | 004_CA01 |
| 36.67 | 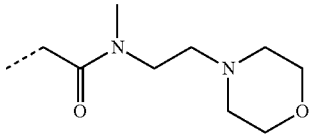 | 594 | 0.70 | 004_CA05 |
| 36.68 | 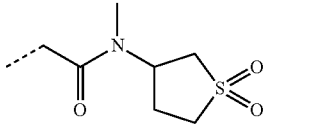 | 596 | 0.87 | 004_CA01 |
| 36.69 | | 601 | 1.14 | 004_CA01 |

TABLE 3-continued
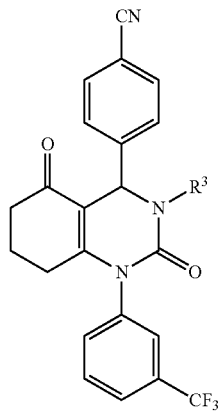
| Example | R³ | MS [M + H]⁺ | Retention time [min] | HPLC-Method |
|---|---|---|---|---|
| 36.70 | 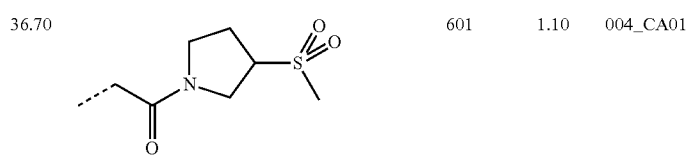 | 601 | 1.10 | 004_CA01 |
| 36.71 | 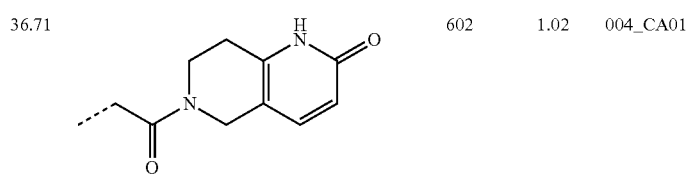 | 602 | 1.02 | 004_CA01 |
| 36.72 | 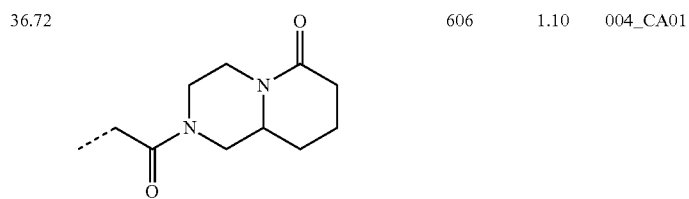 | 606 | 1.10 | 004_CA01 |
| 36.73 | 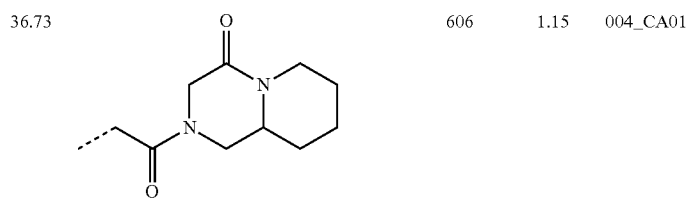 | 606 | 1.15 | 004_CA01 |
| 36.74 | 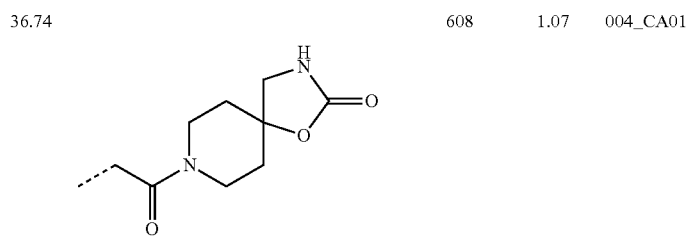 | 608 | 1.07 | 004_CA01 |

TABLE 3-continued

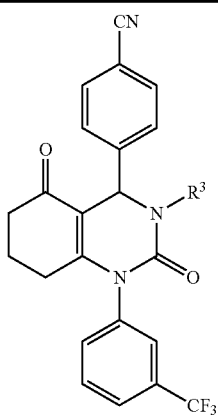

| Example | R³ | MS [M + H]⁺ | Retention time [min] | HPLC-Method |
|---|---|---|---|---|
| 36.75 |  | 616 | 0.72 | 004_CA05 |

Example 37

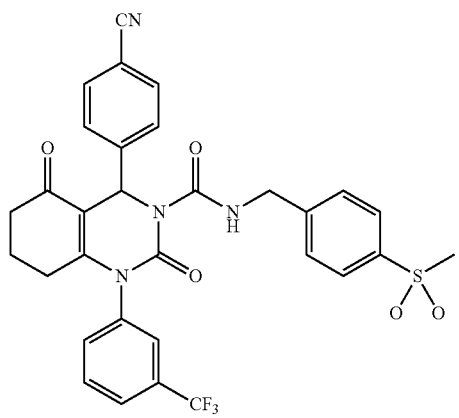 [SMILES: CS(O)(O)c1ccc(CNC(=O)N2C(=O)N(c3cccc(C(F)(F)F)c3)C3=C(C(=O)CCC3)C2c2ccc(C#N)cc2)cc1]

4-(4-Cyanophenyl)-N-(4-(methylsulfonyl)benzyl)-2,
5-dioxo-1-(3-(trifluoromethyl)-phenyl)-1,2,5,6,7,8-
hexahydroquinazoline-3(4H)-carboxamide A mixture of 4-nitrophenyl 4-(4-cyanophenyl)-2,5-dioxo-1-(3-(trifluoromethyl)phenyl)-1,2,5,6,7,8-hexahydro-quinazoline-3(4H)-carboxylate (intermediate 37, 200 mg, 0.347 mmol) and (4-(methylsulfonyl)phenyl)methanamine (193 mg, 1.04 mmol in acetonitrile (5 mL) is stirred at room temperature for 1 h and purified by preparative HPLC (Waters Xbridge™-C$_{18}$, gradient of acetonitrile in water, 0.1% TFA). Yield: 92 mg; ESI mass spectrum [M+H]⁺=623; Retention time HPLC: 0.66 min (X012_S01).

Example 38

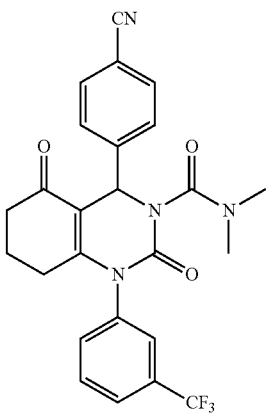 [SMILES: CN(C)C(=O)N1C(=O)N(c2cccc(C(F)(F)F)c2)C2=C(C(=O)CCC2)C1c1ccc(C#N)cc1]

4-(4-Cyanophenyl)-N,N-dimethyl-2,5-dioxo-1-(3-
(trifluoromethyl)phenyl)-1,2,5,6,7,8-hexahydro-
quinazoline-3(4H)-carboxamide A mixture of 4-nitrophenyl 4-(4-cyanophenyl)-2,5-dioxo-1-(3-(trifluoromethyl)phenyl)-1,2,5,6,7,8-hexahydro-quinazoline-3(4H)-carboxylate (intermediate 37, 51 mg, 8 μmol) and dimethylamine (2.0 M in tetrahydrofuran, 220 μL, 440 μmol) in acetonitrile (1.5 mL) is stirred at room temperature for 30 h and purified by preparative HPLC (Waters Xbridge™-C$_{18}$, gradient of acetonitrile in water, 0.1% NH$_3$).

Yield: 14 mg; ESI mass spectrum [M+H]$^+$=483; Retention time HPLC: 1.03 min (Z018_S04).

Example 39

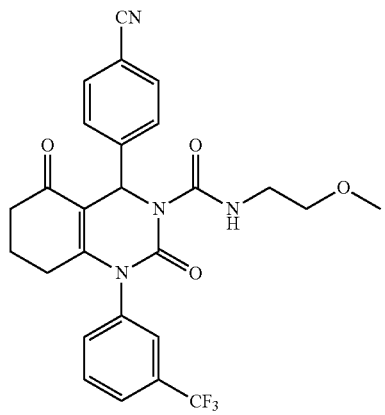 [SMILES: COCCNC(=O)N1C(=O)N(c2cccc(C(F)(F)F)c2)C2=C(C(=O)CCC2)C1c1ccc(C#N)cc1]

4-(4-Cyanophenyl)-N-(2-methoxyethyl)-2,5-dioxo-1-(3-(trifluoromethyl)phenyl)-1,2,5,6,7,8-hexahydro-quinazoline-3(4H)-carboxamide A solution of 4-nitrophenyl 4-(4-cyanophenyl)-2,5-dioxo-1-(3-(trifluoromethyl)phenyl)-1,2,5,6,7,8-hexahydro-quinazoline-3(4H)-carboxylate (intermediate 37, 58 mg, 100 µmol) in acetonitrile (1.5 mL) is added to a solution of 2-methoxyethanamine (43 µL, 500 µmol) in acetonitrile (0.5 mL). The mixture is stirred at room temperature for 2 h and purified by preparative HPLC (Waters Xbridge™-C$_{18}$, gradient of acetonitrile in water, 0.1% NH$_3$). Yield: 33 mg; ESI mass spectrum [M+H]$^+$=513; Retention time HPLC: 0.98 min (Z018_S04).

The following examples of Table 4 are prepared in analogy to 4-(4-cyanophenyl)-N-(2-methoxyethyl)-2,5-dioxo-1-(3-(trifluoromethyl)phenyl)-1,2,5,6,7,8-hexahydroquinazoline-3(4H)-carboxamide (example 39) replacing 2-methoxyethanamine with the appropriate amine as starting material.

TABLE 4

| Example | R³ | MS [M + H]⁺ | Retention time [min] | HPLC-Method |
|---|---|---|---|---|
| 39.1 | –C(=O)NHCH₃ | 469 | 1.24 | 004_CA01 |
| 39.2 | –C(=O)NHCH₂CH₂CH₃ | 497 | 1.36 | 004_CA01 |
| 39.3 | –C(=O)NHCH₂CH₂OH | 499 | 1.12 | 004_CA01 |
| 39.4 | –C(=O)N(azetidin-3-ol) | 511 | 1.08 | 004_CA01 |

TABLE 4-continued
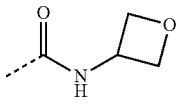
| Example | R³ | MS [M + H]⁺ | Retention time [min] | HPLC-Method |
|---------|-----|-------------|----------------------|-------------|
| 39.5 | 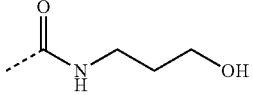 | 511 | 1.19 | 004_CA01 |
| 39.6 | 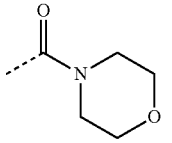 | 513 | 1.14 | 004_CA01 |
| 39.7 | 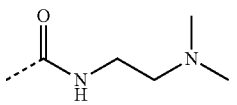 | 525 | 1.16 | 004_CA01 |
| 39.8 | 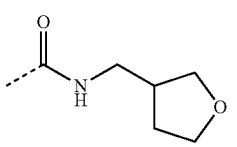 | 526 | 0.87 | 004_CA01 |
| 39.9 | 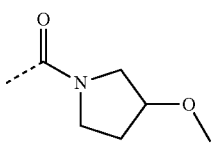 | 539 | 1.24 | 004_CA01 |
| 39.10 | 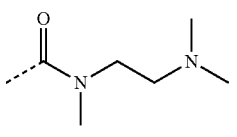 | 539 | 1.19 | 004_CA01 |
| 39.11 | 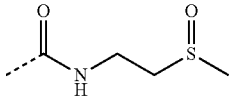 | 540 | 0.87 | 004_CA01 |
| 39.12 |  | 545 | 1.07 | 004_CA01 |

TABLE 4-continued
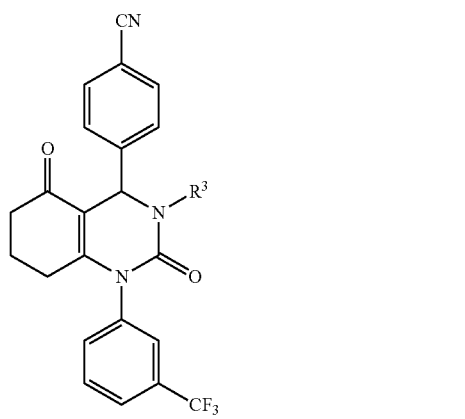
| Example | R³ | MS [M + H]⁺ | Retention time [min] | HPLC-Method |
|---|---|---|---|---|
| 39.13 | | 549 | 1.21 | 004_CA01 |
| 39.14 | | 549 | 1.14 | 004_CA01 |
| 39.15 | | 552 | 1.16 | 004_CA01 |
| 39.16 | | 552 | 1.08 | 004_CA01 |
| 39.17 | | 552 | 1.09 | 004_CA01 |
| 39.18 | | 553 | 1.20 | 004_CA01 |
| 39.19 | | 561 | 1.16 | 004_CA01 |

TABLE 4-continued

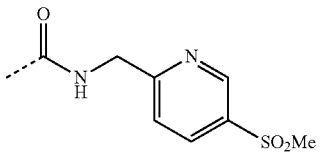

| Example | R³ | MS [M + H]⁺ | Retention time [min] | HPLC-Method |
|---|---|---|---|---|
| 39.20 | 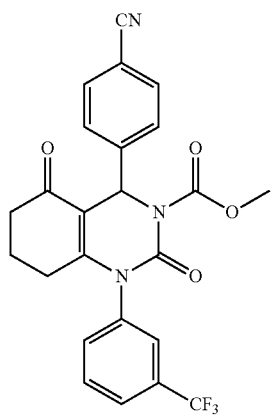 | 624 | 1.20 | 004_CA01 |

Example 40

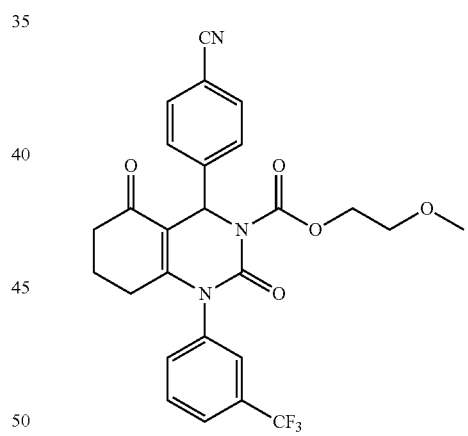

Methyl 4-(4-Cyanophenyl)-2,5-dioxo-1-(3-(trifluoromethyl)phenyl)-1,2,5,6,7,8-hexahydroquinazoline-3(4H)-carboxylate A solution of 4-(2,5-dioxo-1-(3-(trifluoromethyl)phenyl)-1,2,3,4,5,6,7,8-octahydroquinazolin-4-yl)-benzonitrile (example 1, 60 mg, 0.146 mmol) in tetrahydrofuran (0.8 mL) is added to a suspension of sodium hydride (60% in mineral oil, 7 mg, 0.17 mmol) in tetrahydrofuran (0.5 mL). After 20 min methyl chloroformate (11 µL, 0.15 mmol) is added and the mixture is stirred at room temperature over night. Another portion of sodium hydride (60% in mineral oil, 3 mg, 0.07 mmol) is added. After 2 h, the mixture is diluted with water and N,N-dimethylformamide and then purified by preparative HPLC (Waters Xbridge™-C₁₈, gradient of acetonitrile in water, 0.1% NH₃). Yield: 8 mg; ESI mass spectrum [M+H]⁺=470, Retention time HPLC: 1.14 min (V011_S01).

Example 41

2-Methoxyethyl 4-(4-Cyanophenyl)-2,5-dioxo-1-(3-(trifluoromethyl)phenyl)-1,2,5,6,7,8-hexahydroquinazoline-3(4H)-carboxylate A solution of 2-methoxyethanol (7 µL, 89 µmol) in dry tetrahydrofuran (500 µL) is cooled at 78° C. and treated with sodium hydride (60% in mineral oil, 9 mg, 0.14 mmol). After 30 min, 4-nitrophenyl 4-(4-cyanophenyl)-2,5-dioxo-1-(3-(trifluoromethyl)phenyl)-1,2,5,6,7,8-hexahydroquinazoline-3(4H)-carboxylate (intermediate 37, 50 mg, 87 µmol) is added and the mixture is stirred at room temperature for 2 h. Water is added and the mixture is purified by preparative HPLC (Waters Xbridge™-C₁₈, gradient of acetonitrile in water, 0.1% NH₃). Yield: 8 mg; ESI mass spectrum [M+H]⁺=514; Retention time HPLC: 0.64 min (X012_S01).

Example 42

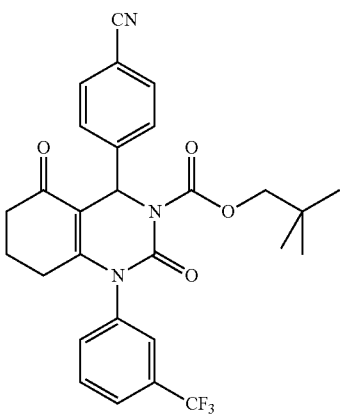 [SMILES: CC(C)(C)COC(=O)N1C(=O)N(c2cccc(C(F)(F)F)c2)C2=C(C(=O)CCC2)C1c1ccc(C#N)cc1]

Neopentyl 4-(4-Cyanophenyl)-2,5-dioxo-1-(3-(trifluoromethyl)phenyl)-1,2,5,6,7,8-hexahydroquinazoline-3(4H)-carboxylate A solution of 2,2-dimethyl-1-propanol (9 mg, 0.10 mmol) in dry tetrahydrofuran (1 mL) is cooled at −78° C. and treated with sodium hydride (60% in mineral oil, 5 mg, 0.11 mmol). After 20 min, a solution of 4-nitrophenyl 4-(4-cyanophenyl)-2,5-dioxo-1-(3-(trifluoromethyl)phenyl)-1,2,5,6,7,8-hexahydroquinazoline-3(4H)-carboxylate (intermediate 37, 60 mg, 0.10 mmol) in tetrahydrofuran (1 mL) is added and the mixture is stirred for 5 h at room temperature. Another portion of 2,2-dimethyl-1-propanol (9 mg, 0.10 mmol) is added and the mixture is stirred over night. Another portion of 2,2-dimethyl-1-propanol (18 mg, 0.20 mmol) is added and the mixture is heated at 50° C. for 2 h. Water is added and the mixture is extracted with dichlormethane. The organic layer is concentrated under reduced it) pressure and the residue is purified by flash chromatography on silica (gradient cyclohexane to cyclohexane/ethyl acetate 1:1). Yield: 12 mg; ESI mass spectrum [M+H]$^+$=526; Retention time HPLC: 0.76 min (X012_S01).

Example 43

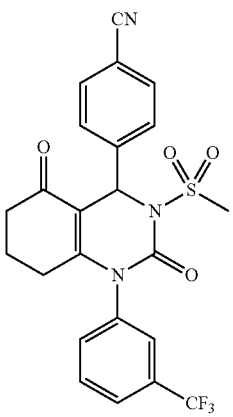 [SMILES: CS(=O)(=O)N1C(=O)N(c2cccc(C(F)(F)F)c2)C2=C(C(=O)CCC2)C1c1ccc(C#N)cc1]

4-(3-(Methylsulfonyl)-2,5-dioxo-1-(3-(trifluoromethyl)phenyl)-1,2,3,4,5,6,7,8-octahydroquinazolin-4-yl)benzonitrile Sodium hydride (60% in mineral oil, 6 mg, 0.15 mmol) and triethylamine (26 µL, 182 µmol) are added to a solution of 4-(2,5-dioxo-1-(3-(trifluoromethyl)phenyl)-1,2,3,4,5,6,7,8-octahydroquinazolin-4-yl)-benzonitrile (example 1, 25 mg, 61 µmol) in tetrahydrofuran (600 µL), and the mixture is stirred at room temperature for 15 min. Methanesulfonyl chloride (6 µL, 0.07 mmol) is added, and the mixture is stirred for 2.5 h and purified by preparative HPLC (Waters Xbridge™-C$_{18}$, gradient of acetonitrile in water, 0.1% NH$_3$). Yield: 13 mg; ESI mass spectrum [M+H]$^+$=490; Retention time HPLC: 0.95 min (Z018_S04).

Example 44

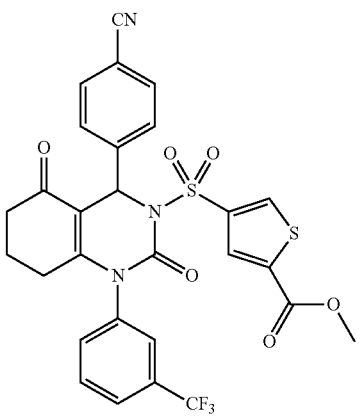 [SMILES: COC(=O)c1cc(S(=O)(=O)N2C(=O)N(c3cccc(C(F)(F)F)c3)C3=C(C(=O)CCC3)C2c2ccc(C#N)cc2)cs1]

Methyl 4-(4-(4-Cyanophenylcyanophenyl)-2,5-dioxo-1-(3-(trifluoromethyl)phenyl)-1,2,5,6,7,8-hexahydroquinazolin-3(4H)-ylsulfonyl)thiophene-2-carboxylate Sodium hydride (60% in mineral oil, 10 mg, 0.26 mmol) is added to a solution of 4-(2,5-dioxo-1-(3-(trifluoromethyl)phenyl)-1,2,3,4,5,6,7,8-octahydroquinazolin-4-yl)-benzonitrile (example 1, 41 mg, 100 µmol) in a mixture of tetrahydrofuran (1.5 mL) and N,N-dimethylformamide (150 µL). The mixture is stirred for 5 min and added to a solution of methyl 4-(chlorosulfonyl)thiophene-2-carboxylate (48 mg, 200 µmol) in tetrahydrofuran (0.5 mL). The mixture is stirred at 45° C. over night and purified by preparative HPLC (Waters SunFire™-C$_{18}$, gradient of acetonitrile in water, 0.1% TFA). Yield: 24 mg; ESI mass spectrum [M+H]$^+$=616; Retention time HPLC: 1.30 min (001_CA04).

The following examples of Table 5 are prepared in analogy to methyl 4-(4-(4-cyanophenyl)-2,5-dioxo-1-(3-(trifluoromethyl)phenyl)-1,2,5,6,7,8-hexahydroquinazolin-3(4H)-yl-sulfonyl)thiophene-2-carboxylate (example 44), using the appropriate sulfonyl chloride as starting material.

TABLE 5

[Structure: 4-(4-cyanophenyl)-1-(3-(trifluoromethyl)phenyl)-substituted tetrahydroquinazoline-2,5-dione core with R³ substituent]

| Example | R³ | MS [M+H]⁺ | Retention time [min] | HPLC-Method |
|---|---|---|---|---|
| 44.1 | -SO₂-ethyl | 504 | 1.30 | 001_CA03 |
| 44.2 | -SO₂-propyl | 518 | 1.01 | Z018_S04 |
| 44.3 | -SO₂-isobutyl | 532 | 1.40 | 001_CA03 |
| 44.4 | -SO₂-(2-furyl) | 542 | 1.25 | 002_CA04 |
| 44.5 | -SO₂-phenyl | 552 | 1.30 | 002_CA04 |
| 44.6 | -SO₂-(3-pyridyl) | 553 | 1.29 | 001_CA03 |
| 44.7 | -SO₂-(1-methylpyrazol-3-yl) | 556 | 1.26 | 001_CA03 |
| 44.8 | -SO₂-CH₂-phenyl | 566 | 1.38 | 001_CA03 |
| 44.9 | -SO₂-CH₂-SO₂-CH₃ | 568 | 1.25 | 001_CA03 |
| 44.10 | -SO₂-(CH₂)₃-C(O)OMe | 576 | 1.31 | 001_CA03 |
| 44.11 | -SO₂-(2-cyanophenyl) | 577 | 1.33 | 001_CA03 |
| 44.12 | -SO₂-CH=CH-phenyl | 578 | 1.42 | 001_CA03 |
| 44.13 | -SO₂-(5-(methoxycarbonyl)-2-methylfuran-3-yl) | 614 | 1.39 | 001_CA03 |

Example 45

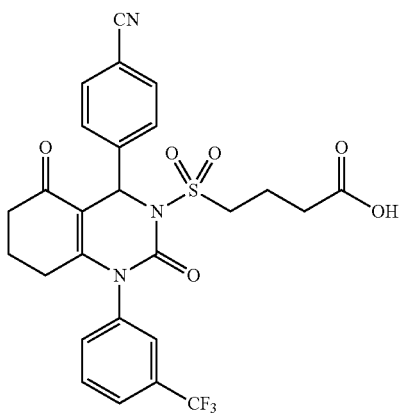 [SMILES: N#Cc1ccc(C2C3=C(CCCC3=O)N(c3cccc(C(F)(F)F)c3)C(=O)N2S(=O)(=O)CCCC(=O)O)cc1]

4-(4-(4-Cyanophenyl)-2,5-dioxo-1-(3-(trifluoromethyl)phenyl)-1,2,5,6,7,8-hexahydroquinazolin-3(4H)-ylsulfonyl)butanoic acid A solution of lithium hydroxide (2 mg, 84 µmol) in water (200 mL) is added to a solution of methyl 4-(4-(4-cyanophenyl)-2,5-dioxo-1-(3-(trifluoromethyl)phenyl)-1,2,5,6,7,8-hexahydroquinazolin-3(4H)-ylsulfonyl)butanoate (example 44.10, 19 mg, 33 µmol) in 1,4-dioxane (1 mL). The mixture is stirred at room temperature for 2 h and purified by it) preparative HPLC (Waters SunFire™-C$_{18}$, gradient of acetonitrile in water, 0.1% TFA). Yield: 6 mg; ESI mass spectrum [M+H]$^+$=562; Retention time HPLC: 0.91 min (Z018_S04).

Example 46

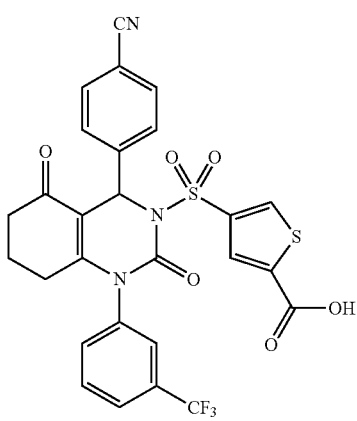 [SMILES: N#Cc1ccc(C2C3=C(CCCC3=O)N(c3cccc(C(F)(F)F)c3)C(=O)N2S(=O)(=O)c2csc(C(=O)O)c2)cc1]

4-(4-(4-Cyanophenyl)-2,5-dioxo-1-(3-(trifluoromethyl)phenyl)-1,2,5,6,7,8-hexahydroquinazolin-3(4H)-ylsulfonyl)thiophene-2-carboxylic acid The title compound is prepared in analogy to 4-(4-(4-cyanophenyl)-2,5-dioxo-1-(3-(tri-fluoromethyl)phenyl)-1,2,5,6,7,8-hexahydroquinazolin-3(4H)-ylsulfonyl)butanoic acid example 45), using methyl 4-(4-(4-cyanophenyl)-2,5-dioxo-1-(3-(trifluoromethyl)phenyl)-1,2,5,6,7,8-hexahydroquinazolin-3(4H)-ylsulfonyl)thiophene-2-carboxylate (example 44, 22 mg, 36 µmol) as starting material. Yield: 9 mg; ESI mass spectrum [M+H]$^+$=602; Retention time HPLC: 0.94 min (Z018_S04).

Example 47

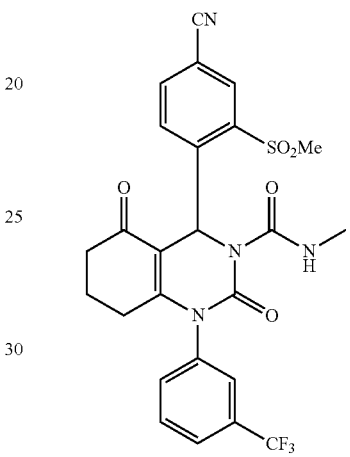

4-(4-Cyano-2-(methylsulfonyl)phenyl)-N-methyl-2,5-dioxo-1-(3-(trifluoromethyl)-phenyl)-1,2,5,6,7,8-hexahydroquinazoline-3(4H)-carboxamide Methylamine (2.0 M in tetrahydrofuran, 69 µL, 138 µmol) is added to a solution of 4-nitrophenyl 4-(4-cyano-2-(methylsulfonyl)phenyl)-2,5-dioxo-1-(3-(trifluoromethyl)phenyl)-1,2,5,6,7,8-hexahydroquinazoline-3(4H)-carboxylate (intermediate 38, 30 mg, 46 µmol) in acetonitrile (1 mL). The mixture is stirred at room temperature for 20 min and purified by reversed phase HPLC (Agilent ZORBAX™ SB-C$_{18}$, gradient of acetonitrile in water, 0.15% formic acid). Yield: 22 mg; ESI mass spectrum M+H]$^+$=547, Retention time HPLC: 1.01 min (Z017_S04).

Examples 47A and 47B

Enantiomers of Example 47

The enantiomers of racemic 4-(4-cyano-2-(methylsulfonyl)phenyl)-N-methyl-2,5-dioxo-1-(3-(trifluoromethyl)phenyl)-1,2,5,6,7,8-hex ahydroquinazoline-3(4H)-carboxamide (example 47, 50 mg, 91 µmol) are separated by preparative supercritical fluid chromatography on a chiral phase (Daicel Chiralpak IB, 10 mm×250 mm, 5 µm, 30% MeOH+ is 0.2% diethylamine in supercritical $CO_2$, 40° C., 120 bar back pressure).

Example 47A

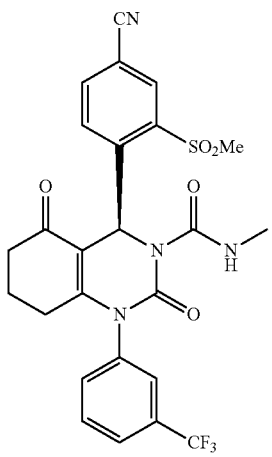 [SMILES: CNC(=O)N1C(=O)N(c2cccc(C(F)(F)F)c2)C2=C(C(=O)CCC2)[C@H]1c1ccc(C#N)cc1S(C)(=O)=O]

(S)-4-(4-Cyano-2-(methylsulfonyl)phenyl)-N-methyl-2,5-dioxo-1-(3-(trifluoromethyl)-phenyl)-1,2,5,6,7,8-hexahydroquinazoline-3(4H)-carboxamide Yield: 22 mg; ESI mass spectrum [M+H]$^+$=547; Retention time: 1.28 min (early eluting enantiomer) (I_IB_30_MeOH_DEA).

Example 47B

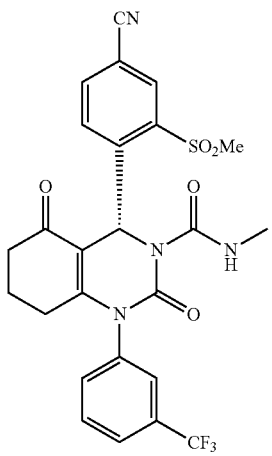 [SMILES: CNC(=O)N1C(=O)N(c2cccc(C(F)(F)F)c2)C2=C(C(=O)CCC2)[C@@H]1c1ccc(C#N)cc1S(C)(=O)=O]

(R)-4-(4-Cyano-2-(methylsulfonyl)phenyl)-N-methyl-2,5-dioxo-1-(3-(trifluoromethyl)-phenyl)-1,2,5,6,7,8-hexahydroquinazoline-3(4H)-carboxamide Yield: 22 mg; ESI mass spectrum [M+H]$^+$=547; Retention time: 2.29 min (late eluting enantiomer) (I_IB_30_MeOH_DEA).

The following examples of Table 6 are prepared in analogy to 4-(4-cyano-2-(methylsul-fonyl)phenyl)-N-methyl-2,5-dioxo-1-(3-(trifluoromethyl)phenyl)-1,2,5,6,7,8-hexahydroquinazoline-3(4H)-carboxamide (example 47) using the appropriate amine as starting material.

TABLE 6

| Example | R³ | MS [M + H]⁺ | Retention time [min] | HPLC-Method |
|---|---|---|---|---|
| 47.1 | | 561 | 1.06 | Z017_S04 |
| 47.2 | | 577 | 0.95 | Z017_S04 |
| 47.3 | | 591 | 0.97 | Z017_S04 |
| 47.4 | | 639 | 0.97 | Z017_S04 |

Example 48

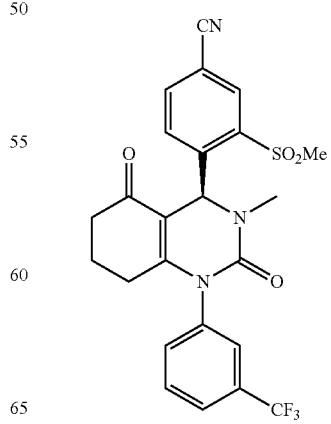

(S)-4-(3-Methyl-2,5-dioxo-1-(3-(trifluoromethyl)phenyl)-1,2,3,4,5,6,7,8-octahydroquinazolin-4-yl)-3-(methylsulfonyl)benzonitrile Lithium diisopropylamide (1.8 M in tetrahydrofuran, 62 μL, 0.11 mmol) is added to a solution of (S)-4-(2,5-dioxo-1-(3-(trifluoromethyl)phenyl)-1,2,3,4,5,6,7,8-octahydroquinazolin-4-yl)-3-(methylsulfonyl)benzonitrile (example 18A, 50 mg, 0.10 mmol) in N,N-dimethylformamide (1 mL). Methyl iodide (8 μL, 0.13 mmol) is added and the mixture is stirred for 1 h. Water is added and the mixture is purified by reversed phase HPLC (Agilent ZORBAX™ SB-$C_{18}$, gradient of acetonitrile in water, 0.15% formic acid). Yield: 20 mg; ESI mass spectrum $[M+H]^+$=504; Retention time HPLC: 1.04 min (Z017_S04).

Example 49

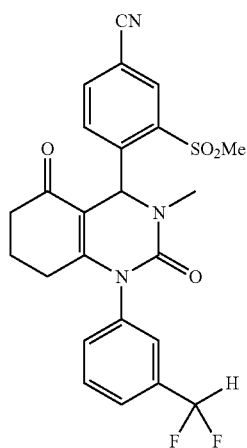

4-(1-(3-(Difluoromethyl)phenyl)-3-methyl-2,5-dioxo-1,2,3,4,5,6,7,8-octahydroquinazolin-4-yl)-3-(methylsulfonyl)benzonitrile The title compound is prepared in analogy to (S)-4-(3-methyl-2,5-dioxo-1-(3-(trifluoromethyl)phenyl)-1,2,3,4,5,6,7,8-octahydroquinazolin-4-yl)-3-(methylsulfonyl)benzonitrile (example 48), using 4-(1-(3-(difluoromethyl)phenyl)-2,5-dioxo-1,2,3,4,5,6,7,8-octahydroquinazolin-4-yl)-3-(methylsulfonyl)benzonitrile (example 19, 60 mg, 0.13 mmol) as starting material. Yield: 20 mg, ESI mass spectrum $[M+H]^+$=486; Retention time HPLC: 0.99 min (Z017_S04).

Example 50

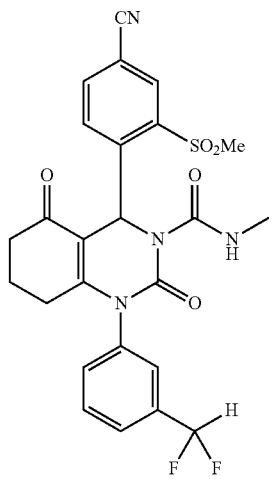 [SMILES: CNC(=O)N1C(=O)N(c2cccc(C(F)F)c2)C2=C(C(=O)CCC2)C1c1ccc(C#N)cc1S(C)(=O)=O]

4-(4-Cyano-2-(methylsulfonyl)phenyl)-1-(3-(difluoromethyl)phenyl)-N-methyl-2,5-dioxo-1,2,5,6,7,8-hexahydroquinazoline-3(4H)-carboxamide The title compound is prepared in analogy to 4-(4-cyano-2-(methylsulfonyl)-phenyl)-N-methyl-2,5-dioxo-1-(3-(trifluoromethyl)phenyl)-1,2,5,6,7,8-hexahydroquinazoline-3(4H)-carboxamide (example 47), using 4-nitrophenyl 4-(4-cyano-2-(methylsulfonyl)-phenyl)-1-(3-(difluoromethyl)phenyl)-2,5-dioxo-1,2,5,6,7,8-hexahydroquinazoline-3(4H)-carboxylate (intermediate 39, 16 mg, 25 μmol), as starting material. Yield: 9 mg, ESI mass spectrum $[M+H]^+$=529; Retention time HPLC: 0.97 min (Z017_S04).

Example 51

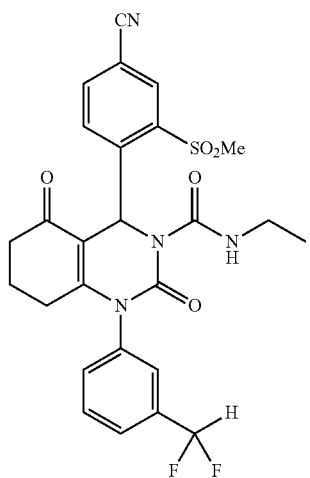 [SMILES: CCNC(=O)N1C(=O)N(c2cccc(C(F)F)c2)C2=C(C(=O)CCC2)C1c1ccc(C#N)cc1S(C)(=O)=O]

4-(4-Cyano-2-(methylsulfonyl)phenyl)-1-(3-(difluoromethyl)phenyl)-N-ethyl-2,5-dioxo-1,2,5,6,7,8-hexahydroquinazoline-3(4H)-carboxamide The title compound is prepared in analogy to 4-(4-cyano-2-(methylsulfonyl)phenyl)-N-methyl-2,5-dioxo-1-(3-(trifluoromethyl)phenyl)-1,2,5,6,7,8-hexahydroquinazoline-3 (4H)-carboxamide (example 47), using 4-nitrophenyl 4-(4-cyano-2-(methylsulfonyl)-phenyl)-1-(3-(difluoromethyl)-phenyl)-2,5-dioxo-1,2,5,6,7,8-hexahydroquinazoline-3 (4H)-carboxylate (intermediate 39, 34 mg, 53 μmol) as starting material and replacing methylamine with ethylamine Yield: 10 mg, ESI mass spectrum [M+H]$^+$=543; Retention time HPLC: 1.02 min (Z018_S04).

Example 52

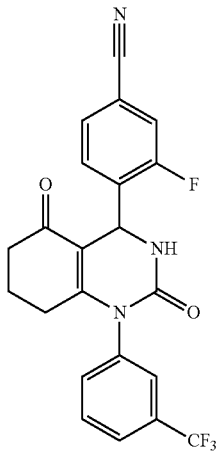

4-(2,5-Dioxo-1-(3-(trifluoromethyl)phenyl)-1,2,3,4,5,6,7,8-octahydroquinazolin-4-yl)-3-fluorobenzonitrile Sodium tert-butoxide (0.51 g, 5.31 mmol) is added to a solution of 1-((4-cyano-2-fluoro-phenyl)(2-ethoxy-6-oxocyclohex-1-enyl)methyl)-3-(3-(trifluoromethyl)phenyl)urea (intermediate 41, 1.82 g, 3.83 mmol) in acetonitrile (6 mL), and the mixture is shaked in an ultrasound bath for 20 min. Water is added, and the mixture is extracted with dichloromethane. The combined organic layers are dried over Na$_2$SO$_4$ and concentrated under reduced pressure. The residue is purified by reversed phase HPLC (Waters SunFire™-C$_{18}$, gradient of acetonitrile in water, 0.1% formic acid). Yield: 695 mg; ESI mass spectrum [M+H]$^+$=430; Retention time HPLC: 1.01 min (Z018_S04).

The following examples of Table 7 are prepared in analogy to 4-(2,5-dioxo-1-(3-(trifluoromethyl)phenyl)-1,2,3,4,5,6,7,8-octahydroquinazolin-4-yl)-3-fluorobenzonitrile (example is 52), using the appropriate starting material as indicated in the table and replacing sodium tert-butoxide with potassium tert-butoxide as base.

TABLE 7

| Example | Starting Material | R$^2$ | MS [M + H]$^+$ | Retention time [min] | HPLC-Method |
|---------|-------------------|-------|----------------|----------------------|-------------|
| 52.1 | intermediate 44 | 2-fluoro-5-(trifluoromethyl)phenyl | 430 | 1.01 | Z017_S04 |
| 52.2 | intermediate 44.1 | 3-fluoro-5-(trifluoromethyl)phenyl | 430 | 1.03 | Z018_S04 |

Example 53

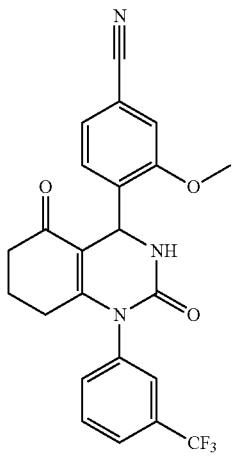 [SMILES: COc1cc(C#N)ccc1C1NC(=O)N(c2cccc(C(F)(F)F)c2)C2=C1C(=O)CCC2]

4-(2,5-Dioxo-1-(3-(trifluoromethyl)phenyl)-1,2,3,4,5,6,7,8-octahydroquinazolin-4-yl)-3-methoxybenzonitrile Under an atmosphere of argon, a mixture of 4-(4-bromo-2-methoxyphenyl)-1-(3-(trifluoromethyl)phenyl)-3,4,7,8-tetrahydroquinazoline-2,5(1H,6H)-dione (intermediate 50, 21 mg, 42 µmol), copper(I) cyanide (10 mg, 0.11 mmol) and tetrakis(triphenylphosphine)-palladium(O) (5 mg, 4 µmol) in N,N-dimethylformamide (1 mL) is heated at 140° C. over it) night. The mixture is cooled at room temperature, diluted with methanol and purified by reversed phase HPLC (Waters SunFire™-C$_{18}$, gradient of acetonitrile in water, 0.1% TFA). Yield: 4 mg; ESI mass spectrum [M+H]$^+$=442; Retention time HPLC: 0.87 min (Z011_S03).

Example 54

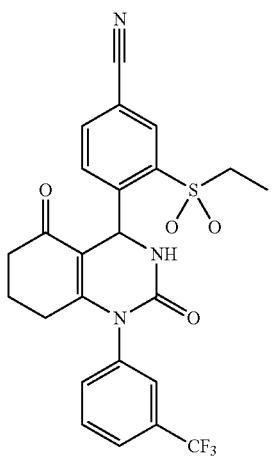 [SMILES: CCS(O)(O)c1cc(C#N)ccc1C1NC(=O)N(c2cccc(C(F)(F)F)c2)C2=C1C(=O)CCC2]

4-(2,5-Dioxo-1-(3-(trifluoromethyl)phenyl)-1,2,3,4,5,6,7,8-octahydroquinazolin-4-yl)-3-(ethylsulfonyl)benzonitrile A mixture of triethyl phosphate (4.6 mL, 26.9 mmol) and phosphorous pentoxide (2.54 g, 17.9 mmol) is heated at 50° C. over night and dilutet with tert-butyl methyl ether (45 mL). Cyclohexane-1,3-dione (3.77 g, 33.6 mmol), 3-(ethylsulfonyl)-4-formylbenzonitrile (5.00 g, 22.4 mmol) and 1-(3-(trifluoromethyl)phenyl)urea (4.57 g, 22.4 mmol) are added, and the mixture is heated at reflux for 4 h. The mixture is cooled at room temperature and concentrated under reduced pressure. The residue is purified by reversed phase HPLC (Agilent ZORBAX™ SB-C$_{18}$, gradient of acetonitrile in water, 0.15% formic acid). Yield: 930 mg; ESI mass spectrum [M+H]$^+$=504; Retention time HPLC: 1.02 min (Z017_S04).

Examples 54A and 54B

Enantiomers of Example 54

The enantiomers of racemic 4-(2,5-dioxo-1-(3-(trifluoromethyl)phenyl)-1,2,3,4,5,6,7,8-octahydroquinazolin-4-yl)-3-(ethylsulfonyl)benzonitrile (example 54, 65 mg, 0.13 mmol) are separated by preparative supercritical fluid chromatography on a chiral phase (Daicel Chiralpak IB, 10 mm×250 mm, 5 µm, 20% MeOH in supercritical CO$_2$, 40° C., 120 bar back pressure).

Example 54A

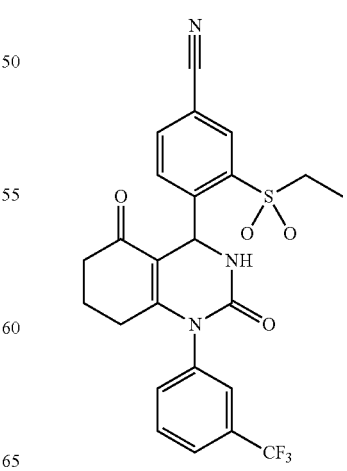

(S)-4-(2,5-Dioxo-1-(3-(trifluoromethyl)phenyl)-1,2,3,4,5,6,7,8-octahydroquinazolin-4-yl)-3-(ethylsulfonyl)benzonitrile Yield: 27 mg; ESI mass spectrum [M+H]$^+$=504; Retention time: 2.13 min (early eluting enantiomer) (I_IB_20_MeOH_DEA).

Example 54B

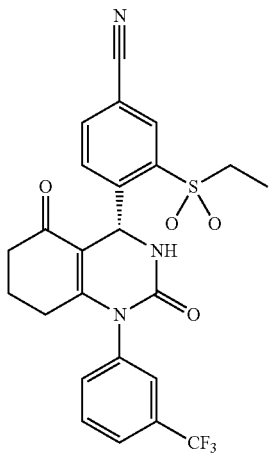 [SMILES: CCS(O)(O)c1cc(C#N)ccc1[C@@H]1NC(=O)N(c2cccc(C(F)(F)F)c2)C2=C1C(=O)CCC2]

(R)-4-(2,5-Dioxo-1-(3-(trifluoromethyl)phenyl)-1,2,3,4,5,6,7,8-octahydroquinazolin-4-yl)-3-(ethylsulfonyl)benzonitrile Yield: 28 mg; ESI mass spectrum [M+H]$^+$=504; Retention time: 3.33 min (late eluting enantiomer) (I_IB_20_MeOH_DEA).

Example 55

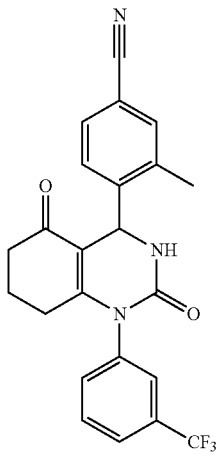

4-(2,5-Dioxo-1-(3-(trifluoromethyl)phenyl)-1,2,3,4,5,6,7,8-octahydroquinazolin-4-yl)-3-methylbenzonitrile A mixture of 4-(amino(6-oxo-2-(3-(trifluoromethyl)phenylamino)cyclohex-1-enyl)methyl)-3-methylbenzonitrile hydrochloride (intermediate 52, 1.06 g, 2.43 mmol), 1,1-carbonyl-diimidazole (495 mg, 3.05 mmol) and triethylamine (685 µL, 4.87 mmol) in acetonitrile (10 mL) is stirred at room temperature over night. Water ist added, and the mixture is extracted with dichloromethane. The phases are separated, and the organic layer is concentrated under reduced pressure. The residue is by purified by preparative HPLC (Waters it) Xbridge™-C$_{18}$, gradient of acetonitrile in water, 0.1% TFA). Yield: 364 mg; ESI mass spectrum [M+H]$^+$=426; Retention time HPLC: 0.65 min (X012_S01).

Example 56

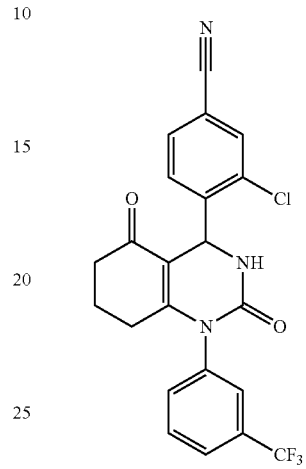

3-Chloro-4-(2,5-dioxo-1-(3-(trifluoromethyl)phenyl)-1,2,3,4,5,6,7,8-octahydroquinazolin-4-yl)benzonitrile The title compound is prepared in analogy to 4-(2,5-dioxo-1-(3-(trifluoromethyl)phenyl)-1,2,3,4,5,6,7,8-octahydroquinazolin-4-yl)-3-methylbenzonitrile (example 55), using 4-(amino(6-oxo-2-(3-(trifluoromethyl)phenylamino)cyclohex-1-enyl)methyl)-3-chloro-benzonitrile hydrochloride (intermediate 54, 620 mg, 1.36 mmol) as starting material. Yield: 191 mg; ESI mass spectrum [M+H]$^+$=446; Retention time HPLC: 0.65 min (X012_S01).

Example 57

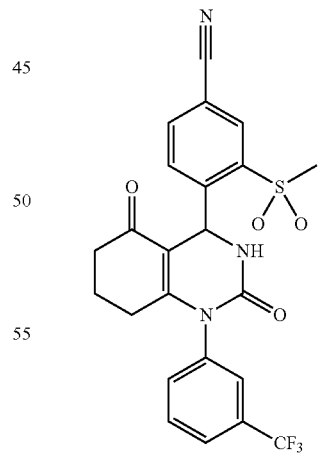

4-(2,5-Dioxo-1-(2-(trifluoromethyl)pyridin-4-yl)-1,2,3,4,5,6,7,8-octahydroquinazolin-4-yl)-3-(methylsulfonyl)benzonitrile A mixture of 4-(amino(6-oxo-2-(2-(trifluoromethyl)pyridin-4-ylamino)cyclohex-1-enyl)-methyl)-3-(methylsulfonyl)benzonitrile hydrochloride (intermediate 57, 970 mg, 1.94 mmol), 1,1-carbonyldiimidazole (392 mg, 2.42 mmol) and triethylamine (68 µL, 0.48 mmol) in acetonitrile (15 mL) is stirred at room temperature for 1 h. All volatiles are removed under reduced pressure, and the residue is treated with iso-propanol. The precipitate is filtered, washed with iso-propanol and dried. Yield: 800 mg; ESI mass spectrum [M+H]$^+$=491; Retention time HPLC: 0.55 min (X012_S02).

Example 58

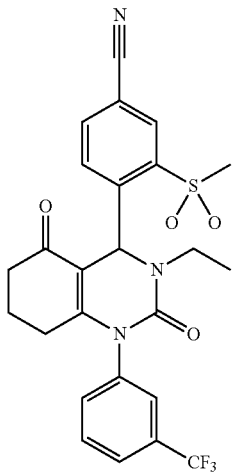 [SMILES: CCN1C(=O)N(c2cccc(C(F)(F)F)c2)C2=C(C(=O)CCC2)C1c1ccc(C#N)cc1S(C)(O)O]

4-(3-Ethyl-2,5-dioxo-1-(3-(trifluoromethyl)phenyl)-1,2,3,4,5,6,7,8-octahydroquinazolin-4-yl)-3-(methylsulfonyl)benzonitrile Ethyl bromide (18 µL, 0.25 mmol) is added to a solution of 4-(2,5-dioxo1-(3-(trifluoromethyl)phenyl)-1,2,3,4,5,6,7,8-octahydroquinazolin-4-yl)-3-(methylsulfonyl)benzonitrile (example 18, 60 mg, 0.12 mmol) and cesium carbonate (80 mg, 0.25 mmol) in N,N-dimethylformamide (2 mL). The mixture is stirred at room temperature over night and purified by preparative HPLC (Waters Xbridge™-C$_{18}$, gradient of acetonitrile in water, 0.1% NH$_3$). Yield: 18 mg; ESI mass spectrum [M+H]$^+$=518; Retention time HPLC: 0.81 min (004_CA05).

The following examples of Table 8 are prepared in analogy to 4-(3-ethyl-2,5-dioxo-1-(3-(trifluoromethyl)phenyl)-1,2,3,4,5,6,7,8-octahydroquinazolin-4-yl)-3-(methyl-sulfonyl)benzonitrile (example 58), using the appropriate alkyl halogenide and the purification method as indicated in the table (Method A: Waters Xbridge™-C$_{18}$, gradient of acetonitrile in water, 0.1% NH$_3$, Method B: Waters Xbridge™-Phenyl, gradient of methanol in water, 0.1% TFA, Method C: Waters SunFire™-C$_{18}$, gradient of acetonitrile in water, 0.1% TFA).

TABLE 8

| Example | R$^3$ | Purification Method | MS [M + H]$^+$ | Retention time [min] | HPLC-Method |
|---|---|---|---|---|---|
| 58.1 | ⸺\O\ | A | 548 | 0.79 | 004_CA05 |
| 58.2 | ⸺\\OH | B | 548 | 1.01 | Z018_S04 |
| 58.3 | ⸺\F F | C | 554 | 1.11 | Z018_S04 |
| 58.4 | ⸺\\O\ | A | 562 | 0.80 | 004_CA05 |

TABLE 8-continued

| Example | R³ | Purification Method | MS [M + H]⁺ | Retention time [min] | HPLC-Method |
|---|---|---|---|---|---|
| 58.5 | (tetrahydropyran-4-yl-methyl) | C | 588 | 1.09 | Z018_S04 |
| 58.6 | (2-(tetrahydropyran-4-yl)ethyl) | A | 602 | 0.83 | 004_CA05 |

Example 59

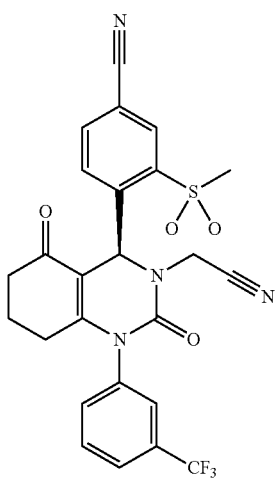 [SMILES: CS(O)(O)c1cc(C#N)ccc1[C@@H]1C2=C(CCCC2=O)N(c2cccc(C(F)(F)F)c2)C(=O)N1CC#N]

(S)-4-(3-(Cyanomethyl)-2,5-dioxo-1-(3-(trifluoromethyl)phenyl)-1,2,3,4,5,6,7,8-octahydroquinazolin-4-yl)-3-(methylsulfonyl)benzonitrile Sodium hydride (60% in mineral oil, 11 mg, 0.28 mmol) is added to a solution of (S)-4-(2,5-dioxo-1-(3-(trifluoromethyl)phenyl)-1,2,3,4,5,6,7,8-octahydroquinazolin-4-yl)-3-(methylsulfonyl)benzonitrile (example 18A, 50 mg, 0.10 mmol) in tetrahydrofuran (3 mL), and the mixture is stirred at room temperature for 20 min 2-Iodoacetonitrile (7 µL, 0.10 mmol) is added, and the mixture is stirred over night. Another portion of 2-iodoaceto-nitrile (7 µL, 0.10 mmol) is added, and the mixture is stirred over night. Another portion of 2-iodoacetonitrile (14 µL, 0.20 mmol) is added, and the mixture is stirred for 2 h, diluted with water and purified by preparative HPLC (Waters SunFire™-C₁₈, gradient of acetonitrile in water, 0.1% TFA). Yield: 6 mg; ESI mass spectrum [M+H]⁺=529; Retention time HPLC: 1.05 min (Z018_S04).

Example 60

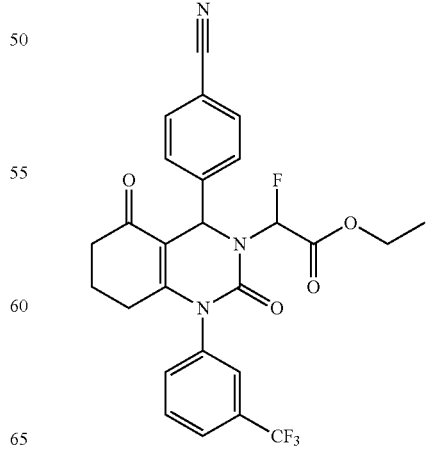

Ethyl 2-(4-(4-Cyanophenyl)-2,5-dioxo-1-(3-(trifluoromethyl)phenyl)-1,2,5,6,7,8-hexahydroquinazolin-3(4H)-yl)-2-fluoroacetate A solution of 4-(2,5-dioxo-1-(3-(trifluoromethyl)phenyl)-1,2,3,4,5,6,7,8-octahydroquinazolin-4-yl)-benzonitrile (example 1, 200 mg, 0.49 mmol) in tetrahydrofuran (4 mL) is cooled in an ice bath. Lithium diisopropylamide (2 M in tetrahydrofuran, 270 µL, 0.54 mmol) is added, and the mixture is stirred for 15 min. Ethyl 2-bromo-2-fluoroacetate (135 mg, 0.73 mmol) is added, and the mixture is warmed at room temperature and stirred over night. Water is added, and the mixture is extracted twice with dichloromethane. The combined organic layers are concentrated under reduced pressure, and the residue is purified by preparative HPLC (Waters Xbridge™-$C_{18}$, gradient of acetonitrile in water, 0.1% TFA). Yield: 70 mg; ESI mass spectrum [M+H]$^+$=516; Retention time HPLC: 0.67 min (X012_S01).

Example 61

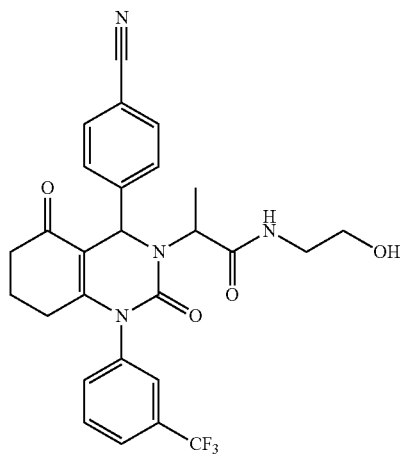 [SMILES: CC(C(=O)NCCO)N1C(=O)N(c2cccc(C(F)(F)F)c2)C2=C(C(=O)CCC2)C1c1ccc(C#N)cc1]

2-(4-(4-Cyanophenyl)-2,5-dioxo-1-(3-(trifluoromethyl)phenyl)-1,2,5,6,7,8-hexahydroquinazolin-3(4H)-yl)-N-(2-hydroxyethyl)propanamide Triethylamine (55 µL, 0.40 mmol) is added to a solution of 2-(4-(4-cyanophenyl)-2,5-dioxo-1-(3-(trifluoromethyl)phenyl)-1,2,5,6,7,8-hexahydroquinazolin-3(4H)-yl)-propanoic acid (intermediate 59, 50 mg, 0.10 mmol) in N,N-dimethylformamide, and the mixture is stirred for 10 min at room temperature. N,N,N',N'-Tetramethyl-O-(benzotriazol-1-yl) uronium tetrafluoroborate (33 mg, 0.10 mmol) is added, and the mixture is stirred for 15 min. Ethanolamine (15 µL, 0.25 mml) is added, and the mixture is stirred for 1 h, diluted with N,N-dimethylformamide and purified by preparative HPLC (Waters SunFire™-$C_{18}$, gradient of acetonitrile in water, 0.1% TFA). Yield: 39 mg; ESI mass spectrum [M+H]$^+$=527; Retention time HPLC: 0.86 min (Z018_S04).

Example 62

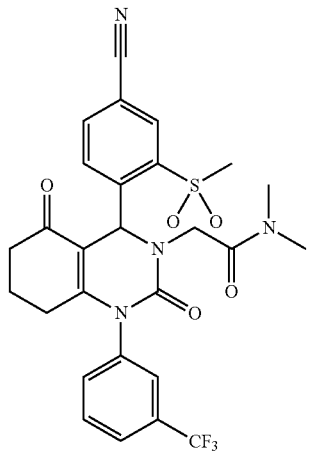 [SMILES: CN(C)C(=O)CN1C(=O)N(c2cccc(C(F)(F)F)c2)C2=C(C(=O)CCC2)C1c1ccc(C#N)cc1S(C)(O)O]

2-(4-(4-Cyano-2-(methylsulfonyl)phenyl)-2,5-dioxo-1-(3-(trifluoromethyl)phenyl)-1,2,5,6,7,8-hexahydroquinazolin-3(4H)-yl)-N,N-dimethylacetamide Step 1

2-(4-(4-Cyano-2-(methylsulfonyl)phenyl)-2,5-dioxo-1-(3-(trifluoromethyl)phenyl)-1,2,5,6,7,8-hexahydroquinazolin-3(4H)-yl)acetic acid tert-Butyl bromoacetate (200 L, 1.35 mmol) is added to a mixture of 4-(2,5-dioxo-1-(3-(trifluoromethyl)phenyl)-1,2,3,4,5,6,7,8-octahydroquinazolin-4-yl)-3-(methylsulfonyl)benzonitrile (example 18, 440 mg, 0.90 mmol) and cesium carbonate (440 mg, 1.35 mmol) in N,N-dimethylformamide (5 mL), and the mixture is stirred at room temperature for 3 h. Another portion of tert-butyl bromoacetate (200 µL, 1.35 mmol) is added, and the mixture is stirred for 2 h. Water is added, and the mixture is extracted with ethyl acetate. The phases are separated and the organic layer is concentrated under reduced pressure. The residue is dissolved in acetonitrile (3 mL), and the mixture is treated with trifluoroacetic acid (10 mL, 123 mmol) and stirred at room temperature for 6 h. All volatiles are removed under reduced pressure, and the residue is directly used in the next step without further purification. Yield: 460 mg.

Step 2

2-(4-(4-Cyano-2-(methylsulfonyl)phenyl)-2,5-dioxo-1-(3-(trifluoromethyl)phenyl)-1,2,5,6,7,8-hexahydroquinazolin-3(4H)-yl)-N,N-dimethylacetamide Triethylamine (50 µL, 0.36 mmol) is added to a solution of 2-(4-(4-cyano-2-(methyl-sulfonyl)phenyl)-2,5-dioxo-1-(3-(trifluoromethyl)phenyl)-1,2,5,6,7,8-hexahydroquinazolin-3(4H)-yl)acetic acid (step 1, 25 mg, 45 µmol) in N,N-dimethylformamide (1 mL), and the mixture is stirred at room temperature for 5 min N,N,N',N'-Tetramethyl-O-(benzotriazol-1-yl)uronium tetrafluoroborate (15 mg, 0.05 mmol) is added, and the mixture is stirred for 5 min Dimethylamine (2 M in tetrahydrofuran, 0.12 mL, 0.24 mmol) is added and the mixture is stirred at room temperature for 1 h and purified by preparative HPLC (Waters SunFire™-$C_{18}$, gradient of acetonitrile in water, 0.1% TFA). Yield: 22 mg; ESI mass spectrum [M+H]⁺=575; Retention time HPLC: 1.02 min (Z018_S04).

The following examples of Table 9 are prepared in analogy to 2-(4-(4-cyano-2-(methyl-sulfonyl)phenyl)-2,5-dioxo-1-(3-(trifluoromethyl)phenyl)-1,2,5,6,7,8-hexahydroquinazolin-3(4H)-yl)-N,N-dimethylacetamide (example 62), using the appropriate amine as reagent and purifying the product by preparative HPLC (Waters Xbridge™-C$_{18}$, gradient of acetonitrile in water, 0.1% TFA).

TABLE 9

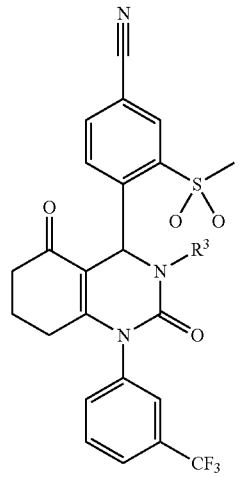

| Example | R³ | MS [M + H]⁺ | Retention time [min] | HPLC-Method |
|---|---|---|---|---|
| 62.1 | | 587 | 0.84 | 005_CA01 |
| 62.2 | | 601 | 0.88 | 005_CA01 |
| 62.3 | | 605 | 0.78 | 005_CA01 |
| 62.4 | | 613 | 0.90 | 005_CA01 |
| 62.5 | | 617 | 0.83 | 005_CA01 |

TABLE 9-continued
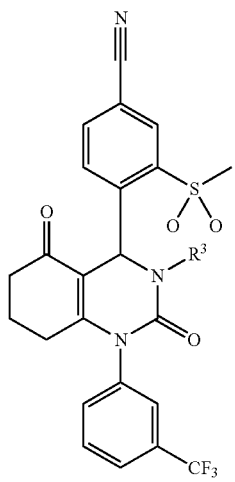
| Example | R³ | MS [M + H]⁺ | Retention time [min] | HPLC-Method |
|---|---|---|---|---|
| 62.6 | | 619 | 0.86 | 005_CA01 |
| 62.7 | | 619 | 0.86 | 005_CA01 |
| 62.8 | | 645 | 0.88 | 005_CA01 |
| 62.9 | | 655 | 0.82 | 005_CA01 |
| 62.10 | 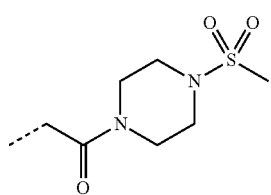 | 616 | 0.72 | 004_CA05 |

Example 63

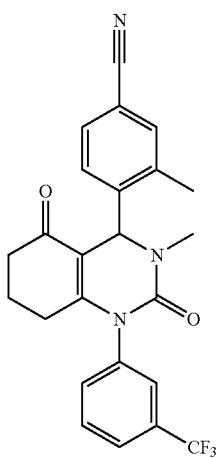 [SMILES: Cc1cc(C#N)ccc1C1C2=C(CCCC2=O)N(c2cccc(C(F)(F)F)c2)C(=O)N1C]

3-Methyl-4-(3-methyl-2,5-dioxo-1-(3-(trifluoromethyl)phenyl)-1,2,3,4,5,6,7,8-octahydroquinazolin-4-yl)benzonitrile Sodium hydride (60% in mineral oil, 6 mg, 0.16 mmol) is added to a solution of 4-(2,5-dioxo-1-(3-(trifluoromethyl)phenyl)-1,2,3,4,5,6,7,8-octahydroquinazolin-4-yl)-3-methylbenzonitrile (example 55, 60 mg, 0.13 mmol) in acetonitrile (3 mL), and the mixture is stirred at room temperature for 20 min. Methyl idodide (16 µL, 0.26 mmol) is added, and the mixture is stirred over night, diluted with N,N-dimethylformamide (1 mL) and purified by preparative HPLC (Waters Xbridge™-C$_{18}$, gradient of acetonitrile in water, 0.1% TFA). Yield: 13 mg; ESI mass spectrum [M+H]$^+$=440; Retention time HPLC: 0.65 min (X012_S01).

Example 64

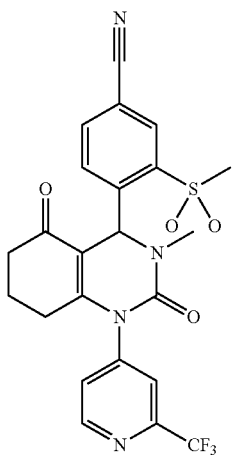 [SMILES: CN1C(=O)N(c2ccnc(C(F)(F)F)c2)C2=C(C(=O)CCC2)C1c1ccc(C#N)cc1S(C)(O)O]

4-(3-Methyl-2,5-dioxo-1-(2-(trifluoromethyl)pyridin-4-yl)-1,2,3,4,5,6,7,8-octahydroquinazolin-4-yl)-3-(methylsulfonyl)benzonitrile Cesium carbonate (265 mg, 0.82 mmol) and methyl idodide (51 µL, 0.82 mmol) are added to a solution of 4-(2,5-dioxo-1-(2-(trifluoromethyl)pyridin-4-yl)-1,2,3,4,5,6,7,8-octahydroquinazolin-4-yl)-3-(methylsulfonyl)benzonitrile (example 57, 200 mg, 0.41 mmol) in N,N-dimethylformamide (3 mL), and the mixture is stirred at room temperature for 2 h. Ethyl acetate is added, and the mixture is extracted three times with water. The organic phase is dried over Mg$_2$SO$_4$ and concentrated under reduced pressure. The residue is it) purified by flash chromatography on silica (gradient dichloromethane/methanol 99:1 to 97:3). Yield: 134 mg; ESI mass spectrum [M+H]$^+$=505; Retention time HPLC: 0.60 min (X012_S02).

Example 65

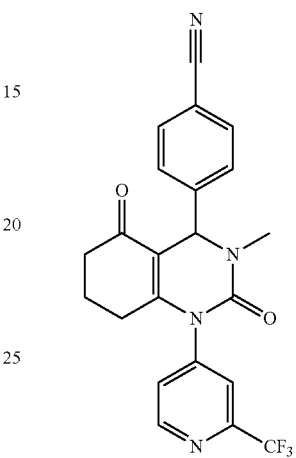

4-(3-Methyl-2,5-dioxo-1-(2-(trifluoromethyl)pyridin-4-yl)-1,2,3,4,5,6,7,8-octahydroquinazolin-4-yl)benzonitrile Cesium carbonate (39 mg, 0.12 mmol) and methyl idodide (6 µL, 0.10 mmol) are added to a solution of 4-(2,5-dioxo-1-(2-(trifluoromethyl)pyridin-4-yl)-1,2,3,4,5,6,7,8-octahydroquinazolin-4-yl)benzonitrile (example 14, 25 mg, 61 µmol) in N,N-dimethylformamide (1 mL). The mixture is stirred at room temperature for 1 h, diluted with aceontrile and purified by preparative HPLC (Waters SunFire™-C$_{18}$, gradient of acetonitrile in water, 0.1% TFA). Yield: 13 mg; ESI mass spectrum [M+H]$^+$=427; Retention time HPLC: 1.02 min (Z018_S04).

Example 66

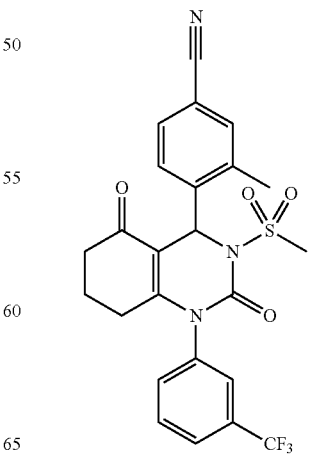

3-Methyl-4-(3-(methylsulfonyl)-2,5-dioxo-1-(3-(trifluoromethyl)phenyl)-1,2,3,4,5,6,7,8-octahydroquinazolin-4-yl)benzonitrile Sodium hydride (60% in mineral oil, 15 mg, 0.38 mmol) is added to a solution of 4-(2,5-dioxo-1-(3-(trifluoromethyl)phenyl)-1,2,3,4,5,6,7,8-octahydroquinazolin-4-yl)-3-methylbenzonitrile (example 55, 60 mg, 0.13 mmol) in tetrahydrofuran (3 mL), and the mixture is stirred at room temperature for 20 min. Methanesulfonyl chloride (22 µL, 0.28 mmol) is added, and the mixture is stirred at room temperature over night. Another portion of sodium hydride (60% in mineral oil, 5 mg, 0.13 mmol) and methanesulfonyl chloride (10 µL, 0.13 mmol) is added, and the mixture is stirred for 1 h and purified by preparative HPLC (Waters Xbridge™-$C_{18}$, gradient of acetonitrile in water, 0.1% TFA). Yield: 28 mg; ESI mass spectrum [M+H]$^+$=504; Retention time HPLC: 0.71 min (X012_S01).

Example 67

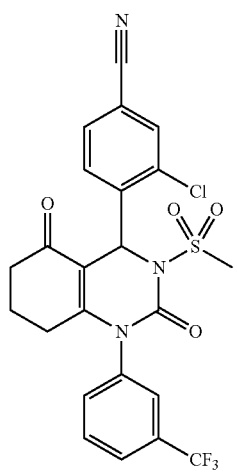 [SMILES: CS(=O)(=O)N1C(=O)N(c2cccc(C(F)(F)F)c2)C2=C(C(=O)CCC2)C1c1ccc(C#N)cc1Cl]

3-Chloro-4-(3-(methylsulfonyl)-2,5-dioxo-1-(3-(trifluoromethyl)phenyl)-1,2,3,4,5,6,7,8-octahydroquinazolin-4-yl)benzonitrile Sodium hydride (60% in mineral oil, 14 mg, 0.36 mmol) is added to a solution of 3-chloro-4-(2,5-dioxo-1-(3-(trifluoromethyl)phenyl)-1,2,3,4,5,6,7,8-octahydroquinazolin-4-yl)-benzonitrile (example 56, 60 mg, 0.13 mmol) in tetrahydrofuran (3 mL), and the mixture is stirred at room temperature for 20 min. Methanesulfonyl chloride (21 µL, 0.27 mmol) is added, and the mixture is stirred at room temperature over night. Water is added, and the mixture is extracted with dichloromethane. The phases are separated, and the organic phase is concentrated under reduced pressure. The residue is purified by preparative HPLC (Waters Xbridge™-$C_{18}$, gradient of acetonitrile in water, 0.1% TFA). Yield: 40 mg; ESI mass spectrum [M+H]$^+$=524; Retention time HPLC: 0.70 min (X012_S01).

Example 68

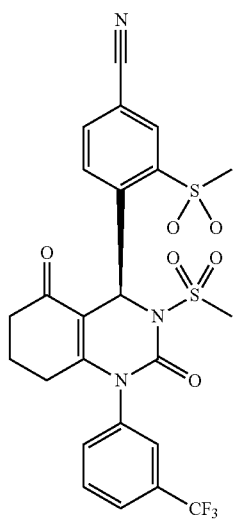 [SMILES: CS(O)(O)c1cc(C#N)ccc1[C@@H]1C2=C(CCCC2=O)N(c2cccc(C(F)(F)F)c2)C(=O)N1S(C)(=O)=O]

(S)-3-(Methylsulfonyl)-4-(3-(methylsulfonyl)-2,5-dioxo-1-(3-(trifluoromethyl)phenyl)-1,2,3,4,5,6,7,8-octahydroquinazolin-4-yl)benzonitrile (S)-4-(2,5-Dioxo-1-(3-(trifluoromethyl)phenyl)-1,2,3,4,5,6,7,8-octahydroquinazolin-4-yl)-3-(methylsulfonyl)benzonitrile (example 18A, 50 mg, 0.10 mmol) is added to a suspension of sodium hydride (60% in mineral oil, 11 mg, 0.29 mmol) and tetrahydrofuran (3 mL), and the mixture is stirred at room temperature for 10 min. Methanesulfonyl chloride (16 µL, 0.22 mol) is added, and the mixture is heated at 50° C. for 2 h. The mixture is cooled at room temperature, diluted with water (0.5 mL) and purified by preparative HPLC (Waters Xbridge™-$C_{18}$, gradient of acetonitrile in water, 0.1% TFA). Yield: 37 mg; ESI mass spectrum [M+H]$^+$=568; Retention time HPLC: 0.81 min (005_CA01).

Example 69

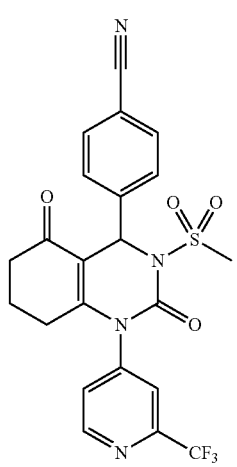 [SMILES: CS(=O)(=O)N1C(=O)N(c2ccnc(C(F)(F)F)c2)C2=C(C(=O)CCC2)C1c1ccc(C#N)cc1]

4-(3-(Methylsulfonyl)-2,5-dioxo-1-(2-(trifluoromethyl)pyridin-4-yl)-1,2,3,4,5,6,7,8-octahydroquinazolin-4-yl)benzonitrile 4-(2,5-Dioxo-1-(2-(trifluoromethyl)pyridin-4-yl)-1,2,3,4,5,6,7,8-octahydroquinazolin-4-yl)benzonitrile (example 14, 40 mg, 97 μmol) is added to a mixture of sodium hydride (60% in mineral oil, 15 mg, 0.19 mmol) and tetrahydrofuran (1 mL), and the mixture is stirred at room temperature for 3 min. Methanesulfonyl chloride (15 μL, 0.19 mmol) is added, and the mixture is heated at 50° C. for 1 h. The mixture is cooled at room temperature, diluted with water, acetonitrile and acetic acid and purified by reversed phase HPLC (Waters SunFire™-$C_{18}$, gradient of acetonitrile in water, 0.1% TFA). Yield: 32 mg; ESI mass spectrum [M+H]$^+$=491; Retention time HPLC: 1.01 min (Z018_S04).

Example 70

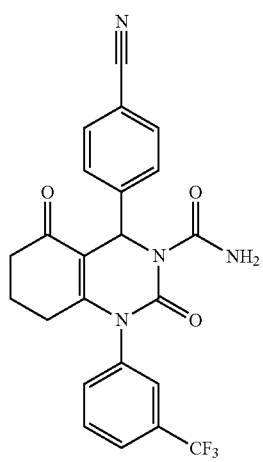 [SMILES: N#Cc1ccc(C2C3=C(CCCC3=O)N(c3cccc(C(F)(F)F)c3)C(=O)N2C(N)=O)cc1]

4-(4-Cyanophenyl)-2,5-dioxo-1-(3-(trifluoromethyl)phenyl)-1,2,5,6,7,8-hexahydroquinazoline-3(4H)-carboxamide N,N-Diisopropylethylamine (51 μL, 0.30 mmol) and ammonium carbonate (22 mg, 0.24 mmol) are added to a solution of 4-nitrophenyl 4-(4-cyanophenyl)-2,5-dioxo-1-(3-(tri-fluoromethyl)phenyl)1,2,5,6,7,8-hexahydroquinazoline-3(4H)-carboxylate (intermediate 37, 40 mg, 59 μmol) in acetonitrile (2 mL), and the mixture is stirred at room temperature over night and purified by preparative HPLC (Waters SunFire™-$C_{18}$, gradient of acetonitrile in water, 0.1% TFA). Yield: 12 mg; ESI mass spectrum [M+H]$^+$=455; Retention time HPLC: 1.05 min (Z018_S04).

The following examples of Table 10 are prepared in analogy to 4-(4-cyanophenyl)-2,5-dioxo-1-(3-(trifluoromethyl)phenyl)-1,2,5,6,7,8-hex ahydroquinazoline-3(4H)-carboxamide (example 70), employing the appropriate amine

TABLE 10

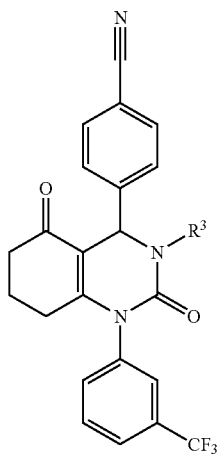

| Example | R$^3$ | MS [M + H]$^+$ | Retention time [min] | HPLC-Method |
|---|---|---|---|---|
| 70.1 | | 483 | 0.94 | 005_CA01 |
| 70.2 | | 494 | 0.87 | 005_CA01 |
| 70.3 | | 495 | 0.95 | 005_CA01 |
| 70.4 | | 497 | 0.99 | 005_CA01 |
| 70.5 | | 509 | 0.99 | 005_CA01 |
| 70.6 | | 519 | 0.93 | 005_CA01 |
| 70.7 | (cyclopropyl)) | 525 | 0.86 | 005_CA01 |
| 70.8 | | 525 | 0.89 | 005_CA01 |

TABLE 10-continued
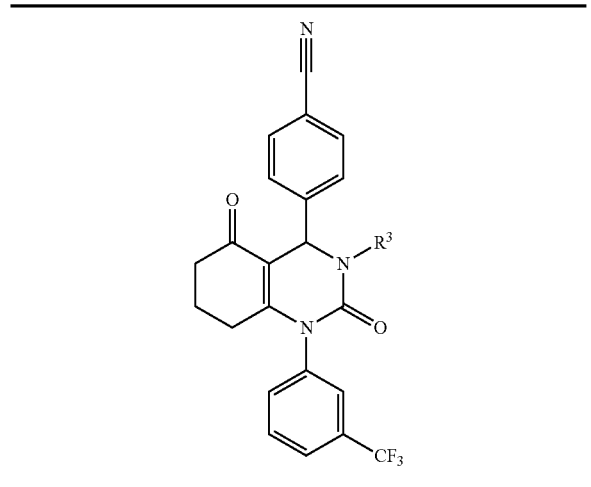
| Example | R³ | MS [M+H]⁺ | Retention time [min] | HPLC-Method |
|---|---|---|---|---|
| 70.9 | | 527 | 0.87 | 005_CA01 |
| 70.10 | | 527 | 0.90 | 005_CA01 |
| 70.11 | | 539 | 0.90 | 005_CA01 |
| 70.12 | | 539 | 0.90 | 005_CA01 |
| 70.13 | | 539 | 0.89 | 005_CA01 |
| 70.14 | | 539 | 0.91 | 005_CA01 |
| 70.15 | | 539 | 0.85 | 005_CA01 |
TABLE 10-continued
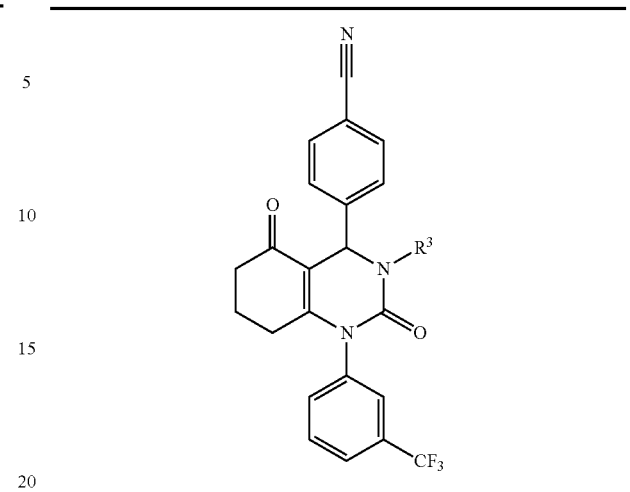
| Example | R³ | MS [M+H]⁺ | Retention time [min] | HPLC-Method |
|---|---|---|---|---|
| 70.16 | | 541 | 0.89 | 005_CA01 |
| 70.17 | | 553 | 0.93 | 005_CA01 |
| 70.18 | | 559 | 1.05 | Z018_S04 |
| 70.19 | | 573 | 0.85 | 005_CA01 |
| 70.20 | | 587 | 0.86 | 005_CA01 |

Example 71

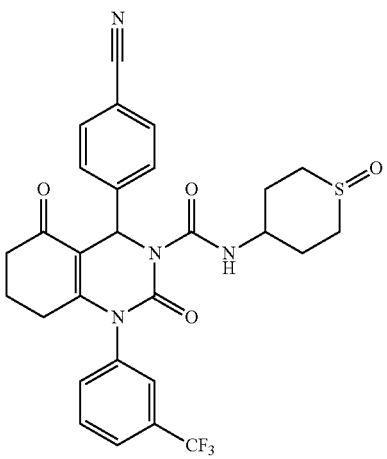 [SMILES: N#Cc1ccc(C2C3=C(CCCC3=O)N(c3cccc(C(F)(F)F)c3)C(=O)N2C(=O)NC2CCS(=O)CC2)cc1]

4-(4-Cyanophenyl)-2,5-dioxo-N-(1-oxo-hexahydro-1λ⁴-thiopyran-4-yl)-1-(3-(trifluoromethyl)phenyl)-1,2,5,6,7,8-hexahydroquinazoline-3(4H)-carboxamide A solution of 4-(4-cyanophenyl)-2,5-dioxo-N-(tetrahydro-2H-thiopyran-4-yl)-1-(3-(tri-fluoromethyl)phenyl)-1,2,5,6,7,8-hexahydroquinazoline-3(4H)-carboxamide (intermediate 60, 131 mg, 0.24 mmol) in ethanol (10 mL) is cooled at −78° C. with an acetone/dry ice bath. Aqueous hydrogen peroxide (1 M, 50 µL, 0.05 mmol) is added, and the mixture is stirred at −78° C. for 30 min. Methyltrioxorhenium(VII) (1 mg, 4 µmol) is added, and the mixture is stirred at −78° C. for 2 h. Aqueous sodium ascorbate (10%, 30 mL) and water (30 mL) is added, and the precipitate is filtered and purified by preparative HPLC (Waters Xbridge™-C₁₈, gradient of acetonitrile in water, 0.1% NH₃). Yield: 22 mg; ESI mass spectrum [M+H]⁺=571; Retention time HPLC: 0.51 min (004_CA07).

Example 72

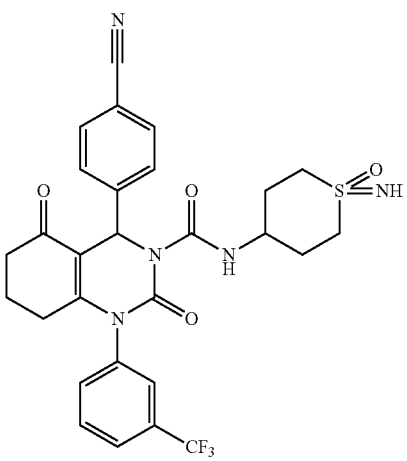 [SMILES: N#Cc1ccc(C2C3=C(CCCC3=O)N(c3cccc(C(F)(F)F)c3)C(=O)N2C(=O)NC2CCS(=N)(=O)CC2)cc1]

4-(4-Cyanophenyl)-2,5-dioxo-N-(1-imino-1-oxo-hexahydro-1λ⁶-thiopyran-4-yl)-1-(3-(trifluoromethyl)phenyl)-1,2,5,6,7,8-hexahydroquinazoline-3(4H)-carboxamide 4-(4-Cyanophenyl)-2,5-dioxo-N-(1-oxo-hexahydro-1λ⁴-thiopyran-4-yl)-1-(3-(trifluoromethyl)phenyl)-1,2,5,6,7,8-hexahydroquinazoline-3(4H)-carboxamide (example 71, 67 mg, 0.12 mmol) is added to a solution of O-mesitylenesulfonylhydroxylamine (25 mg, 0.12 mmol) in dichloromethane (1.0 mL), and the mixture is stirred at room temperature over night. All volatiles are removed under reduced pressure, and the residue is purified by reversed phase HPLC (Waters SunFire™-C₁₈, gradient of acetonitrile in water, 0.1% TFA). Yield: 18 mg; ESI mass spectrum [M+H]⁺=586; Retention time HPLC: 0.92 min (Z018_S04).

Example 73

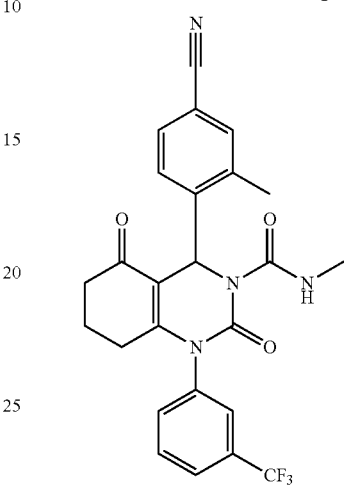

4-(4-Cyano-2-methylphenyl)-N-methyl-2,5-dioxo-1-(3-(trifluoromethyl)phenyl)-1,2,5,6,7,8-hexahydroquinazoline-3(4H)-carboxamide N,N-Diisopropylethylamine (88 µL, 0.51 mmol), 4-dimethylaminopyridine (48 mg, 0.39 mmol) and 4-nitrophenyl chloroformate (78 mg, 0.39 mmol) is added to a solution of 4-(2,5-dioxo-1-(3-(trifluoromethyl)phenyl)-1,2,3,4,5,6,7,8-octahydroquinazolin-4-yl)-3-methylbenzonitrile (example 55, 55 mg, 0.13 mmol) in acetonitrile (1.5 mL), and the mixture is stirred at room temperature over night. Methylamine (2 M in tetrahydrofuran, 97 µL, 0.19 mmol) is added, and the mixture is stirred at room temperature over night and purified by preparative HPLC (Waters Xbridge™-C₁₈, gradient of acetonitrile in water, 0.1% TFA). Yield: 35 mg; ESI mass spectrum [M+H]⁺=483; Retention time HPLC: 0.74 min (X012_S01).

Example 74

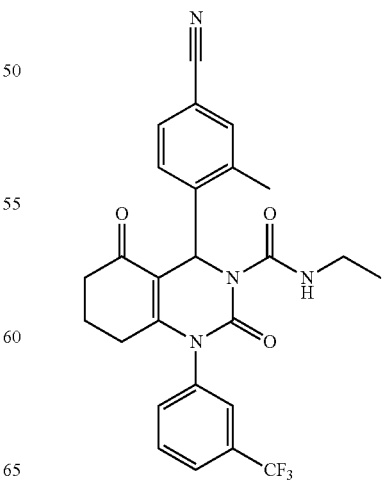

4-(4-Cyano-2-methylphenyl)-N-ethyl-2,5-dioxo-1-(3-(trifluoromethyl)phenyl)-1,2,5,6,7,8-hexahydroquinazoline-3(4H)-carboxamide The title compound is prepared in analogy to 4-(4-cyano-2-methylphenyl)-N-methyl-2,5-dioxo-1-(3-(trifluoromethyl)phenyl)-1,2,5,6,7,8-hexahydroquinazoline-3(4H)-carboxamide (example 73), replacing methylamine with ethylamine as reagent. Yield: 45 mg; ESI mass spectrum [M+H]$^+$=497; Retention time HPLC: 0.77 min (X012_S01).

Example 75

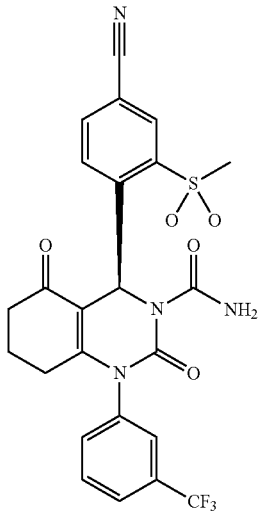 [SMILES: CS(O)(O)c1cc(C#N)ccc1[C@@H]1C2=C(CCCC2=O)N(c2cccc(C(F)(F)F)c2)C(=O)N1C(N)=O]

(S)-4-(4-Cyano-2-(methylsulfonyl)phenyl)-2,5-dioxo-1-(3-(trifluoromethyl)phenyl)-1,2,5,6,7,8-hexahydroquinazoline-3(4H)-carboxamide N,N-Diisopropylethylamine (52 µL, 0.30 mmol), 4-dimethylaminopyridine (13 mg, 0.11 mmol) and 4-nitrophenyl chloroformate (22 mg, 0.11 mmol) is added to a solution of (S)-4-(2,5-dioxo-1-(3-(trifluoromethyl)phenyl)-1,2,3,4,5,6,7,8-octahydroquinazolin-4-yl)-3-(methylsulfonyl)benzonitrile (example 18A, 50 mg, 0.10 mmol) in acetonitrile (2 mL), and the mixture is stirred at room temperature over night. Another portion of 4-dimethyl-aminopyridine (13 mg, 0.11 mmol) and 4-nitrophenyl chloroformate (22 mg, 0.11 mmol) is added, and the mixture is stirred over night. Ammonium carbonate (29 mg, 0.31 mmol) is added, and the mixture is stirred over night. Water is added, and the mixture is purified by reversed phase HPLC (Waters SunFire™-C$_{18}$, gradient of acetonitrile in water, 0.1% TFA). Yield: 19 mg; ESI mass spectrum [M+H]$^+$=533; Retention time HPLC: 1.02 min (Z018_S04).

The following examples of Table 11 are prepared in analogy to (S)-4-(4-cyano-2-(methyl-sulfonyl)phenyl)-2,5-dioxo-1-(3-(trifluoromethyl)phenyl)-1,2,5,6,7,8-hexahydroquinazoline-3(4H)-carboxamide (example 75), using the appropriate amine as reagent and the purification method as indicated in the table (Method A: Waters Xbridge™-Phenyl, gradient of methanol in water, 0.1% TFA; Method B: Waters SunFire™-C$_{18}$, gradient of is acetonitrile in water, 0.1% TFA).

TABLE 11

| Example | R$^3$ | Purification Method | MS [M + H]$^+$ | Retention time [min] | HPLC-Method |
|---|---|---|---|---|---|
| 75.1 | —C(O)NHCH$_2$CN | A | 572 | 1.02 | Z018_S04 |
| 75.2 | —C(O)NH-cyclopropyl | B | 573 | 0.77 | 002_CA03 |

TABLE 11-continued
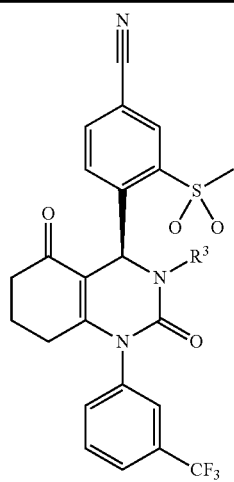
| Example | R³ | Purification Method | MS [M + H]⁺ | Retention time [min] | HPLC-Method |
|---|---|---|---|---|---|
| 75.3 | | B | 575 | 0.80 | 002_CA03 |
| 75.4 | | B | 586 | 1.06 | Z018_S04 |
| 75.5 | | B | 589 | 1.02 | Z018_S04 |
| 75.6 | | A | 591 | 1.05 | Z018_S04 |
| 75.7 | | B | 597 | 0.77 | 002_CA03 |
| 75.8 | | B | 598 | 1.05 | Z018_S04 |
| 75.9 | | B | 599 | 1.17 | Z018_S04 |
| 75.10 | | A | 603 | 1.03 | Z018_S04 |
| 75.11 | | B | 603 | 0.99 | Z018_S04 |

TABLE 11-continued
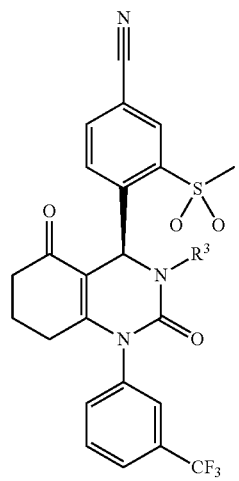
| Example | R³ | Purification Method | MS [M + H]⁺ | Retention time [min] | HPLC-Method |
|---|---|---|---|---|---|
| 75.12 | (acetamide-CH₂-C(CH₃)₂-OH) | A | 605 | 1.02 | Z018_S04 |
| 75.13 | (acetamide-C(CH₃)₂-CH₂OH) | A | 605 | 1.03 | Z018_S04 |
| 75.14 | (acetamide-cis-2-hydroxycyclopentyl) | A | 617 | 1.04 | Z018_S04 |
| 75.15 | (acetamide-cis-2-hydroxycyclopentyl) | A | 617 | 1.04 | Z018_S04 |
| 75.16 | (acetamide-tetrahydropyran-4-yl) | B | 617 | 0.74 | 002_CA03 |
| 75.17 | (acetamide-3-hydroxycyclopentyl) | B | 617 | 1.01 | Z018_S04 |
| 75.18 | (acetamide-2-hydroxycyclopentyl) | B | 619 | 0.98 | Z018_S04 |
| 75.19 | (acetamide-CH₂CH₂-C(CH₃)₂-OH) | A | 619 | 1.04 | Z018_S04 |

TABLE 11-continued

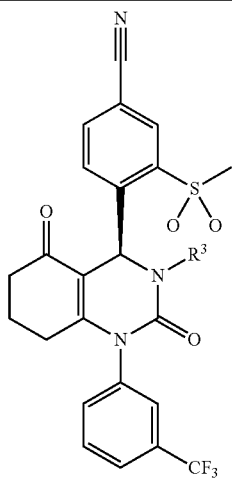

| Example | R³ | Purification Method | MS [M + H]⁺ | Retention time [min] | HPLC-Method |
|---|---|---|---|---|---|
| 75.20 | 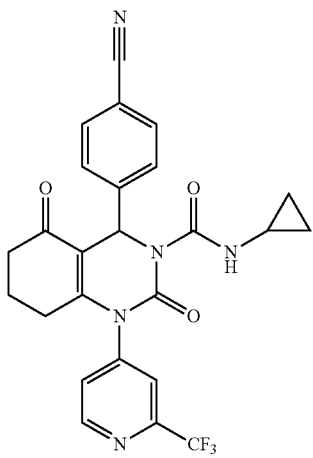 | B | 631 | 0.76 | 002_CA03 |

Example 76

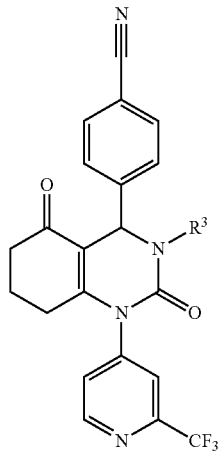

4-(4-Cyanophenyl)-N-cyclopropyl-2,5-dioxo-1-(2-(trifluoromethyl)pyridin-4-yl)-1,2,5,6,7,8-hexahydroquinazoline-3(4H)-carboxamide N,N-Diisopropylethylamine (66 µL, 0.39 mmol), 4-dimethylaminopyridine (13 mg, 0.11 mmol) and 4-nitrophenyl chloroformate (21 mg, 0.11 mmol) are added to a solution of 4-(2,5-dioxo-1-(2-(trifluoromethyl)pyridin-4-yl)-1,2,3,4,5,6,7,8-octahydroquinazolin-4-yl)-benzonitrile (example 14, 40 mg, 97 µmol) in acetonitrile (3 mL), and the mixture is stirred at room temperature for 3 h. Cyclopropylamine (20 µL, 0.29 mmol) is added, and the mixture is stirred at room temperature for 2 h and purified by reversed phase HPLC (Waters SunFire™-C₁₈, gradient of acetonitrile in water, 0.1% TFA). Yield: 20 mg; ESI mass spectrum [M+H]⁺=496; Retention time HPLC: 1.08 min (Z018_S04).

The following examples of Table 12 are prepared in analogy to 4-(4-cyanophenyl)-N-cyclopropyl-2,5-dioxo-1-(2-(trifluoromethyl)pyridin-4-yl)-1,2,5,6,7,8-hexahydroquinazoline-3(4H)-carboxamide (example 76), using the appropriate amine as reagent.

TABLE 12

| Example | R³ | MS [M + H]⁺ | Retention time [min] | HPLC-Method |
|---|---|---|---|---|
| 76.1 | | 470 | 1.03 | Z018_S04 |

TABLE 12-continued

| Example | R³ | MS [M + H]⁺ | Retention time [min] | HPLC-Method |
|---|---|---|---|---|
| 76.2 | -C(O)NH-Et | 484 | 1.08 | Z018_S04 |
| 76.3 | -C(O)NH-iPr | 498 | 1.12 | Z018_S04 |
| 76.4 | -C(O)NH-CH₂C(CH₃)₂OH | 528 | 1.01 | Z018_S04 |

EXAMPLES

Other features and advantages of the present invention will become apparent from the following more detailed examples which illustrate, by way of example, the principles of the invention.

Human Neutrophil Elastase Assay

Materials: Human neutrophil elastase was purchased from Calbiochem (Cat.No.: 324681) and the elastase substrate MeOSuc-Ala-Ala-Pro-Val-AMC from Bachem (Cat.No.: I-1270). All other materials were of the highest grade commercially available.

The following buffers were used: Compound buffer: 100 mM Tris, 500 mM NaCl, adjusted to pH 7.5; Assay buffer: 100 mM Tris, 500 mM NaCl, adjusted to pH 7.5, containing 0.01% BSA.

Assay conditions: Test compounds were prediluted in DMSO and subsequently in compound buffer (5% DMSO final). 5 μL of these compound dilutions were mixed with 10 μl Neutrophil elastase (9 ng/ml in assay buffer) in a black 384 well OptiPlate (Perkin Elmer, Cat No.: 6007270) and incubated for 15 min at room temperature. Subsequently 10 μL substrate solution in assay buffer were added (250 nM final concentration) and the plates were incubated for 60 min at room temperature. After inactivation of the enzyme, fluorescence intensities were measured at 380 nm excitation and 460 nm emission wavelengths.

Each plate contains wells with a high value control (DMSO+enzyme+substrate) and wells with a low value control (DMSO+inactivated enzyme+substrate). $IC_{50}$ values were estimated using a sigmoidal concentration response curve with variable slope. Means of low values were taken as 0%, means of high values as 100%. The $IC_{50}$ values of selected compounds in the Neutrophil Elastase assay are listed in Table 13.

TABLE 13

| Example | $IC_{50}$ [nM] |
|---|---|
| 1 | 28.5 |
| 1A | 9.5 |
| 1B | 6565 |
| 2 | 44.9 |
| 3 | 68.3 |
| 4 | 109.5 |
| 5 | 65.8 |
| 6 | 47.6 |
| 7 | 212.0 |
| 8 | 26.3 |
| 9 | 41.7 |
| 10 | 48.5 |
| 11 | 39.4 |
| 12 | 43.4 |
| 13 | 110.4 |
| 14 | 70.3 |
| 15 | 52.1 |
| 16 | 54.1 |
| 17 | 23.2 |
| 18 | 8.5 |
| 18A | 4.8 |
| 18B | 2509 |
| 19 | 10.7 |
| 19A | 7.3 |
| 19B | 1660 |
| 20 | 7.3 |
| 20A | 2.2 |
| 20B | 1335 |
| 21 | 19.4 |
| 22 | 8.7 |
| 23 | 10.7 |
| 24 | 6.4 |
| 24.1 | 6.6 |
| 24.2 | 9.8 |
| 24.3 | 11.1 |
| 25 | 8.6 |
| 26 | 11.8 |
| 27 | 10.8 |
| 28 | 29.0 |
| 29 | 13.7 |
| 30 | 4.0 |
| 31 | 18.4 |
| 31A | 7.6 |
| 31B | 7015 |
| 32 | 12.0 |
| 32A | 4.6 |
| 32B | 1410 |
| 33 | 9.6 |
| 34 | 3.1 |
| 34A | 1.5 |
| 34B | 570.5 |
| 35 | 1.7 |
| 35A | <1 |
| 35B | 26.8 |
| 36 | 8.2 |
| 36.1 | 6.4 |
| 36.2 | 13.1 |
| 36.3 | 20.8 |
| 36.4 | 2.4 |
| 36.5 | 13.5 |
| 36.6 | 1.2 |
| 36.7 | 3.4 |
| 36.8 | 2.1 |
| 36.9 | 10.6 |
| 36.10 | 20.0 |
| 36.11 | 5.1 |
| 36.12 | 6.6 |
| 36.13 | 20.5 |
| 36.14 | 8.1 |

TABLE 13-continued

| Example | IC$_{50}$ [nM] |
|---|---|
| 36.15 | 17.5 |
| 36.16 | 3.6 |
| 36.17 | 5.5 |
| 36.18 | 4.0 |
| 36.19 | 10.2 |
| 36.20 | 11.4 |
| 36.21 | 2.1 |
| 36.22 | 6.8 |
| 36.23 | 2.1 |
| 36.24 | 10.1 |
| 36.25 | 1.7 |
| 36.26 | 17.8 |
| 36.27 | 7.8 |
| 36.28 | 4.4 |
| 36.29 | 9.5 |
| 36.30 | 5.9 |
| 36.31 | 7.8 |
| 36.32 | 14.0 |
| 36.33 | 17.1 |
| 36.34 | 10.7 |
| 36.35 | 7.0 |
| 36.36 | 7.9 |
| 36.37 | 4.2 |
| 36.38 | 16.9 |
| 36.39 | 26.3 |
| 36.40 | 3.1 |
| 36.41 | 7.4 |
| 36.42 | 9.9 |
| 36.43 | 12.1 |
| 36.44 | 9.3 |
| 36.45 | 2.1 |
| 36.46 | 1.2 |
| 36.47 | 13.8 |
| 36.48 | 6.2 |
| 36.49 | 2.6 |
| 36.50 | 1.7 |
| 36.51 | 1.7 |
| 36.52 | 11.7 |
| 36.53 | 10.7 |
| 36.54 | 2.9 |
| 36.55 | 21.6 |
| 36.56 | 8.0 |
| 36.57 | 10.4 |
| 36.58 | 10.0 |
| 36.59 | 8.6 |
| 36.60 | 3.7 |
| 36.61 | 12.7 |
| 36.62 | 8.2 |
| 36.63 | 13.9 |
| 36.64 | 5.6 |
| 36.65 | 16.2 |
| 36.66 | 5.8 |
| 36.67 | 4.2 |
| 36.68 | 8.7 |
| 36.69 | 3.1 |
| 36.70 | 2.3 |
| 36.71 | 2.2 |
| 36.72 | 3.7 |
| 36.73 | 35.5 |
| 36.74 | 2.1 |
| 36.75 | 2.4 |
| 37 | <1 |
| 38 | 67.1 |
| 39 | 1.0 |
| 39.1 | 1.2 |
| 39.2 | 1.0 |
| 39.3 | <1 |
| 39.4 | 13.4 |
| 39.5 | <1 |
| 39.6 | <1 |
| 39.7 | 63.3 |
| 39.8 | 1.4 |
| 39.9 | <1 |
| 39.10 | 54.8 |
| 39.11 | 23.2 |
| 39.12 | <1 |
| 39.13 | 1.0 |
| 39.14 | 15.0 |
| 39.15 | <1 |
| 39.16 | 46.9 |
| 39.17 | <1 |
| 39.18 | 79.1 |
| 39.19 | <1 |
| 39.20 | <1 |
| 40 | 9.0 |
| 41 | 9.1 |
| 42 | 88.7 |
| 43 | 4.0 |
| 44 | 22.0 |
| 44.1 | 5.1 |
| 44.2 | 3.0 |
| 44.3 | 5.1 |
| 44.4 | 15.6 |
| 44.5 | 34.9 |
| 44.6 | 22.3 |
| 44.7 | 15.9 |
| 44.8 | 9.0 |
| 44.9 | 3.4 |
| 44.10 | 5.2 |
| 44.11 | 11.4 |
| 44.12 | 106.5 |
| 44.13 | 27.3 |
| 45 | 3.4 |
| 46 | 21.5 |
| 47 | <1 |
| 47A | <1 |
| 47B | 94 |
| 47.1 | <1 |
| 47.2 | <1 |
| 47.3 | <1 |
| 47.4 | <1 |
| 48 | 1.0 |
| 49 | 1.3 |
| 50 | <1 |
| 51 | <1 |
| 52 | 26.7 |
| 52.1 | 19.3 |
| 52.2 | 13.8 |
| 53 | 34.0 |
| 54 | 7.5 |
| 54A | 3.2 |
| 54B | 1869 |
| 55 | 18.7 |
| 56 | 34.0 |
| 57 | 73.2 |
| 58 | 1.3 |
| 58.1 | 1.0 |
| 58.2 | 1.2 |
| 58.3 | 3.1 |
| 58.4 | 1.3 |
| 58.5 | 1.9 |
| 58.6 | <1 |
| 59 | 1.8 |
| 60 | 21.6 |
| 61 | 6.6 |
| 62 | 1.2 |
| 62.1 | <1 |
| 62.2 | <1 |
| 62.3 | 1.3 |
| 62.4 | <1 |
| 62.5 | 1.0 |
| 62.6 | <1 |
| 62.7 | <1 |
| 62.8 | 1.6 |
| 62.9 | 1.4 |
| 62.10 | 2.4 |
| 63 | 7.9 |
| 64 | 3.6 |
| 65 | 22.6 |
| 66 | 2.0 |
| 67 | 6.7 |
| 68 | <1 |
| 69 | 23.8 |
| 70 | 6.0 |
| 70.1 | <1 |
| 70.2 | <1 |

TABLE 13-continued

| Example | IC$_{50}$ [nM] |
|---|---|
| 70.3 | <1 |
| 70.4 | 1.4 |
| 70.5 | 1.4 |
| 70.6 | <1 |
| 70.7 | 1.4 |
| 70.8 | <1 |
| 70.9 | 1.7 |
| 70.10 | 2.4 |
| 70.11 | <1 |
| 70.12 | <1 |
| 70.13 | 2.1 |
| 70.14 | <1 |
| 70.15 | <1 |
| 70.16 | 1.1 |
| 70.17 | 1.1 |
| 70.18 | <1 |
| 70.19 | <1 |
| 70.20 | <1 |
| 71 | <1 |
| 72 | <1 |
| 73 | <1 |
| 74 | <1 |
| 75 | <1 |
| 75.1 | <1 |
| 75.2 | <1 |
| 75.3 | <1 |
| 75.4 | <1 |
| 75.5 | <1 |
| 75.6 | <1 |
| 75.7 | <1 |
| 75.8 | <1 |
| 75.9 | <1 |
| 75.10 | <1 |
| 75.11 | <1 |
| 75.12 | <1 |
| 75.13 | <1 |
| 75.14 | <1 |
| 75.15 | <1 |
| 75.16 | <1 |
| 75.17 | <1 |
| 75.18 | <1 |
| 75.19 | <1 |
| 75.20 | <1 |
| 76 | 1.7 |
| 76.1 | 4.4 |
| 76.2 | 1.2 |
| 76.3 | 1.9 |
| 76.4 | 5.5 |

Assay for the Determination of Neutrophil Elastase Inhibitory Activity in Human Plasma Citrated blood from human healthy donors is mixed with zymosan suspension and incubated at room temperature. This leads to the stimulation of neutrophils and the release of neutrophil elastase into the plasma. The stimulated blood is centrifuged to generate the neutrophil elastase enriched plasma.

Preparation of Zymosan Working Solution:

Zymosan (100 mg) is mixed with saline (0.9%, 10 mL) and stored at 4° C. for up to one week (note: zymosan does not dissolve in the saline and is used as a suspension).

Whole blood stimulation:

single 45 ml blood sample is taken into a 50 ml tube containing citrate (3.13%, 5 mL) and the tube is gently inverted 4 times.

Immediately after blood sampling, zymosan working solution (5 mL) is added.

After the addition of zymosan working solution, the tubes are capped, mixed gently and incubated at 22° C. for 15 min on a shaker at 20 rpm.

Make 10 ml aliquots after the incubation time.

Centrifuge the 15 ml tubes at 800 g for 15 mM at 4° C. in a Jouan centrifuge.

Harvest the plasma and make 1-5 ml aliquots.

Store the plasma at −80° C.

Various concentrations of the neutrophil elastase inhibitor are incubated with plasma. Subsequently, the enzyme activity is measured using the fluorogenic substrate MeOSuc-Ala-Ala-Pro-Val-AMC (Bachem Cat. No. 1-1270, substrate concentration: 250 µM, pH 7.5, 25 mM TRIS buffer, 250 mM NaCl) in analogous fashion as described for the human neutrophil assay. A dose response curve is generated to calculate the EC$_{50}$ of the inhibitor. The analysis of the data is performed by the calculation of the percentage of fluorescence in the presence of the test compound compared to the fluorescence of the vehicle control after subtracting the background fluorescence: An inhibitor of the neutrophil elastase enzyme will give values between 100% control (no inhibition) and 0% control (complete inhibition). The human plasma shift of selected compounds can be calculated using the following equation:

Human plasma shift=($EC_{50}$ in human plasma assay)/ ($IC_{50}$ in human neutrophil elastase assay)

The EC$_{50}$ values of selected compounds in the human plasma assay described above are listed in Table 14.

TABLE 14

| Example | EC$_{50}$ [µM] | Example | EC$_{50}$ [µM] |
|---|---|---|---|
| 39.8 | 0.006 | 75.16 | 0.001 |
| 39.19 | 0.009 | 70.9 | 0.015 |
| 39.3 | 0.006 | 75 | <0.001 |
| 18A | 0.003 | 68 | 0.001 |
| 19A | 0.002 | 64 | 0.001 |
| 47A | 0.001 | 58.2 | 0.003 |
| 54A | 0.001 | 47.1 | 0.001 |
| 75.7 | 0.001 | 48 | 0.001 |
| 75.3 | 0.001 | | |

Assay for the Determination of Metabolic Stability with Human Liver Microsomes

The metabolic degradation of the test compound is assayed at 37° C. with pooled human liver microsomes. The final incubation volume of 100 nl per time point contains TRIS buffer pH 7.6 (0.1 M), magnesium chloride (5 mM), microsomal protein (1 mg/ml) and the test compound at a final concentration of 1 nM. Following a short preincubation period at 37° C., the reactions are initiated by addition of beta-nicotinamide adenine dinucleotide phosphate, reduced form (NADPH, 1 mM) and terminated by transfering an aliquot into acetonitrile after different time points. Additionally, the NADPH-independent degradation is monitored in incubations without NADPH, terminated at the last time point. The rol remaining test compound after NADPH independent incubation is reflected by the parameter c(control) (metabolic stability). The quenched incubations are pelleted by centrifugation (10'000 g, 5 min) An aliquot of the supernatant is assayed by LC-MS/MS for the amount of parent compound.

The half-life ($t_{1/2}$ INVITRO) is determined by the slope of the semilogarithmic plot of the concentration-time profile. The intrinsic clearance (CL_INTRINSIC) is calculated by considering the amount of protein in the incubation:

CL_INTRINSIC[µl/min/mg protein]=(ln 2/(half-life [min]*protein content [mg/ml]))*1'000.

The half-life ($t_{1/2}$ INVITRO) values of selected compounds in the metabolic stability assay described above are listed in Table 15.

TABLE 15

| Example | $t_{1/2}$ INVITRO [min] | Example | $t_{1/2}$ INVITRO [min] |
|---|---|---|---|
| 140 | >130 | 75.3 | >130 |
| 39.19 | >130 | 75.16 | >130 |
| 39.3 | >130 | 70.9 | >130 |
| 18A | >130 | 75 | >130 |
| 19A | >130 | 68 | >130 |
| 47A | >130 | 64 | >130 |
| 54A | >130 | 58.2 | >130 |
| 75.7 | >130 | 48 | >130 |

Assay for the Determination of Metabolic Stability with Human Hepatocytes

The metabolic degradation of the test compound is assayed in a human hepatocyte suspension. Human hepatocytes (typically cryopreserved) are incubated in an appropriate buffer system (e.g. Dulbecco's modified eagle medium plus 3.5 µg glucagon/500 mL, 2.5 mg insulin/500 mL and 3.75 mg/500 mL hydrocortison) containing 5% species serum. Following a (typically) 30 mM preincubation in an incubator (37° C., 10% $CO_2$), 5 µl of test compound solution (80 µM; from 2 mM stock solution in DMSO diluted 1:25 with medium) are added into 395 µl hepatocyte suspension (cell density in the range 0.25-5*$10^6$ cells/mL, typically 1*$10^6$ cells/mL; final concentration of test compound 1 µM, final DMSO concentration 0.05%). The cells are incubated for six hours (incubator, orbital shaker) and samples (25 µl) are taken at 0, 0.5, 1, 2, 4 and 6 hours. Samples are transferred into acetonitrile and pelleted by centrifugation (5 min). The supernatant is transferred to a new 96-deepwell plate, evaporated under nitrogen and resuspended. The decline of parent compound is analyzed by LC-MS/MS.

The intrinsic clearance CL_INTRINSIC is calculated as follows:

$$CL\_INTRINSIC = Dose/AUC = (C_0/CD)/(AUD + c_{last}/k)*1'000/60$$

($C_0$: initial concentration in the incubation [µM], CD: cell density of vital cells [$10^6$ cells/mL], AUD: area under the data [µM*h], $c_{last}$: concentration of last data point [µM], k: slope of the regression line for parent decline [$h^{-1}$])

The calculated in vitro hepatic intrinsic clearance can be scaled up to the intrinsic in vivo hepatic clearance and used to predict hepatic in vivo blood clearance (CL) by the use of a is liver model (well stirred model):

$$CL\_INTRINSIC\_INVIVO\ [ml/min/kg] = (CL\_INTRINSIC\ [\mu L/min/10^6\ cells]* hepatocellularity\ [10^6\ cells/g\ liver]*liver\ factor[g/kg\ bodyweight])/1'000$$

$$CL[ml/min/kg] = CL\_INTRINSIC\_INVIVO\ [ml/min/kg]*hepatic\ blood\ flow\ [ml/min/kg]/(CL\_INTRINSIC\_INVIVO\ [ml/min/kg] + hepatic\ blood\ flow\ [ml/min/kg])$$

$$Q_h[\%] = CL[ml/min/kg]/hepatic\ blood\ flow[ml/min/kg])$$

(Hepatocellularity, human: 120*$10^6$ cells/g liver; lver factor, human: 25.7 g/kg bodyweight; blood flow human: 21 ml/(min*kg))

The predicted human hepatic in vivo blood clearance (CL) of selected compounds in the metabolic stability assay described above are listed in Table 16.

TABLE 16

| Example | CL [ml/min/kg] | Example | CL [ml/min/kg] |
|---|---|---|---|
| 140 | 4 | 75.3 | 0 |
| 39.19 | 0 | 75.16 | 0 |
| 18A | 0 | 70.9 | 0 |
| 19A | 0 | 68 | 0 |
| 47A | 0 | 64 | 0 |
| 54A | 2 | 48 | 3 |
| 75.7 | 0 | 58.2 | 3 |

Assay for Determination of Drug Transport Across Human CACO-2 Cells

The assay provides information on the potential of a compound to pass the cell membrane, on the extent of oral absorption as well as on whether the compound is actively transported by uptake and/or efflux transporters. For the measurement of permeability across polarized, confluent human cancer colon carcinoma cells 2 (Caco-2) cell monolayers grown on permeable filter supports are used as the in vitro absorption model. Apparent permeability coefficients (PE) of the compounds across the Caco-2 monolayers are measured (pH 7.2, 37° C.) in apical-to-basal (AB) (absorptive) and basal-to-apical (BA) (secretory) transport direction. AB permeability (PEAB) represents drug absorption from the intestine into the blood and BA permeability (PEBA) drug secretion from the blood back into the intestine via both passive permeability as well as active transport mechanisms mediated by efflux and uptake transporters that are expressed on the Caco-2 cells. The compounds are assigned to permeability/absorption classes by comparison of the AB permeabilities with the AB permeabilities of reference compounds with known in vitro permeability and oral absorption in the human. Identical or similar permeabilities in both transport directions indicate passive permeation, vectorial permeability points to additional active transport mechanisms. Higher PEBA than PEAB suggests the involvement of an apical efflux transporter (like P-gp) and/or basolateral uptake transporter; higher PEAB than PEBA permeability suggests involvement of an apical uptake transporter (like PepT1) and/or basolateral efflux transporter (like MRP3). Active transport is concentration-dependently saturable.

Caco-2 cells (1–2*$10^5$ cells/$cm^2$ area) are seeded on filter inserts (Costar transwell polycarbonate or PET filters, 0.4 nm pore size) and cultured (DMEM) for 10 to 25 days. Compounds are dissolved in appropriate solvent (like DMSO, 1-20 mM stock solutions). Stock solutions are diluted with HTP-4 buffer (128.13 mM NaCl, 5.36 mM KCl, 1 mM $MgSO_4$, 1.8 mM $CaCl_2$, 4.17 mM $NaHCO_3$, 1.19 mM $Na_2HPO_4 \times 7H_2O$, 0.41 mM $NaH_2PO_4 \times H_2O$, 15 mM HEPES, 20 mM glucose, pH 7.2) to prepare the transport solutions (typically 10 nM compound, final DMSO <=0.5%). The transport solution (TL) is applied to the apical or basolateral donor side for measuring A-B or B-A permeability (3 filter replicates), respectively. The receiver side contains HTP-4 buffer supplemented with 2% BSA. Samples are collected at the start and end of experiment from the donor and at various time intervals for up to 2 hours also from the receiver side for concentration measurement by LC-MS/MS or scintillation counting. Sampled receiver volumes are is replaced with fresh receiver solution.

The apparent permeability coefficients (PEAB and PEBA) and efflux ratios (PEBA/PEAB) of selected compounds in the Caco-2 drug transport assay described above are listed in Table 17.

TABLE 17

| Example | PEAB [cm/s] | PEBA [cm/s] | Efflux ratio |
|---|---|---|---|
| 140 | 0.0000242 | 0.0000874 | 3.6 |
| 39.8 | 0.0000164 | 0.0000807 | 4.9 |
| 39.3 | 0.0000128 | 0.0000765 | 6.0 |
| 18A | 0.0000209 | 0.0000882 | 4.2 |
| 19A | 0.0000114 | 0.0000767 | 6.7 |
| 47A | 0.00000986 | 0.0000535 | 5.4 |
| 54A | 0.000026 | 0.0000617 | 2.4 |
| 75.7 | 0.0000084 | 0.0000906 | 10.8 |
| 75.3 | 0.0000228 | 0.0000853 | 3.7 |
| 70.9 | 0.0000303 | 0.0000961 | 3.2 |
| 64 | 0.0000171 | 0.0000757 | 4.4 |
| 47.1 | 0.000015 | 0.000081 | 5.4 |
| 48 | 0.000060 | 0.000098 | 1.6 |
| Example 38 disclosed in US 2011/0034433 | 0.0000002 | 0.0000028 | 17.1 |

Compared to the bicyclic example 38 disclosed in US 2011/0034433 bearing a carbamoyl (R—NH—C(═O)—) substituent at the dihydropyrimidinone nitrogen, numerous examples of the present invention bearing a carbamoyl (R—NH—C(═O)—) substituent at the dihydro-pyrimidinone nitrogen exhibit improved AB permeability and/or a reduced efflux ratio.

Assay for Determination of Aqueous Solubility

The aqueous solubility of a compound is determined by comparing the amount dissolved in aqueous buffer (containing 2.5% DMSO) to the amount dissolved in an acetonitrile/water (1/1) solution. Starting from a 10 mM DMSO stock solution, aliquots are diluted with acetonitrile/water (1/1) and McIlvaine buffer pH 6.8, respectively. After 24 h of shaking, the solutions or suspensions are filtered and analyzed by LC-UV. The amount dissolved in buffer is compared to the amount dissolved in the acetonitrile/water (1/1) solution. Solubility is measured from 0.001 to 0.125 mg/ml at a DMSO concentration of 2.5%. If more than 90% of the compound is dissolved in buffer, the value is marked with ">".

The aqueous solubility of selected compounds in the solubility assay described above is listed in Table 18.

TABLE 18

| Example | Aqueous solubility [mg/mL] | Example | Aqueous solubility [mg/mL] |
|---|---|---|---|
| 140 | 0.053 | 39.8 | 0.098 |
| 39.19 | 0.009 | 75.16 | 0.066 |
| 39.3 | 0.006 | 70.9 | 0.012 |
| 18A | 0.078 | 75 | 0.079 |
| 19A | 0.092 | 68 | 0.057 |
| 47A | 0.086 | 64 | 0.008 |
| 54A | 0.059 | 58.2 | 0.056 |
| 75.7 | 0.005 | 47.1 | 0.073 |
| 75.3 | 0.009 | | |

Assay for Determination of Cytochrome P450 2C9 Inhibition

The inhibition of cytochrome P450 2C9-isoenzyme catalysed hydroxylation of Diclofenac by the test compound is assayed at 37° C. with human liver microsomes. All assays are carried out on a robotic system in 96 well plates. The final incubation volume contains TRIS buffer (0.1 M), $MgCl_2$ (5 mM), human liver microsomes (0.1 mg/ml), Diclofenac (10 μM) and the test compound at five different concentrations or no compound (high it) control) in duplicate (e.g. highest concentration 10-50 μM with subsequent serial 1:4 dilutions). Following a short preincubation period, reactions are started with the cofactor (NADPH, 1 mM) and stopped by cooling the incubation down to 8° C. and subsequently by addition of one volume of acetonitrile. An internal standard solution—usually the stable isotope of the formed metabolite—is added after quenching of incubations. Peak area is analyte (=metabolite formed) and internal standard is determined by LC-MS/MS. The resulting peak area ratio analyte to internal standard in these incubations is compared to a control activity containing no test compound. Within each of the assay runs, the $IC_{50}$ of a positive control inhibitor (sulfaphenazole) is determined Experimental $IC_{50}$ values are calculated by least square regression according to the following equation:

% control activity=(100% control activity/
    $(1+(I/IC_{50})*S))-B$ (I=inhibitor concentration, S=slope factor, B=background activity)

If the inhibition of the reaction is already >50% at the lowest concentration of the test compound, the $IC_{50}$ is assigned "<lowest concentration tested" (usually <0.4 μM). If the inhibition of the reaction is still <50% at the highest concentration of the test compound, the $IC_{50}$ is assigned ">highest concentration tested" (usually >50 μM).

Assay for Determination of Cytochrome P450 2C19 Inhibition

The inhibition of cytochrome P450 2C19-isoenzyme catalysed hydroxylation of Mephenyloin by the test compound is assayed at 37° C. with human liver microsomes. All assays are carried out on a robotic system in 96 well plates. The final incubation volume contains TRIS buffer (0.1 M), $MgCl_2$ (5 mM), human liver microsomes (0.5 mg/ml), (S)-Mephenyloin (70 μM) and the test compound at five different concentrations or no compound (high control) in duplicate (e.g. highest concentration 10-50 μM with subsequent serial 1:4 dilutions). Following a short preincubation period, reactions are started with the cofactor (NADPH, 1 mM) and stopped by cooling the incubation down to 8° C. and subsequently by addition of one volume of acetonitrile. An internal standard solution—usually the stable isotope of the formed metabolite—is added after quenching of incubations. Peak area analyte (=metabolite formed) and internal standard is determined by LC-MS/MS. The resulting peak area ratio analyte to internal standard in these incubations is compared to a control activity containing no test compound. Within each of the assay runs, the $IC_{50}$ of a positive control inhibitor (tranylcypromine) is determined Experimental $IC_{50}$ values are calculated by least square regression according to the following equation:

% control activity=(100% control activity/
    $(1+(I/IC_{50})*S))-B$ (I=inhibitor concentration, S=slope factor, B=background activity)

If the inhibition of the reaction is already >50% at the lowest concentration of the test compound, the $IC_{50}$ is assigned "<lowest concentration tested" (usually <0.4 μM). If the inhibition of the reaction is still <50% at the highest concentration of the test compound, the $IC_{50}$ is assigned ">highest concentration tested" (usually >50 μM).

Combinations

The compounds of general formula 1 may be used on their own or combined with other active substances of formula 1 according to the invention. The compounds of general formula 1 may optionally also be combined with other pharmacologically active substances. These include, β2-adrenoceptor-agonists (short and long-acting), anti-cholinergics (short and long-acting), anti-inflammatory steroids (oral and topical corticosteroids), cromoglycate, methylxanthine, dissociated-glucocorticoidmimetics, PDE3 inhibitors, PDE4-inhibitors, PDE7-inhibitors, LTD4 antagonists, EGFR-inhibitors, Dopamine agonists, PAF antagonists, Lipoxin A4 derivatives, FPRL1 modulators, LTB4-receptor (BLT1, BLT2) antagonists, Histamine H1 receptor antagonists, Histamine H4 receptor antagonists, dual Histamine H1/H3-receptor antagonists, PI3-kinase inhibitors, inhibitors of non-receptor tyrosine kinases as for example LYN, LCK, SYK, ZAP-70, FYN, BTK or ITK, inhibitors of MAP kinases as for example p38, ERK1, ERK2, JNK1, JNK2, JNK3 or SAP, inhibitors of the NF-κB signalling pathway as for example IKK2 kinase inhibitors, iNOS inhibitors, MRP4 inhibitors, leukotriene biosynthese inhibitors as for example 5-Lipoxygenase (5-LO) inhibitors, cPLA2 inhibitors, Leukotriene A4 Hydrolase inhibitors or FLAP inhibitors, MMP9-inhibitors, MMP12-inhibitors, non-steroidale anti-inflammatory agents (NSAIDs), Cathepsin C (or DPPI/Dipeptidylaminopeptidase I) inhibitors, CRTH2 antagonists, DP1-receptor modulators, Thromboxane receptor antagonists, CCR3 antagonists, CCR4 antagonists, CCR1 antagonists, CCR5antagonists, CCR6 antagonists, CCR7 antagonists, CCR8 antagonists, CCR9 antagonists, CCR30 antagonists, CXCR3 antagonists, CXCR4 antagonists, CXCR2 antagonists, CXCR1 antagonists, CXCR5 antagonists, CXCR6 antagonists, CX3CR3 antagonists, Neurokinin (NK1, NK2) antagonists, Sphingosine 1-Phosphate receptor modulators, Sphingosine 1 phosphate lyase inhibitors, Adenosine receptor modulators as for example A2a-agonists, modulators of purinergicreceptors as for example P2X7 inhibitors, Histone Deacetylase (HDAC) activators, Bradykinin (BK1, BK2) antagonists, TACE inhibitors, PPAR gamma modulators, Rho-kinase inhibitors, interleukin 1-beta converting enzyme (ICE) inhibitors, Toll-Like receptor (TLR) modulators, HMG-CoA reductase inhibitors, VLA-4 antagonists, ICAM-1 inhibitors, SHIP agonists, GABAa receptor antagonist, ENaC-inhibitors, Prostasin-inhibitors, Melanocortin receptor (MC1R, MC2R, MC3R, MC4R, MC5R) modulators, CGRP antagonists, Endothelin antagonists, TNFα antagonists, anti-TNF antibodies, anti-GM-CSF antibodies, anti-CD46 antibodies, anti-IL-1 antibodies, anti-IL-2 antibodies, anti-IL-4 antibodies, anti-IL-5 antibodies, anti-IL-13 antibodies, anti-IL-4/IL-13 antibodies, anti-TSLP antibodies, anti-OX40 antibodies, mucoregulators, immunotherapeutic agents, compounds against swelling of the airways, compounds against cough, VEGF inhibitors, but also combinations of two or three active substances.

Preferred are betamimetics, anticholinergics, corticosteroids, PDE4-inhibitors, LTD4-antagonists, EGFR-inhibitors, Cathepsin C inhibitors, CRTH2 inhibitors, 5-LO-inhibitors, Histamine receptor antagonists and SYK-inhibitors, especially Cathepsin C inhibitors, but also combinations of two or three active substances, i.e.:

Betamimetics with corticosteroids, PDE4-inhibitors, CRTH2-inhibitors or LTD4-antagonists, Anticholinergics with betamimetics, corticosteroids, PDE4-inhibitors, CRTH2-inhibitors or LTD4-antagonists, Corticosteroids with PDE4-inhibitors, CRTH2-inhibitors or LTD4-antagonists PDE4-inhibitors with CRTH2-inhibitors or LTD4-antagonists CRTH2-inhibitors with LTD4-antagonists.

Indications

The compounds of the invention and their pharmaceutically acceptable salts have activity as pharmaceuticals, in particular as inhibitors of neutrophil elastase, and thus may be used in the treatment of:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; alpha1-antitrypsin deficiency; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus; acute lung injury; acute respiratory distress syndrome;

2. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis;cutaneous lymphomas, non-melanoma skin cancer and other dysplastic lesions; drug-induced disorders including fixed drug eruptions;

3. eyes: blepharitis; conjunctivitis, including perennial and vernal allergic conjunctivitis; iritis; anterior and posterior uveitis; choroiditis; autoimmune, degenerative or inflammatory disorders affecting the retina; ophthalmitis including sympathetic ophthalmitis; sarcoidosis; infections including viral, fungal, and bacterial;

4. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

5. allograft rejection: acute and chronic following, for example, transplantation of kidney, heart, liver, lung, bone marrow, skin or cornea or following blood transfusion; or chronic graft versus host disease;

6. other auto-immune and allergic disorders including rheumatoid arthritis, irritable bowel syndrome, systemic lupus erythematosus, multiple sclerosis, Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome and Sazary syndrome;

7. oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and,
8. infectious diseases: virus diseases such as genital warts, common warts, plantar warts, hepatitis B, hepatitis C, herpes simplex virus, molluscum contagiosum, variola, human immunodeficiency virus (HIV), human papilloma virus (HPV), cytomegalovirus (CMV), varicella zoster virus (VZV), rhinovirus, adenovirus, coronavirus, influenza, para-influenza; bacterial diseases such as tuberculosis and *mycobacterium avium*, leprosy; other infectious diseases, such as fungal diseases, chlamydia, *Candida*, *aspergillus*, cryptococcal meningitis, *Pneumocystis* carnii, cryptosporidiosis, histoplasmosis, toxoplasmosis, trypanosome infection and leishmaniasis.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For Example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

The actual pharmaceutically effective amount or therapeutic dosage will of course depend on factors known by those skilled in the art such as age and weight of the patient, route of administration and severity of disease. In any case the active ingredient will be administered at dosages and in a manner which allows a pharmaceutically effective amount to be delivered based upon patient's unique condition.

What we claim:
1. A compound of formula 1

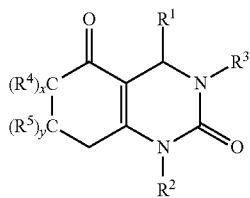

wherein
$R^1$ is phenyl or a five- or six-membered heteroaryl, wherein said heteroaryl comprises one, two or three heteroatoms independently selected from the group consisting of N, O and S; each ring optionally substituted with one, two or three substituents independently selected from the group consisting of halogen, $O_2N-$, $NC-$, $H_2N-$, $HO-$, $R^{1.1}$, $R^{1.1}O-$, $R^{1.2}$, $R^{1.3}S-$, $R^{1.3}(O)S-$ and $R^{1.3}(O)_2S-$;
  $R^{1.1}$ is independently selected from the group consisting of $C_{1-6}$-alkyl-, $C_{3-6}$-cycloalkyl-, $C_{1-6}$-haloalkyl- and $C_{3-6}$-halocycloalkyl-;
  $R^{1.2}$ is $HO-C_{1-6}$-alkyl- or $R^{1.1}-O-C_{1-6}$-alkyl-;
  $R^{1.3}$ is independently selected from the group consisting of H, $HO-$, $R^{1.1}$ and $R^{1.2}$;
$R^2$ is phenyl or a five- or six-membered heteroaryl, wherein said heteroaryl comprises one, two or three heteroatoms independently selected from the group consisting of N, O and S; each ring optionally substituted with one or two substituents independently selected from the group consisting of halogen, $C_{1-4}$-alkyl-, $C_{1-4}$-haloalkyl- and $C_{1-4}$-alkyl-O—;
$R^3$ is a residue independently selected from the group consisting of
  $R^{3.1}-$;
  $R^{3.2}(O)C-$;
  $R^{3.2}O(O)C-$;
  $R^{3.2}O(O)C-A-$;
  $R^{3.2}S-$; $R^{3.2}(O)S-$; $R^{3.2}(O)_2S-$;
  $(R^{3.2})_2N(O)C-$; and
  $(R^{3.2})_2N(O)C-A-$;
  $R^{3.1}$ is independently selected from the group consisting of H, $R^{3.3}R^{3.4}$, $C_{1-6}$-alkyl-$C_{3-6}$-cycloalkyl- and $C_{3-6}$-cycloalkyl-$C_{1-6}$-alkyl-, each optionally substituted with one or two substituents independently selected from among $R^{3.1.1}$;
    $R^{3.1.1}$ is selected from the group consisting of $HO-$, halogen, $NC-$, $R^{3.3}O-$, $R^{3.5}$, $R^{3.6}$ and $R^{3.7}$ or
    $R^{3.1.1}$ denotes a ring independently selected from phenyl and a four-membered heterocyclic ring containing one element independently selected from among N, O, S, S(O) and $S(O)_2$; or
    $R^{3.1.1}$ denotes a five- or six-membered heterocyclic or heteroaryl ring containing one, two or three elements independently selected from among N, O, S, S(O) and $S(O)_2$; each of the rings optionally substituted with one or two substituents independently selected from among $HO-$, $O=$, halogen, $NC-$, $R^{3.3}$, $R^{3.3}O-$, $R^{3.3}-(O)C-$, $R^{3.4}$, $R^{3.5}$, $R^{3.6}$ and $R^{3.7}$ or two substituents are together $R^{3.8}$;
  $R^{3.2}$ is independently selected from among $R^{3.1}$, phenyl, a four-membered heterocyclic ring containing one element independently selected from the group consisting of N, O, S, S(O) and $S(O)_2$; or a five- or six-membered heterocyclic or heteroaryl ring containing one, two or three elements independently selected from the group consisting of N, O, S, S(O) and $S(O)_2$; each ring optionally substituted with one or two substituents independently selected from the group consisting of $HO-$, $O=$, $NC-$, halogen, $R^{3.3}$, $R^{3.3}O-$, $R^{3.3}-(O)C-$, $R^{3.4}$, $R^{3.5}$, $R^{3.6}$, $R^{3.7}$ or two substituents are together $R^{3.8}$;
    or two $R^{3.2}$ are together a three-, four-, five- or six-membered monocyclic or a six-, seven-, eight-, nine- or ten-membered bicyclic heterocyclic or heteroaryl ring optionally containing additional to the nitrogen one or two elements independently selected from the group consisting of N, O, S, S(O) and $S(O)_2$; optionally substituted with one or two substituents, independently selected from the group consisting of $HO-$, F, $O=$, $NC-$, $R^{3.3}$, $R^{3.3}O-$, $R^{3.3}-(O)C-$, $R^{3.4}$, $R^{3.5}$, $R^{3.6}$, $R^{3.7}$, phenyl, a five- or six-membered heterocyclic or heteroaryl ring containing one, two or three elements independently selected from the group consisting of N, O, S, S(O) or $S(O)_2$; or two substituents are together $R^{3.8}$;
  $R^{3.3}$ is independently selected from the group consisting of $C_{1-6}$-alkyl-, $C_{3-6}$-cycloalkyl-, $C_{1-6}$-haloalkyl-, $c_{3-6}$-halocycloalkyl-;
  $R^{3.4}$ is $HO-C_{1-6}$-alkyl- or $R^{3.3}-O-C_{1-6}$-alkyl-;
  $R^{3.5}$ is independently selected from the group consisting of $H_2N-$, $R^{3.3}-HN-$, $(R^{3.3})_2N-$, $R^{3.3}-(O)C-HN-$, $R^{3.3}-(O)C-(R^{3.3})N-$;
  $R^{3.6}$ is independently selected from the group consisting of $R^{3.3}-(O)S-$, $R^{3.3}-(O)_2S-$, $R^{3.3}(HN)S-$, $R^{3.3}(HN)(O)S-$, $R^{3.3}(R^{3.3}N)S-$, $R^{3.3}(R^{3.3}N)(O)S-$, $R^{3.3}(R^{3.4}N)S—$, $R^{3.3}(R^{3.4}N)(O)S—$; $R^{3.3}(NC—N)S—$, $R^{3.3}(NC—N)(O)S—$;

$R^{3.7}$ is independently selected from the group consisting of HO(O)C—, $H_2N(O)C—$, $R^{3.3}—O—(O)C—$, $R^{3.3}—NH—(O)C—$, $(R^{3.3})_2N—(O)C—$;

$R^{3.8}$ is independently selected from the group consisting of $C_{1-6}$-alkylene or $C_{1-6}$-haloalkylene, wherein optionally one or two $CH_2$-groups independently from each other are replaced by —HN—, —$(R^{3.3})N—$, —$(R^{3.4})N—$, —$(R^{3.3}(O)C—)N—$, —$(R^{3.4}(O)C—)N—$, —O—, —S—, —S(O)— or —$S(O)_2$—;

A is —$CH_2$—, —$CH_2$—$CH_2$— or —$CH_2$—$CH_2$—$CH_2$—; optionally substituted with one or two substituents independently selected from the group consisting of halogen, $R^{3.3}$ $R^{3.3}$O— and $R^{3.4}$ or two substituents together are $R^{3.8}$;

$R^4$ is independently selected from the group consisting of halogen, $C_{1-6}$-alkyl-, $C_{3-6}$-cycloalkyl-, $C_{1-6}$-haloalkyl-, $C_{3-6}$-halocycloalkyl-, HO—$C_{1-6}$-alkyl-, $C_{1-6}$-alkyl—O—$C_{1-6}$-alkyl-;

or two $R^4$ are together $C_{1-6}$-alkylene or $C_{1-6}$-haloalkylene, wherein optionally one $CH_2$-group can be replaced by —O—, —S—, —S(O)— or —$S(O)_2$—;

x is 0, 1 or 2;

$R^5$ is independently selected from the group consisting of halogen, NC—, $R^{5.1}$;

HO(O)C—, $H_2N(O)C—$, $R^{5.1}$—O—(O)C—, $R^{5.1}$—NH—(O)C—, $(R^{5.1})_2N—(O)C—$;

phenyl or a five- or six-membered heterocyclic or heteroaryl ring containing one, two or three elements independently selected from the group consisting of N, O, S, S(O) or $S(O)_2$; each ring optionally substituted with one, two or three substituents independently selected from the group consisting of halogen, HO—, O=, NC—, $O_2N—$, $H_2N—$, $R^{5.1}$, $R^{5.1}$O—, $R^{5.1}$—HN—, $(R^{5.1})_2N—$, $R^{5.1}$—(O)C—HN—, $R^{5.1}$—(O)C—$(R^{5.1})N—$, $R^{5.1}$—(O)S—, $R^{5.1}$—$(O)_2S—$, $R^{5.1}$—(HN)S—, $R^{5.1}$—(HN)(O)S—, $R^{5.1}$—$(R^{5.1}N)S—$, $R^{5.1}$—$(R^{5.1}N)(O)S—$, $R^{5.1}$—(NC—N)S—, $R^{5.1}$—(NC—N)(O)S—, HO(O)C—, $H_2N(O)C—$, $R^{5.1}$—O—(O)C—, $R^{5.1}$—NH—(O)C—, $(R^{5.1})_2N—(O)C—$;

$R^{5.1}$ is independently selected from the group consisting of $C_{1-6}$-alkyl-, $C_{3-6}$-cycloalkyl-, $C_{1-6}$-alkyl-$C_{3-6}$-cycloalkyl-, $C_{3-6}$-cycloalkyl-$C_{1-6}$-alkyl-, $C_{1-6}$-haloalkyl-, $C_{3-6}$-halocycloalkyl-, HO—$C_{1-6}$-alkyl-, $C_{1-6}$-alkyl—O—$C_{1-6}$-alkyl-, $C_{3-6}$-cycloalkyl—O—$C_{1-6}$-alkyl-, $C_{1-6}$-haloalkyl—O—$C_{1-6}$-alkyl-, $C_{3-6}$-halocycloalkyl—O—$C_{1-6}$-alkyl-, or two $R^{5.1}$ are together $C_{1-6}$-alkylene or $C_{1-6}$-haloalkylene, wherein optionally one or two $CH_2$-groups are replaced by —HN—, —$(C_{1-6}$-alkyl-)N—, —$(C_{3-6}$-cycloalkyl-)N—, —$(C_{1-6}$-haloalkyl-)N—, —$(C_{3-6}$-halocycloalkyl-)N—, —(HO—$C_{1-6}$-alkyl-)N—, —$(C_{1-6}$-alkyl—O—$C_{1-6}$-alkyl-)N—, —$(C_{3-6}$-cycloalkyl—O—$C_{1-6}$-alkyl-)N—, —$(C_{1-6}$-alkyl—(O)C—)N—, —$(C_{3-6}$-cycloalkyl—(O)C—)N—, —$(C_{1-6}$-haloalkyl—(O)C—)N—, —(HO—$C_{1-6}$-alkyl—(O)C—)N—, —$(C_{1-6}$-alkyl—O—$C_{1-6}$-alkyl—(O)C—)N—, —$(C_{3-6}$-cycloalkyl—O—$C_{1-6}$-alkyl—(O)C—)N—, —O—, —S—, —S(O)— or —$S(O)_2$—;

y is 0, 1 or 2;

or a salt thereof.

2. A compound of formula 1, according to claim 1, wherein $R^1$ is $R^{1.c}$ and $R^{1.c}$ is phenyl or pyridinyl; each ring optionally substituted by one, two or three residues independently selected from the group consisting of F, Cl, NC—, $R^{1.1}$ $R^{1.1}$O— and $R^{1.3}(O)_2S—$; and $R^{1.1}$ is independently selected from the group consisting of $C_{1-6}$-alkyl-, $C_{3-6}$-cycloalkyl-, $C_{1-6}$-haloalkyl-, $C_{3-6}$-halocycloalkyl-;

$R^{1.2}$ is HO—$C_{1-6}$-alkyl- or $R^{1.1}$—O—$C_{1-6}$-alkyl-;

$R^{1.3}$ is independently selected from the group consisting of H, HO—, $R^{1.1}$ or $R^{1.2}$;

or a salt thereof.

3. A compound of formula 1, according to claim 1, wherein $R^1$ is $R^{1.h}$ and $R^{1.h}$ is phenyl or pyridinyl; each ring optionally substituted by one or two residues independently selected from the group consisting of NC—, $Me(O)_2S$ and $Et(O)_2S$; or a salt thereof.

4. A compound of formula 1, according to claim 1, wherein $R^2$ is $R^{2.b}$ and $R^{2.b}$ is phenyl or a six-membered heteroaryl; comprising one or two nitrogen atoms; each ring optionally substituted with one or two substituents independently selected from the group consisting of halogen, $C_{1-4}$-alkyl-, $C_{1-4}$-haloalkyl-; or a salt thereof.

5. A compound of formula 1, according to claim 1, wherein $R^2$ is $R^{2.g}$ and $R^{2.g}$ is phenyl or pyridinyl, optionally substituted with a substituent independently selected from among $F_3C$ and $F_2HC—$; or a salt thereof.

6. A compound of formula 1, according to claim 1, wherein A is $A^b$ and $A^b$ is —$CH_2$—, optionally substituted with one or two substituents independently selected from the group consisting of F, Me, Et, i-Pr, MeO, EtO, $HOCH_2$—and $MeOCH_2$—; or a salt thereof.

7. A compound of formula 1, according to claim 1, wherein $R^4$ is $R^{4.a}$ and $R^{4.a}$ is independently selected from the group consisting of fluorine, $C_{1-6}$-alkyl- , $C_{3-6}$-cycloalkyl- , $C_{1-6}$-haloalkyl, $C_{3-6}$-halocycloalkyl-, HO—$C_{1-6}$-alkyl- and $C_{1-6}$-alkyl—O—$C_{1-6}$-alkyl-; or two $R^{4.a}$ are together $C_{1-6}$-alkylene or $C_{1-6}$-haloalkylene, wherein optionally one $CH_2$-group can be replaced by —O—; or a salt thereof.

8. A compound of formula 1, according to claim 1, wherein $R^3$ is a residue independently selected from the group consisting of $R^{3.1}$—;

$R^{3.2}O(O)C—$ or $R^{3.2}O(O)C—CH_2—$;

$R^{3.2}(O)_2S—$;

$(R^{3.2})_2N(O)C—$ or $(R^{3.2})_2N(O)C—CH_2—$;

$R^{3.1}$ is independently selected from the group consisting of H, $R^{3.3}$, $R^{3.4}$ , $C_{1-6}$-alkyl-$C_{3-6}$-cycloalkyl-, $C_{3-6}$-cycloalkyl-$C_{1-6}$-alkyl-, each optionally substituted with one or two substituents independently selected from among $R^{3.1.1}$;

$R^{3.1.1}$ is selected from the group consisting of HO—, halogen, NC—, $R^{3.3}$O—, $R^{3.5}$, $R^{3.6}$ and $R^{3.7}$; or $R^{3.1.1}$ is selected from the group consisting of a ring independently selected from phenyl and a four-membered heterocyclic ring containing one element independently selected from among N, O, S, S(O) and $S(O)_2$; or $R^{3.1.1}$ denotes a five- or six-membered heterocyclic or heteroaryl ring containing one, two or three elements independently selected from among N, O, S, S(O) and $S(O)_2$; each of the rings optionally substituted with one or two substituents independently selected from among HO—, O=, halogen, $R^{3.3}$, $R^{3.3}$O—, $R^{3.3}$—(O)C—, $R^{3.4}$, $R^{3.5}$, $R^{3.6}$ and $R^{3.7}$ or two substituents are together $R^{3.8}$;

$R^{3.2}$ is independently selected from among $R^{3.1}$, phenyl or a five- or six-membered heterocyclic or heteroaryl ring containing one, two or three elements independently selected from the group consisting of N, O, S, S(O) or $S(O)_2$;

each ring optionally substituted with one or two substituents independently selected from the group consisting of HO—, O=,NC—, halogen, $R^{3.5}$, $R^{3.3}$O—, $R^{3.3}$, —(O)C—, $R^{3.4}$,$R^{3.5}$, $R^{3.6}$ and $R^{3.7}$; or two substituents are together $R^{3.8}$;

or two R[3.2] are together a five- or six-membered monocyclic or an eight-, nine-or ten-membered bicyclic heterocyclic or heteroaryl ring optionally containing additional to the nitrogen one or two elements independently selected from the group consisting of N, O, S, S(O) and S(O)$_2$; optionally substituted with one or two substituents, independently selected from the group consisting of HO—, F, O=, R[3.3], R[3.3]O—, R[3.3]—(O)C—, R[3.4], R[3.5], R[3.7] and R[3.6] or two substituents are together R[3.8];

R[3.3] is independently selected from the group consisting of C$_{1-6}$-alkyl-, C$_{3-6}$-cycloalkyl-, C$_{1-6}$-haloalkyl-, C$_{3-6}$-halocycloalkyl-;

R[3.4] is HO—C$_{1-6}$-alkyl- or R[3.3]—O—C$_{1-6}$-alkyl-;

R[3.5] is independently selected from the group consisting of H$_2$N—, R[3.3]—HN—, (R[3.3])$_2$N—, R[3.3]—(O)C—HN—;

R[3.6] is independently selected from the group consisting of R[3.3]—(O)S—, R[3.3]—(O)$_2$S—, R[3.3](HN)S—, R[3.3](HN)(O)S—, R[3.3](R[3.3]N)S—, R[3.3](R[3.4]N)(O)S—, R[3.3](R[3.4]N)S—, R[3.3](R[3.4]N)(O)S—;

R[3.7] is independently selected from the group consisting of HO(O)C—, H$_2$N(O)C—, R[3.3]—O—(O)C—, R[3.3]—NH—(O)C—, (R[3.3])$_2$N—(O)C—;

R[3.8] is independently selected from among C$_{1-6}$-alkylene and C$_{1-6}$-haloalkylene, wherein optionally one or two CH$_2$-groups independently from each other are replaced by —HN—, —(R[3.3])N—, —(R[3.4])N—, —(R[3.3](O)C—)N—, —(R[3.4](O)C—)N—, —O—, —S—, —S(O)—or —S(O)$_2$—;

or a salt thereof.

9. A compound of formula 1, according to claim 1, wherein R[3] is independently selected from the group consisting of HO(O)C—H$_2$C—, MeO(O)C—H$_2$C—, H$_2$N(O)C—H$_2$C—, MeHN(O)C—H$_2$C—, Me$_2$N(O)C—H$_2$C—, morpholinyl—(O)C—H$_2$C—, azetidinyl—(O)C—H$_2$C—, pyrrolidinyl—(O)C—H$_2$C—, MeHN(O)C—, EtHN(O)C—, HO(CH$_2$)$_2$HN(O)C—, HO(CH$_2$)$_3$HN(O)C—, Me(O)S(CH$_2$)$_2$HN(O)C—, Me(O)$_2$S(CH$_2$)$_2$HN(O)C—, Et(O)$_2$S—and Me(O)$_2$S—; or a salt thereof.

10. A compound selected from the group consisting of

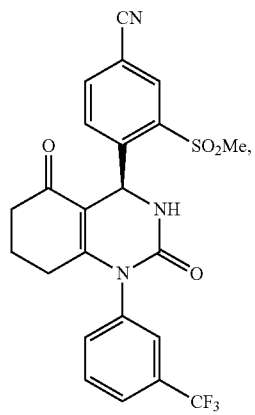

1.a

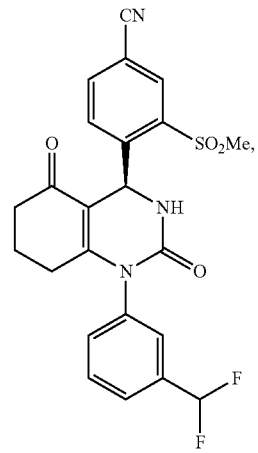

1.b

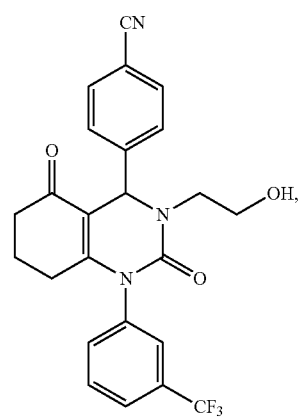

1.c

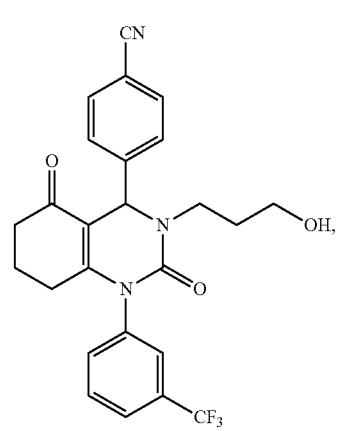

1.d

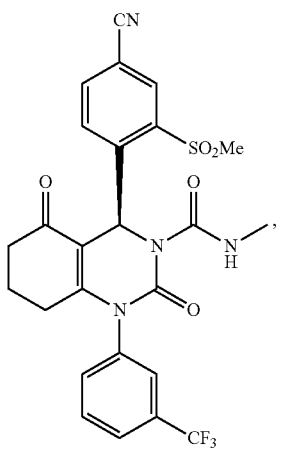
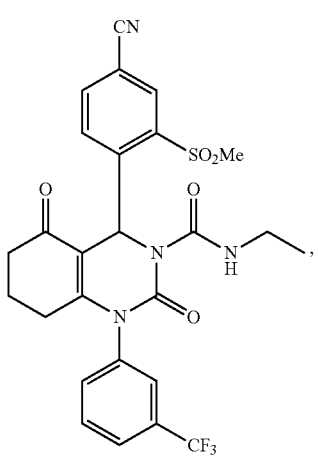
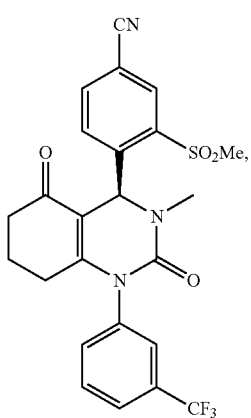
1.e
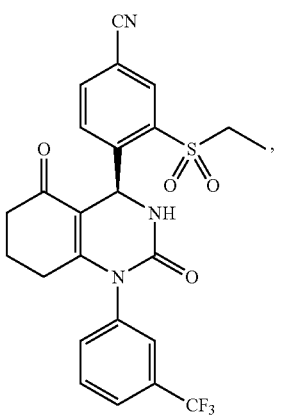
1.f
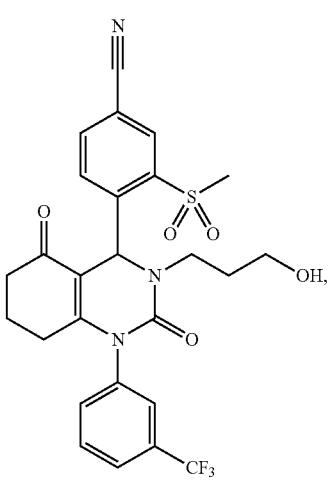
1.g
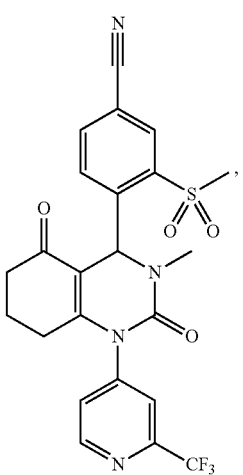
1.h
1.i
1.j

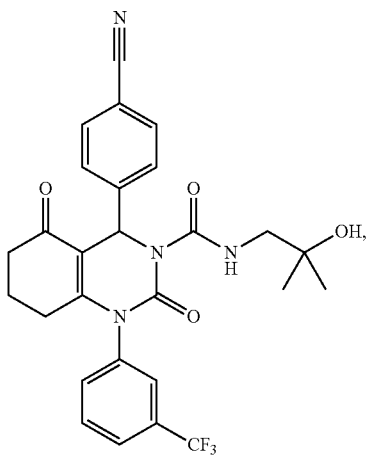

1.k

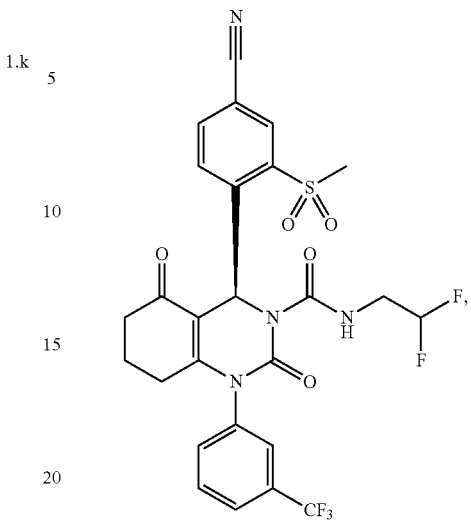

1.m

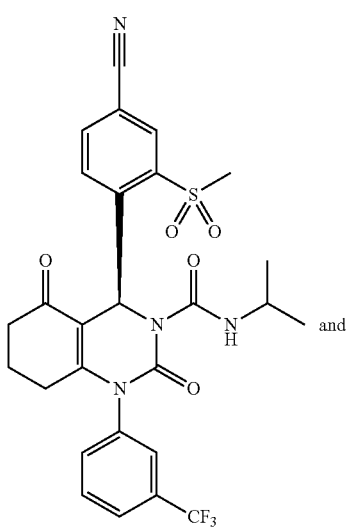

1.l and or a salt thereof.

11. A compound according to claim 1, wherein the configuration of formula 1 is formula 1'

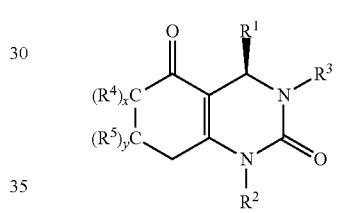

1' or a salt thereof.

12. A method for treating rheumatoid arthritis, which method comprises administration, to a host suffering from rheumatoid arthritis, a therapeutically effective amount of a compound of formula 1 according to claim 1.

13. A pharmaceutical composition, comprising a compound according to claim 1 and a pharmaceutically acceptable carrier.

* * * * *